US009534000B2

(12) United States Patent
Chari

(10) Patent No.: US 9,534,000 B2
(45) Date of Patent: Jan. 3, 2017

(54) CYTOTOXIC BENZODIAZEPINE DERIVATIVES AND METHODS OF PREPARATION

(75) Inventor: Ravi V. J. Chari, Newton, MA (US)

(73) Assignee: ImmunoGen, Inc., Waltham, MA (US)

( * ) Notice: Subject to any disclaimer, the term of this patent is extended or adjusted under 35 U.S.C. 154(b) by 482 days.

(21) Appl. No.: 13/984,762

(22) PCT Filed: Feb. 15, 2012

(86) PCT No.: PCT/US2012/025292
§ 371 (c)(1),
(2), (4) Date: Nov. 22, 2013

(87) PCT Pub. No.: WO2012/112708
PCT Pub. Date: Aug. 23, 2012

(65) Prior Publication Data
US 2014/0088089 A1 Mar. 27, 2014

Related U.S. Application Data

(66) Substitute for application No. 61/483,499, filed on May 6, 2011.

(60) Provisional application No. 61/443,062, filed on Feb. 15, 2011, provisional application No. 61/443,092, filed on Feb. 15, 2011.

(51) Int. Cl.
A61K 31/5517 (2006.01)
A61K 47/48 (2006.01)
C07D 519/00 (2006.01)
C07D 487/04 (2006.01)
A61K 45/06 (2006.01)
C07K 16/30 (2006.01)
A61K 39/00 (2006.01)

(52) U.S. Cl.
CPC ......... C07D 519/00 (2013.01); A61K 31/5517 (2013.01); A61K 45/06 (2013.01); A61K 47/4863 (2013.01); A61K 47/48215 (2013.01); A61K 47/48276 (2013.01); A61K 47/48384 (2013.01); A61K 47/48561 (2013.01); A61K 47/48569 (2013.01); C07D 487/04 (2013.01); C07K 16/30 (2013.01); A61K 2039/505 (2013.01); C07K 2317/24 (2013.01); C07K 2317/92 (2013.01)

(58) Field of Classification Search
CPC ........................... A61K 31/5517; A61K 47/48
See application file for complete search history.

(56) References Cited

U.S. PATENT DOCUMENTS 3,763,183 A 10/1973 Carabateas
3,860,600 A 1/1975 Carabateas
8,426,402 B2 4/2013 Li et al.
8,765,740 B2 7/2014 Li et al.
8,802,667 B2 8/2014 Li et al.
8,809,320 B2 8/2014 Li et al.
8,889,669 B2 11/2014 Li et al.
9,169,272 B2 10/2015 Li et al.
2009/0036431 A1 2/2009 Gauzy et al.
2010/0316656 A1 12/2010 Bouchard et al.
2011/0256157 A1 10/2011 Howard et al.
2012/0238731 A1 9/2012 Fishkin et al.
2013/0302359 A1 11/2013 Li et al.

FOREIGN PATENT DOCUMENTS

| EP | 0219292 A2 | 4/1987 |
|---|---|---|
| EP | 2019104 A1 | 1/2009 |
| JP | 57131791 | 8/1982 |
| RU | 2005133443 A | 4/2006 |
| RU | 2005133442 A | 5/2006 |
| WO | 93/18045 A1 | 9/1993 |
| WO | 00/12507 A2 | 3/2000 |
| WO | 00/12508 A2 | 3/2000 |
| WO | 2004/087716 A1 | 10/2004 |
| WO | 2004/087717 A1 | 10/2004 |
| WO | 2005/040170 A2 | 5/2005 |
| WO | 2005/085250 A1 | 9/2005 |
| WO | 2005/110423 A2 | 11/2005 |
| WO | 2007/039752 A1 | 4/2007 |
| WO | 2009/016516 A2 | 2/2009 |
| WO | 2009/016647 A1 | 2/2009 |
| WO | 2010/043880 A1 | 4/2010 |
| WO | 2010/091150 A1 | 8/2010 |

(Continued)

OTHER PUBLICATIONS

Internationa Preliminary Report on Patentability on International Application PCT/US2010/023150, dated Aug. 9, 2011.
Internationa Preliminary Report on Patentability on International Application PCT/US2012/025252 dated Jun. 14, 2013.
International Preliminary Report on Patentability on International Application PCT/US2012/025257, dated Aug 21, 2013.
International Preliminary report on Patentability on the Application PCT/US2012/025292, dated Aug 21, 2013.

(Continued)

Primary Examiner — Samira Jean-Louis
(74) Attorney, Agent, or Firm — McCarter & English, LLP; Yu Lu; Xin Zhang

(57) ABSTRACT

The invention relates to novel benzodiazepine derivatives with antiproliferative activity and more specifically to novel benzodiazepine compounds, such as those in formulas (V)-(VII). The invention also provides conjugates of the benzodiazepine compounds linked to a cell-binding agent. The invention further provides compositions and methods useful for inhibiting abnormal cell growth or treating a proliferative disorder in a mammal using the compounds or conjugates of the invention. The present invention is further directed to methods of preparing a conjugate of a cell-binding agent and a cytotoxic compound. The methods comprise the use of an imine reactive compound to enable efficient conjugations of cytotoxic compounds with cell binding agents.

28 Claims, 51 Drawing Sheets

(56) References Cited

FOREIGN PATENT DOCUMENTS

| WO | 2011/106528 A1 | 9/2011 |
|---|---|---|
| WO | 2011/130613 A1 | 10/2011 |
| WO | 2011/130616 A1 | 10/2011 |
| WO | 2012/112687 A1 | 8/2012 |
| WO | 2014/031566 A1 | 2/2014 |

OTHER PUBLICATIONS

International Search Report and Written Opinion dated Mar. 31, 2010, issued in International Application No. PCT/US10/23150.
International Search report and Written Opinion issued in International application PCT/US2012/025252, dated Jun. 26, 2012.
International Search Report and Wrtten Opinion issued in International Application PCT/US2012/025257, dated Jun. 29, 2012.
Kamal et al., "Design, synthesis, and evaluation of mixed imine-amine pyrrolobenzodiazepine dimers wtih efficient DNA binding affinity and potent cytotoxicity," Bioorg. Med. Chem. (2004) 12:5427-5436.
Kamal et al., "Development of Pyrrolo[2,1-c][1,4]benzodiazepine β-Galactoside Prodrugs for Selective Therapy of Cancer by ADEPT and PMT," ChemMedChem (2008) 3:794-802.
Li et al., "Design, Synthesis and Evalaution of a Novel NDA-Interactive Agent: A Promising New Class of Cytotoxic Molecules for Use in Antibody-Drug Conjugates," 239th ACS National Meeting, San Francisco, CA 2010 [MEDI 251].
Masterson et al "Synthesis and biological evalaution of Novel pyrrolo[2,1-c][1,4]benzodiazepine prodrugs for use in antibody-directed enzyme prodrug therapy," Bioorg. Med. Chem. Lett. (2006) 16:252-256.
Miller et al., "Potent antigen-specific anti-tumor activity observed with antibody-drug conjugates (ADCs) made using a new class of DNA-crosslinking agents," poster presentation at the AACR-NCI-EORTC, Abstract B126 (Nov. 2009).
Miller et al., "Abstract B126, Potent antigen-specific anti-tumor activity observed with antibody-drug conjugates (ADCs) made using a new class of DNA-crosslinking agents," Mol. Cancer Ther., 8(12) Suppl 1 (2009).
Thurston et al., "Synthesis and reactivity of a novel oxazolo[2,3-c][1,4]benziodiazepine ring system with DNA recognition potential: a new class of anthramycins," J. Chem. Soc., No. 12, p. 874 (1990).
Tozuka et al., "Studies on tomamycin. III. Syntheses and antitumor activity of tomamycin analogs", J. Antibiotics., 36 (12):1699-1708 (1983).
Guo et al., "Synthesis and Evaluation of a Cyclic Imine Derivative Conjugated to a Fluorescent Molecule for Labeling Proteins," Bioorg. Med. Chem. Lett., 19(4):1210-1213 (2009).

Synthetic scheme of dimers 4e and 5e

Synthetic scheme of dimers 37d and 38d

Synthetic scheme of compound 4b with 5-ethyl-2-methylpyridine borane (PEMB)

Synthetic scheme of compound 5b with sodium triacetoxyborohydride (STAB)

One-step conjugation scheme to prepare dimer-antibody immunoconjugates

One-step conjugation scheme to prepare dimer-antibody immunoconjugates

One-step conjugation scheme to prepare dimer-antibody immunoconjugates

One-step conjugation scheme to prepare dimer-antibody immunoconjugates

One-step conjugation scheme to prepare dimer-antibody immunoconjugates

Synthetic Scheme of Linker 5e

Alternate Synthsis of 4-(benzyloxy)-5-methoxy-2-nitrobenzoic acid used in the Preperation of IBD Monomer Alternate Synthesis of (5-((2-(2-(2-methoxyethoxy)ethoxy)ethyl)(2-methyl-2-(methyldisulfanyl)propyl)amino)-1,3-phenylene)dimethanol (1b)

Alternate Synthesis of (5-((2-(2-(2-methoxyethoxy)ethoxy)ethyl)(2-methyl-2-(methyldisulfanyl)propyl)amino)-1,3-phenylene)dimethanol (1b)

CYTOTOXIC BENZODIAZEPINE DERIVATIVES AND METHODS OF PREPARATION

REFERENCE TO RELATED APPLICATIONS

This application is a 35 U.S.C. §371 national stage filing of International Application No. PCT/US2012/025292, filed on Feb. 15, 2012, which claims the benefit of the filing date under 35 U.S.C. §119(e), of U.S. Provisional Application No. 61/443,062, filed on Feb. 15, 2011, U.S. Provisional Application No. 61/483,499, filed on May 6, 2011, and U.S. Provisional Application No. 61/443,092, filed on Feb. 15, 2011, the entire contents of which, including all drawings, formulae, specifications, and claims, are incorporated herein by reference.

FIELD OF THE INVENTION

The present invention relates to novel cytotoxic compounds, and cytotoxic conjugates comprising these cytotoxic compounds and cell-binding agents. More specifically, this invention relates to novel benzodiazepine compounds derivatives thereof, intermediates thereof, conjugates thereof, and pharmaceutically acceptable salts thereof, which are useful as medicaments, in particular as antiproliferative agents.

This invention also describes the use of imine reactive reagents for the preparation of conjugates of cell-binding agents with DNA-binding cytotoxic drugs containing one or more imine functional groups.

BACKGROUND OF THE INVENTION

Benzodiazepine derivatives are useful compounds for treating various disorders, and include medicaments such as, antiepileptics (imidazo[2,1-b][1,3,5]benzothiadiazepines, U.S. Pat. No. 4,444,688; U.S. Pat. No. 4,062,852), antibacterials (pyrimido[1,2-c][1,3,5]benzothiadiazepines, GB 1476684), diuretics and hypotensives (pyrrolo(1,2-b)[1,2,5] benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

Recently, it has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo[1,2-b][1,2,5]benzothiadiazepines and pyrrolo[1,2-b][1,2,5]benzodiazepine derivatives (WO2007/015280), tomaymycin derivatives (e.g., pyrrolo[1,4]benzodiazepines), such as those described in WO 00/12508, WO2005/085260, WO2007/085930, and EP 2019104. Benzodiazepines are also known to affect cell growth and differentiation (Kamal A., et al., Bioorg Med. Chem. 2008 Aug. 15; 16(16):7804-10 (and references cited therein); Kumar R, Mini Rev Med. Chem. 2003 June; 3(4):323-39 (and references cited therein); Bednarski J J, et al., 2004; Sutter A. P, et al., 2002; Blatt N B, et al., 2002), Kamal A. et al., Current Med. Chem., 2002; 2; 215-254, Wang J-J., J. Med. Chem., 2206; 49:1442-1449, Alley M. C. et al., Cancer Res. 2004; 64:6700-6706, Pepper C. J., Cancer Res 2004; 74:6750-6755, Thurston D. E. and Bose D. S., Chem Rev 1994; 94:433-465; and Tozuka, Z., et al., Journal of Antibiotics, (1983) 36; 1699-1708. General structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove and crosslink DNA enables them to interfere with DNA processing, hence their potential for use as antiproliferative agents.

The first pyrrolobenzodiazepine to enter the clinic, SJG-136 (NSC 694501) is a potent cytotoxic agent that causes DNA inter-strand crosslinks (S. G Gregson et al., 2001, J. Med. Chem., 44: 737-748; M. C. Alley et al., 2004, Cancer Res., 64: 6700-6706; J. A. Hartley et al., 2004, Cancer Res., 64: 6693-6699; C. Martin et al., 2005, Biochemistry., 44: 4135-4147; S. Arnould et al., 2006, Mol. Cancer. Ther., 5: 1602-1509). Results from a Phase I clinical evaluation of SJG-136 revealed that this drug was toxic at extremely low doses (maximum tolerated dose of 45 µg/m$^2$, and several adverse effects were noted, including vascular leak syndrome, peripheral edema, liver toxicity and fatigue. DNA damage was noted at all doses in circulating lymphocytes (D. Hochhauser et al., 2009, Clin. Cancer Res., 15: 2140-2147). Thus, there exists a need for improved benzodiazepine derivatives that are less toxic and still therapeutically active for treating a variety of proliferative disease states, such as cancer.

Monoclonal antibodies are increasingly being explored as therapeutic agents against cancer. Several monoclonal antibodies against cancer cell-surface antigens have already been approved for cancer treatment, such as rituximab for non-Hodgkin's lymphoma, trastuzumab for breast cancer, cetuximab for head and neck and colorectal cancer, cetuximab, panitimumab, and bevacizumab for colorectal cancer, and alemtuzumab for chronic lymphocytic leukemia (Strome, S. E., Sausville, E. A., and Mann, D., 2007, The Oncologist, 12, 1084-1095). However, the cytotoxic activity of a "naked" antibody can be limited to the mechanisms of receptor function inhibition, complement-dependent cytotoxicity (CDC), and antibody-dependent cell-mediated cytotoxicity (ADCC).

An approach to enhance the cytotoxic activity of antibody toward target cancer cells is by linking antibody with cytotoxic effectors (A. D. Ricart, and A. W. Tolcher, 2007, Nat. Clin. Pract. Oncol. 4, 245-255; Lambert, J., 2010, Drugs of the Future 35, 471-480). The antibody-cytotoxic drug conjugate (ADC) binds specifically to cancer cells, followed by conjugate internalization and degradation, which results in the intracellular release of the toxic drug and ultimately to the death of the cancer cells. The cytotoxic drugs that have been employed in linkage with antibodies include antitubulin drugs such as maytansinoids and auristatins, DNA-binding drugs such as calicheamicin that causes sequence-specific double-stranded DNA cleavage. Another class of DNA-binding cytotoxic drugs includes imine-containing pyrrolobenzodiazepines (PBD) such as N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo[1,2-b][1,2,5]benzothiadiazepines and pyrrole[1,2-b][1,2,5]benzodiazepine derivatives (WO2007/015280), tomaymycin derivatives (e.g., pyrrolo[1,4]benzodiazepines), such as those described in WO 00/12508, WO2005/085260, WO2007/085930, EP 2019104, and U.S. Pat. No. 6,156,746). Other DNA-binding benzodiazepine drugs are described in US Patent Publication No. 2010/0203007A1. These benzodiazepine drugs containing imine bonds bind to the minor groove of DNA and interfere with DNA function, resulting in cell death.

There is a need for new methods for preparing conjugates of cell-binding agent and cytotoxic drugs bearing an imine group.

SUMMARY OF THE INVENTION

Cytotoxic benzodiazepine dimers disclosed in the art possess two imine functionalities in their free form or reversibly protected form, such as a hydrate, alkoxylate or sulfonate. The presence of these two imine functionalities results in crosslinking of DNA (S. G. Gregson et al., 2001, *J. Med. Chem.*, 44: 737-748). The present invention is partly based on the unexpected finding that cell binding agent conjugates of new cytotoxic benzodiazepine derivatives, such as pyrrolobenzodiazapene dimers that are devoid of two imine functionalities (e.g., one imine functionality and one amine functionality), and thus incapable of crosslinking DNA, display a much higher therapeutic index (ratio of maximum tolerated dose to minimum effective dose) in vivo compared to benzodiazepine derivatives that can crosslink DNA that are previously disclosed in the art.

Thus one object of the invention is to provide cytotoxic compound comprising a linking group with a reactive group bonded thereto capable of covalently linking the cytotoxic compound to a cell binding agent (CBA, see below), wherein the cytotoxic compound is represented by any one of the following formulas:

a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

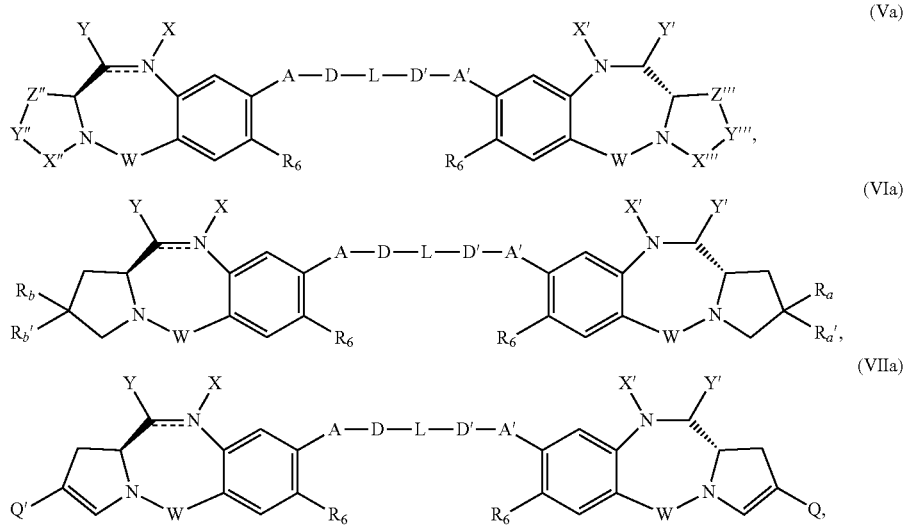

or a pharmaceutically acceptable salt thereof, wherein:
the double line ═ between N and C represents a single bond or a double bond, provided that when it is a double bond X is absent and Y is —H, or a linear or branched alkyl having 1 to 4 carbon atoms, and when it is a single bond, X is —H, the linking group with the reactive group bonded thereto, or an amine protecting moiety;

Y is —H or a leaving group selected from —OR, —OCOR', —OCOOR', —OCONR'R", —NR'R", —OCOR', —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C═NH)NR'R", an amino acid, or a peptide represented by —NRCOP', wherein P' is an amino acid or a polypeptide containing between 2 to 20 amino acid units, —SR, —SOR', —SO_2M, —SO_3M, —OSO_3M, halogen, cyano and an azido; or, Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or M is —H or a pharmaceutically acceptable cation;
$R_6$ is —H, —R, —OR, —SR, —NR'R", —NO_2, halogen or the linking group with the reactive group bonded thereto;
R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;
R' and R" are each independently selected from —H, —OH, —OR, —NHR, —NR_2, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3- to 18-membered heterocyclic ring having 1 to 6 heteroatoms independently selected from O, S, N and P;

$R^c$ is —H or a substituted or unsubstituted linear or branched alkyl having 1 to 4 carbon atoms, or the linking group with the reactive group bonded thereto;

n is an integer from 1 to 24;

W is selected from C=O, C=S, $CH_2$, BH, SO and $SO_2$;

X' is selected from —H, an amine-protecting group, the linking group with the reactive group bonded thereto, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 0.6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

A and A' are the same or different, and are independently selected from —O—, oxo (—C(=O)—), —CRR'O—, —CRR'—, —S—, —CRR'S—, —$NR_5$ and —CRR'N($R_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2)_n$—;

L is absent, the linking group with the reactive group bonded thereto, a polyethylene glycol unit (—$OCH_2CH_2)_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; the phenyl or heterocyclic or heteroaryl ring can be optionally substituted, wherein the substituent can comprise the linking group with the reactive group bonded thereto;

X" and X''' are the same or different, and are independently selected from —$(CH_2)_{n'}$—, —NR'—, —CO—, —BH—, —SO— or —$SO_2$—;

Y" and Y''' are the same or different, and are independently selected from —O—, —$(CH_2)_{n'}$—, —NR'— or —S—;

Z" and Z''' are the same or different, and are independently selected from —$(CH_2)_{n'}$—, —$CR_7R_8$—, —$NR_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH unit;

Ar and Ar' are each independently absent, or represent an aryl group;

$Q_2$ and $Q_2'$ are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)$NH_2$], —OR, —NR'R", —$NO_2$, —NCO, —NR'COR", —SR, a sulfoxide represented by —SOR', a sulfone represented by —$SO_2R'$, a sulfonate —$SO_3M$, a sulfate —$OSO_3M$, a sulfonamide represented by $SO_2NR'R"$, cyano, an azido, —COR', —OCOR' or —OCONR'R"; and $R^{c'}$ is absent or selected from linear or branched alkyl, alkenyl or alkynyl having 1 to 5 carbon atoms.

In certain embodiments, X is not the linking group with the reactive group bonded thereto. In certain embodiments, the double line ═══ between N and C represents a single bond, Y is not —H.

In certain embodiments, Y is a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —$SO_2M$, —$SO_3M$, —$OSO_3M$, halogen, cyano and an azido.

A second object of the invention is to provide conjugates of cell binding agents with the novel benzodiazepine compounds or derivatives thereof of the present invention. These conjugates are useful as therapeutic agents, which are delivered specifically to target cells and are cytotoxic.

Specifically, a conjugate of the invention may comprise: a cytotoxic compound and a cell binding agent (CBA), wherein the cytotoxic compound comprises a linking group which covalently links the cytotoxic compound to the CBA, and wherein the cytotoxic compound is represented by any one of the following formulas:

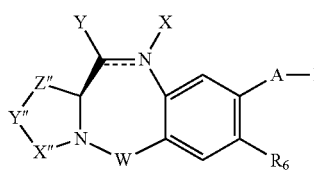 (Vb)

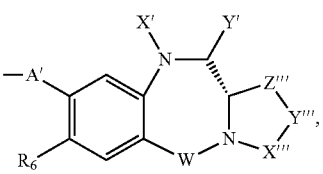

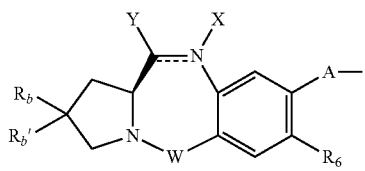 (VIb)

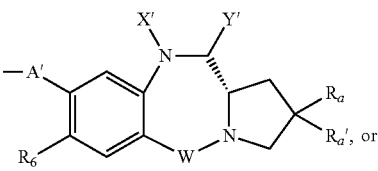

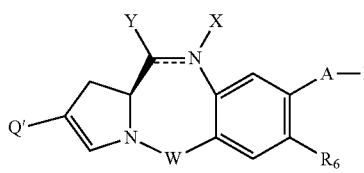 (VIIb)

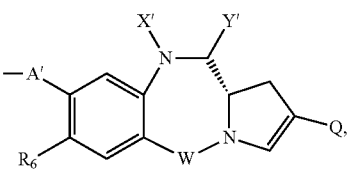

or a pharmaceutically acceptable salt thereof, wherein:

the double line $\doubleequals$ between N and C represents a single bond or a double bond, provided that when it is a double bond X is absent and Y is —H, or a linear or branched alkyl having 1 to 4 carbon atoms, and when it is a single bond, X is —H, the linking group, or an amine protecting moiety;

Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

M is —H or a pharmaceutically acceptable cation;

R$_6$ is —H, —R, —OR, —SR, —NR'R", —NO$_2$, halogen or the linking group;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group;

n is an integer from 1 to 24;

W is selected from C=O, C=S, CH$_2$, BH, SO and SO$_2$;

X' is selected from —H, an amine-protecting group, the linking group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group, a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can be the linking group;

X" and X''' are the same or different, and are independently selected from —(CH$_2$)$_{n'}$—, —NR'—, —CO—, —BH—, —SO— or —SO$_2$—;

Y" and Y''' are the same or different, and are independently selected from —O—, —(CH$_2$)$_{n'}$—, —NR'— or —S—;

Z" and Z''' are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and R$^{c'}$ is absent or selected from linear or branched alkyl, alkenyl or alkynyl having 1 to 5 carbon atoms.

In certain embodiments, X is not the linking group. In certain embodiments, the double line = between N and C represents a single bond, Y is not —H.

In certain embodiments, Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido. In certain embodiments, Y is not —H.

The present invention also includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier). The present invention additionally includes a composition (e.g., a pharmaceutical composition) comprising novel benzodiazepine compounds, derivatives thereof, or conjugates thereof (and/or solvates, hydrates and/or salts thereof), and a carrier (a pharmaceutically acceptable carrier), further comprising a second therapeutic agent. The present compositions are useful for inhibiting abnormal cell growth or treating a proliferative disorder in a mammal (e.g., human). The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds, derivatives thereof, or conjugates thereof, (and/or solvates and salts thereof) or a composition thereof, alone or in combination with a second therapeutic agent. The present invention includes a method of synthesizing and using novel benzodiazepine compounds, derivatives thereof, and conjugates thereof for in vitro, in situ, and in vivo diagnosis or treatment of mammalian cells, organisms, or associated pathological conditions.

The compounds of this invention, derivatives thereof, or conjugates thereof, and compositions comprising them, are useful for treating or lessening the severity of disorders, such as, characterized by abnormal growth of cells (e.g., cancer). Other applications for compounds and conjugates of this invention include, but are not limited to, treating conditions such as cancer, rheumatoid arthritis, multiple sclerosis, graft versus host disease (GVHD), transplant rejection, lupus, myositis, infection, immune deficiency such as AIDS and inflammatory diseases in a mammal (e.g., human).

The present invention also describes the use of imine-reactive reagents for treating an imine-containing drug, which resulted in an unexpected improvement in its conjugation reaction with cell binding agents (CBA) such as antibodies. The reagents are such that the cell killing properties of the drug are not diminished and the integrity of the CBA (antibody) is fully maintained.

In one embodiment, the present invention is directed to a method for preparing a conjugate comprising a cell-binding agent (CBA) conjugated to a cytotoxic compound with a linking group, the method comprising reacting a modified cytotoxic compound with a modified CBA at a pH of about 4 to about 9, wherein:

a) the modified CBA comprises a residue of a bifunctional crosslinking agent bonded to the CBA, and the residue comprises the linking group and a thiol-reactive group; and b) the modified cytotoxic compound comprises a thiol group, and a group represented by:

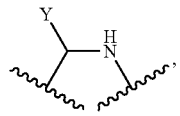

wherein:

(1) the modified cytotoxic compound is represented by one of the following formulae, or a pharmaceutically acceptable salt thereof:

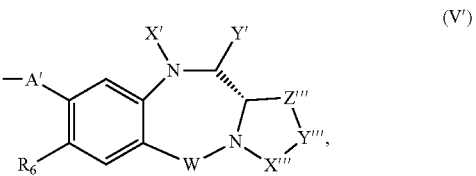 (V')

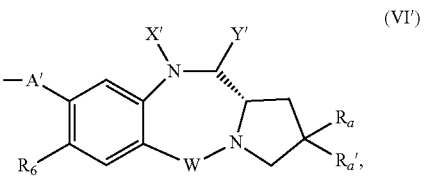 (VI')

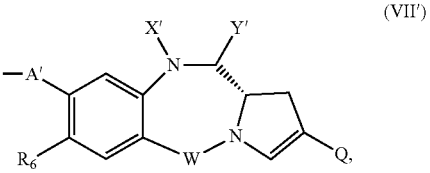 (VII')

and, (2) the modified cytotoxic compound and the linking group portion of the conjugate is represented by one of the following formulae:

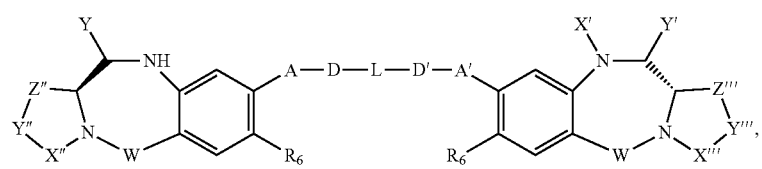 (Vb')

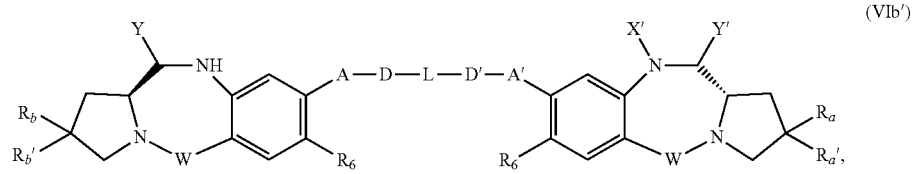 (VIb')

-continued

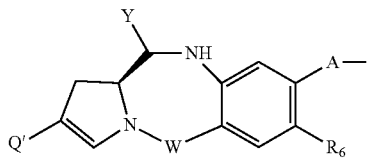 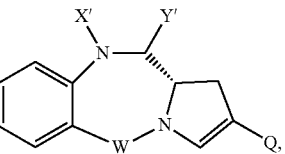

(VIIb′)

Y is a leaving group, and is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS (OR$^i$), R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

X′ is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y′ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$^c$ is —H or a substituted or unsubstituted linear or branched alkyl having 1 to 4 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R′ and R″ are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR′R″, —NO$_2$, or halogen;

A and A′ are the same or different, and are independently selected from —O—, oxo (—C(=O)—), —CRR′O—, —CRR′—, —S—, —CRR′S—, —N(R$_5$)— and —CRR′N(R$_5$)—, R$_5$ for each occurrence is independently —H or an optionally substituted linear or branched alkyl having 1 to 10 carbon atoms;

D and D′ are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X″ and X‴ are the same or different, and are independently selected from —(CH$_2$)$_{n'}$—, —NR′—, —CO—, —BH—, —SO— or —SO$_2$—;

Y″ and Y‴ are the same or different, and are independently selected from —O, —(CH$_2$)$_{n'}$—, —NR′— or —S—;

Z″ and Z‴ are the same or different, and are independently selected from —(CH$_2$)$_{n'}$—, —CR$_7$R$_8$—, —NR$_9$—, —O—, and —S—;

n′ is selected from 0, 1, 2 and 3;

R$_7$ and R$_8$ are the same or different, and are each independently selected from —H, —OH, —SH, —COOH, —NHR′, a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R";

R$^{c'}$ is absent or selected from linear or branched alkyl, alkenyl or alkynyl having 1 to 5 carbon atoms; and wherein at least one of X', Y', R$_6$, R$^c$, L (e.g., through an optionally substituted group), Q, Q', Q$_2$ or Q$_2$' is bonded to the linking group in formulas (Vb'), (VIb'), or (VIIb').

In certain embodiments, the modified cytotoxic compound is produced by reacting an imine reactive reagent with an imine-containing cytotoxic compound bearing the thiol group having one of the following formulas, or a pharmaceutically acceptable salt thereof:

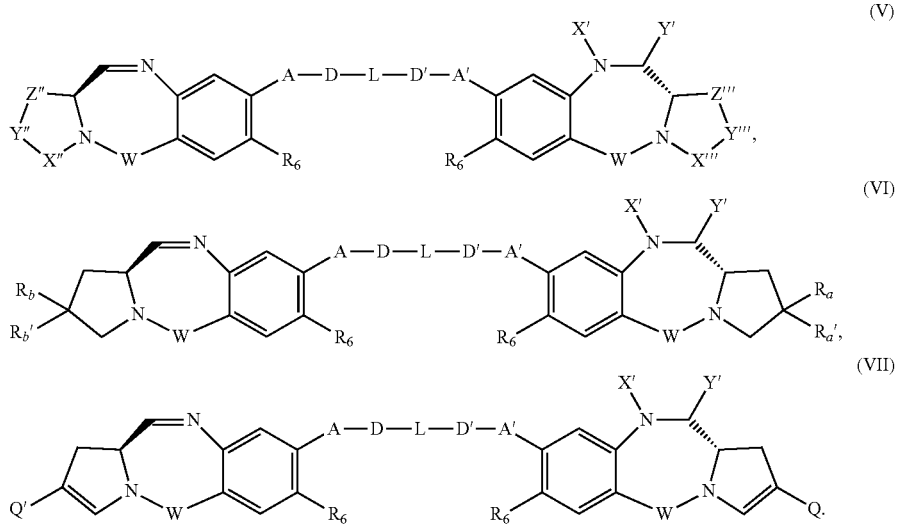

In another embodiment, the present invention is directed to a method for preparing a conjugate comprising a cell-binding agent (CBA) conjugated to a cytotoxic compound with a linking group, the method comprising reacting the CBA with an imine-containing cytotoxic compound, an imine reactive reagent, and a bifunctional crosslinking agent comprising the linking group to form the conjugate, wherein:

the imine-containing cytotoxic compound is represented by one of the following formulae, or a pharmaceutically acceptable salt thereof:

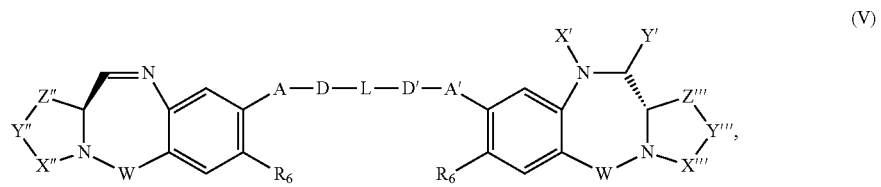

-continued

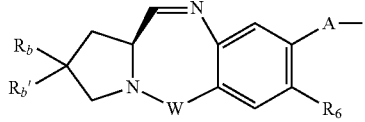 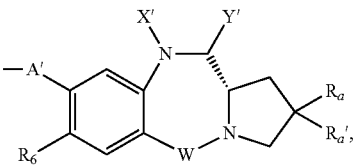 (VI)

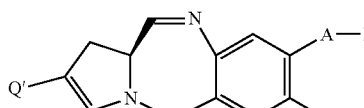 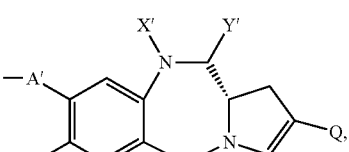 (VII)

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$^c$ is —H or a substituted or unsubstituted linear or branched alkyl having 1 to 4 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, or halogen;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O—, —(CH$_2$)$_{n'}$—, —NR'— or —S—;

Z" and Z'" are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q₁ and Q₁' are each independently absent, a linear, branched or cyclic alkyl from 1 to 6 carbon atoms or a —CH═CH unit;

Ar and Ar' are each independently absent or represent an aryl group;

Q₂ and Q₂' are each independently selected from —H, a substituted or unsubstituted linear, branched or cyclic alkyl, alkenyl or alkynyl having from 1 to 10 carbon atoms, a polyethylene glycol unit —R$^c$'—(OCH₂CH₂)$_n$—R$^c$, or a substituent selected from a halogen, guanidinium [—NH(C═NH)NH₂], —OR, —NR'R", —NO₂, —NCO, —NR'COR", —SR, a sulfoxide represented by —SOR', a sulfone represented by —SO₂R', a sulfonate —SO₃M, a sulfate —OSO₃M, a sulfonamide represented by SO₂NR'R", cyano, an azido, —COR', —OCOR' or —OCONR'R";

R$^c$' is absent or selected from linear or branched alkyl, alkenyl or alkynyl having 1 to 5 carbon atoms; and wherein at least one of X', Y', R₆, R$^c$, L (e.g., through an optionally substituted group), Q, Q', Q₂ or Q₂' is bonded to the linking group in the conjugate.

In another embodiment, the present invention is directed to a method for preparing a conjugate comprising a cell-binding agent (CBA) conjugated to a cytotoxic compound with a linking group, the method comprising:

a) reacting a modified cytotoxic compound with a bifunctional crosslinking agent comprising the linking group, a group reactive with the CBA (such as a thiol group, a maleimide group, a haloacetamide group, or an amine group), and a group reactive with the modified cytotoxic compound, to form a second modified cytotoxic compound covalently bonded to a residue of the bifunctional crosslinking agent, wherein the residue comprises the linking group and the group reactive with the CBA;

wherein the modified cytotoxic compound is represented by one of the following formulas, or a pharmaceutically acceptable salt thereof:

(PO₃SH₃, PO₂S₂H₂, POS₃H₂, PS₄H₂ or a salt of PO₃S$^{3-}$, PO₂S₂$^{3-}$, POS₃$^{3-}$ or PS₄$^{3-}$ formed with a cation), thio phosphate ester (R$^i$O)₂PS(OR$^i$), R$^i$S—, R$^i$SO, R$^i$SO₂, R$^i$SO₃, thiosulfate (HS₂O₃ or a salt of S₂O₃$^{2-}$ formed with a cation), dithionite (HS₂O₄ or a salt of S₂O₄$^{2-}$ formed with a cation), phosphorodithioate (P(═S)(OR$^{k'}$)(S)(OH) or a salt thereof formed with a cation), hydroxamic acid (R$^{k'}$C(═O)NOH or a salt formed with a cation), formaldehyde sulfoxylate (HOCH₂SO₂⁻ or a salt of HOCH₂SO₂⁻ formed with a cation, such as HOCH₂SO₂⁻Na⁺) or a mixture thereof, wherein R$^i$ is a linear or branched alkyl having 1 to 10 carbon atoms and is substituted with at least one substituent selected from —N(R$^j$)₂, —CO₂H, —SO₃H, and —PO₃H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

X' is selected from —H, an amine-protecting group, an optionally substituted linear, branched or cyclic alkyl, alkenyl or alkynyl having from 1 to 10 carbon atoms, a polyethylene glycol unit —(CH₂CH₂O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected

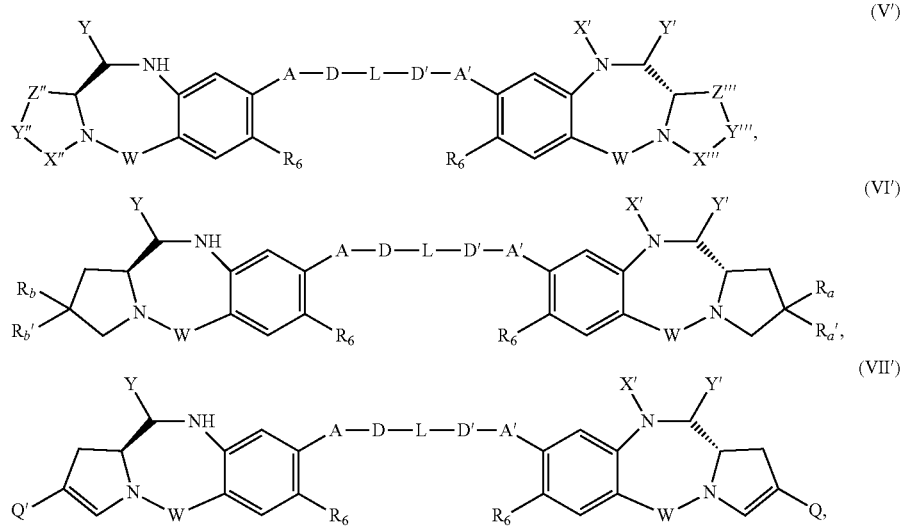

wherein:

Y is a leaving group, and is a sulfite (HSO₃, HSO₂ or a salt of HSO₃⁻, SO₃$^{2-}$ or HSO₂⁻ formed with a cation), metabisulfite (H₂S₂O₅ or a salt of S₂O₅$^{2-}$ formed with a cation), mono-, di-, tri-, and tetra-thiophosphate from nitrogen, oxygen, and sulfur, an optionally substituted 3 to 18-membered heterocyclic ring having 1 to 6 heteroatoms;

R$^c$ is —H or a substituted or unsubstituted linear or branched alkyl having 1 to 4 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, or halogen;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X" and X"' are the same or different, and are independently selected from —(CH$_2$)$_{n'}$—, —NR'—, —CO—, —BH—, —SO— or —SO$_2$—;

Y" and Y"' are the same or different, and are independently selected from —O, —(CH$_2$)$_{n'}$—, —NR'— or —S—;

Z" and Z"' are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$, and/or R$_b$ and R$_{b'}$, together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R";

R$^{c'}$ is absent or selected from linear or branched alkyl, alkenyl or alkynyl having 1 to 5 carbon atoms; and b) reacting the second modified cytotoxic compound with the CBA through the group reactive with the CBA, at a pH of about 4 to about 9, to form the conjugate, wherein at least one of X', Y', R$_6$, R$^c$, L (e.g., through an optionally substituted group), Q, Q', Q$_2$ or Q$_2$' is bonded to the linking group in the conjugate.

In any of the above embodiments, the imine-containing cytotoxic compound may be represented by any one of the following formulas, or a pharmaceutically acceptable salt thereof:

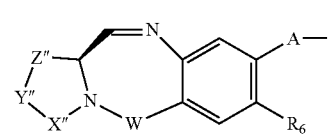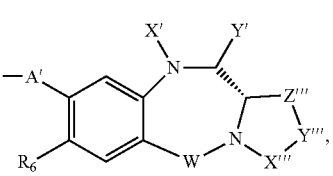

(V)

-continued

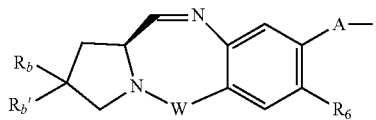

(VI)

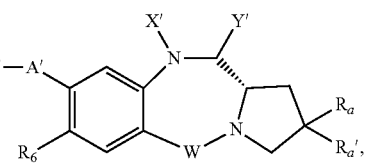

(VII)

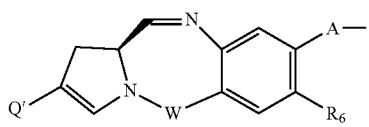

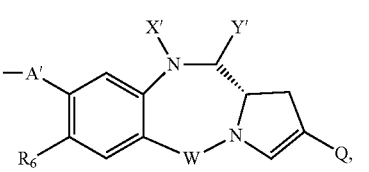

wherein:
X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$^c$ is —H or a substituted or unsubstituted linear or branched alkyl having 1 to 4 carbon atoms;

R$_6$ is —H, —R, —OR, —SR, —NR'R", —NO$_2$, or halogen;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;
W is selected from C=O, C=S, CH$_2$, BH, SO and SO$_2$;
A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, and is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X" and X''' are the same or different, and are independently selected from —(CH$_2$)$_{n'}$—, —NR'—, —CO—, —BH—, —SO— or —SO$_2$—;

Y" and Y''' are the same or different, and are independently selected from —O—, —(CH$_2$)$_{n'}$—, —NR'— or —S—;

Z" and Z''' are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;
Q' is Q$_1$'-Ar'-Q$_2$';

Q₁ and Q₁' are each independently absent, a linear, branched or cyclic alkyl from 1 to 6 carbon atoms or a —CH=CH unit;

Ar and Ar' are each independently absent or represent an aryl group;

Q₂ and Q₂' are each independently selected from —H, a substituted or unsubstituted linear, branched or cyclic alkyl, alkenyl or alkynyl having from 1 to 10 carbon atoms, a polyethylene glycol unit —$R^{c'}$—(OCH₂CH₂)ₙ—$R^c$, or a substituent selected from a halogen, guanidinium [—NH(C=NH)NH₂], —OR, —NR'R", —NO₂, —NCO, —NR'COR", —SR, a sulfoxide represented by —SOR', a sulfone represented by —SO₂R', a sulfonate —SO₃M, a sulfate —OSO₃M, a sulfonamide represented by SO₂NR'R", cyano, an azido, —COR', —OCOR' or —OCONR'R"; and $R^{c'}$ is absent or selected from linear or branched alkyl, alkenyl or alkynyl having 1 to 5 carbon atoms.

In yet another embodiment, the present invention is directed to a method for preparing a conjugate comprising a cell-binding agent (CBA) conjugated to a cytotoxic compound with a linking group, the method comprising reacting a second modified cytotoxic compound with the CBA at a pH of about 4 to about 9, wherein the second modified cytotoxic compound has the structure of one of the following formulas, or a pharmaceutically acceptable salt thereof:

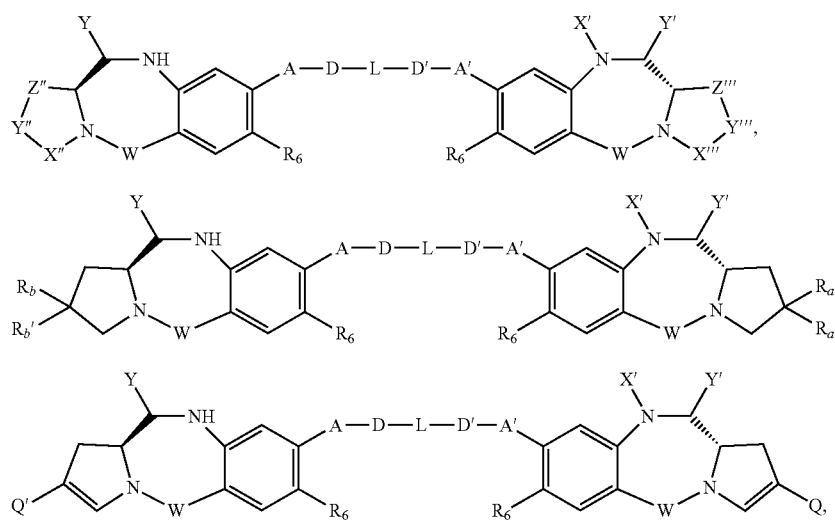

said second modified cytotoxic compound comprising:

a) a residue of a bifunctional crosslinking agent bonded to the cytotoxic compound, and the residue comprises the linking group and a reactive group selected from a reactive ester and a thiol-reactive group, and b) a group represented by:

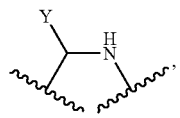

wherein:

Y is a sulfite (HSO₃, HSO₂ or a salt of HSO₃⁻, SO₃²⁻ or HSO₂⁻ formed with a cation), metabisulfite (H₂S₂O₅ or a salt of $S_2O_5^{2-}$ formed with a cation), mono-, di-, tri-, and tetra-thiophosphate (PO₃SH₃, PO₂S₂H₂, POS₃H₂, PS₄H₂ or a salt of $PO_3S^{3-}$, $PO_2S_2^{3-}$, $POS_3^{3-}$ or $PS_4^{3-}$ formed with a cation), thio phosphate ester ($(R^iO)_2PS(OR^i)$, $R^iS$—, $R^iSO$, $R^iSO_2$, $R^iSO_3$, thiosulfate (HS₂O₃ or a salt of $S_2O_3^{2-}$ formed with a cation), dithionite (HS₂O₄ or a salt of $S_2O_4^{2-}$ formed with a cation), phosphorodithioate (P(=S)($OR^{k'}$)(S)(OH) or a salt thereof formed with a cation), hydroxamic acid ($R^{k'}C(=O)NOH$ or a salt formed with a cation), formaldehyde sulfoxylate (HOCH₂SO₂⁻ or a salt of HOCH₂SO₂⁻ formed with a cation, such as HOCH₂SO₂⁻Na⁺) or a mixture thereof, wherein $R^i$ is a linear or branched alkyl having 1 to 10 carbon atoms and is substituted with at least one substituent selected from —$N(R^j)_2$, —CO₂H, —SO₃H, and —PO₃H; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from —H, an amine-protecting group, the linking group with the reactive group bonded thereto, an optionally substituted linear, branched or cyclic alkyl, alkenyl or alkynyl having from 1 to 10 carbon atoms, a polyethylene glycol unit —(CH₂CH₂O)ₙ—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$^c$ is —H or a substituted or unsubstituted linear or branched alkyl having 1 to 4 carbon atoms, or the linking group with the reactive group bonded thereto;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, halogen or the linking group with the reactive group bonded thereto;

A and A' are the same or different, and are independently selected from —O—, oxo (—C(=O)—), —CRR'O—, —CRR'—, —S—, —CRR'S—, —NR$_5$ and —CRR'N(R$_5$)—;

R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O—, —(CH$_2$)$_{n'}$—, —NR'— or —S—;

Z" and Z'" are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent, or represent an aryl group;

Q$_2$ and Q$_2$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and R$^{c'}$ is absent or selected from linear or branched alkyl, alkenyl or alkynyl having 1 to 5 carbon atoms.

In certain embodiments, the second modified cytotoxic compound is produced by reacting an imine reactive reagent with an imine-containing cytotoxic compound bearing the linking group and the reactive group having the following structure:

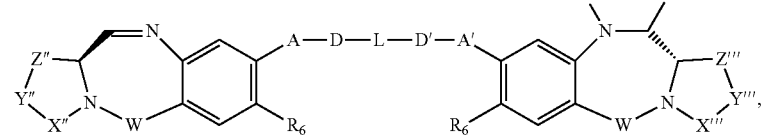

(Va)

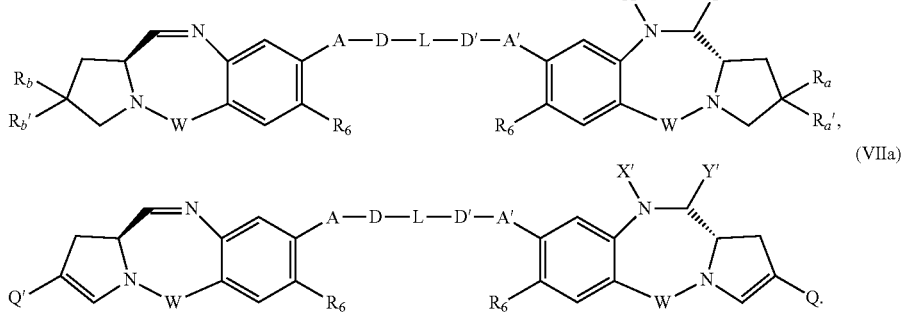

(VIa)

(VIIa)

In any of the above embodiments, the second modified cytotoxic compound is represented by any one of the following formulas:

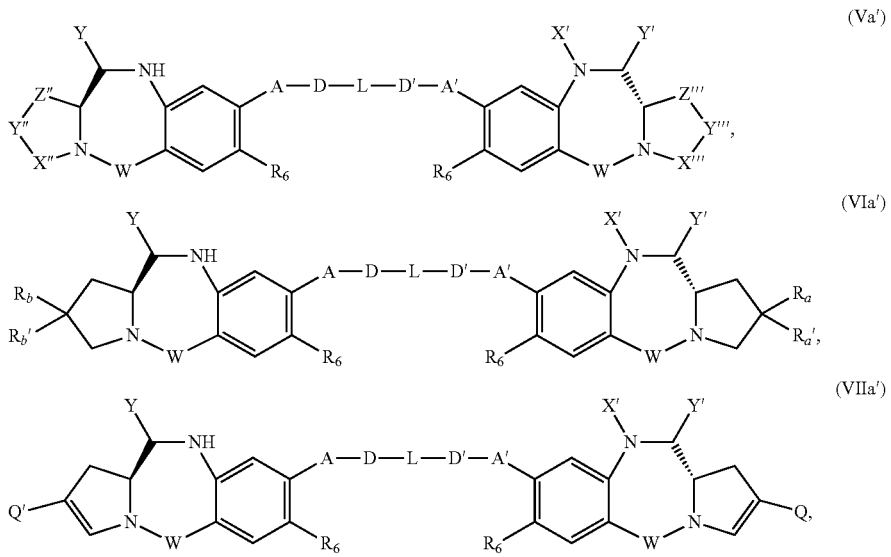

(Va')

(VIa')

(VIIa')

or a pharmaceutically acceptable salt thereof, wherein:

Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^jO)_2PS(OR^j)$, $R^jS-$, $R^jSO$, $R^jSO_2$, $R^jSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from —H, an amine-protecting group, the linking group with the reactive group bonded thereto, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

R$^c$ is —H or a substituted or unsubstituted linear or branched alkyl having 1 to 4 carbon atoms, or the linking group with the reactive group bonded thereto;

R$_6$ is —H, —R, —OR, —SR, —NR'R", —NO$_2$, halogen or the linking group with the reactive group bonded thereto;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

n is an integer from 1 to 24;

W is selected from C=O, C=S, CH$_2$, BH, SO and SO$_2$;

A and A' are the same or different, and are independently selected from —O—, oxo (—C(=O)—), —CRR'O—, —CRR'—, —S—, —CRR'S—, —NR$_5$ and —CRR'N(R$_5$)—;

R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O—, —(CH$_2$)$_{n'}$—, —NR'— or —S—;

Z" and Z'" are the same or different, and are independently selected from —(CH$_2$)$_{n'}$—, —CR$_7$R$_8$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent, or represent an aryl group;

Q$_2$ and Q$_2$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and R$^{c'}$ is absent or selected from linear or branched alkyl, alkenyl or alkynyl having 1 to 5 carbon atoms.

In any of the above embodiments, the cytotoxic compound and the linking group of the conjugate is represented by any one of the following formulas:

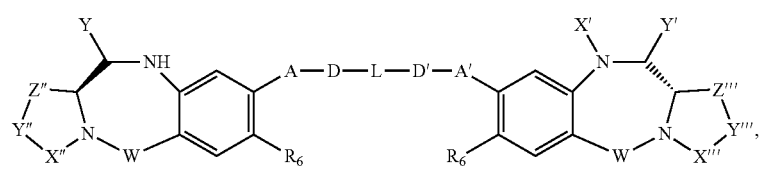

(Vb')

-continued

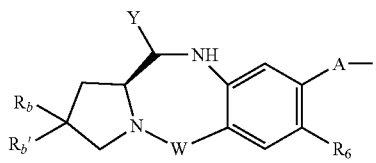 (VIb')


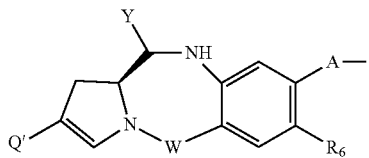 (VIIb')

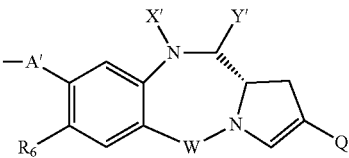

or a pharmaceutically acceptable salt thereof, wherein:

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_2M$, —$SO_3M$, —$OSO_3M$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

M is —H or a pharmaceutically acceptable cation, such as $Na^+$;

X' is selected from —H, an amine-protecting group, the linking group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group;

$R_6$ is —H, —R, —OR, —SR, —NR'R", —$NO_2$, halogen or the linking group;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3-18-membered heterocyclic ring having 1 to 6 heteroatoms independently selected from O, S, N and P;

n is an integer from 1 to 24;

W is selected from C=O, C=S, $CH_2$, BH, SO and $SO_2$;

A and A' are the same or different, and are independently selected from —O—, oxo (—C(=O)—), —CRR'O—, —CRR'—, —S—, —CRR'S—, —$N(R_5)$— and —CRR'N($R_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2$)$_n$—;

L is absent, the linking group, a polyethylene glycol unit (—$OCH_2CH_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; the phenyl or heterocyclic or heteroaryl ring can be optionally substituted, wherein the substituent can comprise the linking group;

X″ and X‴ are the same or different, and are independently selected from —(CH$_2$)$_{n'}$—, —NR'—, —CO—, —BH—, —SO— or —SO$_2$—;

Y″ and Y‴ are the same or different, and are independently selected from —O—, —(CH$_2$)$_{n'}$—, —NR'— or —S—;

Z″ and Z‴ are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, the linking group, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R″, —NO$_2$, —NCO, —NR'COR″, —SR, a sulfoxide represented by —SOR', a sulfone represented by —SO$_2$R', a sulfonate —SO$_3$M, a sulfate —OSO$_3$M, a sulfonamide represented by SO$_2$NR'R″, cyano, an azido, —COR', —OCOR' or —OCONR'R″; and R$^{c'}$ is absent or selected from linear or branched alkyl, alkenyl or alkynyl having 1 to 5 carbon atoms.

As used herein, when referring to a group (e.g., R$^c$, L, X' etc.) "is/be" (or "is not") the linking group or the linking group with the reactive group bounded thereto, it is meant that the group "comprises" (or "does not comprise") the linking group or the linking group with the reactive group bounded thereto.

Figure 1:
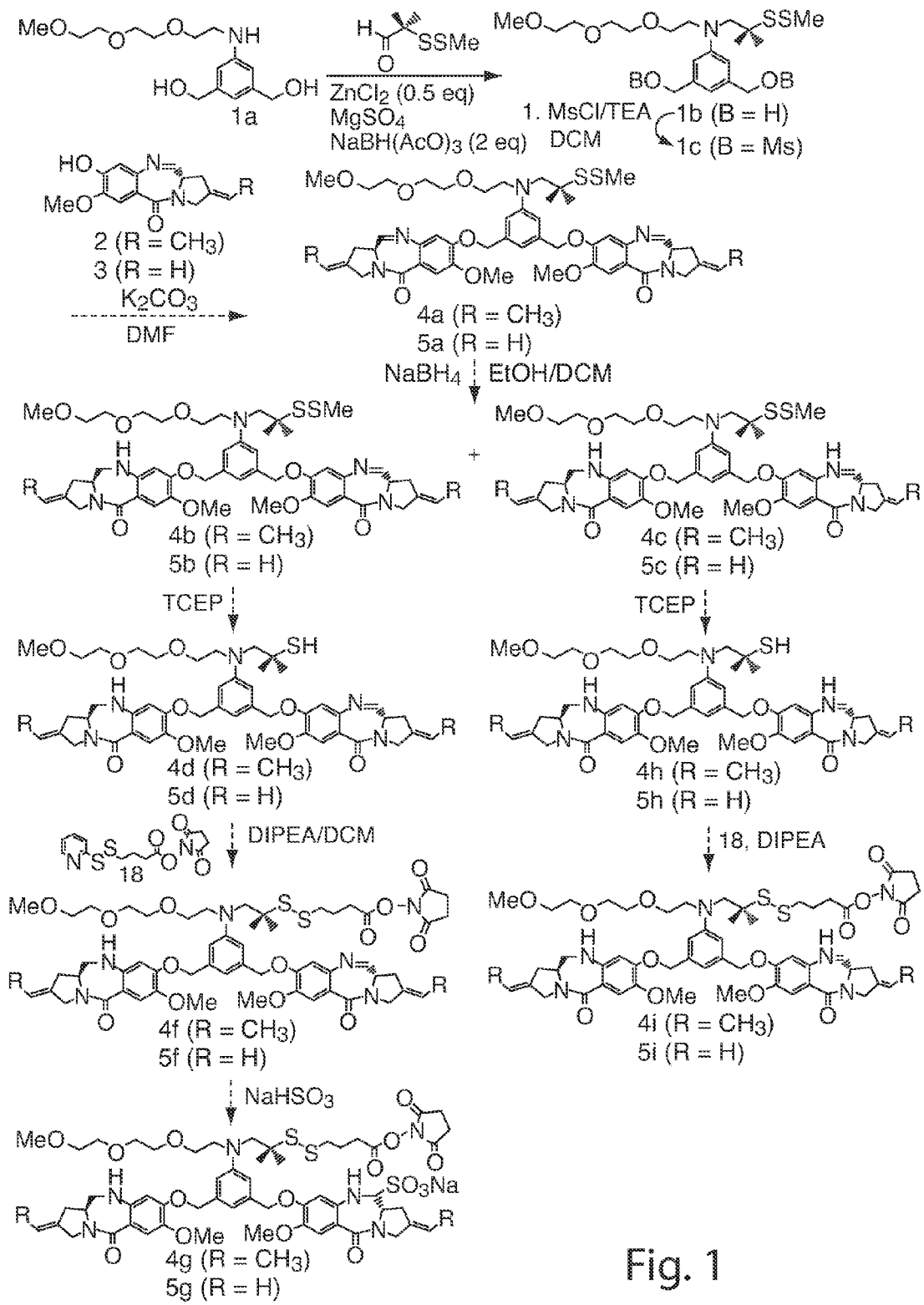
FIGS. 1-31 shows illustrative synthesis schemes for the benzodiazepine cytotoxic compounds (with or without a linking group attached thereto) and conjugates of the invention. Although most of the schemes show a specific compound of one of the formulas (V)-(VII), similar schemes are expected to apply to compounds of all formulas (V)-(VII).
Figure 2:
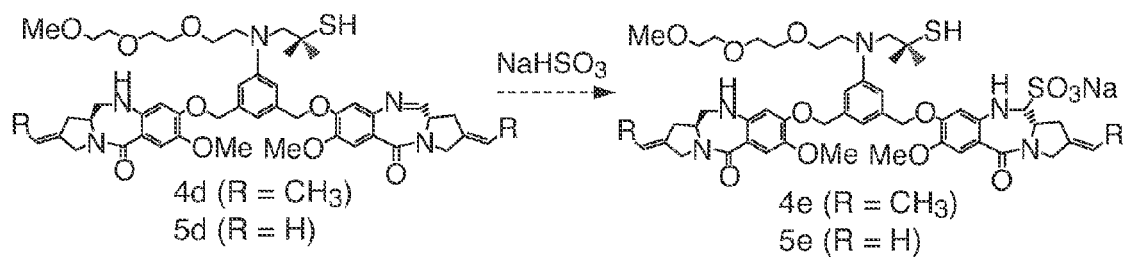
Figure 3:
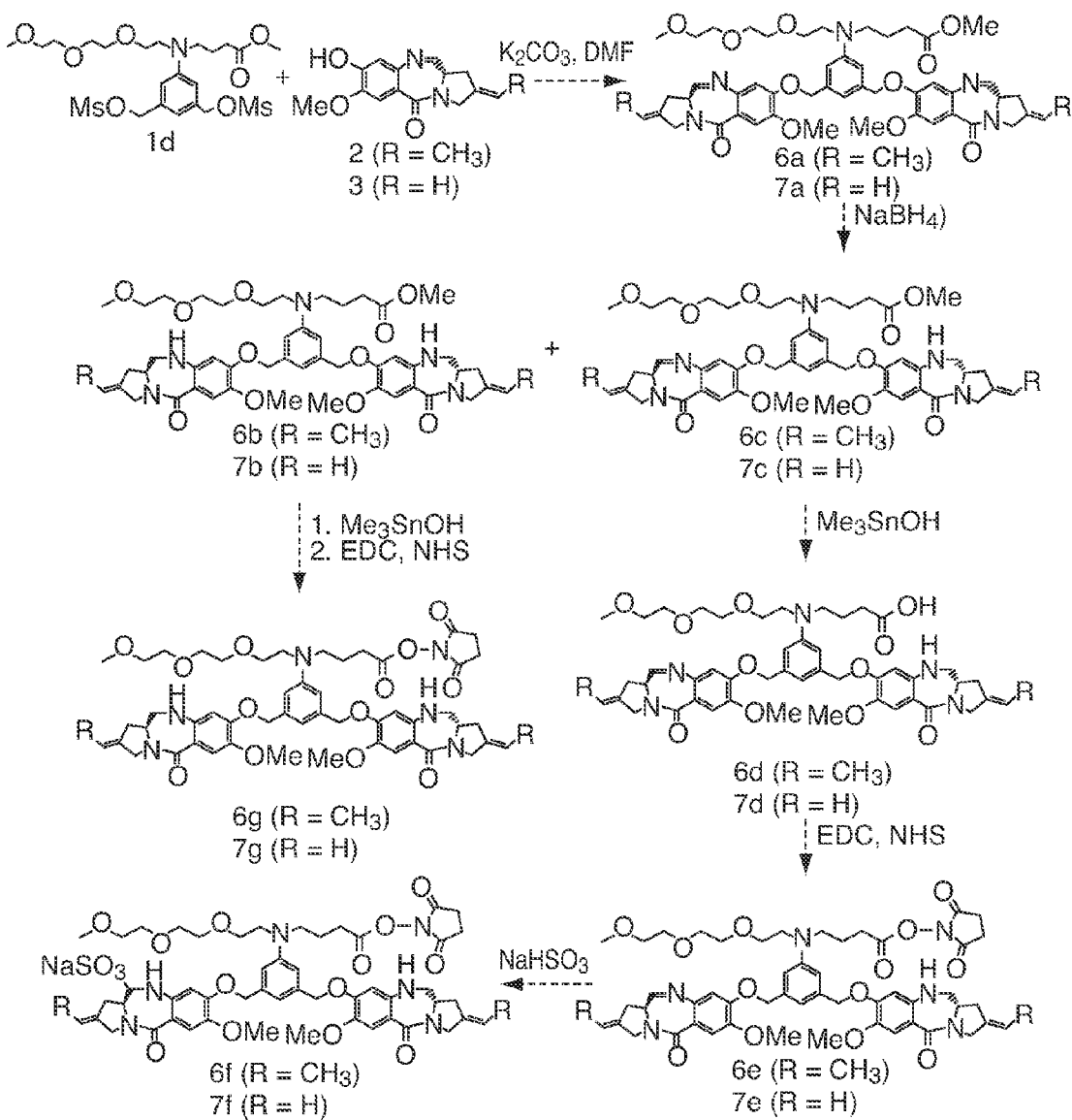
Figure 4:
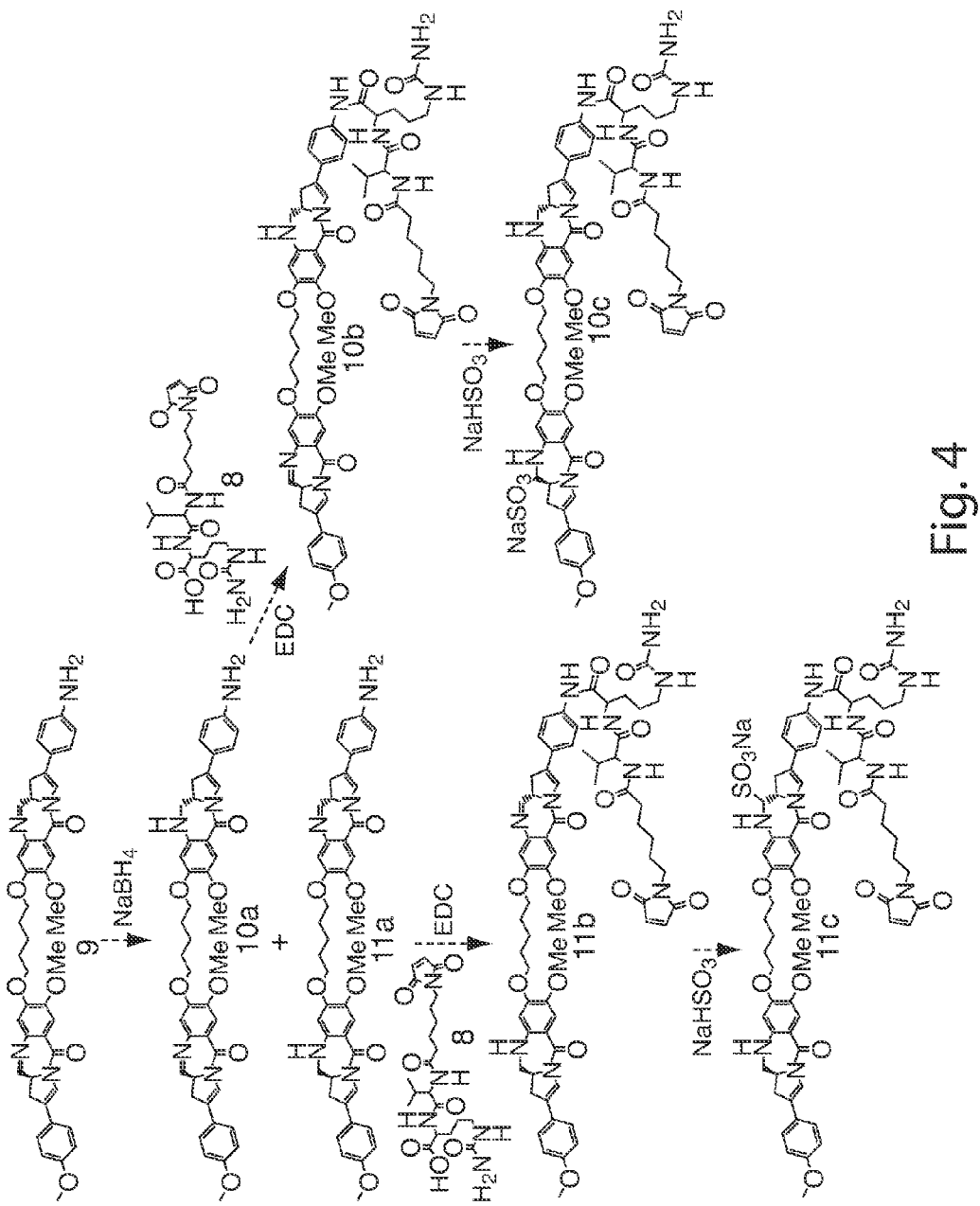
Figure 5:
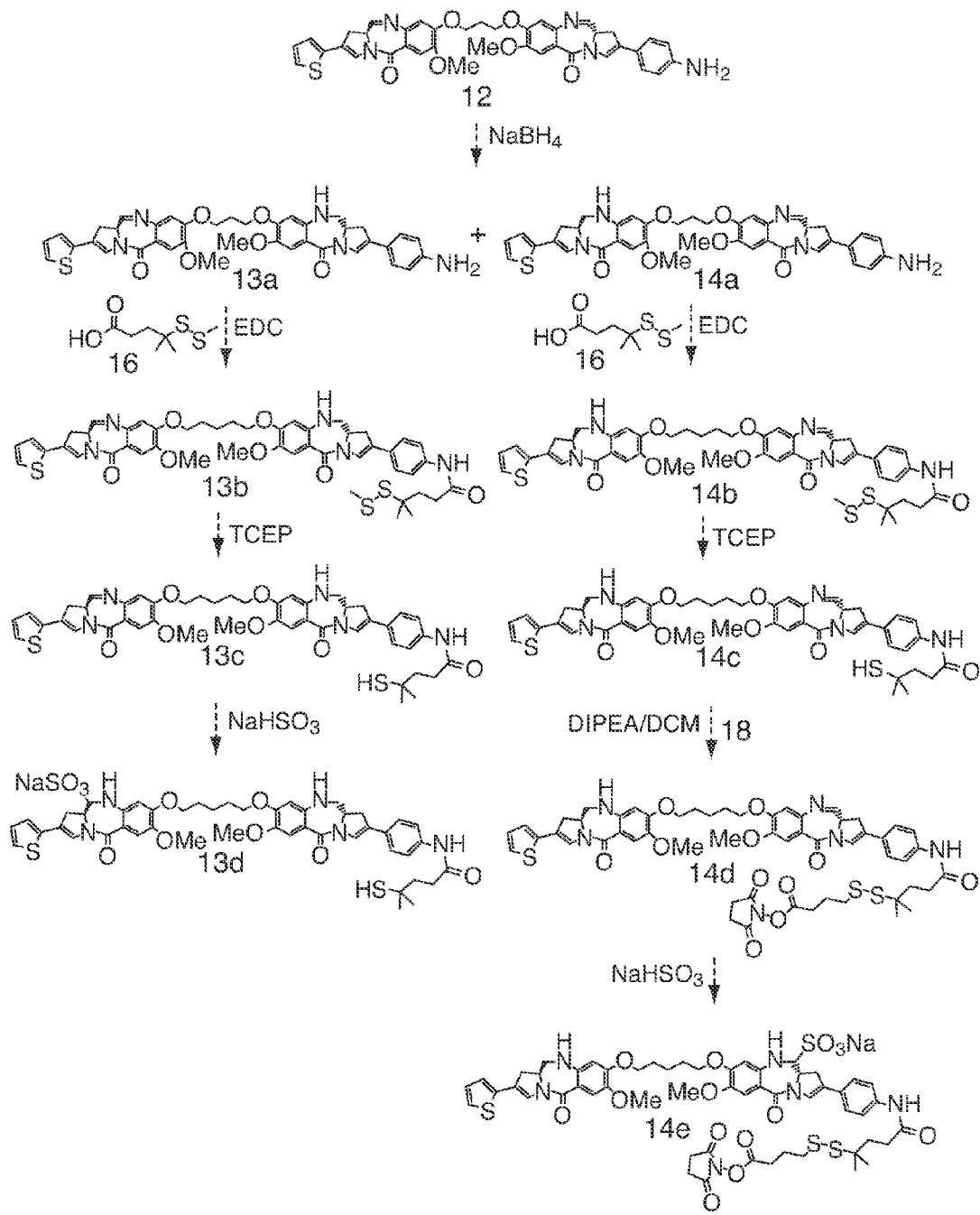
Figure 6:
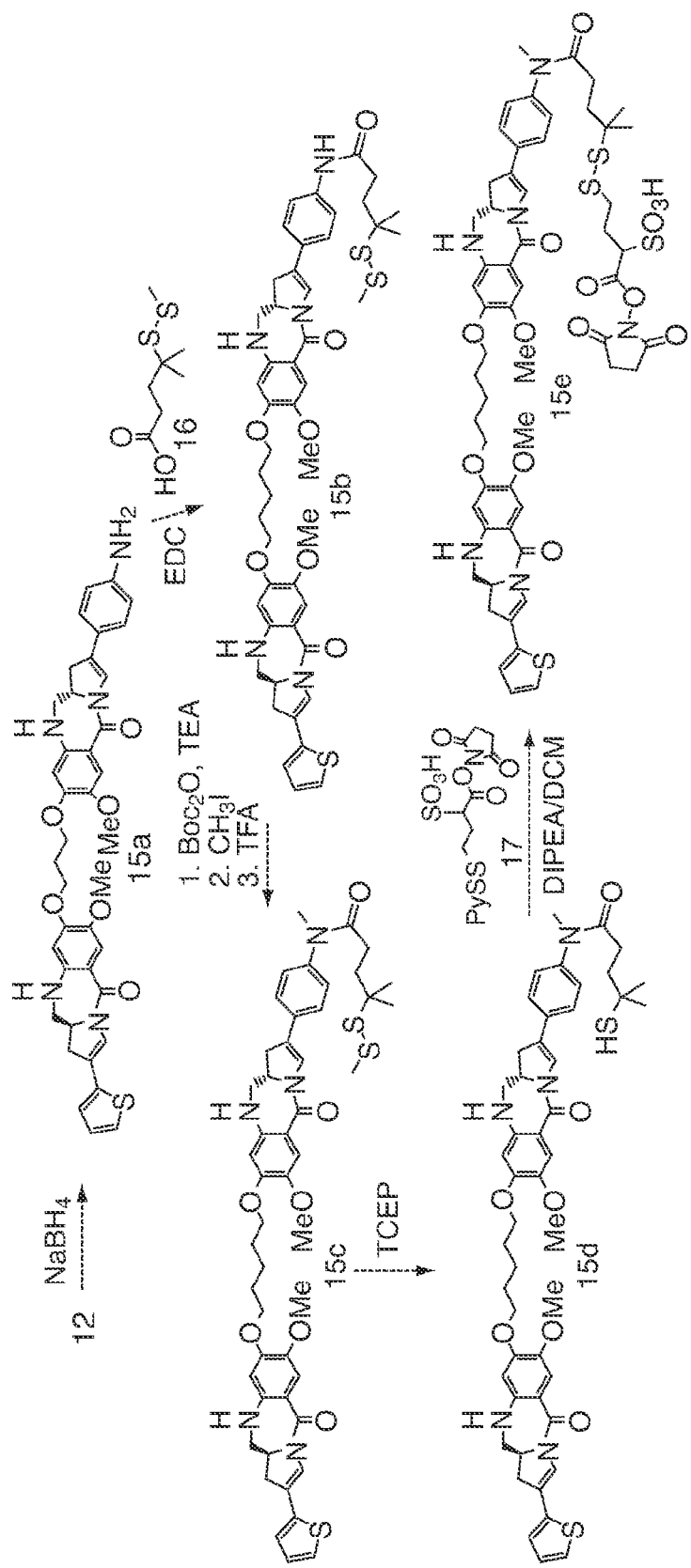
Figure 7:
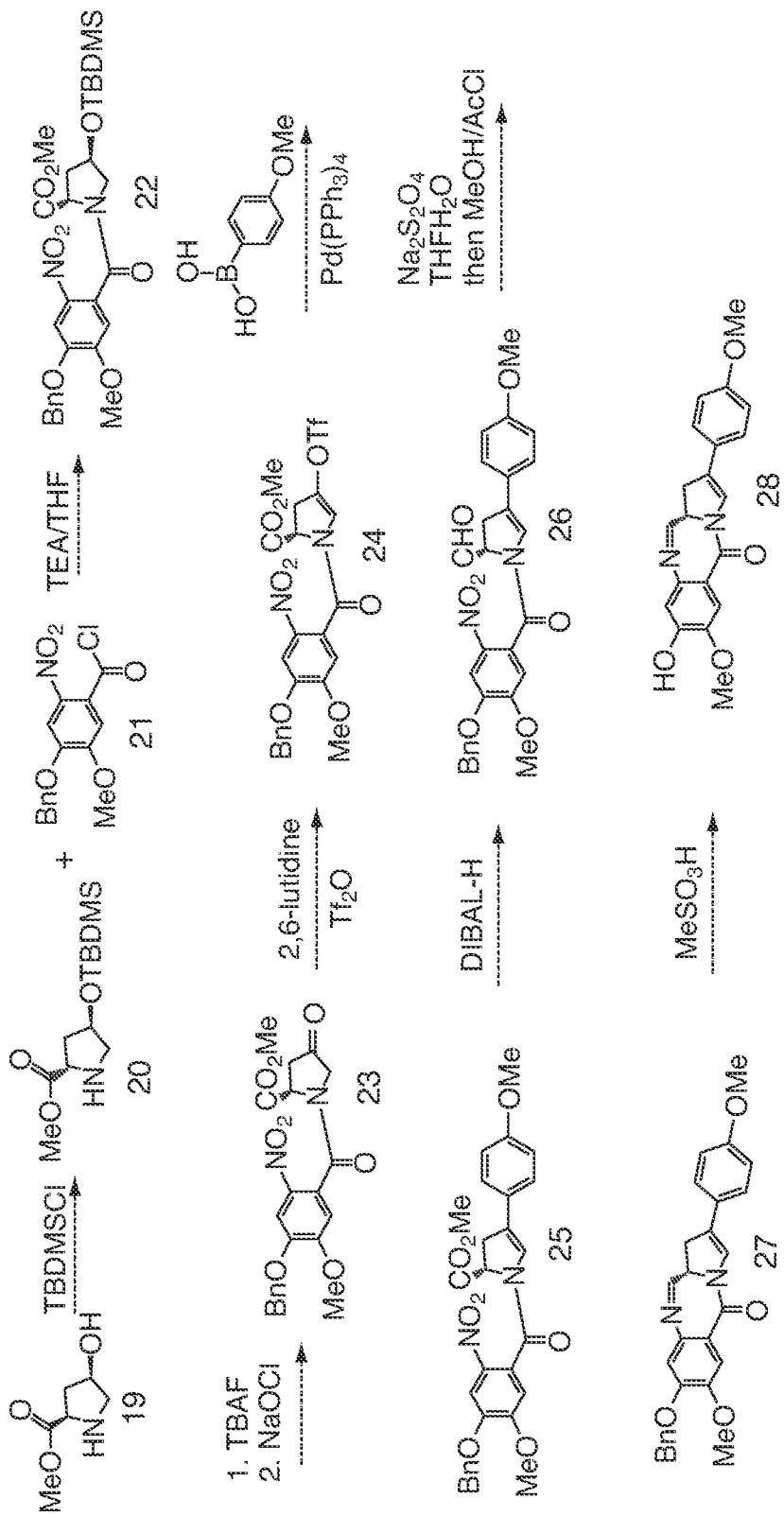
Figure 8:
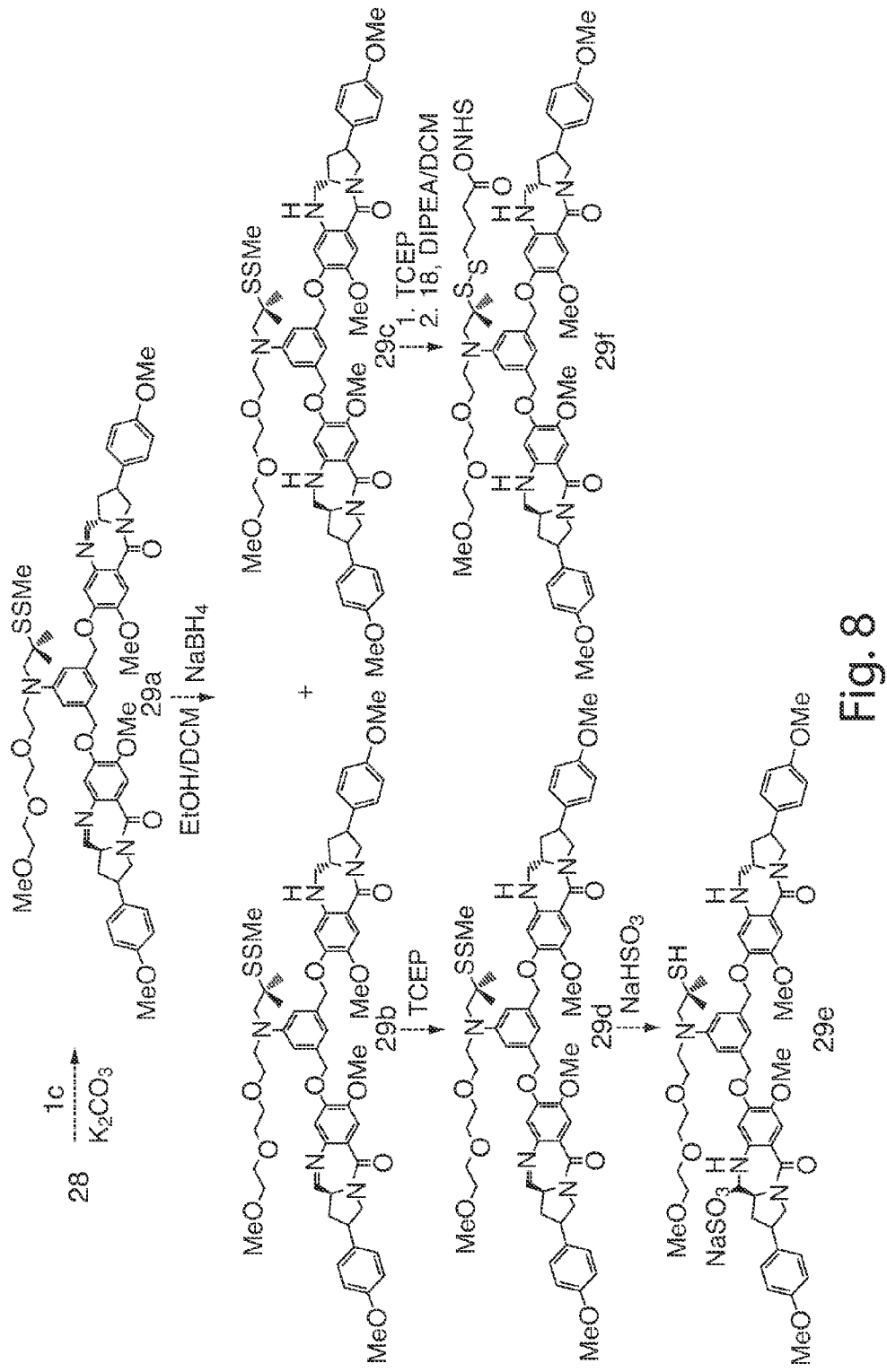

Figures and data in the co-owned co-pending U.S. utility and PCT applications, claiming the benefit of the filing date of the same three provisional applications as the instant application, each filed on the same day, provide additional proof that indolobenzodiazepine compounds/conjugates similar to the instant pyrrolobenzodiazepine compounds/conjugates of the invention have less toxicity compared to their corresponding di-imine compounds/conjugates, while preserving largely the same (if not better) in vitro or in vivo biological activity. In addition, methods of the invention for conjugate production, when used to produce indolobenzodiazepine conjugates similar to the instant pyrrolobenzodiazepine conjugates, produces significantly better quality conjugates. Such data and figure in these co-owned co-pending applications are expressly incorporated herein by reference.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-2-methyl-1-propyl, —CH$_2$CH(CH$_3$)$_2$), 2-butyl, 2-methyl-2-propyl, 1-pentyl, 2-pentyl 3-pentyl, 2-methyl-2- butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6], or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclcyl include the oxidized forms such as NO, SO, and $SO_2$.

The term "halo" or "halogen" refers to F, Cl, Br, or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C=NH)$NH_2$], —$OR^{100}$, $NR^{101}R^{102}$, —$NO_2$, —$NR^{101}COR^{102}$, —$SR^{100}$, a sulfoxide represented by —$SOR^{101}$, a sulfone represented by —$SO_2R^{101}$, a sulfonate —$SO_3M$, a sulfate —$OSO_3M$, a sulfonamide represented by —$SO_2NR^{101}R^{102}$, cyano, an azido, —$COR^{101}$, —$OCOR^{101}$, —$OCONR^{101}R^{102}$ and a polyethylene glycol unit (—$OCH_2CH_2)_nR^{101}$ wherein M is H or a pharmaceutically acceptable cation (such as $Na^+$ or $K^+$), $R^{101}$, $R^{102}$ and $R^{103}$ are each independently selected from H, linear, branched or cyclic alkyl, alkenyl or alkynyl having from 1 to 10 carbon atoms, a polyethylene glycol unit (—$OCH_2CH_2)_n$—$R^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and $R^{104}$ is H or a linear or branched alkyl having 1 to 4 carbon atoms, wherein the alkyl, alkenyl, alkynyl, aryl, heteroaryl and heterocyclcyl in the groups represented by $R^{100}$, $R^{101}$, $R^{102}$, $R^{103}$ and are option ally substituted with one or more (e.g., 2, 3, 4, 5, 6 or more) substituents independently selected from halogen, —OH, —CN, —$NO_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —$NR^{102}R^{103}$, —$CF_3$, —$OR^{101}$, aryl, heteroaryl, heterocycyl, —$SOR^{101}$, —$SO_2R^{101}$ and —$SO_3M$.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any biologically active derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms. In one embodiment, cytotoxic compound comprises a linking group or a linking group with a reactive group bonded thereto. Alternatively, cytotoxic compound does not comprise a linking group or a linking group with a reactive group bonded thereto.

The term "conjugate" as used herein refers to a compound described herein or a derivative thereof that is linked to a cell binding agent.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein (e.g., compounds and drug-linker compounds of the formulas describe herein), or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs."

One preferred form of prodrug of the invention includes compounds (with or without any linker groups) and conjugates of the invention comprising an adduct formed between an imine bond of the compounds/conjugates and an imine reactive reagent. Another preferred form of prodrug of the invention includes compounds such as those of formula (I)-(IV), wherein when the double line $=\!=$ between N and C represents a single bond, X is H or an amine protecting group, and the compound becomes a prodrug. A prodrug of the invention may contain one or both forms of prodrugs described herein (e.g., containing an adduct formed between an imine bond of the compounds/conjugates and an imine reactive reagent, and/or containing a Y leaving group when X is —H).

The term "imine reactive reagent" refers to a reagent that is capable of reacting with an imine group. Examples of imine reactive reagent includes, but is not limited to, sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO$)$_2$PS(O$R^i$), $R^i$SH, $R^i$SOH, $R^i$SO$_2$H, $R^i$SO$_3$H), various amines (hydroxylamine (e.g., NH$_2$OH), hydrazine (e.g., NH$_2$NH$_2$), NH$_2$O—$R^i$, $R^i$NH—$R^i$, NH$_2$—$R^i$), NH$_2$—CO—NH$_2$, NH$_2$—C(=S)—NH$_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)(OR$^k$)(SH)(OH) or a salt thereof formed with a cation), hydroxamic acid (R$^k$C(=O)NHOH or a salt formed with a cation), hydrazide (R$^k$CONHNH$_2$), formaldehyde sulfoxylate (HOCH$_2$SO$_2$H or a salt of HOCH$_2$SO$_2^-$ formed with a cation, such as HOCH$_2$SO$_2^-$ Na$^+$), glycated nucleotide (such as GDP-mannose), fludarabine or a mixture thereof, wherein R$^i$ and R$^{i'}$ are each independently a linear or branched alkyl having 1 to 10 carbon atoms and are substituted with at least one substituent selected from —N(R$^j$)$_2$, —CO$_2$H, —SO$_3$H, and —PO$_3$H; R$^i$ and can be further optionally substituted with a substituent for an alkyl described herein; R$^{i'}$ is a linear or branched alkyl having 1 to 6 carbon atoms; and R$^k$ is a linear, branched or cyclic alkyl, alkenyl or alkynyl having 1 to 10 carbon atoms, aryl, heterocyclyl or heteroaryl (preferably, R$^k$ is a linear or branched alkyl having 1 to 4 carbon atoms; more preferably, R$^k$ is methyl, ethyl or propyl). Preferably, the cation is a monovalent cation, such as Na$^+$ or K$^+$. Preferably, the imine reactive reagent is selected from sulfites, hydroxylamine, urea and hydrazine. More preferably, the imine reactive reagent is NaHSO$_3$ or KHSO$_3$.

As used herein and unless otherwise indicated, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or precancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, head/brain and neck cancer, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

A "therapeutic agent" encompasses both a biological agent such as an antibody, a peptide, a protein, an enzyme or a chemotherapeutic agent.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

Chemotherapeutic agents may also include any of the generic drugs or biosimilars of the brand-name drugs referenced herein, or improvements thereof, including improved formulations, prodrugs, delivery means (sustained release, bioadhesive coating, targeted delivery etc.), and dosage forms.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, N.J.) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups connected to a "linking group"; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-STAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds include N-succinimidyl-4-(4-nitropyridyl-2-dithio) butanoate and other bifunctional crosslinking agents that are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio) butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, the linking group with a reactive group attached at one end, such as a reactive ester, is selected from the following "List 1":

—O(CR$_{20}$R$_{21}$)$_m$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X",

—O(CR$_{20}$R$_{21}$)$_m$(CR$_{26}$CR$_{27}$)$_{m'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X",

—O(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —O(CR$_{20}$R$_{21}$)$_m$(piperazino)$_{n'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —O(CR$_{20}$R$_{21}$)$_m$(pyrrolo)$_{n'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —O(CR$_{20}$R$_{21}$)$_m$A"$_{m'}$(CR$_{22}$R$_{23}$)$_n$(OCH$_2$CH$_2$)$_p$(CR$_{40}$R$_{41}$)$_{p'}$Y"(R$_{24}$R$_{25}$)$_q$(CO)$_t$X", —S(CR$_{20}$R$_{21}$)$_m$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —S(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —S(CR$_{20}$R$_{21}$)$_m$(alkynyl)$_n$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —S(CR$_{20}$R$_{21}$)$_m$(piperazino)$_{n'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —S(CR$_{20}$R$_{21}$)$_m$(pyrrolo)$_{n'}$(CR$_{22}$R$_{23}$)$_n$(OCH$_2$CH$_2$)$_p$(CR$_{40}$R$_{41}$)$_{p'}$Y"(CR$_{24}$R$_{25}$)$_q$(CO)$_t$X", —S$(CR_{20}R_{21})_m$A"$_{m''}$$(CR_{22}R_{23})_n$$(OCH_2CH_2)_p$$(CR_{40}R_{41})_{p''}$Y"$(CR_{24}R_{25})_q$$(CO)_t$X", —$NR_{33}$(C=O)$_{p''}$$(CR_{20}R_{21})_m$$(CR_{22}R_{23})_n$$(OCH_2CH_2)_p$$(CR_{40}R_{41})_{p''}$Y"$(CR_{24}R_{25})_q$$(CO)_t$X", —$NR_{33}$(C=O)$_{p''}$$(CR_{20}R_{21})_m$$(CR_{26}=C_{27})_{m'}$$(CR_{22}R_{23})_n$$(OCH_2CH_2)_p$$(CR_{40}R_{41})_{p''}$Y"$(CR_{24}R_{25})_q$$(CO)_t$X", —$NR_{33}$(C=O)$_{p''}$$(CR_{20}R_{21})_m$(alkynyl)$_{n'}$$(CR_{22}R_{23})_n$$(OCH_2CH_2)_p$$(CR_{40}R_{41})_{p''}$Y"$(CR_{24}R_{25})_q$—$(CO)_t$X", —$NR_{33}$(C=O)$_{p''}$$(CR_{20}R_{21})_m$(piperazino)$_{t'}$$(CR_{22}R_{23})_n$$(OCH_2CH_2)_p$$(CR_{40}R_{41})_{p''}$Y"$(CR_{24}R_{25})_q$$(CO)_t$X", —$NR_{33}$(C=O)$_{p''}$$(CR_{20}R_{21})_m$(pyrrolo)$_{t'}$$(CR_{22}R_{23})_n$$(OCH_2CH_2)_p$$(CR_{40}R_{41})_{p''}$Y"$(CR_{24}R_{25})_q$$(CO)_t$X", —$NR_{33}$(C=O)$_{p''}$$(CR_{20}R_{21})_m$A"$_{m''}$$(CR_{22}R_{23})_n$$(OCH_2CH_2)_p$$(CR_{40}R_{41})_{p''}$Y"$(CR_{24}R_{25})_q$$(CO)_t$X", —$(CR_{20}R_{21})_m$$(CR_{22}R_{23})_n$$(OCH_2CH_2)_p$$(CR_{40}R_{41})_{p''}$Y"$(CR_{24}R_{25})_q$$(CO)_t$X", —$(CR_{20}R_{21})_m$$(CR_{26}=CR_{27})_{m'}$$(CR_{22}R_{23})_n$$(OCH_2CH_2)_p$$(CR_{40}R_{41})_{p''}$Y"$(CR_{24}R_{25})_q$$(CO)_t$X", —$(CR_{20}R_{21})_m$(alkynyl)$_{n'}$$(CR_{22}R_{23})_n$$(OCH_2CH_2)_p$$(CR_{40}R_{41})_{p''}$Y"$(CR_{24}R_{25})_q$$(CO)_t$X", —$(CR_{20}R_{21})_m$(piperazino)$_{t'}$$(CR_{22}R_{23})_n$$(OCH_2CH_2)_p$$(CR_{40}R_{41})_{p''}$Y"$(CR_{24}R_{25})_q$$(CO)_t$X", —$(CR_{20}R_{21})_m$A"$_{m''}$$(CR_{22}R_{23})_n$$(OCH_2CH_2)_p$$(CR_{40}R_{41})_{p''}$Y"$(CR_{24}R_{25})_q$$(CO)_t$X", —$(CR_{20}R_{21})_m$$(CR_{29}=N-NR_{30})_{n''}$$(CR_{22}R_{23})_n$$(OCH_2CH_2)_p$ $(CR_{40}R_{41})_{p''}$Y"$(CR_{24}R_{25})_q$$(CO)_t$X", —$(CR_{20}R_{21})_m$$(CR_{29}=N-NR_{30})_{n''}$$(CR_{26}=CR_{27})_{m'}$$(CR_{22}R_{23})_n$$(OCH_2CH_2)_p$$(CR_{40}R_{41})_{p''}$$(CR_{24}R_{25})_q$$(CO)_t$X", —$(CR_{20}R_{21})_m$$(CR_{29}=N-NR_{30})_{n''}$(alkynyl)$_{n'}$$(CR_{22}R_{23})_n$$(OCH_2CH_2)_p$$(CR_{40}R_{41})_{p''}$Y"$(CR_{24}R_{25})_q$$^-(CO)_t$X", —$(CR_{20}R_{21})_m$$(CR_{29}=N-NR_{30})_{n''}$A"$_{m''}$$(CR_{22}R_{23})_n$$(OCH_2CH_2)_p$$(CR_{40}R_{41})_{p''}$Y"$(CR_{24}R_{25})_q$$(CO)_t$X", wherein:

m, n, p, q, m', n', t' are integer from 1 to 10, or are optionally 0;

t, m", n", and p" are 0 or 1;

X" is selected from $OR_{36}$, $SR_{37}$, $NR_{38}R_{39}$, wherein $R_{36}$, $R_{37}$, $R_{38}$, $R_{39}$ are H, or linear, branched or cyclic alkyl, alkenyl or alkynyl having from 1 to 20 carbon atoms and, or, a polyethylene glycol unit —$(OCH_2CH_2)_n$–$R_{37}$, optionally, is a thiol protecting group when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y" is absent or is selected from O, S, S—S or $NR_{32}$, wherein $R_{32}$ has the same definition as given above for R; or when Y" is not S—S and t=0, X" is selected from a maleimido group, a haloacetyl group or $SR_{37}$, wherein $R_{37}$ has the same definition as above;

A" is an amino acid selected from glycine, alanine, leucine, valine, lysine, citrulline and glutamate or a polypeptide containing between 2 to 20 amino acid units;

$R_{20}$, $R_{21}$, $R_{22}$, $R_{23}$, $R_{24}$, $R_{25}$, $R_{26}$, and $R_{27}$ are the same or different, and are —H or a linear or branched alkyl having from 1 to 5 carbon atoms;

$R_{29}$ and $R_{30}$ are the same or different, and are —H or alkyl from 1 to 5 carbon atoms;

$R_{33}$ is —H or linear, branched or cyclic alkyl, alkenyl or alkynyl having from 1 to 12 carbon atoms, a polyethylene glycol unit R—$(OCH_2CH_2)_n$—, or $R_{33}$ is —$COR_{34}$, —$CSR_{34}$, —$SOR_{34}$, or —$SO_2R_{34}$, wherein $R_{34}$ is H or linear, branched or cyclic alkyl, alkenyl or alkynyl having from 1 to 20 carbon atoms or, a polyethylene glycol unit —$(OCH_2CH_2)_n$; and one of $R_{40}$ and $R_{41}$ is optionally a negatively or positively charged functional group and the other is H or alkyl, alkenyl, alkynyl having 1 to 4 carbon atoms.

Any of the above linking groups may be present in any of the compounds, drug-linker compounds, or conjugates of the invention, including replacing the linking groups of any of the formulas described herein.

The term "amino acid" refers to naturally occurring amino acids or non-naturally occurring amino acid represented by $NH_2$—C($R^{aa'}R^{aa}$)—C(=O)OH, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl. The term "amino acid" also refers to the corresponding residue when one hydrogen atom is removed from the amine and/or carboxy end of the amino acid, such as —NH—C($R^{aa'}R^{aa}$)—C(=O)O—.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health; age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

The term "thiol reactive group" refers to a functional group that will react with a thiol moiety. Examples of thiol reactive group includes, but is not limited to, maleimido, vinylpyridine, vinyl sulfone, vinyl sulfonamide, a haloacetyl-based group (e.g., haloacetamido) or a disulfide (e.g., —$SSR^d$, wherein $R^d$ is a linear or branched alkyl having 1 to 4 carbon atoms, phenyl, nitrophenyl, dinitrophenyl, carboxynitrophenyl, pyridyl, 2-nitropyridyl, 4-nitropyridyl, or 3-carboxy-4-nitropyridyl).

The term "reactive ester" refers to an ester contains a leaving group that is readily displaced by an amine group or a hydroxyl group. Examples of reactive ester includes, but is not limited to, N-hydroxysuccinimide ester, N-hydroxy sulfosuccinimide ester, nitrophenyl ester, dinitrophenyl ester, tetrafluorophenyl ester, sulfo-tetrafluorophenyl ester, and pentafluorophenyl ester. Preferably, the reactive ester is N-hydroxysuccinimide (NHS) ester.

The term "an imine-containing drug" or "an imine-containing cytotoxic compound" refers to a compound described herein (without a linker group) that has at least one imine functional group. Preferably, the imine-containing drug contains one imine functional group.

Cytotoxic Compounds

The present invention is directed to cytotoxic compounds described herein (e.g., compounds of formulas (Va), (VIa) and (VIIa), etc). In one embodiment, the cytotoxic compounds of the present invention do not include any compounds described in US 2010/0203007 (the entire teaching of which is incorporated herein by reference), such as those specifically disclaimed in the proviso below.

In a first specific embodiment, the invention provides a cytotoxic compound comprising a linking group with a reactive group bonded thereto capable of covalently linking the cytotoxic compound to a cell binding agent (CBA), wherein said cytotoxic compound is represented by any one of the following formulas (Va), (VIa), or (VIIa):

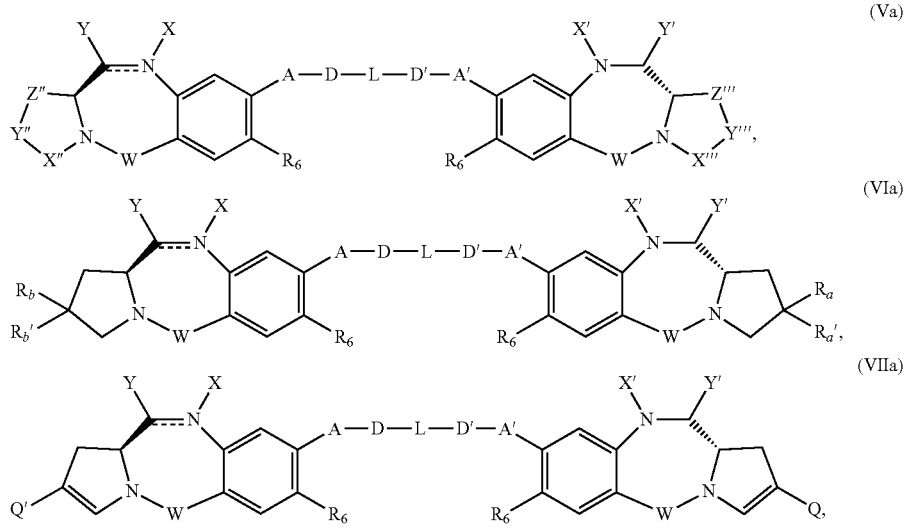

or a pharmaceutically acceptable salt thereof, wherein:

the double line $\doublebond$ between N and C represents a single bond or a double bond, provided that when it is a double bond X is absent and Y is —H, or a linear or branched alkyl having 1 to 4 carbon atoms, and when it is a single bond, X is —H, the linking group with the reactive group bonded thereto, or an amine protecting moiety;

Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

M is —H or a pharmaceutically acceptable cation;

R$_6$ is —H, —R, —OR, —SR, —NR'R", —NO$_2$, halogen or the linking group with the reactive group bonded thereto;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group with the reactive group bonded thereto;

n is an integer from 1 to 24;

W is selected from C=O, C=S, $CH_2$, BH, SO and $SO_2$;

X' is selected from —H, an amine-protecting group, the linking group with the reactive group bonded thereto, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

A and A' are the same or different, and are independently selected from —O—, oxo (—C(=O)—), —CRR'O—, —CRR'—, —S—, —CRR'S—, —$NR_5$ and —CRR'N($R_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2$)_n—;

L is absent, the linking group with the reactive group bonded thereto, a polyethylene glycol unit (—$OCH_2CH_2$)_n—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto;

X" and X'" are the same or different, and are independently selected from —$(CH_2)_{n'}$—, —NR'—, —CO—, —BH—, —SO— or —$SO_2$—;

Y" and Y'" are the same or different, and are independently selected from —O—, —$(CH_2)_{n'}$—, —NR'— or —S—;

Z" and Z'" are the same or different, and are independently selected from —$(CH_2)_{n'}$—, —$CR_7R_8$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH unit;

Ar and Ar' are each independently absent, or represent an aryl group;

$Q_2$ and $Q_2'$ are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)$NH_2$], —OR, —NR'R", —$NO_2$, —NCO, —NR'COR", —SR, a sulfoxide represented by —SOR', a sulfone represented by —$SO_2R'$, a sulfonate —$SO_3M$, a sulfate —$OSO_3M$, a sulfonamide represented by $SO_2NR'R"$, cyano, an azido, —COR', —OCOR' or —OCONR'R"; and $R^{c'}$ is absent or selected from linear or branched alkyl, alkenyl or alkynyl having 1 to 5 carbon atoms.

In certain embodiments, X is not the linking group with the reactive group bonded thereto. In certain embodiments, the double line ═ between N and C represents a single bond, Y is not —H.

In certain embodiments, Y is —H or a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —$SO_2M$, —$SO_3M$, —$OSO_3M$, halogen, cyano and an azido. Preferably, Y is (Sodium) Bisulfite adduct, (Sodium) Hydrosulfite adduct, or (Sodium) Metabisulfite adduct. In certain embodiments, Y is not —H.

In certain embodiments, L is absent, or is selected from an optionally substituted phenyl group and an optionally substituted pyridyl group, wherein the phenyl and the pyridyl group bears the linking group with the reactive group bonded thereto, or L is an amine group bearing the linking group with the reactive group bonded thereto (i.e., —N(linking group)-), or L is a linear, branched or cyclic alkyl or alkenyl having from 1 to 6 carbon atoms and bearing the linking group with the reactive group bonded thereto.

In a second specific embodiment, the cytotoxic dimers of formula (Va), (VIa), and (VIIa) are represented by the following formulas:

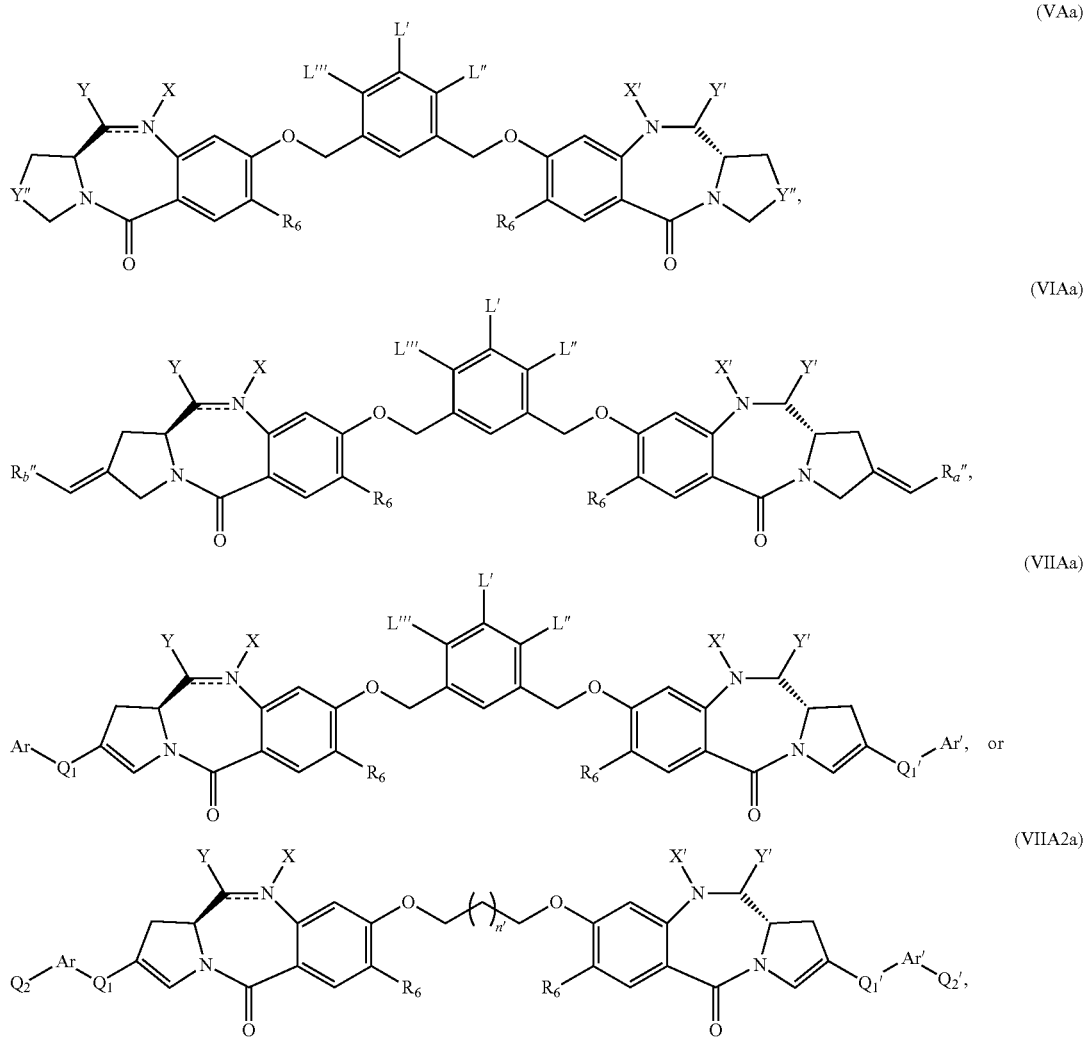

wherein:
- the double line ═ between N and C represents a single bond or a double bond, provided that when it is a double bond X is absent and Y is —H, and when it is a single bond, X is selected from —H, the linking group with the reactive group bonded thereto, or an amine protecting group (preferably X is —H);
- Y is selected from —H, —OR', —OCOR', —SR, —NR'R", —SO₃M, —SO₂M, or —OSO₃M, wherein M is —H or a pharmaceutically acceptable cation such as Na⁺ or K⁺. Preferably, Y is selected from —OH, —OMe, —OEt, —NHOH or —SO₃M. Even more preferably, Y is —OH or —SO₃M, preferably M is —H or Na⁺;
- R is —H, an optionally substituted linear, branched or cyclic alkyl, alkenyl or alkynyl having from 1 to 10 carbon atoms or a PEG group —(CH₂CH₂O)ₙ—R$^c$, wherein n is an integer from 1 to 24 and R$^c$ is a linear or branched alkyl having 1 to 4 carbon atoms;
- R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH₂CH₂O)ₙ—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH₂CH₂O)ₙ—R$^c$;
- X' is selected from the group consisting of —H, —OH, a substituted or unsubstituted linear, branched or cyclic alkyl, alkenyl or alkynyl having from 1 to 10 carbon atoms, phenyl, and an amine-protecting group. Preferably, X' is —H, —OH or -Me. More preferably, X' is —H;
- Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or -Me. More preferably Y' is —H;
- R₆ is —OR$^c$ or —SR$^c$, wherein R$^c$ is a linear or branched alkyl having 1 to 4 carbon atoms. Preferably, R₆ is —OMe or —SMe. Even more preferably, R₆ is —OMe;
- A and A' are selected from —O— and —S—. Preferably, A and A' are —O—;

$R_a''$ and $R_b''$ are the same or different, and are selected from —H and -Me;

one of $Q_2$ and $Q_2'$ is selected from —H, —R, —OR, —NR'R'', —NR'(C=O)OR'', —SR, and —NO$_2$, the other is the linking group with the reactive group bonded thereto.

L', L'', and L''' are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R'', —NO$_2$, —NR'COR'', —SR, a sulfoxide represented by —SOR', a sulfone represented by —SO$_2$R', a sulfonate —SO$_3^-$M$^+$, a sulfate —OSO$_3^+$M$^-$, a sulfonamide represented by —SO$_2$NR'R'', cyano, an azido, —COR', —OCOR', —OCONR'R'' and the linking group with the reactive group bonded thereto, provided only one of L', L'', and L''' is the linking group with the reactive group bonded thereto. Preferably, L' is the linking group with the reactive group bonded thereto. Alternatively, one of L', L'' or L''' is the linking group with the reactive group bonded thereto, while the others are —H. More preferably, L' is the linking group with the reactive group bonded thereto, and L'' and L''' are —H.

In certain embodiments, X is not the linking group with the reactive group bonded thereto. In certain embodiments, the double line 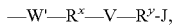 between N and C represents a single bond, Y is not —H.

In certain embodiments, A and A' are both —O—, $R_6$ is —OMe.

In a third specific embodiment, L' in formula (VAa), (VIAa) or (VIIAa), or one of $Q_2$ and $Q_2'$ in formula (VIIA2a) is represented by the following formula:

—W'—R$^x$—V—R$^y$-J, wherein:

W' and V are the same or different, and are each independently absent, or selected from -+CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ and R$^y$ are the same or different, and are each independently absent or an optionally substituted linear, branched or cyclic alkyl, alkenyl or alkynyl having 1 to 10 carbon atoms, an aryl bearing 6 to 10 carbon atoms or a 3- to 8-membered hetereocyclic ring bearing 1 to 3 heteroatoms selected from O, N or S;

R$^e$ and R$^{e'}$ are the same or different, and are selected from —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms. Preferably, R$^{101}$ and R$^{102}$ are each independently a linear or branched alkyl having 1 to 6 carbon atoms;

n is an integer from 1 to 24; and

J comprises the reactive group bonded thereto, and is selected from a maleimide, a haloacetamido, —SH, —SSR$^d$, —CH$_2$SH, —CH(Me)SH, —C(Me)$_2$SH, —NHR$^{c1}$, —CH$_2$NHR$^{c1}$, —NR$^{c1}$NH$_2$, —COOH, and —COE, wherein —COE represents a reactive ester selected from, but not limited to, N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester, and wherein R$^{c1}$ is —H or a substituted or unsubstituted linear or branched alkyl having 1 to 4 carbon atoms, and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl).

In certain embodiments, J is —SH, —SSR$^d$, a maleimide, or a N-hydroxysuccinimide ester.

In certain embodiments, R$^{e'}$ is —H or -Me; R$^e$ is a linear or branched alkyl having 1 to 6 carbon atoms or —(CH$_2$—CH$_2$—O)$_n$—R$^k$; n is an integer from 2 to 8; preferably R$^k$ is —H, -Me or —CH$_2$CH$_2$—NMe$_2$, and the remainder of the variables are as described above in the third specific embodiment.

In certain embodiments, V is an amino acid or a peptide having 2 to 8 amino acids. In certain embodiments, V is valine-citrulline, gly-gly-gly, or ala-leu-ala-leu.

In certain embodiments,

W' is —O—, —N(R$^e$)— or —N(R$^e$)—C(=O)—;

R$^e$ is H, a linear or branched alkyl having 1 to 4 carbon atoms, or —(CH$_2$—CH$_2$—O)$_n$—R$^k$;

R$^x$ is a linear or branched alkyl having 1 to 6 carbon atoms;

V is absent, —(O—CH$_2$—CH$_2$)$_n$—, —C(=O)—NH—, —S—, —NH—C(=O)—;

R$^y$ is absent or a linear or branched alkyl having 1 to 4 carbon atoms; and

J is —SH, —SSR$^d$ or —COE (preferably, N-hydroxysuccinimide ester). The remainder of the variables is as described in the third specific embodiment.

In certain embodiments,

W' is —O—, —N(R$^e$)— or —N(R$^e$)—C(=O)—;

R$^e$ is H, Me, or —(CH$_2$—CH$_2$—O)$_n$-Me;

n is an integer from 2 to 6;

R$^x$ is linear or branched alkyl bearing 1 to 6 carbon atoms;

V and R$^y$ are absent; and

J is —COE, preferably N-hydroxysuccinimide ester. The remainder of the variables is as described in the third specific embodiment.

In a fourth specific embodiment, L' is represented by the following formula:

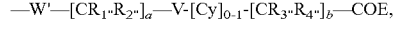

wherein:

$R_{1''}$, $R_{2''}$, and $R_{3''}$ are each independently —H or a linear or branched alkyl bearing 1 to 4 carbon atoms, preferably -Me;

$R_{4''}$ is —H, a linear or branched alkyl bearing 1 to 4 carbon atoms (preferably -Me), —SO$_3$H, or —SO$_3^-$M$^+$, wherein M$^+$ is a pharmaceutically acceptable cation;

a is an integers from 0-5 (e.g., from 0 to 2, 3, 4, or 5), and b is an integer from 0-6 (e.g., from 0 to 3, 4, 5, or 6); and, Cy is an optionally substituted 5-membered heterocyclic ring bearing an N heteroatom, preferably Cy is

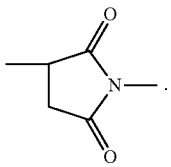

In certain embodiments, W' is —N(R$^e$)—.

In certain embodiments, such as in the third and/or the fourth specific embodiment, R$^e$ is —(CH$_2$—CH$_2$—O)$_{2-6}$—R$^k$, wherein R$^k$ is a —H, a linear, branched cyclic alkyl having 1 to 6 carbon atoms.

In certain embodiments, such as in the third and/or the fourth specific embodiment, V is —S— or —SS—.

In a fifth specific embodiments, L', such as the one in the third and/or the fourth specific embodiment, is represented by the following formula:

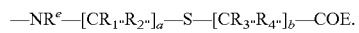

—NR$^e$—[CR$_{1''}$R$_{2''}$]$_a$—S—[CR$_{3''}$R$_{4''}$]$_b$—COE.

In certain embodiments, L' in formula (VAa), (VIAa) or (VIIAa), or one of Q$_2$ and Q$_2$' in formula (VIIA2a) is:

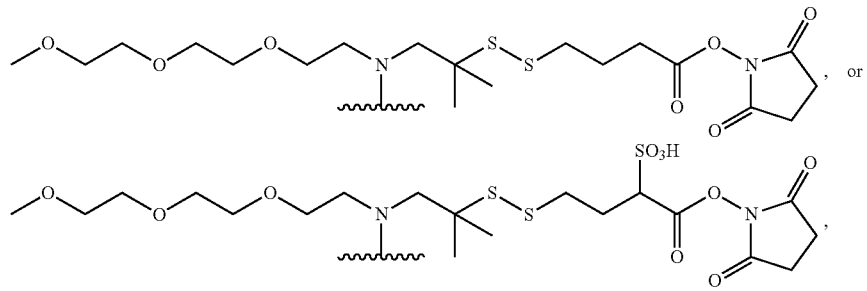

wherein Y is —H or —SO$_3$M (e.g., Y is —SO$_3$M), and M is —H or a pharmaceutically acceptable cation.

In a sixth specific embodiments, L', such as the one in the third and/or the fourth specific embodiment, is represented by the following formula:

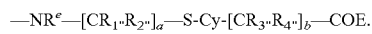

—NR$^e$—[CR$_{1''}$R$_{2''}$]$_a$—S-Cy-[CR$_{3''}$R$_{4''}$]$_b$—COE.

In certain embodiments, L' in formula (VAa), (VIAa) or (VIIAa), or one of Q$_2$ and Q$_2$' in formula (VIIA2a) is:

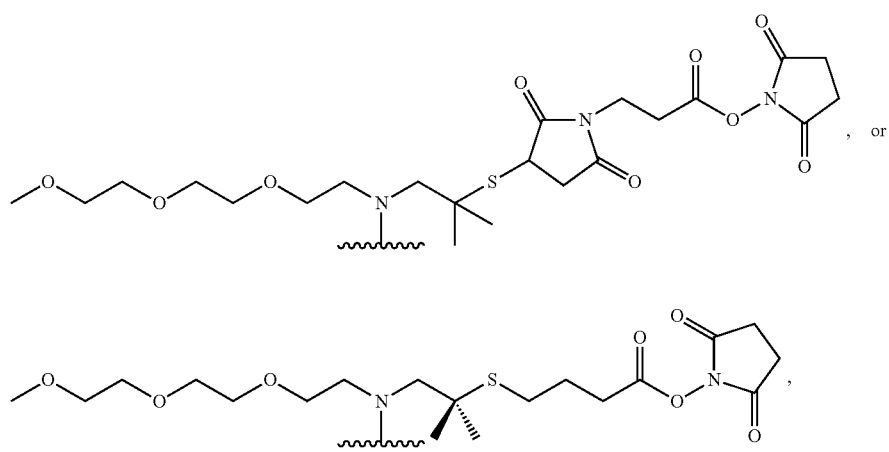

wherein Y is —H or —SO$_3$M (e.g., Y is —SO$_3$M), and M is —H or a pharmaceutically acceptable cation.

In a seventh specific embodiment, L' in formula (VAa), (VIAa) or (VIIAa), or one of Q$_2$ and Q$_2$' in formula (VIIA2a) is represented by the following formula:

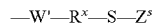

—W'—R$^x$—S—Z$^s$ wherein:

W' is absent, or selected from —O—, —N(R$^e$)—, —N(R$^e$)—C(=O)—, —N(C(=O)R$^e$)—, —S— or —CH$_2$—S—, —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms. Preferably, R$^{101}$ and R$^{102}$ are each independently a linear or branched alkyl having 1 to 6 carbon atoms;

Z$^s$ is —H, —SR$^m$;

R$^m$ is R$^d$ or a substituted or unsubstituted linear or branched alkyl having 1 to 4 carbon atoms bearing a reactive ester, selected from N-hydroxysuccinimide esters, N-hydroxyphtalimide esters, N-hydroxy sulfosuccinimide esters, para-nitrophenyl esters, dinitrophenyl esters, pentafluorophenyl esters;

$R^d$ is selected from phenyl, nitrophenyl, dinitrophenyl, carboxynitrophenyl, pyridyl or nitropyridyl; and, n is an integer from 1 to 24; and the remainder of the variables are as described above in the third specific embodiment.

Preferably, $R^k$ is —H or -Me, and n is an integer from 2 to 8. Preferably, $R^x$ is a linear or branched alkyl having 1 to 6 carbon atoms; and the remainder of the variables is as described above in the third, fourth, and/or the fifth specific embodiment.

In a eighth specific embodiment, L' in formula (VAa), (VIAa) or (VIIAa), or one of $Q_2$ and $Q_2'$ in formula (VIIA2a) is represented by the following formula:

—W'—$R^x$—S—$Z^s$ wherein:

the double line 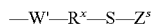 between N and C represents a single bond or a double bond, provided that when it is a double bond, X is absent and Y is —H, and when it is a single bond, X is selected from —H, the linking group with the reactive group bonded thereto, or an amine protecting group (preferably X is —H);

Y is —H, or a leaving group selected from —OR, —OCOR', —SR, —NR'R," —SO$_3$M, —SO$_2$M or —OSO$_3$M, wherein M is —H or a pharmaceutically acceptable cation such as Na$^+$ or K$^+$;

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(=O)—, —N(C(=O)R$^e$)—, —S—, —CH$_2$—S—, or —CH$_2$NR$^e$—;

$R^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

$Z^s$ is —H, or is selected from any one of the following formulas:

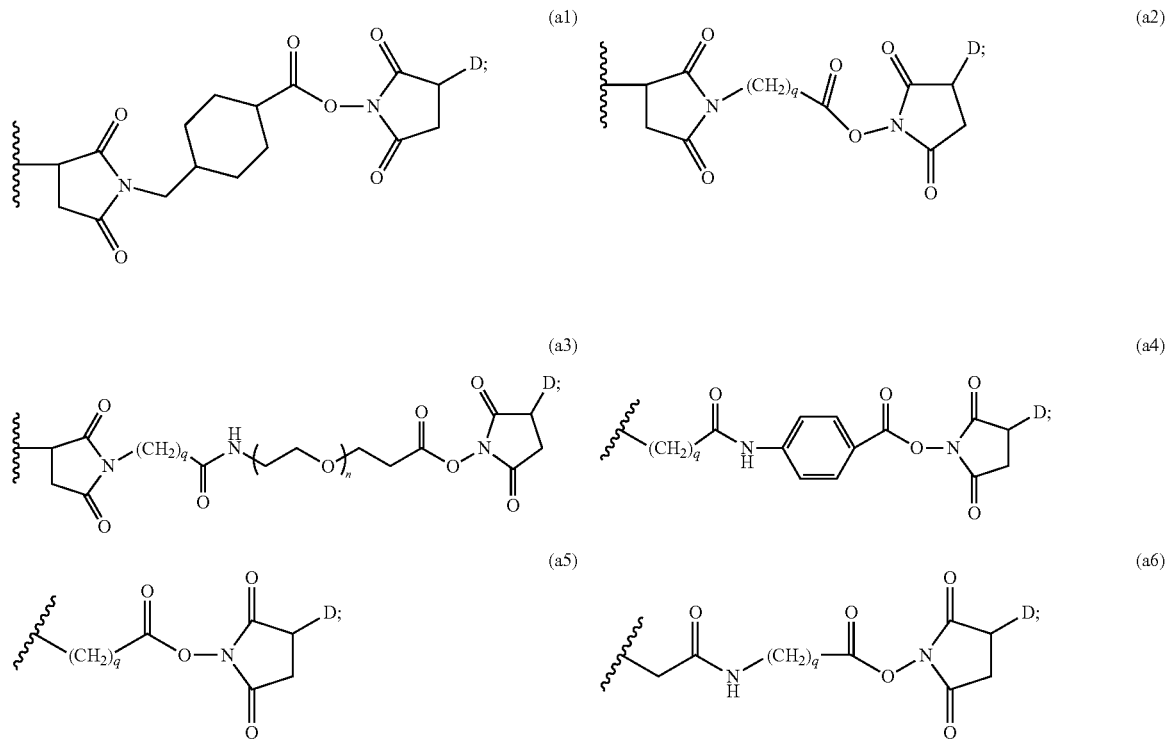

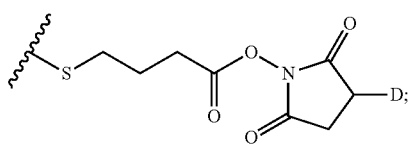 (a7)

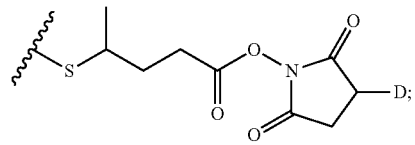 (a8)

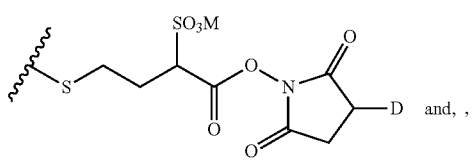 (a9)

and,

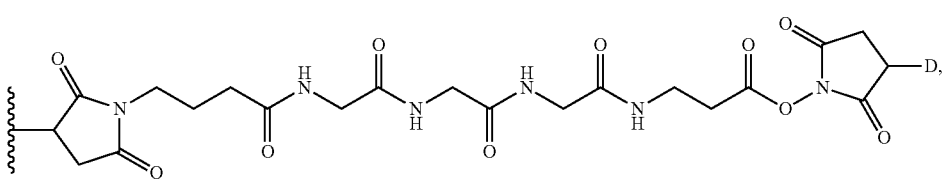 (a10)

wherein:
q is an integer from 1 to 5;
n is an integer from 2 to 6;
D is or —SO$_3$M;
M is —H or a pharmaceutically acceptable cation, such as Na$^+$ or K$^+$.

In certain embodiments, $Z^s$ is represented by any one of the following formulas:

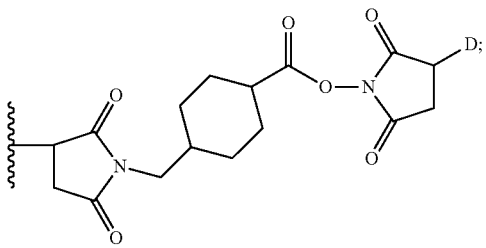 (a1)

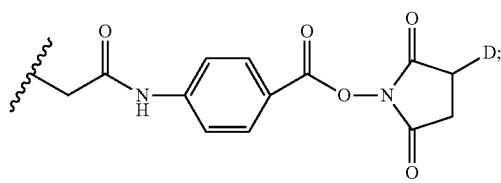 (a4')

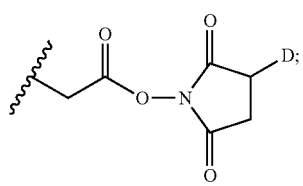 (a5')

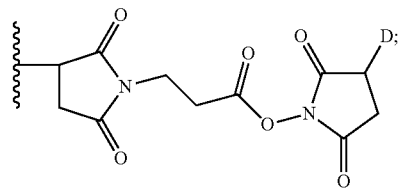 (a12)

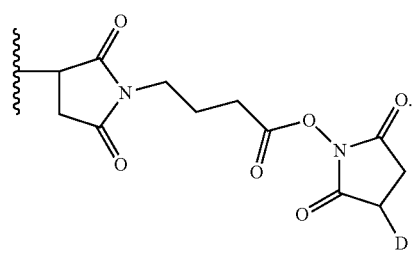 (a13)

In certain embodiments, W' is —N(R$^e$)—.
In certain embodiments, R$^e$ is —(CH$_2$—CH$_2$—O)$_n$—R$^k$, wherein R$^k$ is a —H, a linear, branched cyclic alkyl having 1 to 6 carbon atoms.
In certain embodiments, R$^k$ is —H or -Me, n is 4, and q is 2.
In certain embodiments, R$^x$ is a linear or branched alkyl having 1 to 6 carbon atoms.
In certain embodiments, R$^x$ may be —(CH$_2$)$_p$—(CR$^f$R$^g$)—, wherein R$^f$ and R$^g$ are each independently selected from H or a linear or branched alkyl having 1 to 4 carbon atoms; and p is 0, 1, 2 or 3.
In certain embodiments, R$^f$ and R$^g$ are the same or different, and are selected from —H and -Me; and p is 1.

In a ninth specific embodiment, the compounds of formula (VAa), (VIAa), (VIIAa) or (VIIA2a) described in the eighth specific embodiment, the variables are as described below:
the double line ═ between N and C represents a single bond or a double bond, provided that when it is a double bond X is absent and Y is —H, and when it is a single bond, X is —H; Y is —H, —OH or —SO$_3$M;
M is —H or a pharmaceutically acceptable cation (e.g., Na$^+$);

X' and Y' are both —H;
A and A' are both —O—;
R$_6$ is —OMe; and
R$^x$ is a linear or branched alkyl having 1 to 6 carbon atoms.

In a related embodiment, Y is —OH or —SO$_3$M.

In another embodiment, for the compounds of formula (VAa), (VIAa), (VIIAa), or (VIIA2a) described in the eighth specific embodiment, the variables are as described below:
W' is —O—, —N(R$^e$)—, —N(R$^e$)—C(=O)—, —N(COR$^e$)—, —S— or —CH$_2$—S—;
R$^x$ is absent or selected from a linear, branched or cyclic alkyl having 1 to 6 carbon atoms;
R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a primary, secondary or tertiary amino group or a 5- or 6-membered Nitrogen containing heterocycle, such as piperidine or morpholine;
n is an integer from 1 to 24; and the remainder of the variables are as described above in the ninth specific embodiment.

Preferably, R$^k$ is —H or -Me, and n is an integer from 2 to 8. Preferably, R$^x$ is a linear or branched alkyl having 1 to 6 carbon atoms.

Preferably, R$^x$ is —(CH$_2$)$_p$—(CR$^f$R$^g$)—, wherein R$^f$ and R$^g$ are each independently selected from H or a linear or branched alkyl having 1 to 4 carbon atoms; p is 0, 1, 2 or 3. More preferably, R$^f$ and R$^g$ are the same or different, and are selected from —H and -Me; and p is 1.

In another preferred embodiment, the linker is represented by any one of the formula selected from formulas (a1), (a4'), (a5'), (a12) and (a13) shown above; and the remainder of the variables are as described above in the ninth specific embodiment.

In a tenth specific embodiment, for compounds of formula (VAa), (VIAa), (VIIAa), or (VIIA2a) described in the seventh specific embodiment, the variables are as described below:
the double line ═ between N and C represents a single bond or a double bond, provided that when it is a double bond X is absent and Y is —H, and when it is a single bond, X is —H; Y is —H, —OH or —SO$_3$M (e.g., Y is —OH or —SO$_3$M);
M is —H or Na$^+$;
X' and Y' are both —H;
A and A' are both —O—;
R$_6$ is —OMe;
R$^x$ is a linear or branched alkyl having 1 to 6 carbon atoms; and the remainder of the variables is as described above in the third, fourth, or the fifth specific embodiment.

Preferably, R$^x$ is —(CH$_2$)$_p$—(CR$^f$R$^g$)—, wherein R$^f$ and R$^g$ are each independently selected from H or a linear or branched alkyl having 1 to 4 carbon atoms; p is 0, 1, 2 or 3. More preferably, R$^f$ and R$^g$ are the same or different, and are selected from —H and -Me; and p is 1.

In any of the specific embodiments above (e.g., the first to the 10$^{th}$ specific embodiments), the double line ═ between N and C may represent a double bond.

In any of the specific embodiments above (e.g., the first to the 10$^{th}$ specific embodiments), the double line ═ between N and C may represent a single bond, X is —H, the linking group with the reactive group bonded thereto, or an amine protecting group (e.g., X is —H or an amine protecting group); and Y is selected from —H, —OR, —OCOR', —SR, —NR'R," an optionally substituted 5- or 6-membered nitrogen-containing heterocycle, —SO$_3$M, —SO$_2$M and a sulfate —OSO$_3$M (e.g., Y is —OR, —OCOR', —SR, —NR'R," an optionally substituted 5- or 6-membered nitrogen-containing heterocycle, —SO$_3$M, —SO$_2$M and a sulfate —OSO$_3$M).

In certain embodiments, Y is selected from —H, —SO$_3$M, —OH, —OMe, —OEt or —NHOH (e.g., Y is —SO$_3$M, —OH, —OMe, —OEt or —NHOH).

In certain embodiments, Y is —H, —SO$_3$M or —OH (e.g., Y is —SO$_3$M or —OH).

In certain embodiments, M is —H, Na$^+$ or K$^+$.

In any of the specific embodiments above (e.g., the first to the 10$^{th}$ specific embodiments), W, when present, is C=O.

In any of the specific embodiments above (e.g., the first to the 10$^{th}$ specific embodiments), X' is selected from the group consisting of —H, —OH, an optionally substituted linear, branched or cyclic alkyl, alkenyl or alkynyl having from 1 to 10 carbon atoms, phenyl, the linking group with the reactive group bounded thereto, and an amine-protecting group.

In certain embodiments, X' is —H, —OH, -Me or the linking group with the reactive group bounded thereto.

In certain embodiments, X' is —H.

In any of the specific embodiments above (e.g., the first to the 10$^{th}$ specific embodiments), Y' is selected from the group consisting of —H, an oxo group, a substituted or unsubstituted linear, branched or cyclic alkyl, alkenyl or alkynyl having from 1 to 10 carbon atoms.

In certain embodiments, Y' is —H or oxo.

In certain embodiments, Y' is —H.

In any of the specific embodiments above (e.g., the first to the 10$^{th}$ specific embodiments), A and A' are the same or different, and are selected from O, S, NR$_5$ and oxo (C=O). A and A' may be same or different and selected from —O— and —S—. Preferably, both A and A' are —O—.

In any of the specific embodiments above (e.g., the first to the 10$^{th}$ specific embodiments), D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. Preferably, D and D' are linear or branched alkyl bearing 1 to 4 carbon atoms.

In a eleventh embodiment, the cytotoxic compound of the present invention as described in the first, third, and eighth embodiment is represented by the following:
the double line ═ between N and C represents a double bond;
Y is —H;
W is C=O;
R$_6$ is —OMe;
X' is —H;
Y' is —H; and
A and A' are —O—.

In certain embodiments, the invention provides a cytotoxic compound with the formula Ia:

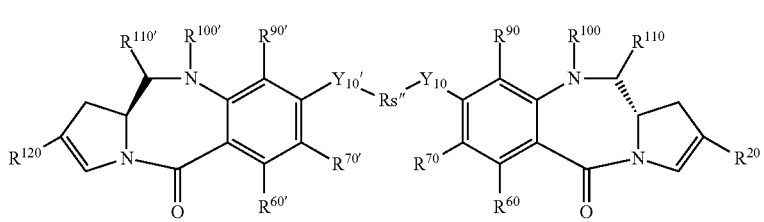

wherein:

R²⁰ is of formula IIa:

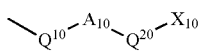

where $A_{10}$ is a $C_{5-7}$ aryl group, $X_{10}$ is selected from the group consisting of OH, SH, CO₂H, C(=O)H, N=C=O, CONHNH₂,

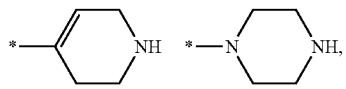

and NHR^N, wherein R^N is selected from the group consisting of H and $C_{1-4}$ alkyl, and either:

(i) $Q^{10}$ is a single bond, and $Q^{20}$ is selected from a single bond and —Z—(CH₂)ₙ—, where Z is selected from a single bond, O, S, and NH and n' is from 1 to 3; or (ii) $Q^{10}$ is —CH=CH—, and $Q^{20}$ is a single bond;

$R^{120}$ is selected from:

(iia) $C_{1-5}$ saturated aliphatic alkyl;

(iib) $C_{3-6}$ saturated cycloalkyl;

(iic)

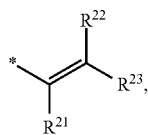

wherein each of $R^{21}$, $R^{22}$, and $R^{23}$ are independently selected from H, $C_{1-3}$ saturated alkyl, $C_{2-3}$ alkenyl, $C_{2-3}$ alkynyl, and cyclopropyl, where the total number of carbon atoms in the $R^{120}$ group is no more than 5;

(iid)

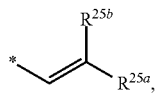

wherein one of $R^{25a}$ and $R^{25b}$ is H and the other is phenyl, which phenyl is optionally substituted by a group selected from halo, methyl, methoxy, pyridyl, or thiophenyl; and (iie)

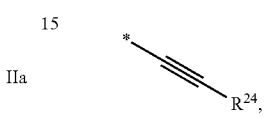

where $R^{24}$ is selected from H, $C_{1-3}$ saturated alkyl, $C_{2-3}$ alkenyl, $C_{2-3}$ alkynyl, cyclopropyl, and phenyl, which phenyl is optionally substituted by a group selected from halo, methyl, methoxy, pyridyl, and thiophenyl;

$R^{60}$ and $R^{90}$ are independently selected from H, $R_{10}$, OH, $OR_{10}$, SH, $SR_{10}$, NH₂, $NHR_{10}$, $NR_{10}R_{10}'$, nitro, Me₃Sn, and halo; where $R_{10}$ and $R_{10}'$ are independently selected from optionally substituted $C_{1-12}$ alkyl, $C_{3-20}$ heterocyclyl, and $C_{5-20}$ aryl groups;

$R^{70}$ is selected from H, $R_{10}$, OH, $OR_{10}$, SH, $SR_{10}$, NH₂, $NHR_{10}$, $NR_{10}R_{10}'$, nitro, Me₃Sn, and halo;

either:

(a) $R^{100'}$ is selected from —H, an amine-protecting group, an optionally substituted linear, branched or cyclic alkyl, alkenyl or alkynyl having from 1 to 10 carbon atoms, a polyethylene glycol unit —(CH₂CH₂O)ₙ—R^c, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P; and $R^{110'}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

when the nitrogen and carbon atoms to which $R^{100}$ and $R^{110}$ are bound, form a nitrogen-carbon double bond; $R^{100}$ is absent; $R^{110}$ is —H, or a linear or branched alkyl having 1 to 4 carbon atoms; or when the nitrogen and carbon atoms to which $R^{100}$ and $R^{110}$ are bound, form a nitrogen-carbon single bond; $R^{100}$ is H or an amine-protecting group, and $R^{110}$ is H, an oxo group, O-Prot°, wherein Prot° is an oxygen protecting group, or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or $R^{110}$ is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; or (b) $R^{100}$ is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P; and $R^{110}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

when the nitrogen and carbon atoms to which $R^{100'}$ and $R^{110'}$ are bound, form a nitrogen-carbon double bald; $R^{100'}$ is absent; $R^{110'}$ is —H, or a linear or branched alkyl having 1 to 4 carbon atoms; or when the nitrogen and carbon atoms to which $R^{100'}$ and $R^{110'}$ are bound, form a nitrogen-carbon single bond; $R^{100'}$ is H or an amine-protecting group, and $R^{110'}$ is H, an oxo group, O-Prot$^o$, wherein Prot$^o$ is an oxygen protecting group, or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or $R^{110'}$ is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —N(R)$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms;

n is an integer from 1 to 24;

R$_s$" is a $C_{3-12}$ alkylene group, which chain may be interrupted by one or more heteroatoms, and/or aromatic rings;

$Y_{10}$ and $Y_{10}'$ are selected from O, S, or NH;

$R^{60'}$, $R^{70'}$, and $R^{90'}$ are selected from the same groups as $R^{60}$, $R^{70}$, and $R^{90}$ respectively.

In certain embodiments, (a) when the nitrogen and carbon atoms to which $R^{100}$ and $R^{110}$ are bound, form a nitrogen-carbon double bond; $R^{100}$ is absent; and $R^{110}$ is —H; or when the nitrogen and carbon atoms to which $R^{100}$ and $R^{110}$ are bound, form a nitrogen-carbon single bond;

(a)(i) $R^{100}$ is H, and $R^{110}$ is OH, OR$^A$, or SO$_z$M, where R$^A$ is $C_{1-4}$ alkyl; z is 2 or 3; and M is a monovalent pharmaceutically acceptable cation;

(a)(ii) $R^{100}$ is carbamate nitrogen protecting group, and $R^{110}$ is O-Prot$^o$, wherein Prot$^o$ is an oxygen protecting group; or (a)(iii) $R^{100}$ is a hemi-aminal nitrogen protecting group and $R^{110}$ is an oxo group; or (b) when the nitrogen and carbon atoms to which $R^{100'}$ and $R^{110'}$ are bound, form a nitrogen-carbon double bond; $R^{100'}$ is absent; and $R^{110'}$ is —H; or when the nitrogen and carbon atoms to which $R^{100'}$ and $R^{110'}$ are bound, form a nitrogen-carbon single bond;

(b)(i) $R^{100'}$ is H, and $R^{110'}$ is OH, $OR^4$, or $SO_zM$, where $R^4$ is $C_{1-4}$ alkyl; z is 2 or 3; and M is a monovalent pharmaceutically acceptable cation;

(b)(ii) $R^{100'}$ is carbamate nitrogen protecting group, and $R^{110'}$ is O-Prot$^o$, wherein Prot$^o$ is an oxygen protecting group; or (b)(iii) $R^{100'}$ is a hemi-aminal nitrogen protecting group and $R^{110'}$ is an oxo group.

In certain embodiments, under condition (a), $R^{100'}$ is selected from the group consisting of —H, —OH, a linear, branched or cyclic alkyl, alkenyl or alkynyl having from 1 to 10 carbon atoms, phenyl, and an amine-protecting group. $R^{110'}$ is selected from the group consisting of —H, an oxo group, a linear, branched or cyclic alkyl, alkenyl or alkynyl having from 1 to 10 carbon atoms; or under condition (b), $R^{100}$ is selected from the group consisting of —H, —OH, a linear, branched or cyclic alkyl, alkenyl or alkynyl having from 1 to 10 carbon atoms, phenyl, and an amine-protecting group. $R^{110}$ is selected from the group consisting of —H, an oxo group, a linear, branched or cyclic alkyl, alkenyl or alkynyl having from 1 to 10 carbon atoms.

In certain embodiments, $R^{70}$ is selected from H, OH, and $OR_{10}$. Preferably, $R^{70}$ is a $C_{1-4}$ alkyloxy group.

In certain embodiments, $Y_{10}$ is O.

In certain embodiments, $R_s"$ is $C_{3-7}$ alkylene.

In certain embodiments, $R^{90}$ is H.

In certain embodiments, $R^{60}$ is selected from H and halo.

In certain embodiments, $A_{10}$ is phenyl.

In certain embodiments, $X_{10}$ is selected from OH, SH, or $NH_2$.

In certain embodiments, $Q^{10}$ is a single bond.

In certain embodiments, $Q^{20}$ is a single bond. In certain embodiments, $Q^{20}$ is $—Z—(CH_2)_{n'}—$, Z is O or S and n' is 1 or 2.

In certain embodiments, $Q^{10}$ is —CH=CH—.

In certain embodiments, $R^{120}$ is a $C_{1-5}$ saturated aliphatic alkyl group. Preferably, $R^{120}$ is methyl, ethyl, or propyl.

In certain embodiments, $R^{120}$ is a $C_{3-6}$ saturated cycloalkyl group. Preferably, $R^{120}$ is cyclopropyl.

In certain embodiments, $R^{120}$ is a group of formula:

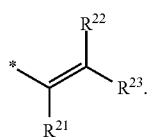

Preferably, the total number of carbon atoms in the $R^{120}$ group is no more than 4. Preferably, the total number of carbon atoms in the $R^{120}$ group is no more than 3. Preferably, one of $R^{21}$, $R^{22}$, and $R^{23}$ is H, with the other two groups being selected from H, $C_{1-3}$ saturated alkyl, $C_{2-3}$ alkenyl, $C_{2-3}$ alkynyl, and cyclopropyl. Preferably, two of $R^{21}$, $R^{22}$, and $R^{23}$ are H, with the other group being selected from H, $C_{1-3}$ saturated alkyl, $C_{2-3}$ alkenyl, $C_{2-3}$ alkynyl, and cyclopropyl.

In certain embodiments, $R^{120}$ is a group of formula:

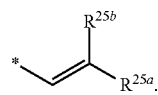

Preferably, $R^{120}$ is the group

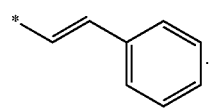 [SMILES: */C=C/c1ccccc1]

In certain embodiments, $R^{120}$ is a group of formula:

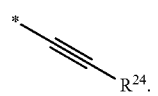

Preferably, $R^{24}$ is selected from H, methyl, ethyl, ethenyl, and ethynyl. More preferably, $R^{24}$ is selected from H and methyl.

In certain embodiments, the nitrogen and carbon atoms to which $R^{100}$ and $R^{110}$ are bound, form a nitrogen-carbon double bond; $R^{100}$ is absent; and $R^{110}$ is —H; or the nitrogen and carbon atoms to which $R^{100'}$ and $R^{110'}$ are bound, form a nitrogen-carbon double bond; $R^{100'}$ is absent; and $R^{110'}$ is —H.

In certain embodiments, $R^{60'}$, $R^{70'}$, $R^{90'}$, and $Y_{10}'$ are the same as $R^{60}$, $R^{10}$, $R^{90}$, and $Y_{10}$ respectively.

The synthesis of such cytotoxic compounds can be based on the methods/schemes described herein, and methods/schemes essentially identical to those in WO 2001/130613 A1 and WO 2001/130616 A1 (both incorporated herein by reference).

The invention further provides the use of a compound of the invention, or a pharmaceutically acceptable salt or solvate thereof, in the manufacture of a medicament for treating a proliferative disease or an autoimmune disease.

The invention additionally provides the use of a Conjugate of the invention, or a pharmaceutically acceptable salt or solvate thereof, for treating a proliferative disease or an autoimmune disease.

Drug Compounds & Drug-Linker Compounds

The cytotoxic compounds described above comprise a linking group with a reactive group bonded thereto, which compounds may result from reacting a bifunctional cross-linking reagent with "linker-less" compounds to form the so-called drug-linker compounds. Alternatively, drug compounds that are otherwise identical to the drug-linker compounds, but without the linker moiety are also encompassed by the present invention.

Thus in certain embodiments, the invention provides a cytotoxic compound without linking group, but may be capable of reacting with a bifunctional crosslinking agent to form a compound of the invention, such as any one of the $1^{st}$ to the $11^{th}$ specific embodiments described above; or to form a cell-binding agent conjugate of the invention (such as those described below). The linkerless cytotoxic compounds of the invention are represented by any one of the following formulas (V), (VI), or (VII):

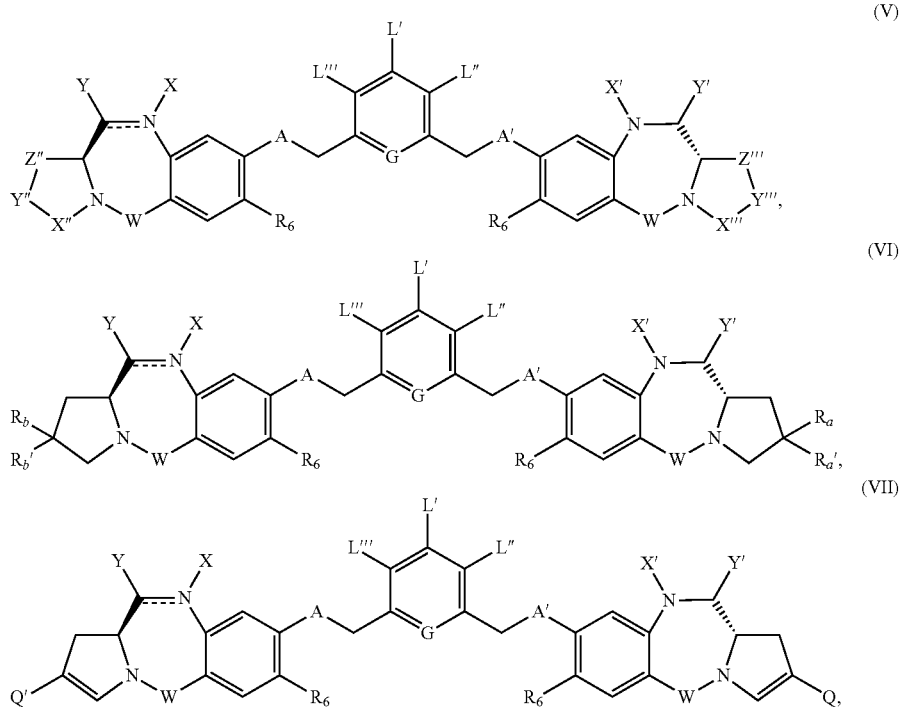

(V)

(VI)

(VII)

or a pharmaceutically acceptable salt thereof, wherein:

the double line ⚌ between N and C represents a single bond or a double bond, provided that when it is a double bond, X is absent and Y is —H, or a linear or branched alkyl having 1 to 4 carbon atoms, and when it is a single bond, X is —H, or an amine protecting moiety; preferably, the double line ⚌ between N and C represents a double bond;

Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH) NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido, wherein M is —H or a pharmaceutically acceptable cation; such as Na$^+$ or K$^+$. Preferably, M is —H or Na$^+$. Preferably, Y is selected from —SO$_3$M, —OH, —OMe, —OEt or —NHOH. More preferably, Y is —SO$_3$M or —OH; or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS (OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are the same or different, and are independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms;

n is an integer from 1 to 24;

W is selected from C=O, C=S, $CH_2$, BH, SO, and $SO_2$;

X' is selected from the group consisting of —H, —OH, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms (e.g., phenyl), an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P. Preferably, X' is —H, —OH, or -Me. More preferably, X' is —H;

Y' is selected from the group consisting of —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms. Preferably, Y' is —H or oxo. More preferably, Y' is —H;

$R_6$ is —H, —R, —OR, —SR, —NR'R", —$NO_2$, halogen, —$OR^c$ or —$SR^c$, wherein $R^c$ is —H, a linear or branched alkyl having 1 to 4 carbon atoms. Preferably, $R_6$ is —OMe or —SMe: Even more preferably, $R_6$ is —OMe;

A and A' are the same or different, and are independently selected from —O—, oxo (—C(=O)—), —CRR'O—, —CRR'—, —S—, —CRR'S—, —$N(R_5)$— and —$CRR'N(R_5)$—. Preferably, A and A' are the same or different, and are selected from —O— and —S—. More preferably, A and A' are —O—;

$R_5$ for each occurrence is independently —H or an optionally substituted linear or branched alkyl having 1 to 10 carbon atoms;

L', L", and L'" are the same or different, and are independently selected from —H, halogen, an optionally substituted linear, branched or cyclic alkyl, haloalkyl, alkoxy, haloalkoxy, —$NO_2$, or —CN;

X" and X'" are the same or different, and are independently selected from —$(CH_2)_{n'}$—, —NR'—, —CO—, —BH—, —SO— or —$SO_2$—;

Y" and Y'" are the same or different, and are independently selected from —O, —$(CH_2)_{n'}$—, —NR'— or —S—;

Z" and Z'" are the same or different, and are independently selected from —$(CH_2)_{n'}$—, —$CR_7R_8$—, —$NR_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$, and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH unit;

Ar and Ar' are each independently absent, or represent an aryl group;

$Q_2$ and $Q_2'$ are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)$NH_2$], —OR, —NR'R", —$NO_2$, —NCO, —NR'COR", —SR, a sulfoxide represented by —SOR', a sulfone represented by —$SO_2R'$, a sulfonate —$SO_3M$, a sulfate —$OSO_3M$, a sulfonamide represented by $SO_2NR'R"$, cyano, an azido, —COR', —OCOR' or —OCONR'R"; and $R^{c'}$ is absent or selected from linear or branched alkyl, alkenyl or alkynyl having 1 to 5 carbon atoms.

In certain embodiments, the compound is represented by any one of the following formulas:

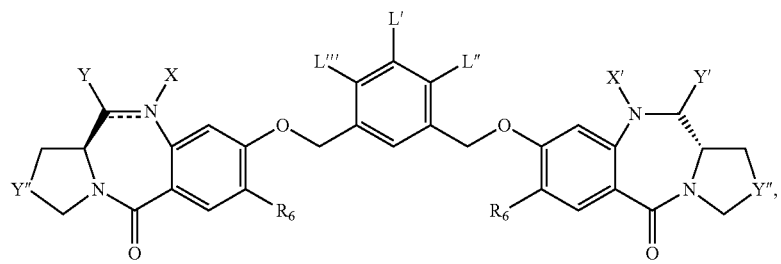

(VA)

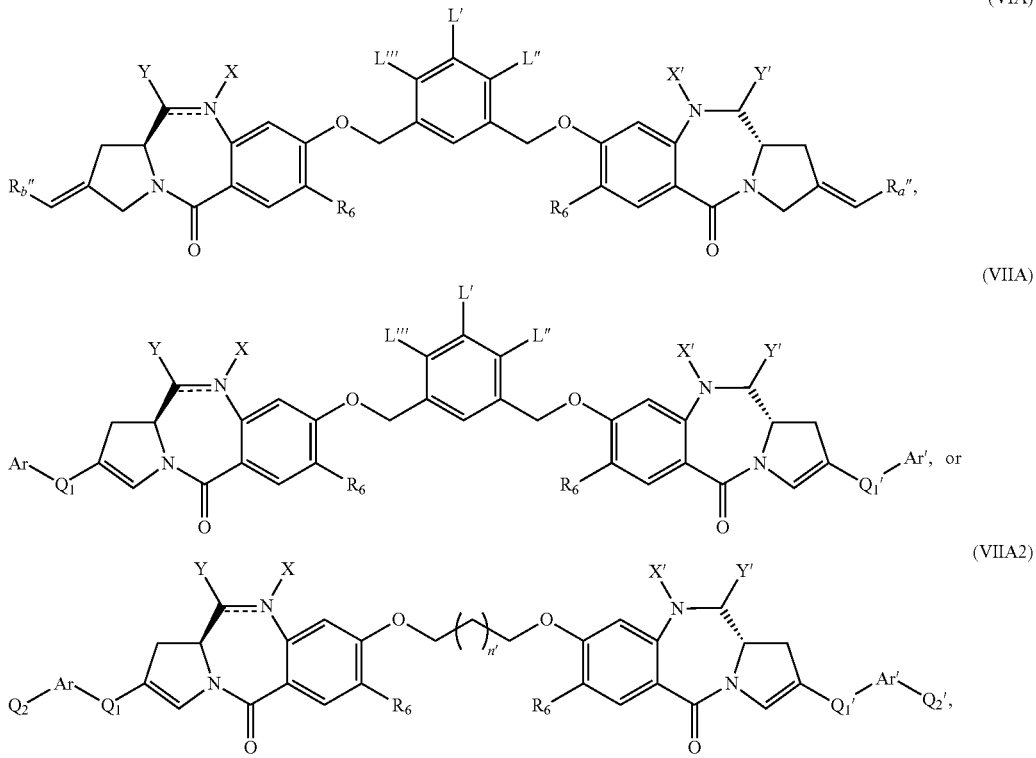

wherein:

L', L", and L''' are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, an azido, —COR', —OCOR', —OCONR'R" and the linking group with the reactive group bonded thereto, provided only one of L', L", and L''' is the linking group with the reactive group bonded thereto;

R$_a$" and R$_b$" are the same or different, and are selected from —H and -Me; one of Q$_2$ and Q$_2$' is selected from —H, —R, —OR, —NR'R", —NR'(C=O)OR", —SR, and —NO$_2$, the other is the linking group with the reactive group bonded thereto.

In certain embodiments, the double line ⹀ between N and C represents a single bond, Y is not —H.

In certain embodiments, the double line ⹀ between N and C represents a single bond or a double bond, provided that when it is a double bond X is absent and Y is —H, and when it is a single bond, X is selected from —H, or an amine protecting group (preferably X is —H); W is C=O; A and A' are both —O—; W is —(C=O)—; R$_6$ is —H, or optionally substituted C1-C10 linear, C1-C10 branched, or C3-C7 cyclic alkyl, —O-alkyl, or —O-halo-alkyl, such as —OMe; X' is selected from the group consisting of —H, —OH, a substituted or unsubstituted linear, branched or cyclic alkyl, alkenyl or alkynyl having from 1 to 10 carbon atoms, phenyl, and an amine-protecting group; and Y' is selected from the group consisting of —H, an oxo group, a substituted or unsubstituted linear, branched or cyclic alkyl, alkenyl or alkynyl having from 1 to 10 carbon atoms.

Preferably, when Y is not —H, Y is selected from —OR, —OCOR', —SR, —NR'R", —SO$_3$M, —SO$_2$M, or —OSO$_3$M, wherein M is —H or a pharmaceutically acceptable cation such as Na$^+$ or K$^+$. Preferably, Y is selected from —H, —OH, —OMe, —OEt, —NHOH or —SO$_3$M (e.g., Y is —OH, —OMe, —OEt, —NHOH or —SO$_3$M). Even more preferably, Y is —H, —OH or —SO$_3$M (e.g., Y is —OH or —SO$_3$M), preferably M is —H or Na$^+$.

In certain embodiments, the double line ⹀ between N and C represents a single bond or a double bond, provided that when it is a double bond X is absent and Y is —H, and when it is a single bond, X is selected from —H, or an amine protecting group (preferably X is —H); W is C=O; X' and Y' are —H; A and A' are both —O—; W is —(C=O)—; R$_6$ is —H, or optionally substituted C1-C10 linear, C1-C10 branched, or C3-C7 cyclic alkyl, —O-alkyl, or —O-haloalkyl, such as —OMe.

Bifunctional Crosslinking Agents

The bifunctional crosslinking agents can be any bifunctional linker known in the art. For example, the bifunctional linkers can be used for making the drug-linker compounds are those that form disulfide bonds, thioether bonds, acid labile bonds, photolabile bonds, peptidase labile bonds and esterase labile bonds with the cytotoxic compounds (see for example, U.S. Pat. Nos. 5,208,020; 5,475,092; 6,441,163; 6,716,821; 6,913,748; 7,276,497; 7,276,499; 7,368,565; 7,388,026 and 7,414,073, all of which are incorporated herein by reference). Preferably, the bifunctional crosslinking agents are those that form disulfide bonds, thioether and peptidase labile bonds with the cytotoxic compounds. Other bifunctional crosslinking agents that can be used in the present invention include non-cleavable linkers, such as those described in U.S. publication number US 2005/0169933, or charged linkers or hydrophilic linkers and are described in US 2009/0274713, US 2010/01293140 and WO 2009/134976, each of which is expressly incorporated herein by reference. The bifunctional crosslinking agents that can be used for making the (drug-linker) compounds of the present invention also include those described in *Thermo Scientific Pierce Crosslinking Technical Handbook*, the entire teaching of which is incorporated herein by reference.

Synthesis of Cytotoxic Compounds

Figure 9:
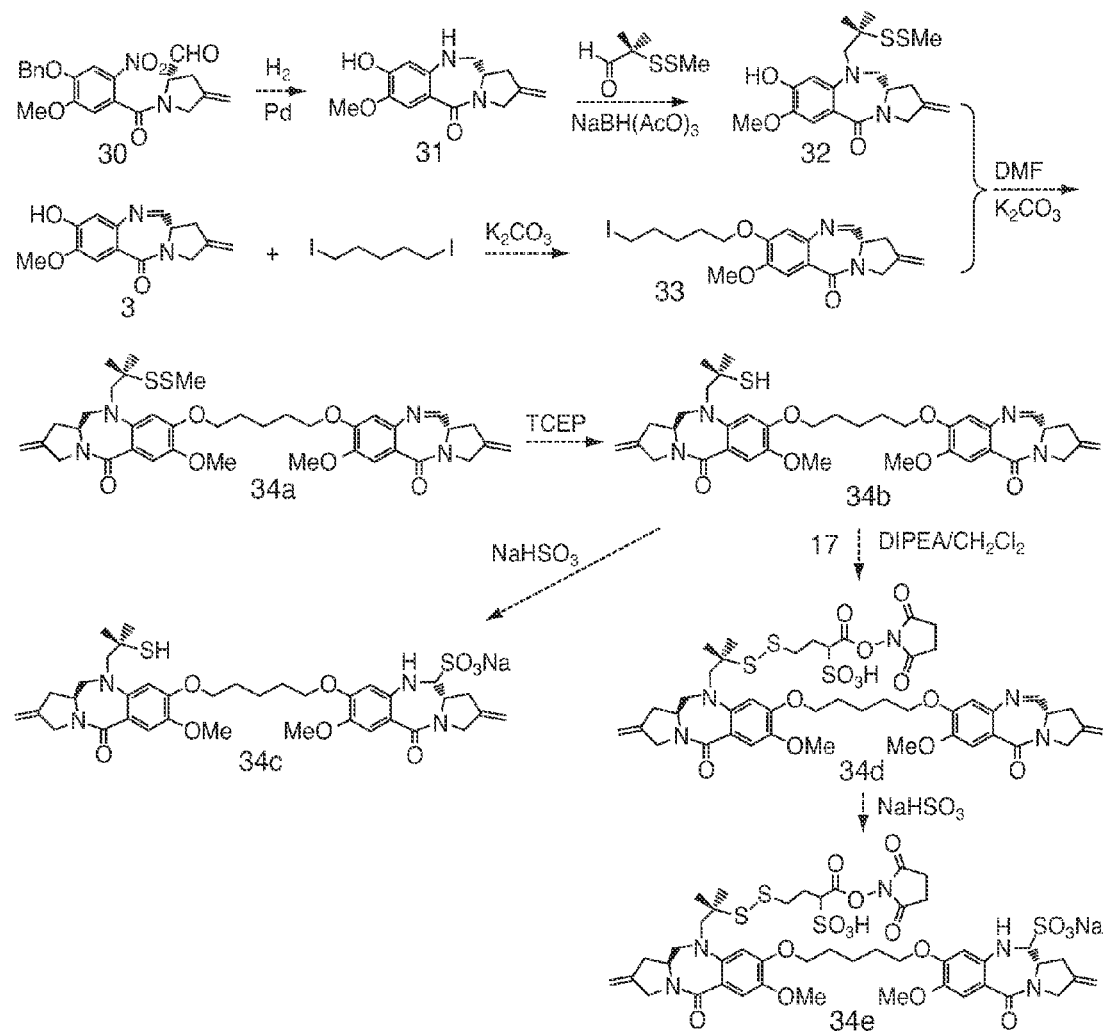
Figure 10:
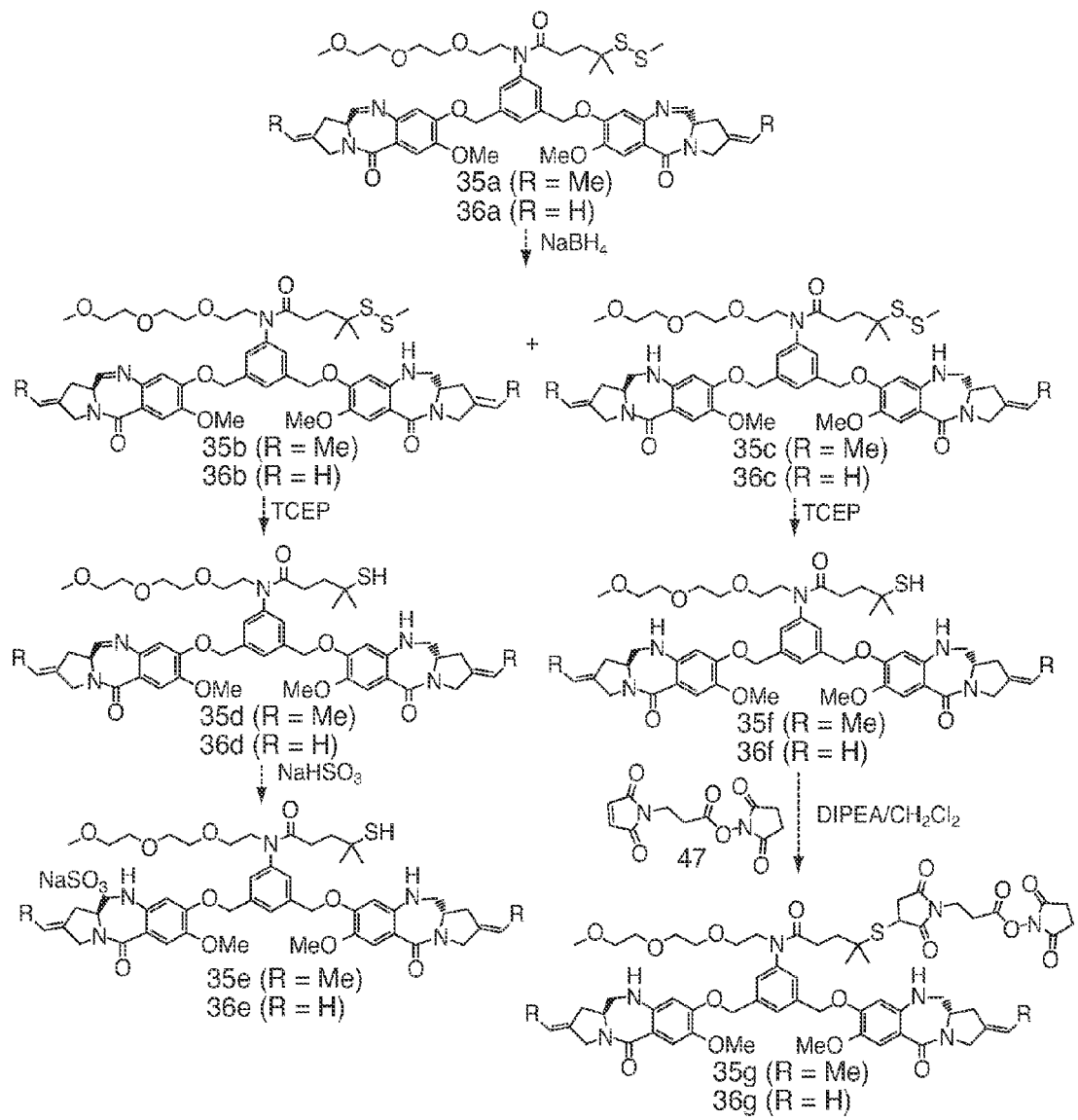
Figure 11:
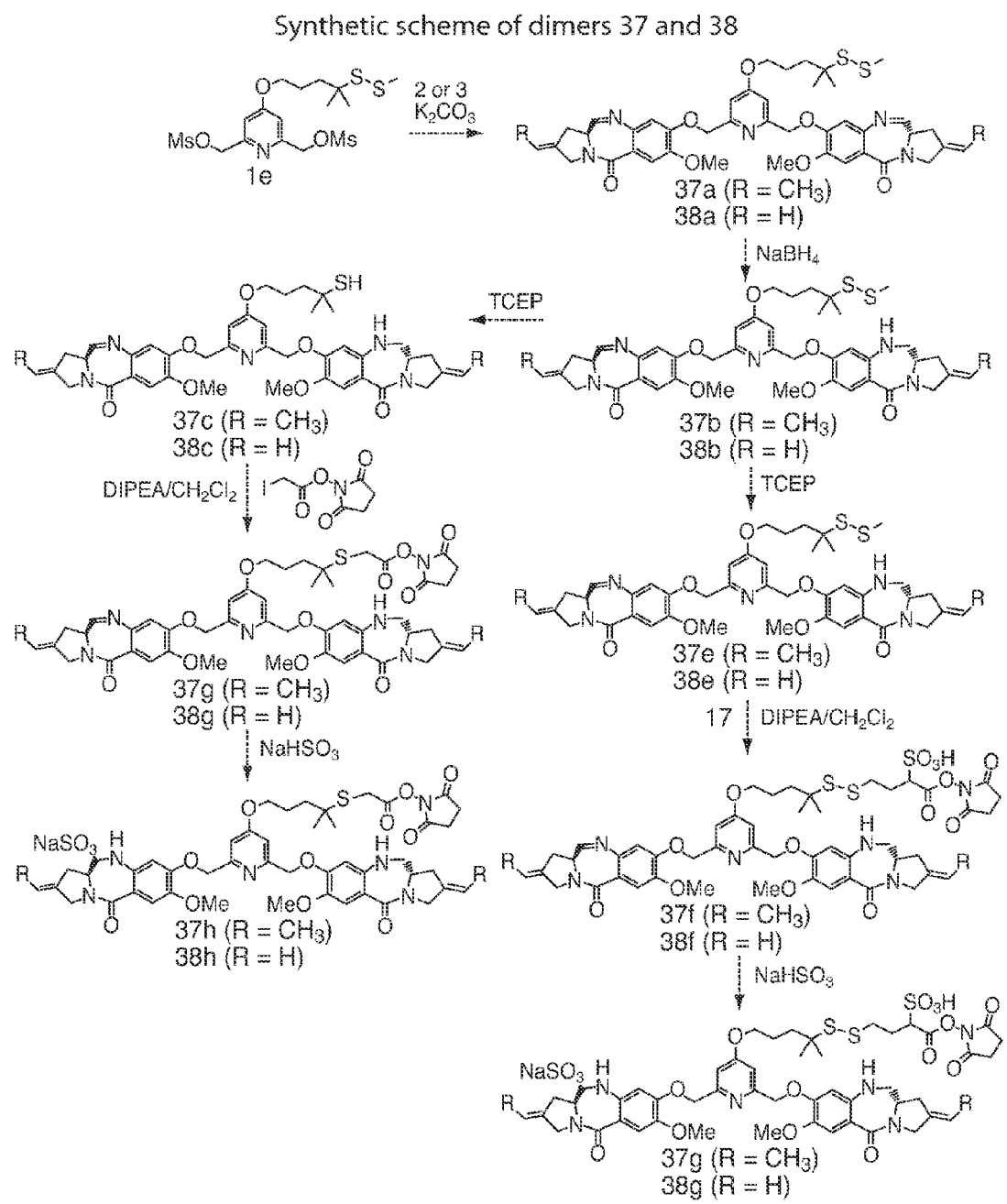
Figure 12:
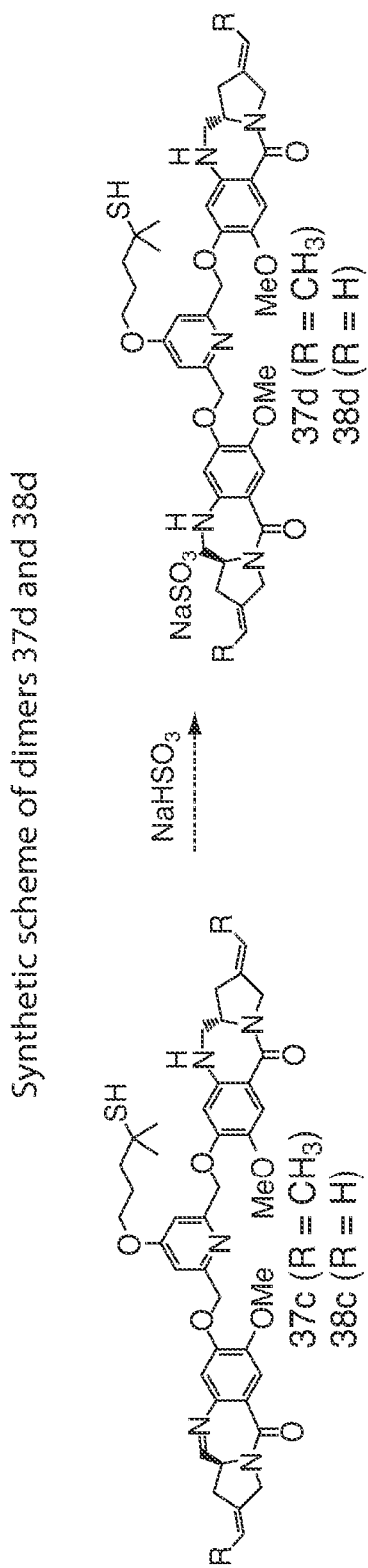
Figure 13:
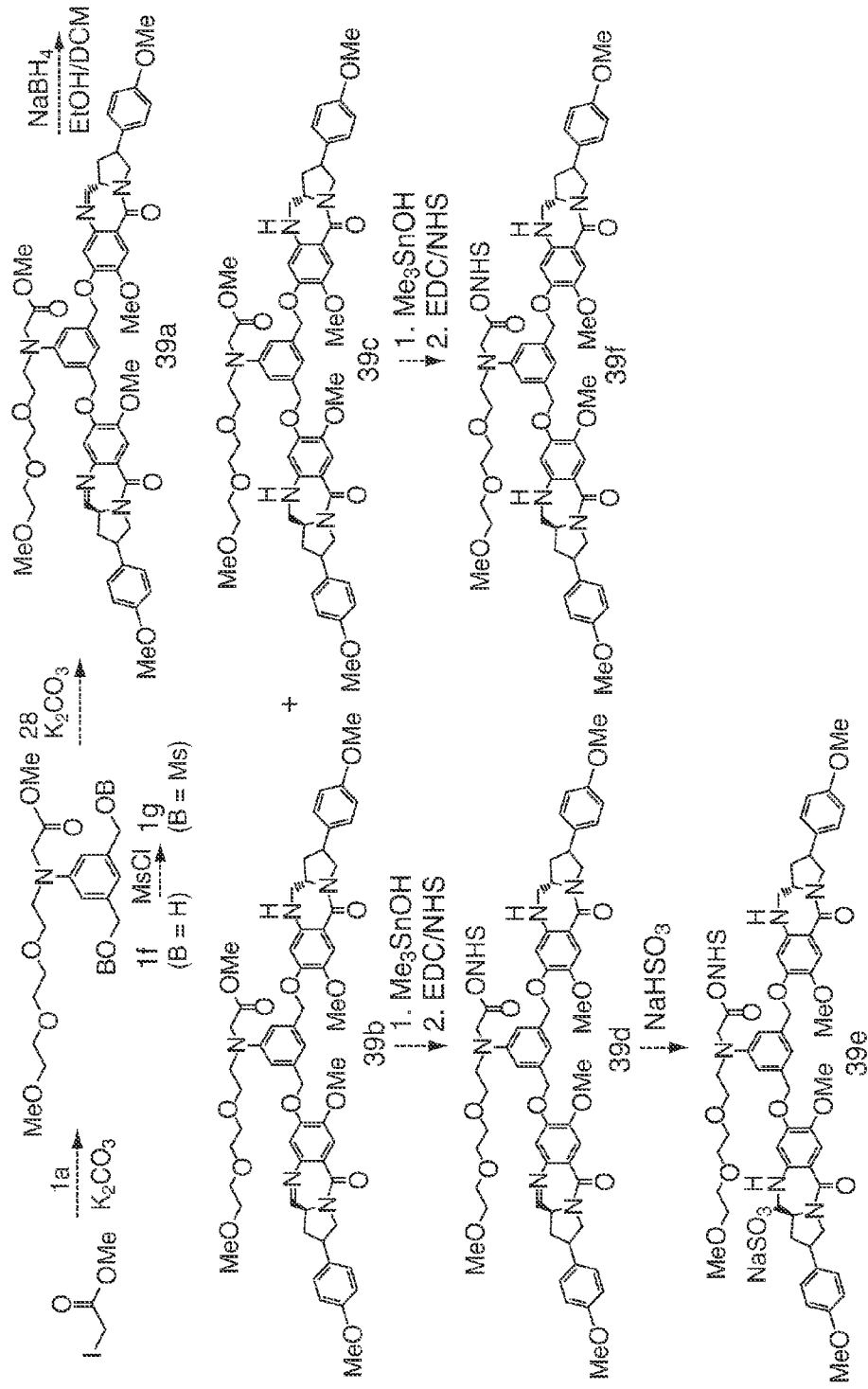
Figure 14:
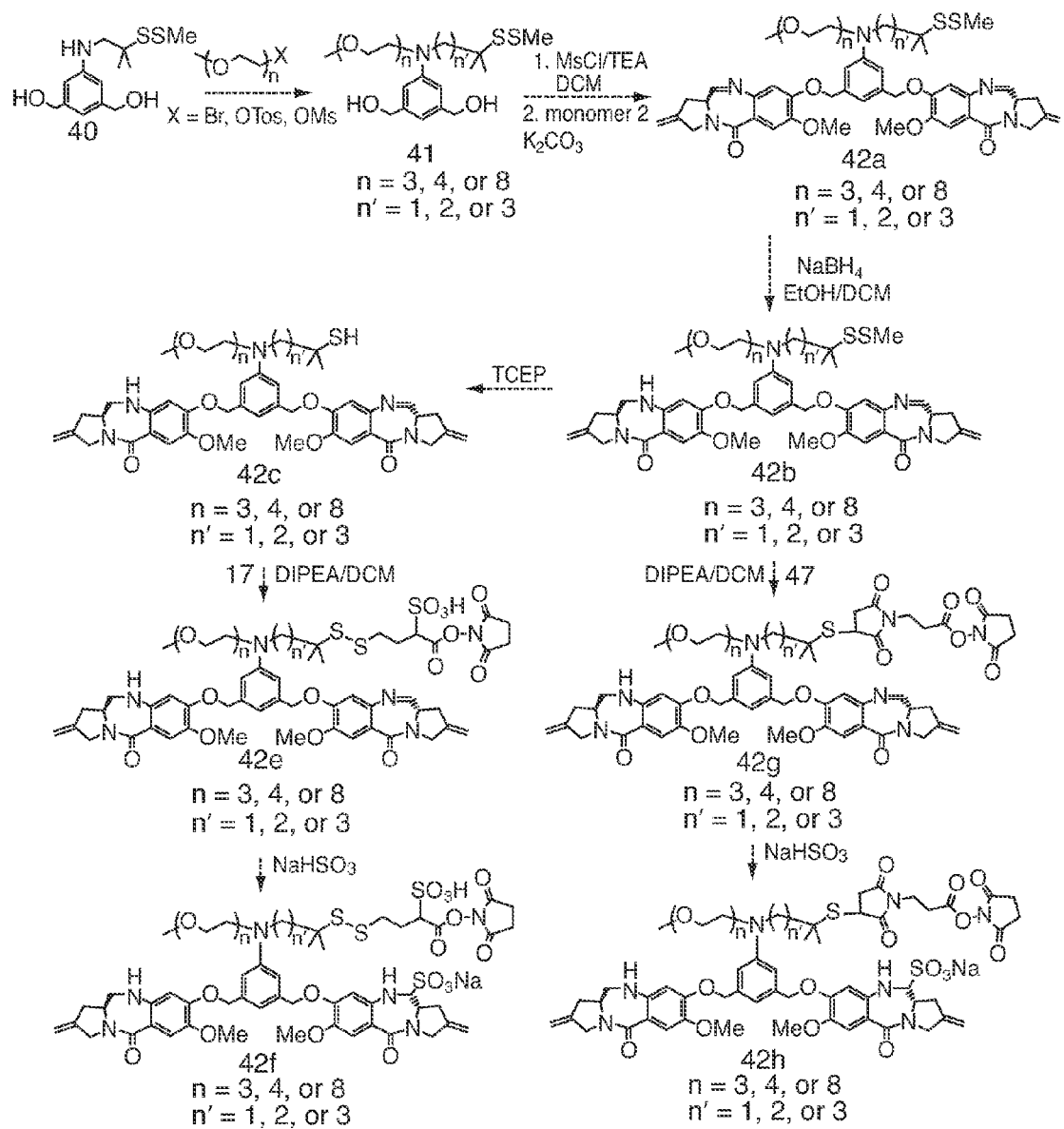
Figure 15:
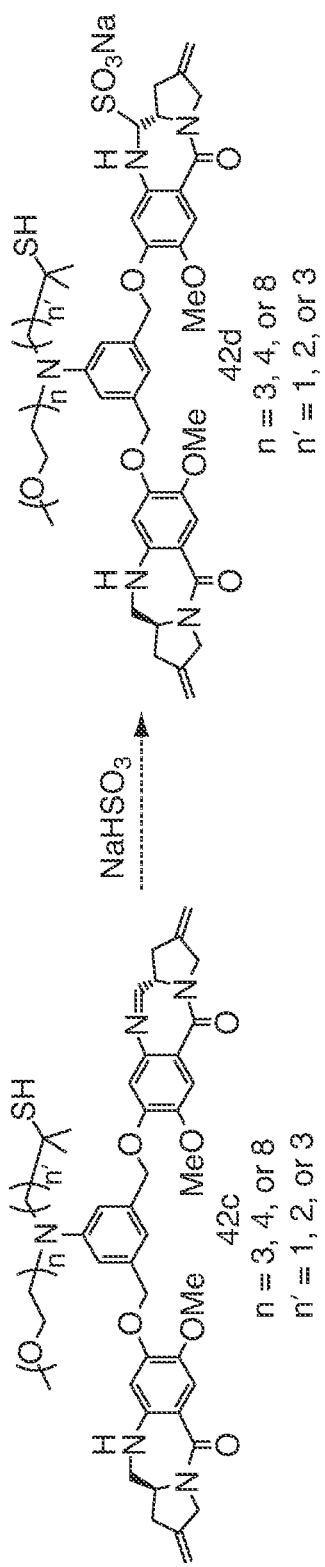
Figure 16:
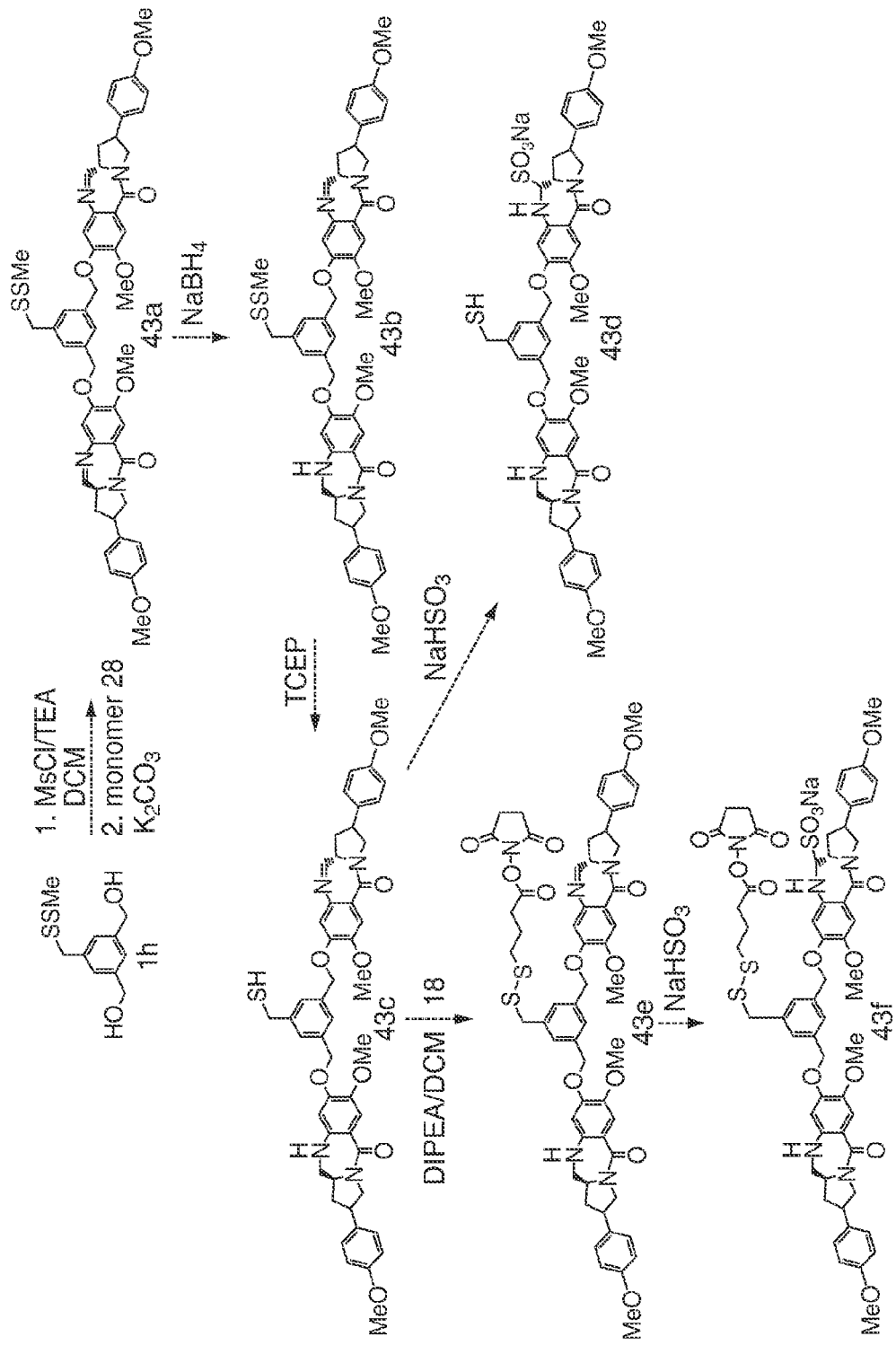
Figures 1, 17:
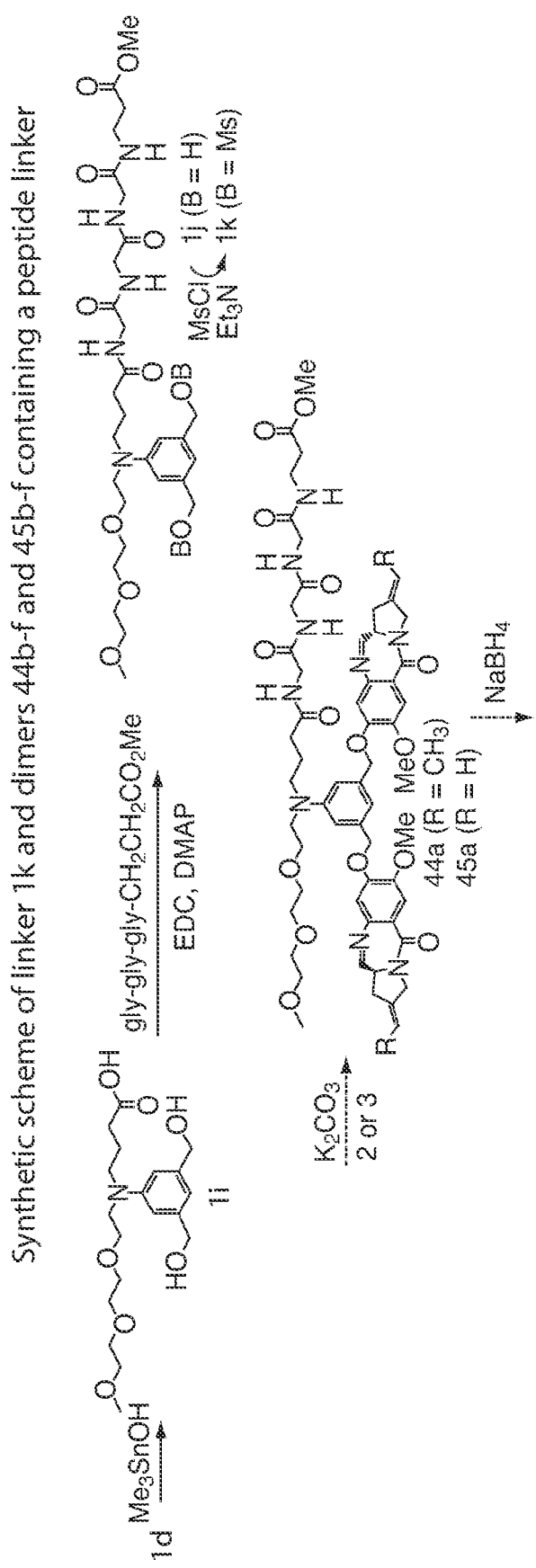
Figures 2, 17:
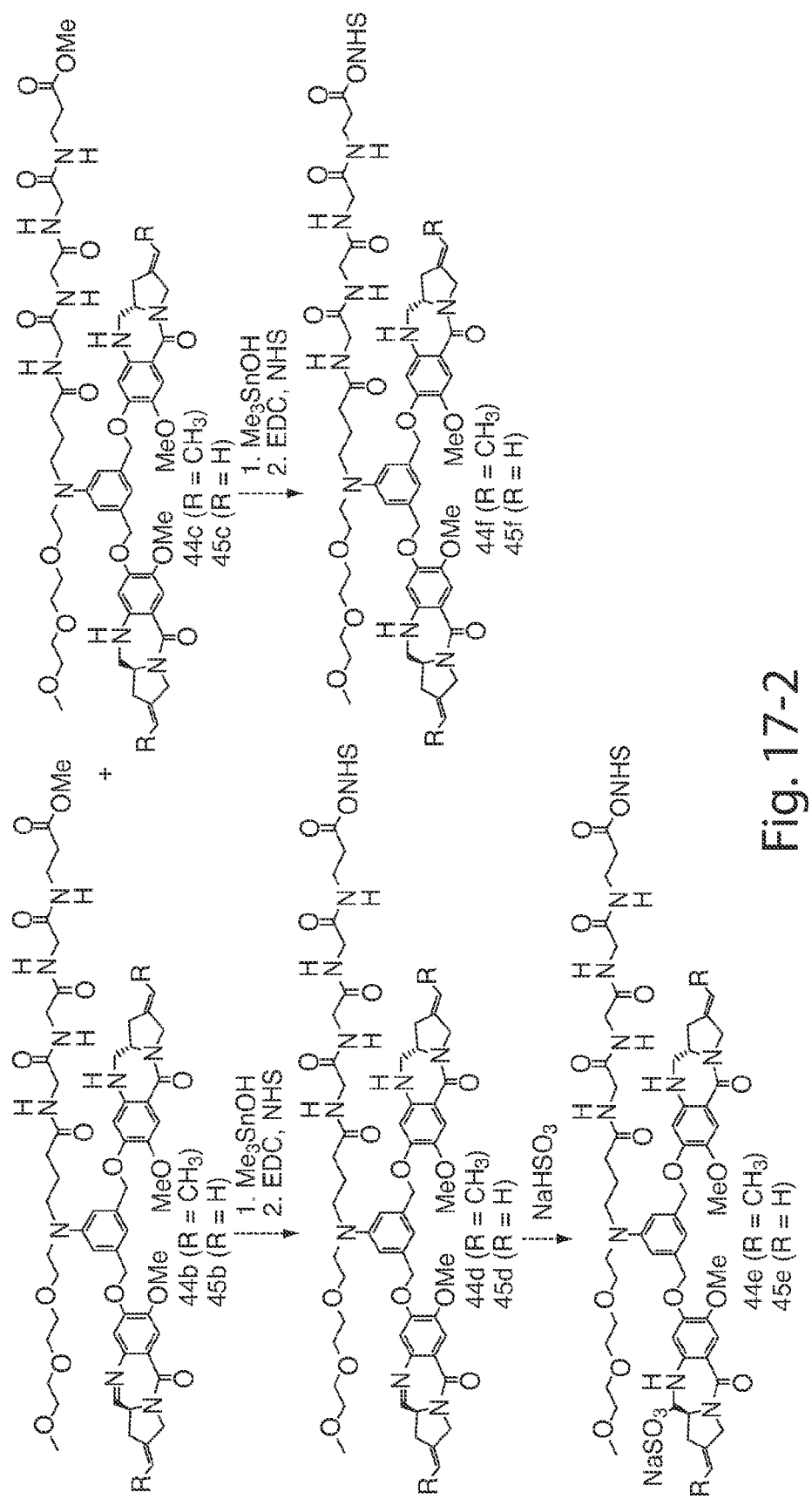
Figure 18:
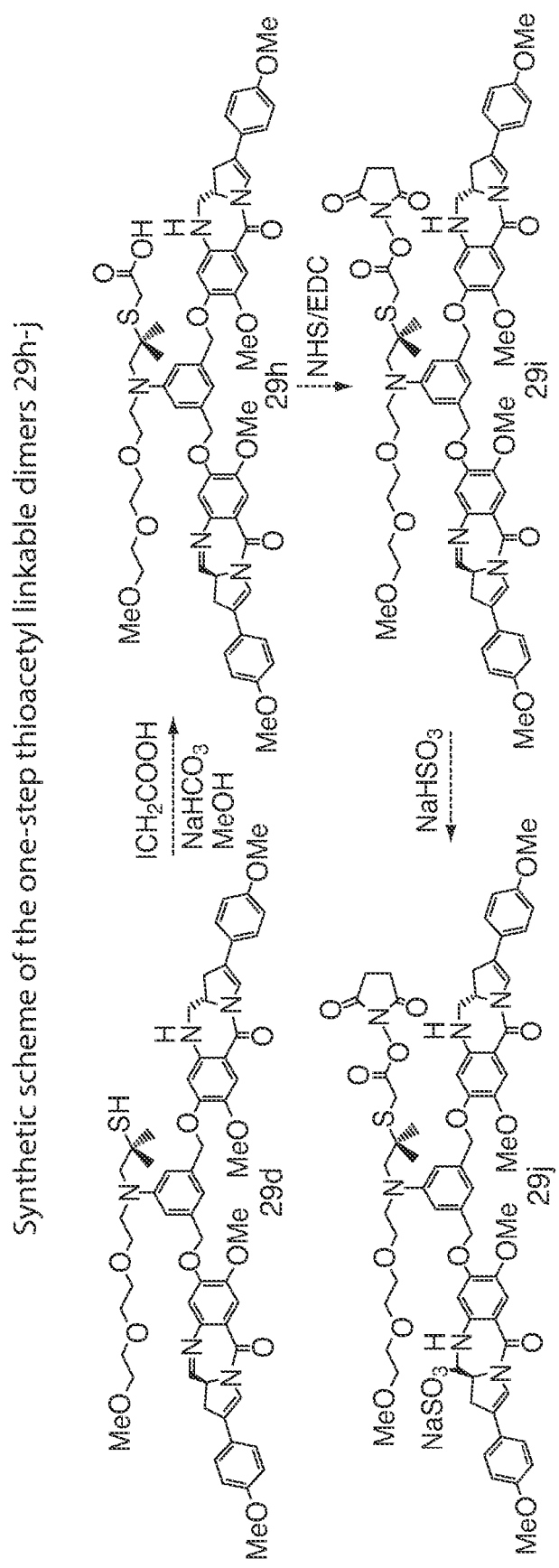
Figure 19:
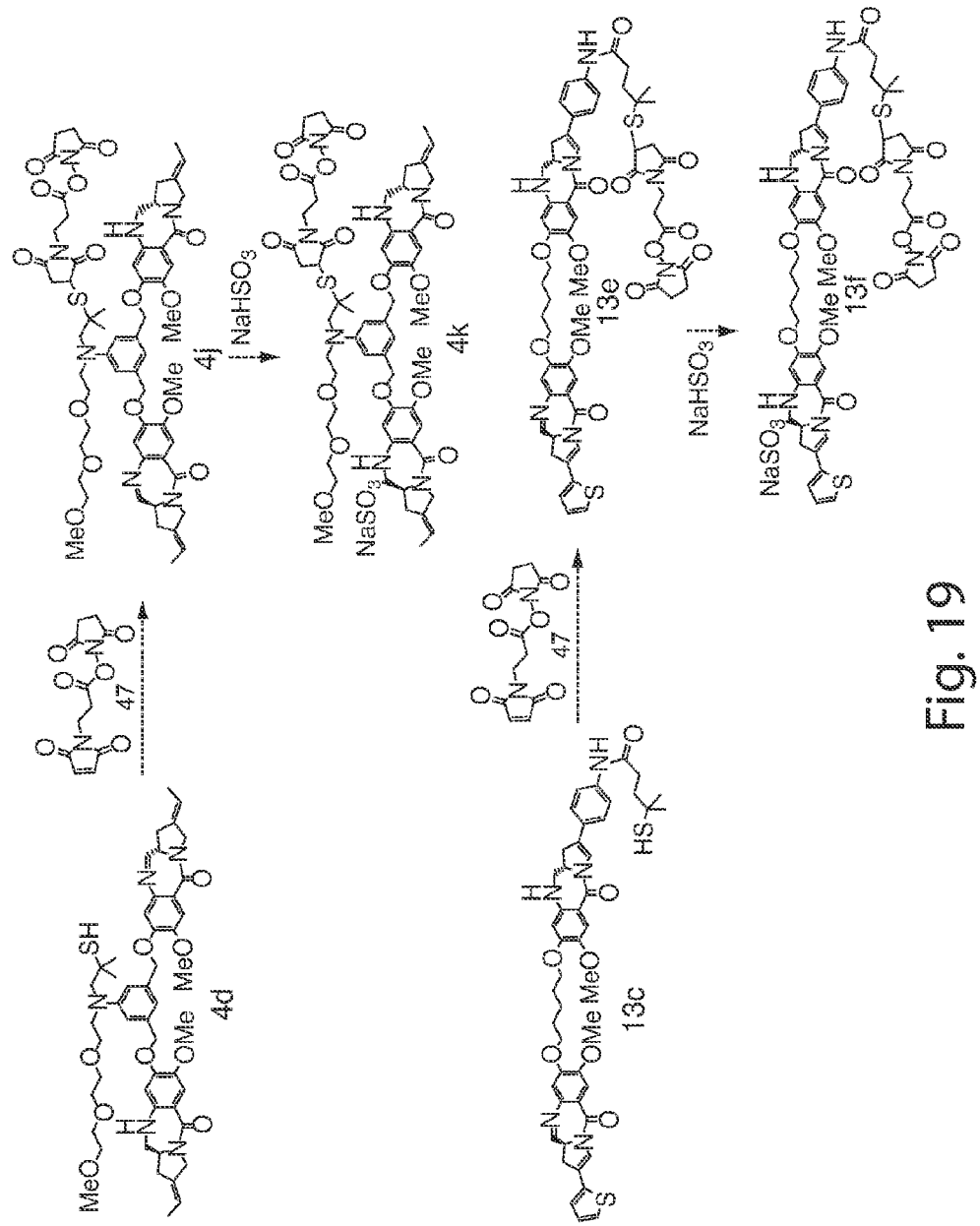
Figure 20:
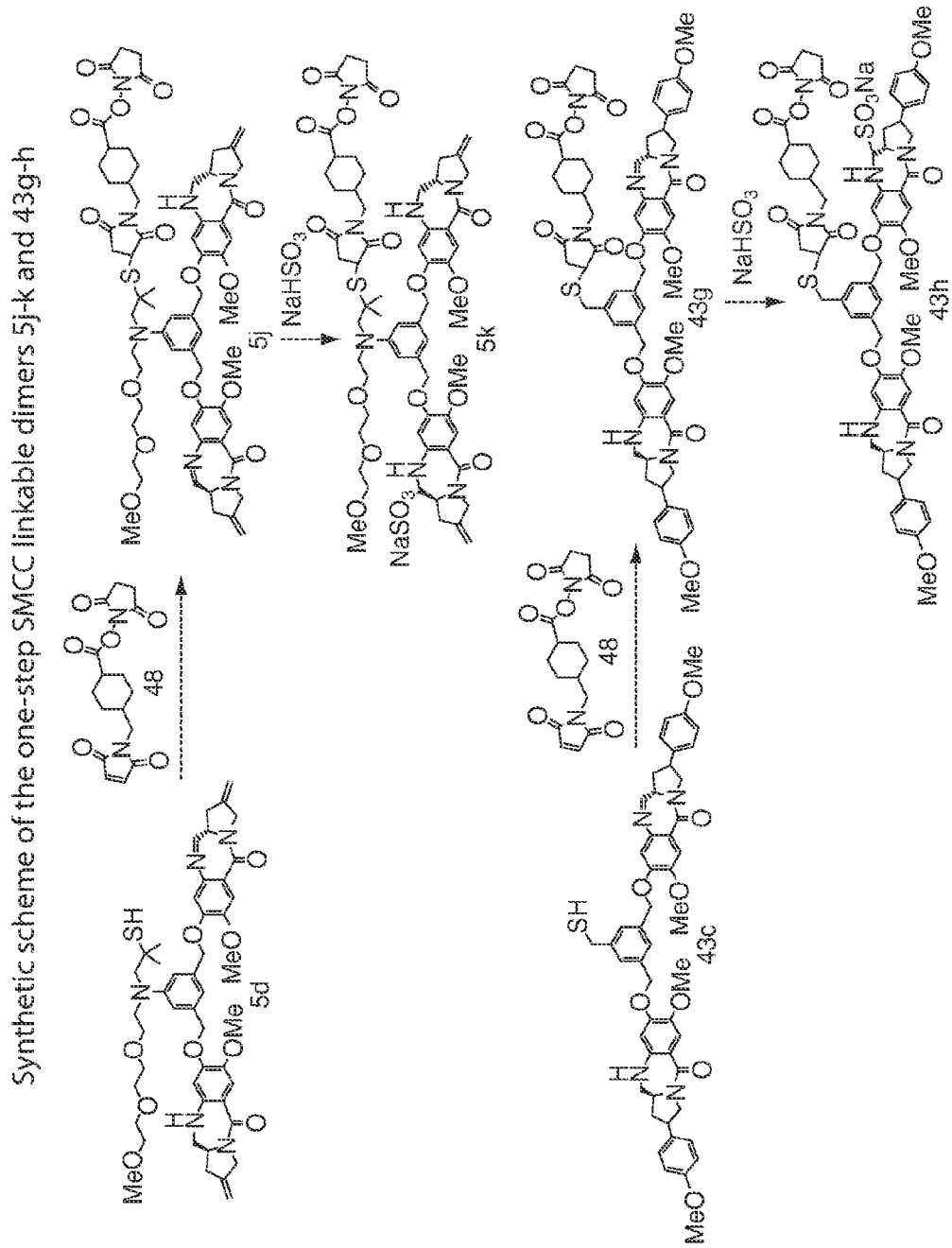
Figure 21:
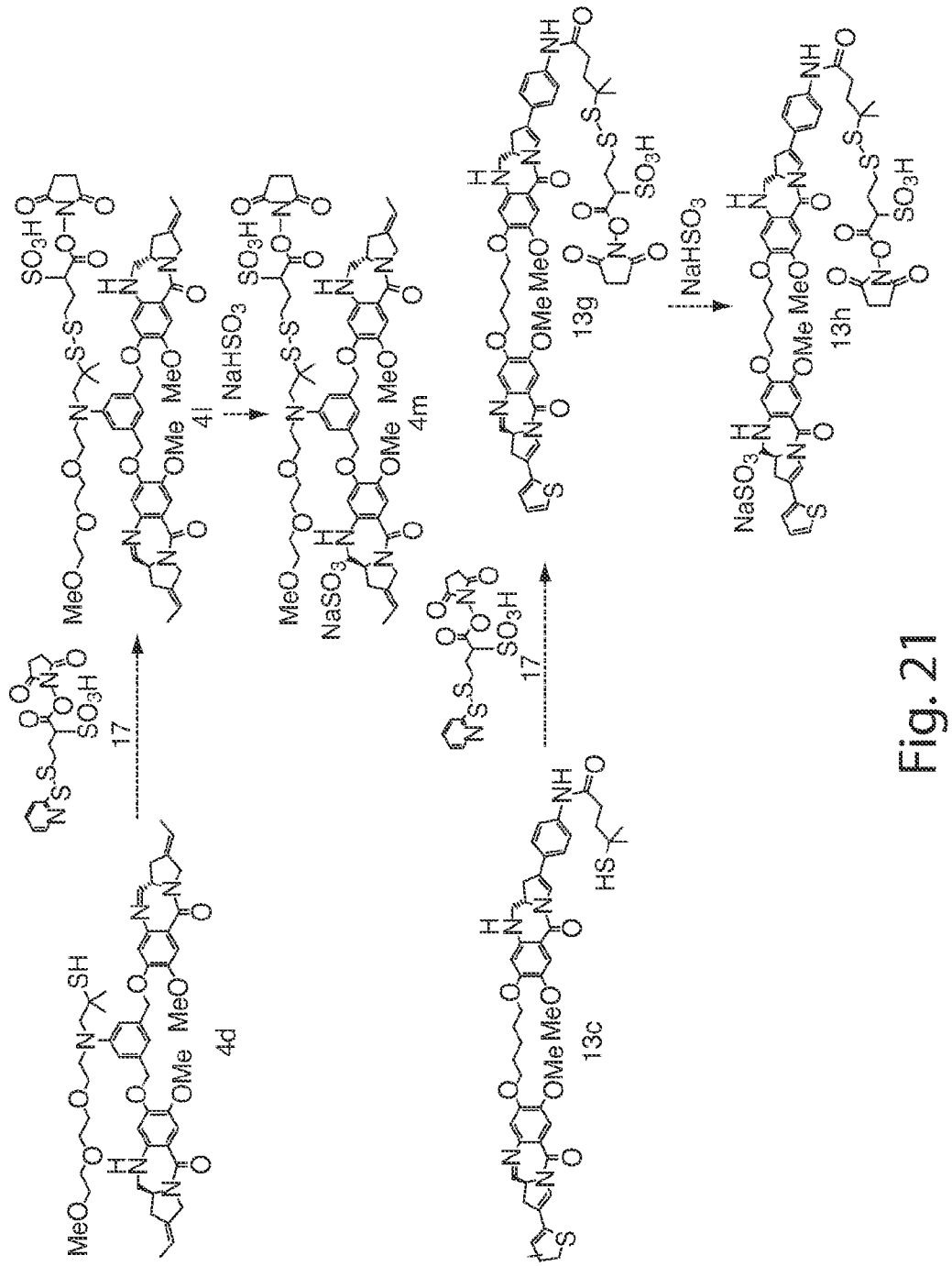
Figure 22:
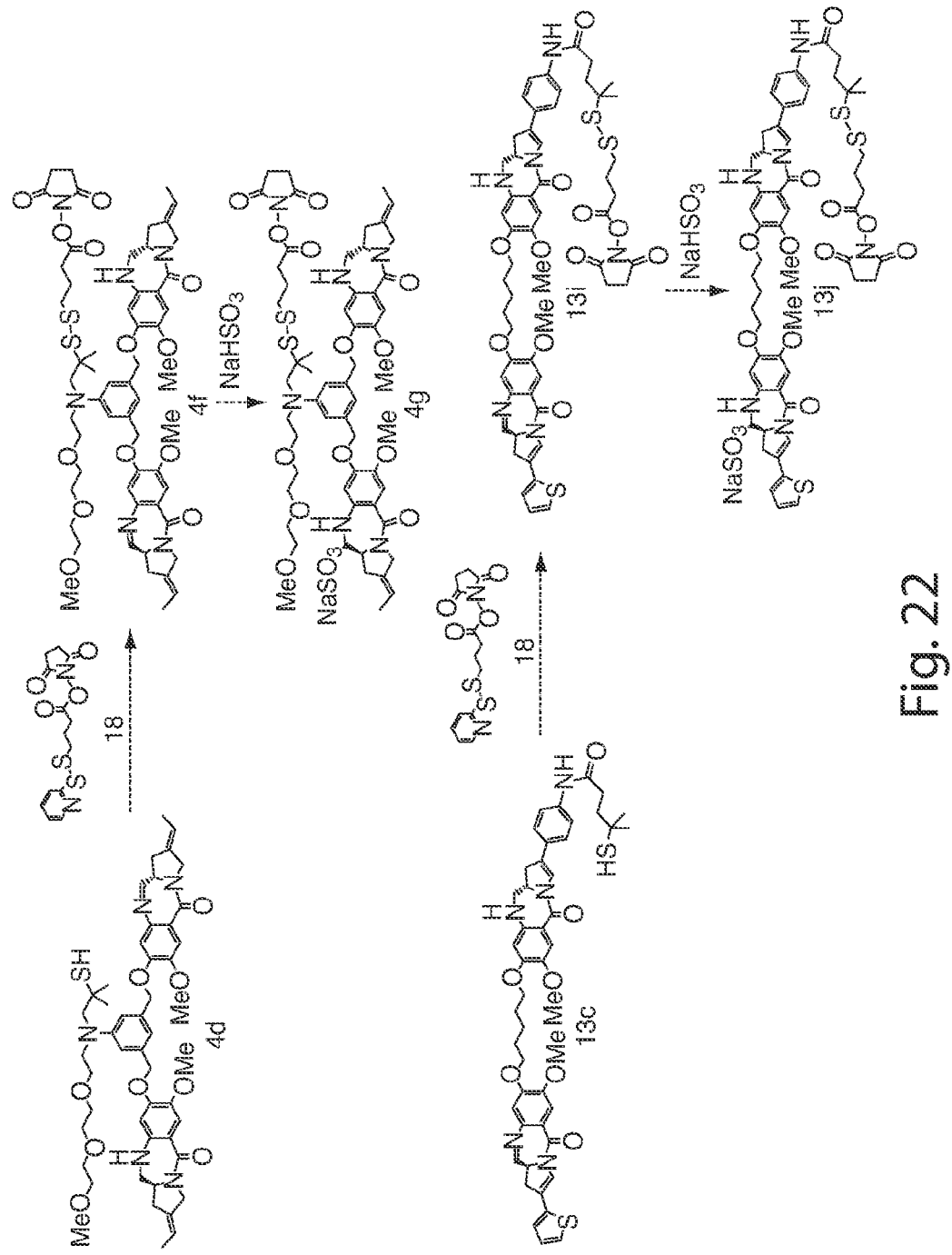
Figure 23:
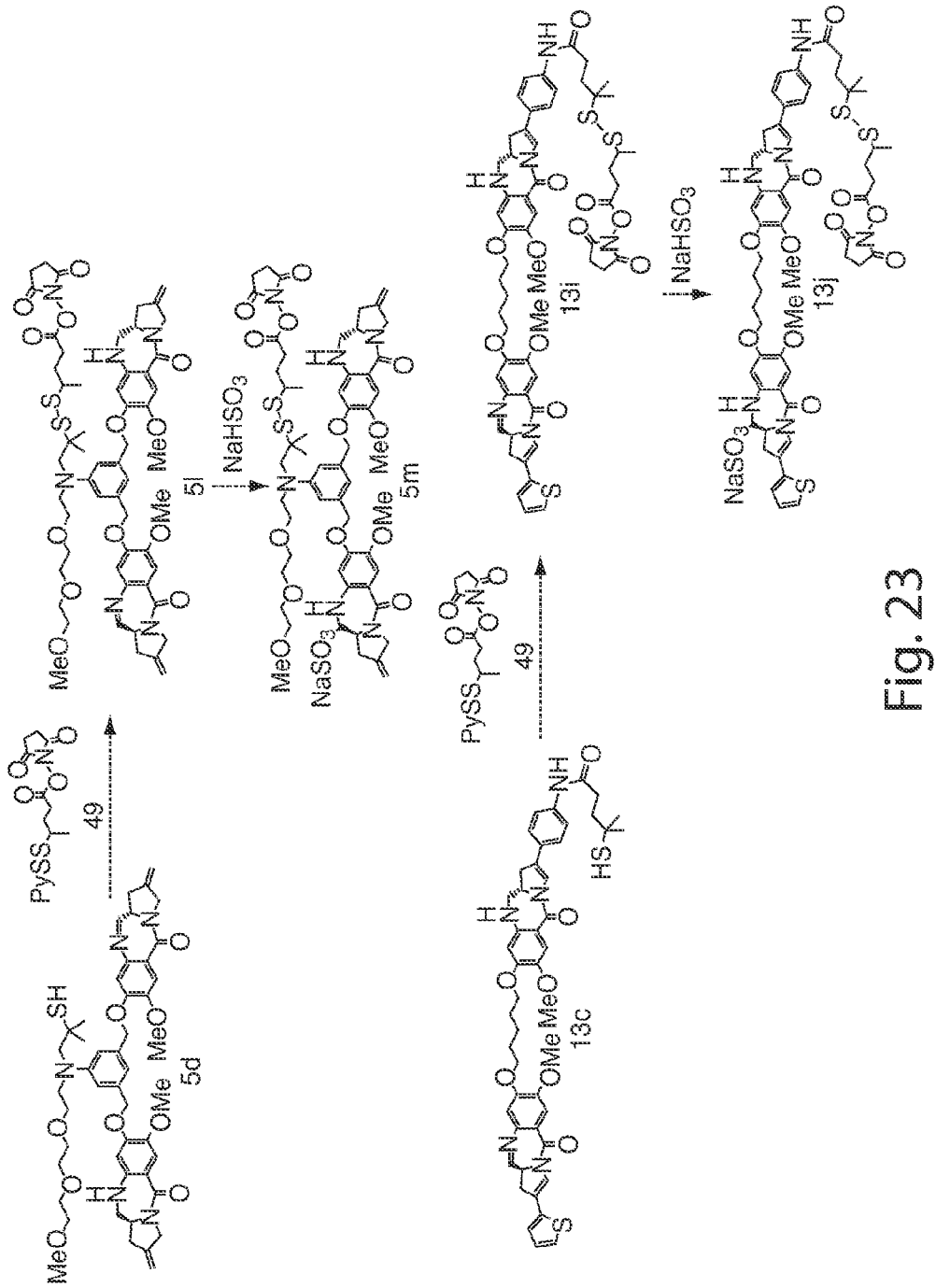
Figure 24:
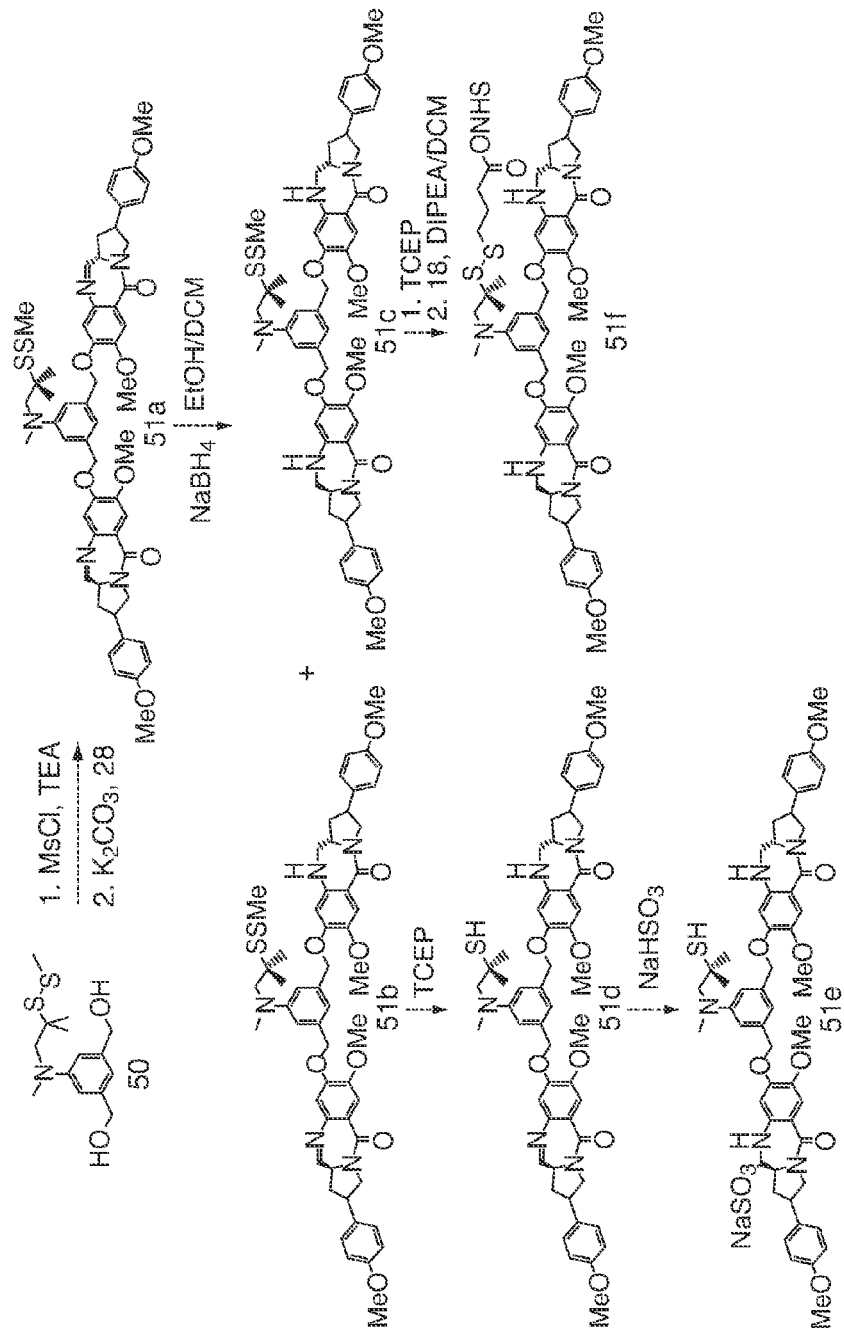
Figure 25:
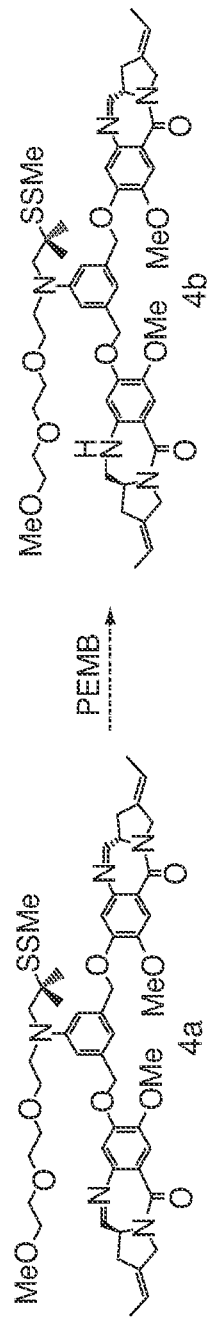
Figure 26:
Figure 32:
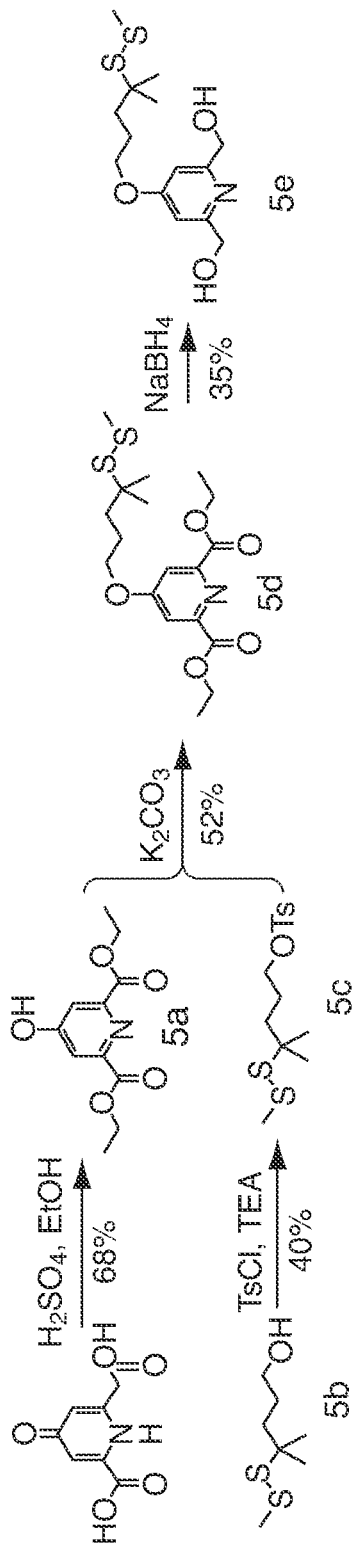
FIG. 32 shows the synthesis scheme for Linker 5e.
Figure 33:
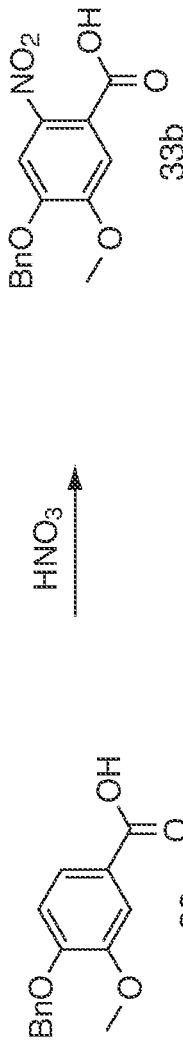
FIG. 33 shows an alternate scheme for synthesizing 4-(benzyloxy)-5-methoxy-2-nitrobenzoic acid used in the preparation of IBD monomer.
Figure 34:
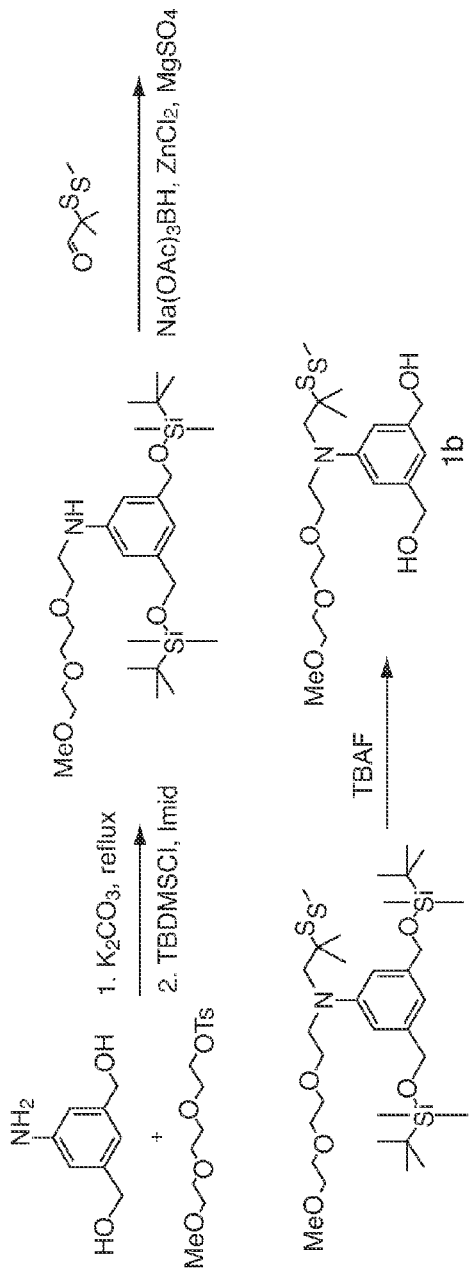
FIG. 34 is an alternate synthesis scheme for (5-((2-(2-(2-methoxyethoxy)ethoxy)ethyl)(2-methyl-2-(methyldisulfanyl)propyl)amino)-1,3-phenylene)dimethanol (1b).
Figure 35:
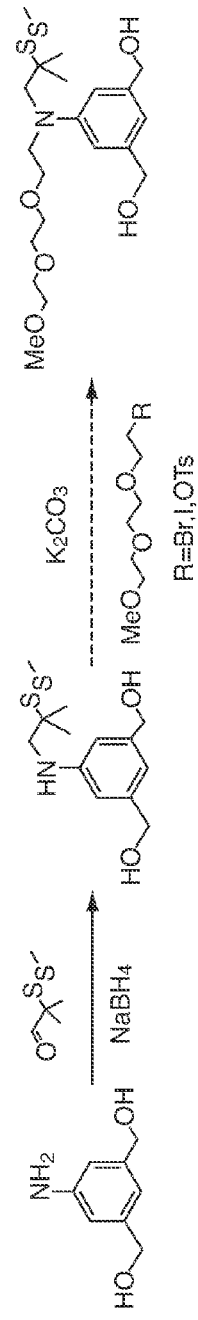
FIG. 35 is an alternate synthesis scheme for (5-((2-(2-(2-methoxyethoxy)ethoxy)ethyl)(2-methyl-2-(methyldisulfanyl)propyl)amino)-1,3-phenylene)dimethanol (1b).

Representative processes for preparing the cytotoxic dimer compounds and precursors thereof, as well as conjugates with cell-binding agents of the present invention, are shown in FIGS. 1-36. In general, the dimers were prepared by reacting a monomer with linker compounds which possess two leaving groups such as halogen, triflate, mesylate, or tosylate such as that described for the synthesis of dimer compounds in FIG. 1. Synthesis of representative dimers which bear a thiol or disulfide moiety to enable linkage to cell binding agents via reducible or non-reducible bonds are shown in, for example, FIGS. 2, 8, 12, 15, etc. In FIG. 1 a linker containing a short polyethylene glycol moiety and an alkyl disulfide was prepared through reductive amination of 1a. Conversion of 1b to its corresponding mesylate and coupling with a PBD (pyrrolobenzodiazepine) monomer unit gave dimer 4a or 5a, which was reduced to the monoimine, converted to the free thiol, and coupled with 18 to give compound 4i/5i (without a bisulfite adduct) or 4g/5g (with a bisulfite adduct) of the present invention. In FIG. 9, a modified form of PBD monomer was prepared and coupled to give a dimer of the present invention in which the reduced imine was converted to a linker. FIG. 10 describes a dimer possessing a short polyethylene glycol moiety and an amide disulfide which was reduced to thiol 35f or 36f and converted to a reactive ester. FIG. 32 describes the synthesis of pyridyl disulfide containing linker 5e which can be converted to a mono-imine thiol of the present invention before being converted to a reactive ester. Synthesis of representative dimers which possess linkers that can react with cell binding agents are prepared by converting the methyl esters to the corresponding reactive esters of a leaving group such as, but not limited to, N-hydroxysuccinimide esters, N-hydroxyphthalimide esters, N-hydroxy sulfo-succinimide esters, para-nitrophenyl esters, pentafluorophenyl esters are shown in FIGS. 12 and 17.

Representative processes for preparing the cytotoxic dimer compounds of the present invention suitable for one-step conjugation with a cell binding agent are shown in FIGS. 1 and 18-23. In all of these examples a dimer containing a thiol moiety is reacted with a bifunctional crosslinking reagent possessing a reactive group such as, but not limited to, a thiopyridyl, a maleimide, iodide, bromide, or tosylate on one side and a reactive substituent suitable for reaction with a cell binding agent such as, but not limited to, N-hydroxysuccinimide esters, N-hydroxyphtalimide esters, N-hydroxy sulfo-succinimide esters, paranitrophenyl esters, pentafluorophenyl esters.

Figure 27:
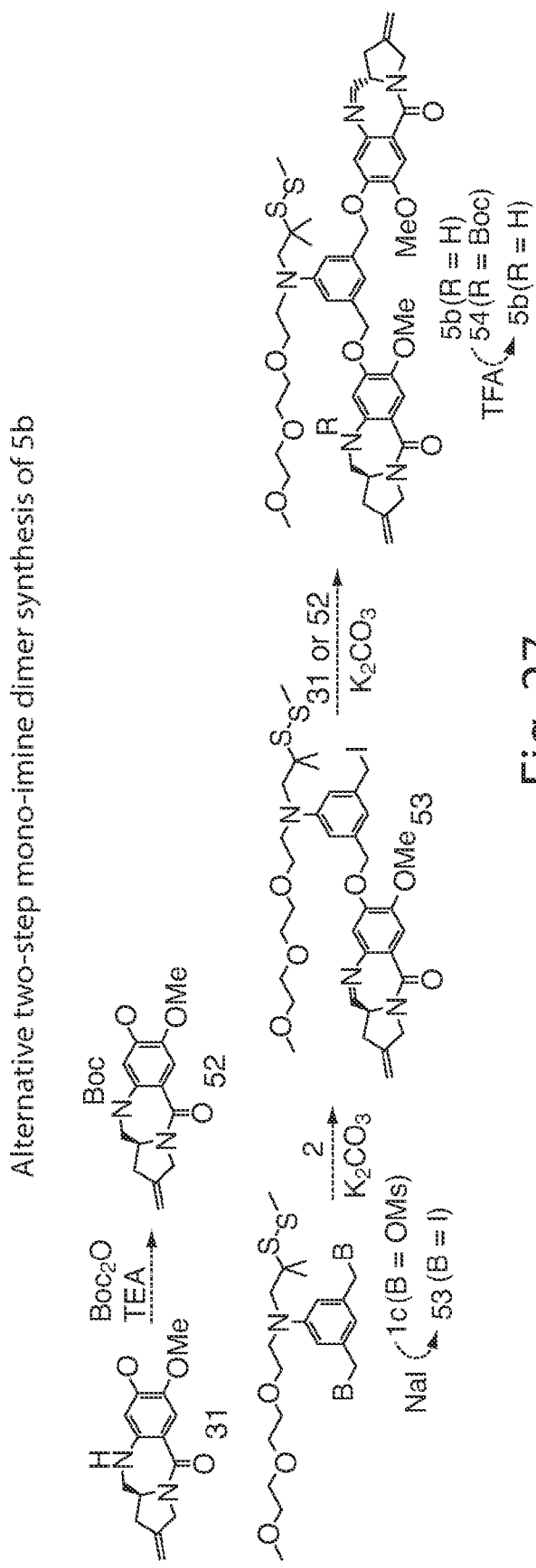
Figure 28:
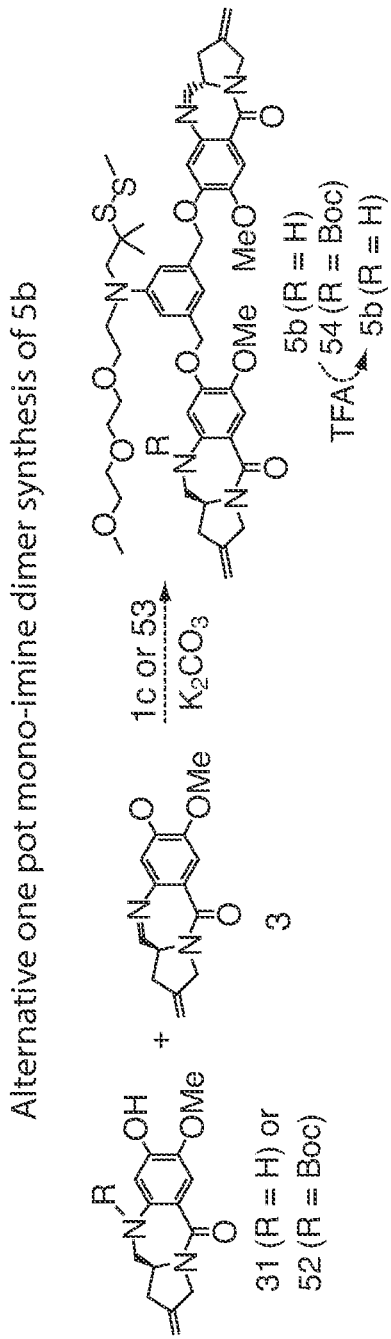
Figure 29A:
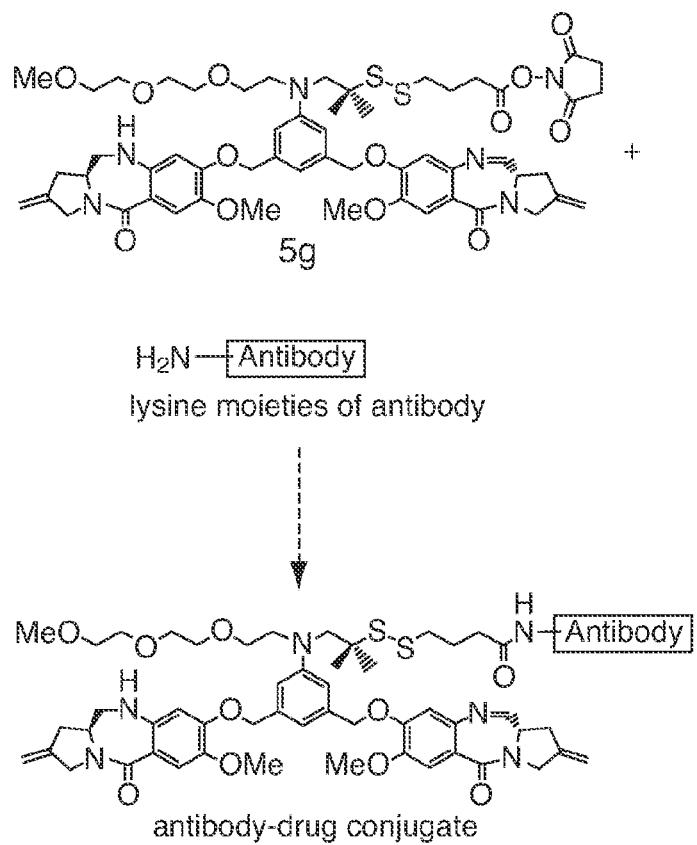
Figure 29B:
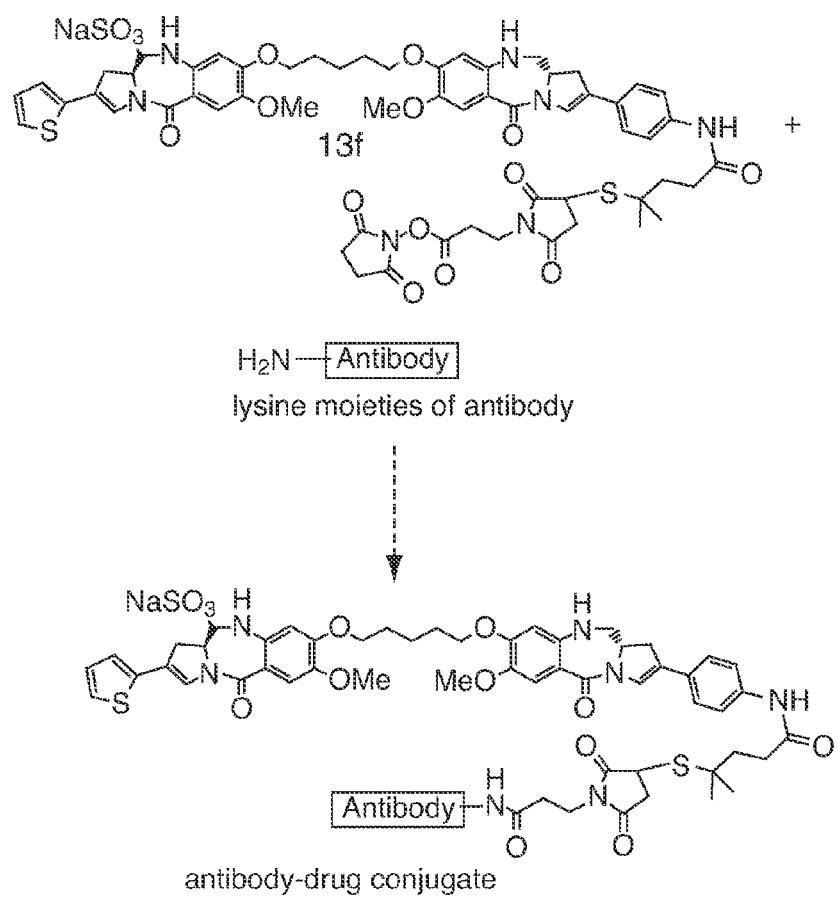
Figure 29C:
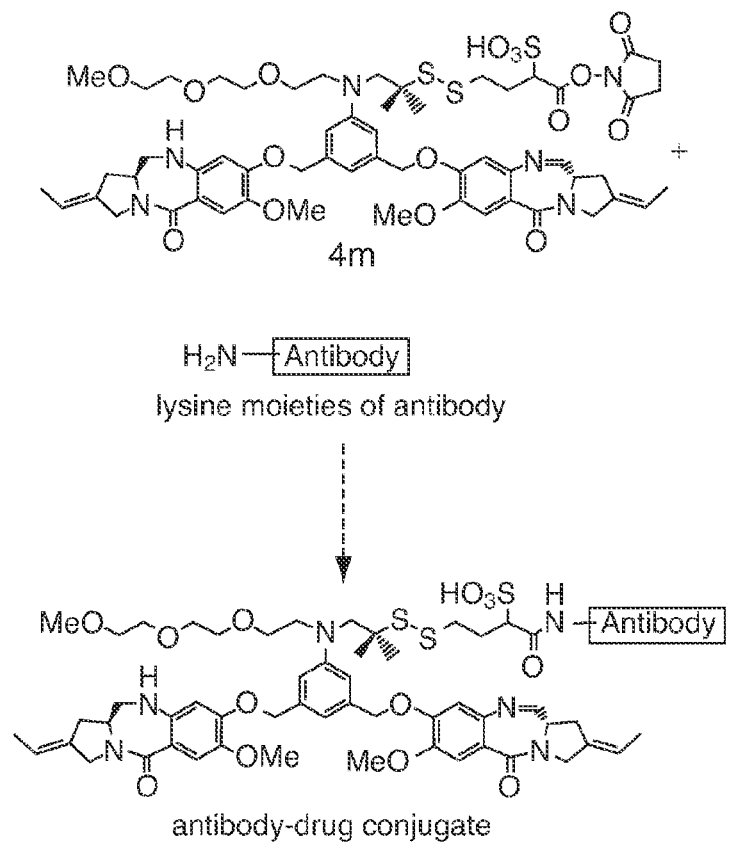
Figure 29D:
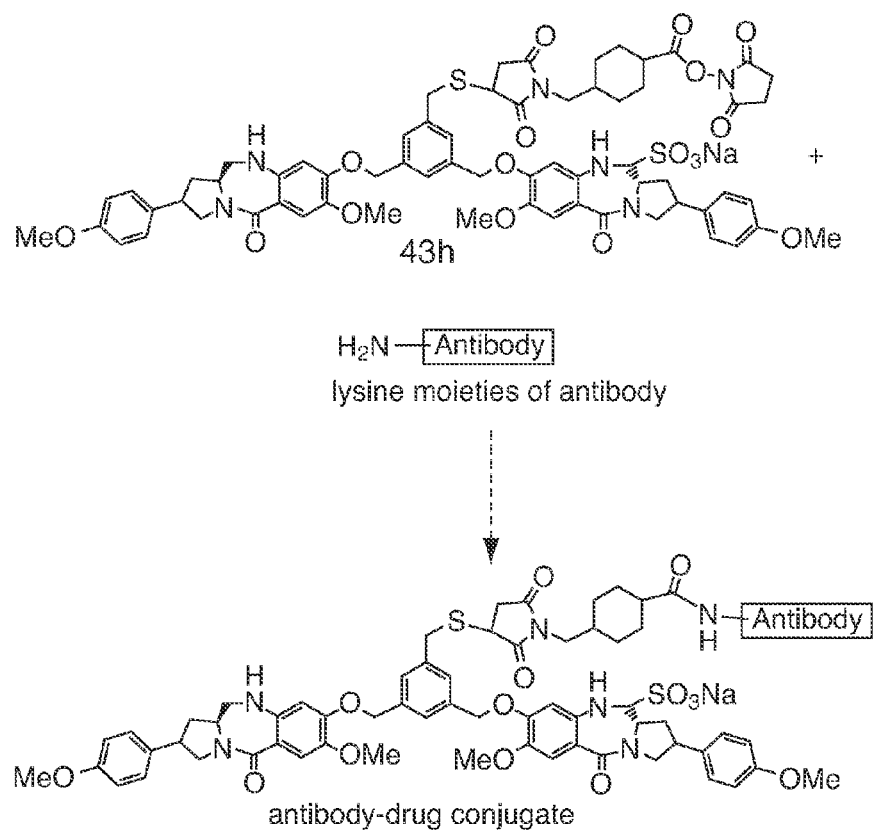
Figure 29E:
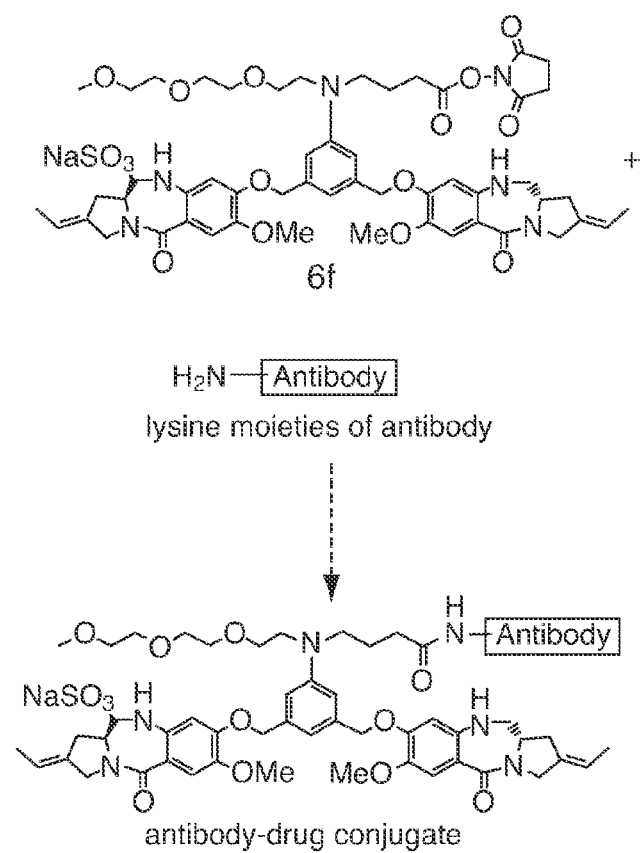
Figure 29F:
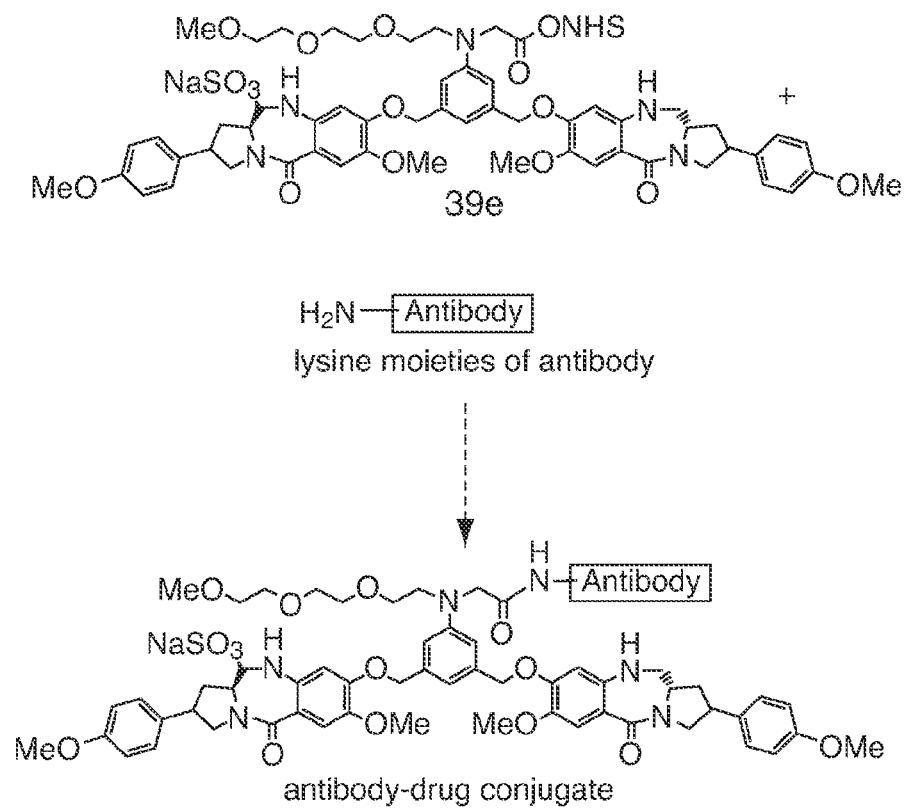

Alternative synthetic processes for preparing representative cytotoxic dimer compounds of the present invention are shown in FIGS. 27-28. In these figures, the synthesis of the mono reduced dimer (i.e., having one imine group) is accomplished by a two step coupling method, in which a reduced form of monomer is either initially coupled to the linker followed by coupling with the PBD monomer or the dimer is prepared using a mixture of both reduced monomer and the PBD monomer in the coupling with the reactive linker. While the di-reduced dimer is potentially a byproduct of the second synthetic pathway previously described (such as FIG. 28), a more direct route is possible in which two reduced monomers are coupled to the linker directly.

Cell-Binding Agents

The effectiveness of the conjugates of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins (such as folate etc., which may bind to a cell surface receptor thereof, e.g., a folate receptor), nutrient-transport molecules (such as transferrin), or any other cell-binding molecule or substance.

In certain embodiments, the cell-binding agents are proteins or polypeptides, or compounds comprising proteins or polypeptides. Preferably, the proteins or polypeptides comprise one or more Lys residues with side chain —$NH_2$ groups. Alternatively or in addition, the proteins or polypeptides comprise one or more Cys residues. The side chain —SH groups of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains).

The Lys side chain —$NH_2$ groups and/or the Cys side chain —SH groups may be covalently linked to the linkers, which are in turn linked to the dimer compounds of the invention, thus conjugating the cell-binding agents to the dimer compounds of the invention. Each protein-based cell-binding agents may contain multiple Lys side chain —$NH_2$ groups and/or the Cys side chain —SH groups available for linking the compounds of the invention through the bifunctional crosslinkers.

More specific examples of cell-binding agents that can be used include:

polyclonal antibodies;

monoclonal antibodies;

fragments of antibodies such as Fab, Fab', and F(ab')$_2$, Fv, minibodies, diabodies, tribodies, tetrabodies (Parham, *J. Immunol.* 131:2895-2902 (1983); Spring et al. *J. Immunol.* 113:470-478 (1974); Nisonoff et al. *Arch. Biochem. Biophys.* 89:230-244 (1960), Kim et al., Mol, Cancer Ther., 7: 2486-2497 (2008), Carter, Nature Revs., 6: 343-357 (2006));

interferons (e.g. α, β, γ);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, *Immunology Today* 5:155-158 (1984));

transferrin (O'Keefe et al. *J. Biol. Chem.* 260:932-937 (1985));

vitamins, such as folate;

Protein scaffolds based on a consensus sequence of fibronectin type III (FN3) repeats (also known as Centyrins; See U.S. Patent Publication 2010/0255056, incorporated herein by reference);

Designer Ankyrin Repeat Proteins (DARPins; U.S. Patent Application Nos. 20040132028; 20090082274; 20110118146; 20110224100, incorporated herein by reference), C. Zahnd et al. 2010, Cancer Res., 70; 1595-1605, incorporated herein by reference); and, Fibronectin domain scaffold proteins (Adnectins: US Patent Application Nos. 20070082365; 20080139791, incorporated herein by reference).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine IgG1 antibody that binds specifically to the CD33 Antigen {J. D. Griffin et al 8 Leukemia Res., 521 (1984)} and can be used if the target cells express CD33 as in the disease of acute myelogenous leukemia (AML). The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like-growth factor-I and -II (IGF-I and IGF-II); des(1-3)-IGF-I (brain IGF-I), insulin-like growth factor binding proteins, melanotransferrin, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, c-kit, 1GF1R, PSGR, NGEP, PSMA, PSCA, LGR5, B7H4, and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In one embodiment, the cell-binding agent is humanized monoclonal antibodies. In another embodiment, the cell-binding agent is huMy9-6, or other related antibodies, which are described in U.S. Pat. Nos. 7,342,110 and 7,557,189 (incorporated herein by reference). In another embodiment, the cell-binding agent is an anti-folate receptor antibody described in U.S. Provisional Application Nos. 61/307,797, 61/346,595, 61/413,172 and U.S. application Ser. No. 13/033,723 (published as US 2012-0009181 A1). The teachings of all these applications are incorporated herein by reference in its entirety.

In certain embodiments, the cell-binding agent may be a monoclonal antibody or antigen-binding portions thereof sharing sequences critical for antigen-binding with an antibody disclosed herein, such as huMy9-6 or its related antibodies described in U.S. Pat. Nos. 7,342,110 and 7,557,189 (incorporated herein by reference). These derivative antibodies may have substantially the same or identical (1) light chain and/or heavy chain CDR3 regions; (2) light chain and/or heavy chain CDR1, CDR2, and CDR3 regions; or (3)

light chain and/or heavy chain regions, compared to an antibody described herein. Sequences within these regions may contain conservative amino acid substitutions, including substitutions within the CDR regions. Preferably, there is no more than 1, 2, 3, 4, or 5 conservative substitutions. In certain embodiments, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the $K_d$ and/or $k_{off}$ values of the derivative antibodies are within 10-fold (either higher or lower), 5-fold (either higher or lower), 3-fold (either higher or lower), or 2-fold (either higher or lower) of an antibody described herein. These derivative antibodies may be fully human antibodies, or humanized antibodies, or chimeric antibodies. The derivative antibodies may be produced according to any art-recognized methods.

In one embodiment, the anti-folate receptor antibody is a humanized antibody or antigen binding fragment thereof that specifically binds a human folate receptor 1, wherein the antibody comprises: (a) a heavy chain CDR1 comprising GYFMN (SEQ ID NO: 1); a heavy chain CDR2 comprising RIHPYDGIDTFYNQXaa$_1$FXaa$_2$Xaa$_3$ (SEQ ID NO: 2); and a heavy chain CDR3 comprising YDGSRAMDY (SEQ ID NO: 3); and (b) a light chain CDR1 comprising KASQSVSFAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 7).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCKASGYTFTGYFMN-WVKQSPGQSLEWIGRIHP YDGDTFYNQKFQG-KATLTVDKSSNTAHMELLSLTSEDFAVYYCTRYDG-SRAM DYWGQGTTVTVSSASTKGPSVFPLAPSSKSTSGG-TAALGCLVKDYFPEPVTVSW NSGALTSGVHTFPAV-LQSSGLYSLSSVVTVPSSSLGTQTYICNVNHKPSNTK-VDK KVEPKSCDKTHTCPPCPAPELLGGPSVFLFPPKP-KDTLMISRTPEVTCVVVDVSH EDPEVKFN-WYVDGVEVHNAKTKPREEQYNSTYRVVSVLTVL-HQDWLNGKEY KCKVSNKALPAPIEKTISKAK-GQPREPQVYTLPPSRDELTKNQVSLTCLVKGFYP SDIAVEWESNGQPENNYKTTPPVLDSDGSFFLYSKLT-VDKSRWQQGNVFSCSV MHEALHNHYTQK-SLSLSPGK (SEQ ID NO: 8).

In another embodiment, the anti-folate antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1 comprising the light chain having the amino acid sequence of DIVLTQSPLSLAVSLGQPAIISCKASQSVSFAGTSLMH-WYHQKPGQQPRLLIYRA SNLEAGVPDRFSGSGSK-TDFTLNISPVEAEDAATYYCQQSREYPYTFGGGT-KLEI KRTVAAPSVFIFPPSDEQLKSGTASVVCLLNNFY-PREAKVQWKVDNALQSGNSQ ESVTEQDSKD-STYSLSSTLTLSKADYEKHKVY-ACEVTHQGLSSPVTKSFNRGEC (SEQ ID NO: 9); or DIVLTQSPLSLAVSLGQPAIISCKASQSVSFAGTSLMH-WYHQKPGQQPRLLIYRA SNLEAGVPDRFSGSGSK-TDFTLTISPVEAEDAATYYCQQSREYPYTFGGGT-KLEI KRTVAAPSVFIFPPSDEQLKSGTASVVCLLNNFY-PREAKVQWKVDNALQSGNSQ ESVTEQDSKD-STYSLSSTLTLSKADYEKHKVY-ACEVTHQGLSSPVTKSFNRGEC (SEQ ID NO: 10).

In another embodiment the anti-folate receptor antibody is a humanized antibody or antigen binding fragment thereof that specifically binds the human folate receptor 1 comprising the heavy chain having the amino acid sequence of SEQ ID NO: 8, and the light chain having the amino acid sequence of SEQ ID NO: 9 or SEQ ID NO: 10. Preferably, the antibody comprises the heavy chain having the amino acid sequence of SEQ ID NO: 8 and the light chain having the amino acid sequence of SEQ ID NO: 10 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof comprising a heavy chain variable domain at least about 90%, 95%, 99% or 100% identical to QVQLVQSGAEV-VKPGASVKISCKASGYTFTGYFMN-WVKQSPGQSLEWIGRIHP YDGDTFYNQKFQG-KATLTVDKSSNTAHMELLSLTSEDFAVYYCTRYDGS RAM DYWGQGTTVTVSS (SEQ ID NO: 11), and a light chain variable domain at least about 90%, 95%, 99% or 100% identical to DIVLTQSPLSLAVSLGQPAIISCK-ASQSVSFAGTSLMHWYHQKPGQQPRLLIYRA SNLEAGVPDRFSGSGSKTDFTLNISPVEAEDAATYY-CQQSREYPYTFGGGTKLEI KR (SEQ ID NO: 12); or DIVLTQSPLSLAVSLGQPAIISCKASQSVSFAGTSLMH-WYHQKPGQQPRLLIYR ASNLEAGVPDRFSGSGSK-TDFTLTISPVEAEDAATYYCQQSREYPYTFGGGTKLE IKR (SEQ ID NO: 13).

A cell-binding agent, such as an antibody, can be modified with a heterobifunctional crosslinker bearing an amine-reactive group, such as N-hydroxysuccinimide group (NHS group), a thiol-reactive maleimido, vinylpyridine, vinyl sulfone, vinyl sulfonamide or a haloacetyl-based group, or a thiol group.

Thiol residues in antibody can be introduced by a number of methods known in the art, including: a) modification of antibody with thiol-generating reagents such as 2-iminothiolane or homocysteine thiolactone, or b) via reaction with a disulfide-containing heterobifunctional crosslinking agent such as SPP, SPDP, SPDB, sulfo-SPDB followed by reduction of the disulfide bond with DTT or TCEP to generate a free thiol, c) mutagenesis to incorporate non-native cysteine residues, such as cysteine-engineered antibodies (US2007/0092940 A1, US 2010/0003766 A1, U.S. Pat. No. 7,723,485 B2), or d) reduction of native disulfide bonds (del Rosario, R. B. et al., Cancer Res. Suppl. 1990, 50, 804s-808s).

A thiol-reactive group, such as maleimido, vinylpyridine, vinyl sulfone, vinyl sulfonamide or a haloacetyl-based group in antibody can be introduced by modifying an antibody with a heterobifunctional crosslinking agent bearing a thiol-reactive group (including but not limited to SPDB, sulfo- SMCC, SMCC, LC-SMCC, KMUA, BMPS, GMBS, sulfo-GMBS, EMCS, sulfo-EMCS, AMAS, SVSB, SPP, NHS-(PEG)n-mal, where n=1 to 24, preferably 2, 4, 8, 12, and 24). Crosslinking agents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Thiol reactive compounds which contain a vinylpyridine are described (Friedman M. et. Al. *Int. J. Peptide Protein Res.* 1974, 6, 183-185; Mak A. et. Al. Anal. Biochem. 1978, 84, 432-440). Thiol reactive compounds which contain a vinyl sulfone moiety have been described (Masri M. S. J. Protein Chem. 1988, 7, 49-54; Morpurgo, M. et. Al. Bioconjugate Chem. 1996, 7, 363-368) Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

The modified antibody can be purified by any suitable methods known in the art, for example, gel filtration, TFF or ion-exchange chromatography or affinity chromatography.

All references cited herein and in the examples that follow are expressly incorporated by reference in their entireties.

Cell-Binding Agent-Drug Conjugates

The present invention provides improved methods to produce cell-binding agent-drug conjugates, comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers.

The present invention also provides cell-binding agent-drug conjugates so made.

Figure 36:
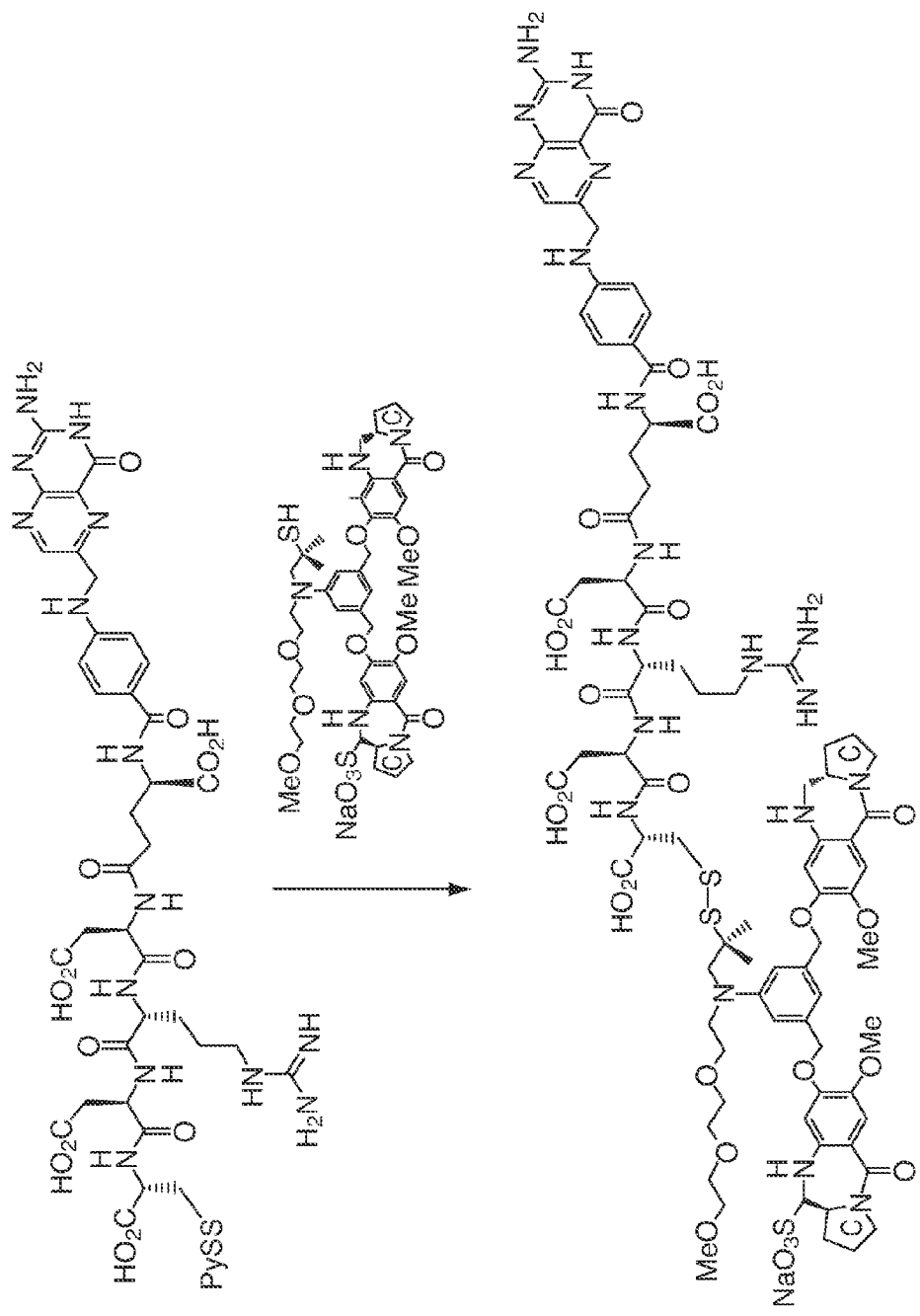
FIG. 36 shows a representative synthesis scheme for a Sulfonated folate/cytotoxic compound conjugate.

Representative conjugates of the invention are antibody/cytotoxic compound, antibody fragment/cytotoxic compound, epidermal growth factor (EGF)/cytotoxic compound, melanocyte stimulating hormone (MSH)/cytotoxic compound, thyroid stimulating hormone (TSH)/cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound. A representative folate/cytotoxic compound conjugate (with the "C" ring generically representing the common structures of formulas (V)-(VII)) is depicted below, with the optional —$SO_3^-N^+$ adduct on the imine bond of one of the two drug monomers. A representative synthesis scheme for this conjugate is shown in FIG. 36.

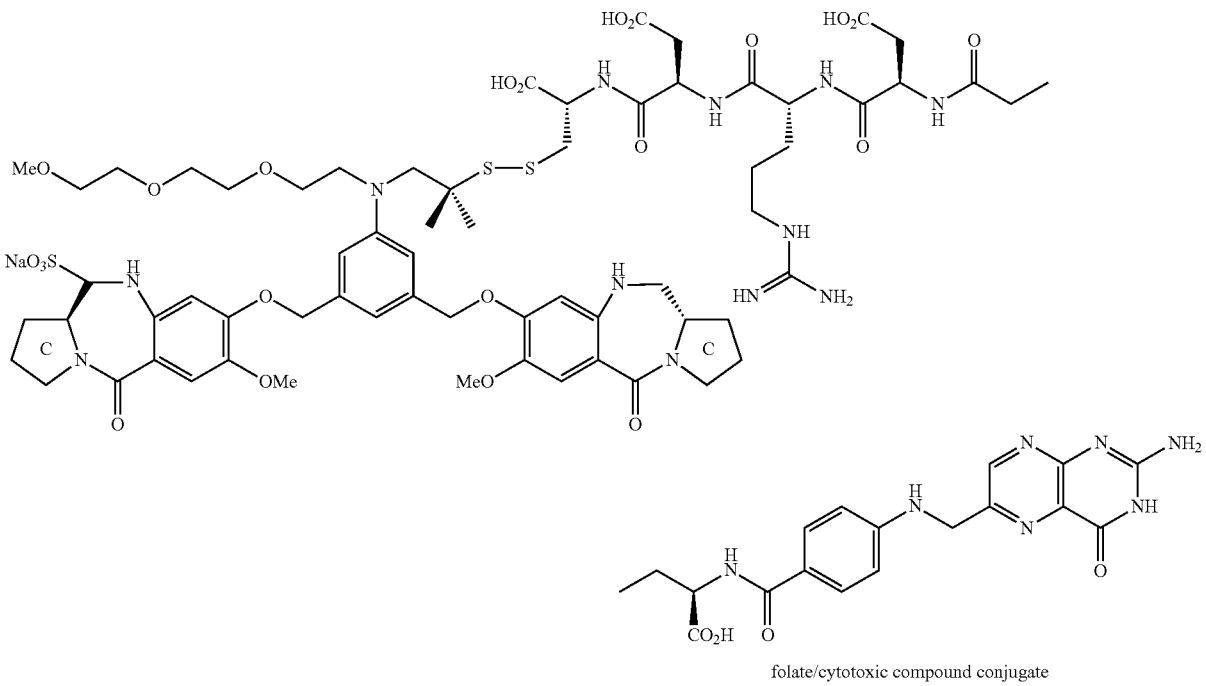

folate/cytotoxic compound conjugate

In a preferred embodiment, the present invention provides conjugates comprising a pyrrolobenzodiazepine dimer compound (e.g., compounds of formulas (V)-(VII), etc.) and the cell-binding agent linked through a covalent bond. The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

In a preferred aspect, representative cytotoxic conjugates of the invention are antibody/pyrrolobenzodiazepine dimer compound, antibody fragment/pyrrolobenzodiazepine dimer compound, epidermal growth factor (EGF)/pyrrolobenzodiazepine dimer compound, melanocyte stimulating hormone (MSH)/pyrrolobenzodiazepine dimer compound, thyroid stimulating hormone (TSH)/pyrrolobenzodiazepine dimer compound, somatostatin/pyrrolobenzodiazepine dimer compound, folate/pyrrolobenzodiazepine dimer compound, estrogen/pyrrolobenzodiazepine dimer compound, estrogen analogue/pyrrolobenzodiazepine dimer compound, prostate specific membrane antigen (PSMA) inhibitor/pyrrolobenzodiazepine dimer compound, matriptase inhibitor/pyrrolobenzodiazepine dimer compound, designed ankyrin repeat proteins (DARPins)/pyrrolobenzodiazepine dimer compound, androgen/pyrrolobenzodiazepine dimer compound, and androgen analogue/pyrrolobenzodiazepine dimer compound.

The invention also provide methods of producing such conjugates according to the methods of the invention described here.

Thus in the twelfth specific embodiment, the invention provides a conjugate comprising: a cytotoxic compound and a cell binding agent (CBA), wherein the cytotoxic compound comprises a linking group which covalently links the cytotoxic compound to the CBA, and wherein the cytotoxic compound is represented by any one of the following formulas:

and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof; wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

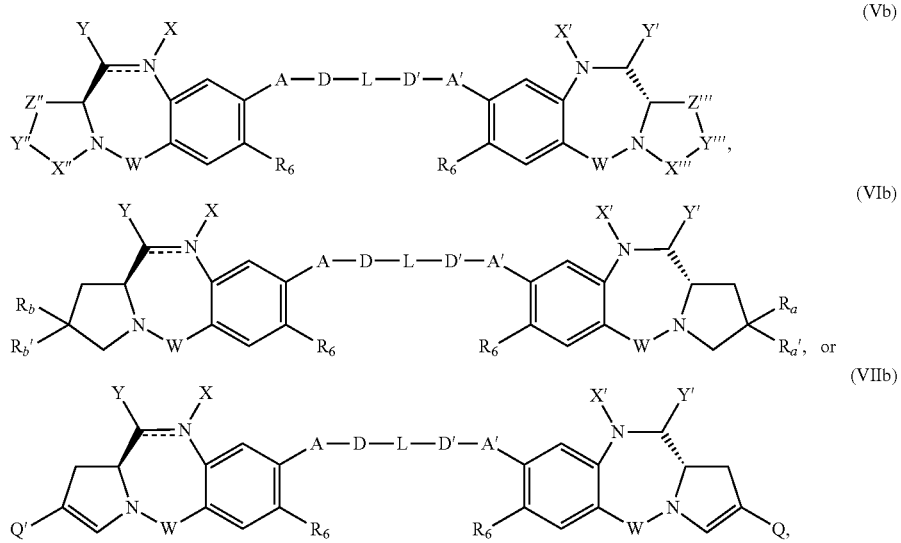

or a pharmaceutically acceptable salt thereof, wherein:

the double line ═══ between N and C represents a single bond or a double bond, provided that when it is a double bond X is absent and Y is —H, or a linear or branched alkyl having 1 to 4 carbon atoms, and when it is a single bond, X is —H, the linking group, or an amine protecting moiety;

Y is —H or a leaving group selected from —OR, —OCOR', —OCOOR', —OCONR'R'', —NR'R'', —NR'COR'', —NR'NR'R'', an optionally substituted 5- or 6-membered nitrogen-containing heterocycle (e.g., piperidine, tetrahydropyrrole, pyrazole, morpholine), a guanidinum represented by —NR'(C═NH)NR'R'', an amino acid, or a peptide represented by —NRCOP', wherein P' is an amino acid or a polypeptide containing between 2 to 20 amino acid units, —SR, —SOR', —SO_2M, —SO_3M, —OSO_3M, halogen, cyano and an azido; or, Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R'' are each independently selected from —H, —OH, —OR, —NHR, —NR_2, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3-18-membered heterocyclic ring having 1 to 6 heteroatoms independently selected from O, S, N and P;

$R^c$ is —H or a substituted or unsubstituted linear or branched alkyl having 1 to 4 carbon atoms, or the linking group;

n is an integer from 1 to 24;

W is selected from C=O, C=S, CH$_2$, BH, SO and SO$_2$;

X' is selected from —H, an amine-protecting group, the linking group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

$R_6$ is —H, —R, —OR, —SR, —NR'R", —NO$_2$, halogen or the linking group;

A and A' are the same or different, and are independently selected from —O—, oxo (—C(=O)—), —CRR'O—, —CRR'—, —S—, —CRR'S—, —N(R$_5$)— and —CRR'N(R$_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group, a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can be the linking group;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O, —(CH$_2$)$_{n'}$—, —NR'— or —S—;

Z" and Z'" are the same or different, and are independently selected from —(CH$_2$)$_{n'}$—, —CR$_7$R$_8$—, —NR$_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —(OCH$_2$CH$_2$)$_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, the linking group, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and $R^{c'}$ is absent or selected from linear or branched alkyl, alkenyl or alkynyl having 1 to 5 carbon atoms.

In certain embodiments, X is not the linking group. In certain embodiments, the double line ═ between N and C represents a single bond, Y is not —H.

In certain embodiments, Y is a leaving group selected from —OR, —OCOR', —OCOOR', —OCONR'R", —NR'R", —NR'COR", —NR'NR'R", an optionally substituted 5 or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido.

In certain embodiments, L is absent, or is selected from an optionally substituted phenyl group and an optionally substituted pyridyl group, wherein the phenyl and the pyridyl group bears the linking group, or L is an amine group bearing the linking group (i.e., —N(linking group)-), or L is a linear, branched or cyclic alkyl or alkenyl having from 1 to 6 carbon atoms and bearing the linking group.

In the 13$^{th}$ specific embodiment, the compound is represented by any one of the following formulas:

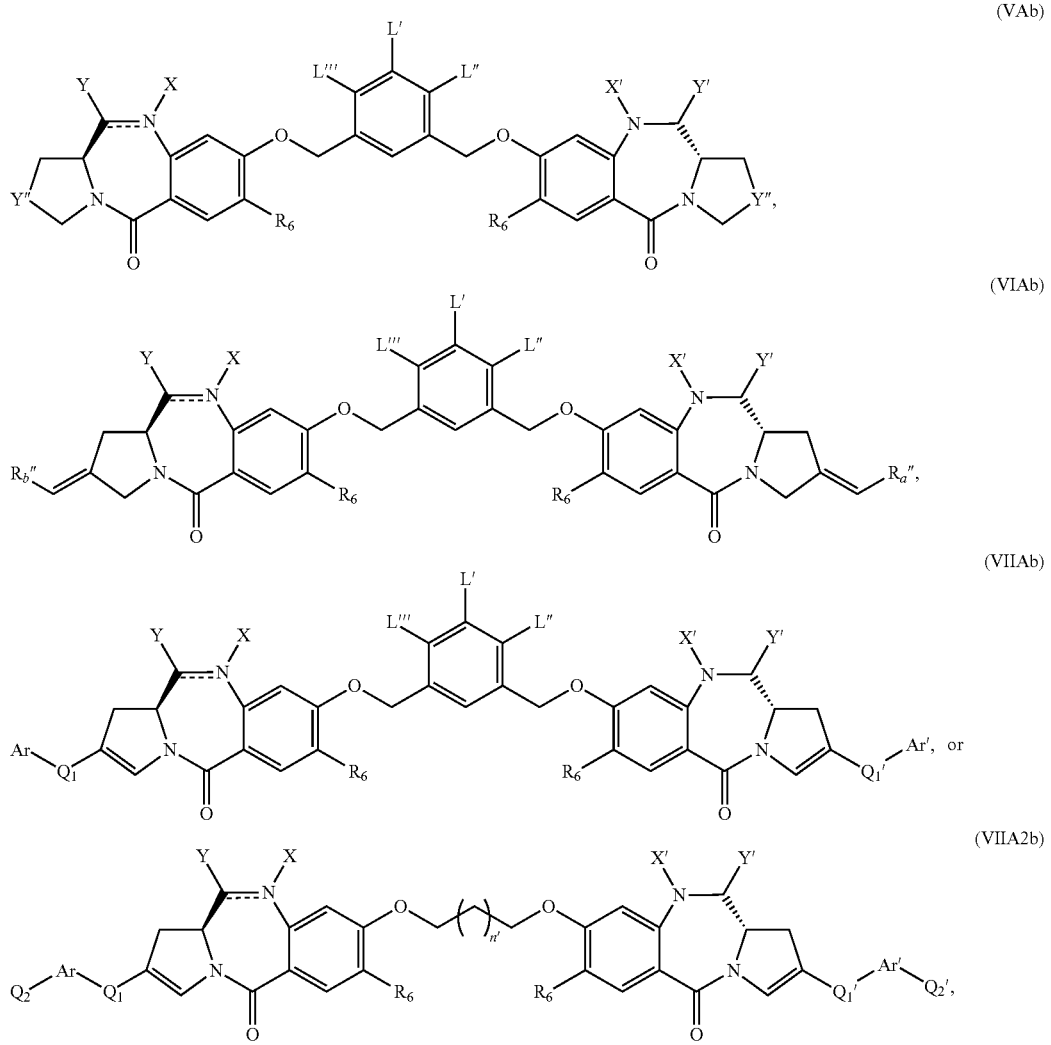

(VAb)

(VIAb)

(VIIAb)

(VIIA2b)

wherein:

L', L", and L'" are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SON, a sulfate —OSO$_3$M, a sulfonamide represented by —SO$_2$NR'R", cyano, an azido, —COR', —OCOR', —OCONR'R" and the linking group, provided only one of L', L", and L'" is the linking group; and R$_a$" and R$_b$" are the same or different and are selected from —H and -Me; one of Q$_2$ and Q$_2$' is selected from —H, —R, —OR, —NR'R", —NR'(C=O)OR", —SR, and —NO$_2$, the other is the linking group. The remaining groups are as described in the twelfth specific embodiment above.

In certain embodiments, one of L', L", or L'" is the linking group, while the others are —H. Preferably, L' is the linking group, and L" and L'" are —H.

In certain embodiments, A and A' are both —O—, R$_6$ is —OMe.

In a 14$^{th}$ specific embodiment, L' in formula (VAb), (VIAb) or (VIIAb), or one of Q$_2$ and Q$_2$' in formula (VIIA2b) is represented by the following formula:

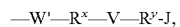

wherein:

W' and V are the same or different, and are each independently absent, or selected from —CR$^e$R$^{e'}$—, —O—, —O—C(=O)—, —C(=O)—O—, —S—, —SO—, —SO$_2$—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ and R$^y$ are the same or different, and are each independently absent or an optionally substituted linear, branched or cyclic alkyl, alkenyl, or alkynyl having 1 to 10 carbon atoms, an aryl bearing 6 to 10 carbon atoms or a 3- to 8-membered hetereocyclic ring bearing 1 to 3 heteroatoms selected from O, N or S;

$R^e$ and $R^{e'}$ are the same or different, and are selected from —H, a linear, branched or cyclic alkyl, alkenyl, or alkynyl having 1 to 10 carbon atoms or —($CH_2$—$CH_2$—O)$_n$—$R^k$, wherein $R^k$ is a —H, a linear, branched cyclic alkyl having 1 to 6 carbon atoms, optionally bearing a secondary amino (e.g., —$NHR^{101}$) or tertiary amino (—$NR^{101}R^{102}$) group or a 5- or 6-membered nitrogen containing heterocycle, such as piperidine or morpholine, wherein $R^{101}$ and $R^{102}$ are each independently a linear, branched, or cyclic alkyl, alkenyl or alkynyl having 1 to 10 carbon atoms; preferably, $R^{101}$ and $R^{102}$ are each independently a linear or branched alkyl having 1 to 6 carbon atoms;

n is an integer from 1 to 24; and

J is covalently linked to the CBA, and is selected from a succinimide, a acetamido, —S—, —SS—, —$CH_2$S—, —CH(Me)S—, —C(Me)$_2$S—, —$NR^{c1}$—, —$CH_2NR^{c1}$—, —$NR^{c1}N$—, and —C(=O)—, wherein $R^{c1}$ is —H or a substituted or unsubstituted linear or branched alkyl having 1 to 4 carbon atoms.

In certain embodiments, J is —S—, —SS—, a succinimide, or —C(=O)—.

In certain embodiments, $R^{e'}$ is —H or -Me; $R^e$ is a linear or branched alkyl having 1 to 6 carbon atoms or —($CH_2$—$CH_2$—O)$_n$—$R^k$; n is an integer from 2 to 8; and $R^k$ is —H, -Me or —$CH_2CH_2$—$NMe_2$, and the remainder of the variables are as described above in the fifteenth specific embodiment.

In certain embodiments, V is an amino acid or a peptide having 2 to 8 amino acids.

In certain embodiments, V is valine-citrulline, gly-gly-gly, or ala-leu-ala-leu.

In certain embodiments,

W' is —O—, —N($R^e$)— or —N($R^e$)—C(=O)—;

$R^e$ is H, a linear or branched alkyl having 1 to 4 carbon atoms, or —($CH_2$—$CH_2$—O)$_n$—$R^k$;

$R^x$ is a linear or branched alkyl having 1 to 6 carbon atoms;

V is absent, —(O—$CH_2$—$CH_2$)$_n$—, —C(=O)—NH—, —S—, —NH—C(=O)—;

$R^y$ is absent or a linear or branched alkyl having 1 to 4 carbon atoms; and

J is —S—, —SS—, or —C(=O)—, and the remaining groups are as defined in the 14$^{th}$ specific embodiment.

In certain embodiments,

W' is —O—, —N($R^e$)— or —N($R^e$)—C(=O)—;

$R^e$ is —H, -Me, or —($CH_2$—$CH_2$—O)$_n$-Me;

n is an integer from 2 to 6;

$R^x$ is linear or branched alkyl bearing 1 to 6 carbon atoms;

V and $R^y$ are absent; and

J is —C(=O)—. The remaining groups are as defined in the 14$^{th}$ specific embodiment.

In a 15$^{th}$ specific embodiment, L' in the 14$^{th}$ specific embodiment is represented by the following formula:

—W'—[$CR_{1''}R_{2''}$]$_a$—V—[Cy]$_{0-1}$—[$CR_{3''}R_{4''}$]$_b$—C(=O)—, wherein:

$R_{1''}$, $R_{2''}$, and $R_{3''}$ are each independently —H or a linear or branched alkyl bearing 1 to 4 carbon atoms, preferably -Me;

$R_{4''}$ is —H, a linear or branched alkyl bearing 1 to 4 carbon atoms (preferably -Me), —$SO_3H$, or —$SO_3^-M^+$, wherein $M^+$ is a pharmaceutically acceptable cation;

a is an integers from 0-5 (e.g., from 0 to 2, 3, 4, or 5), and b is an integer from 0-6 (e.g., from 0 to 3, 4, 5, or 6); and, Cy is an optionally substituted 5-membered heterocyclic ring bearing an N heteroatom, preferably Cy is

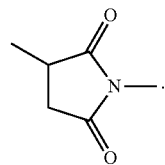

In certain embodiments, such as in the 14$^{th}$ or the 15$^{th}$ specific embodiment, W' is —N($R^e$)—.

In certain embodiments, such as in the 14$^{th}$ or the 15$^{th}$ specific embodiment, $R^e$ is —($CH_2$—$CH_2$—O)$_{2-6}$—$R^k$, wherein $R^k$ is a linear or branched alkyl having 1 to 6 carbon atoms.

In certain embodiments, such as in the 14$^{th}$ or the 15$^{th}$ specific embodiment, V is —S— or —SS—.

In an 16$^{th}$ specific embodiment, L' in the 14$^{th}$ or the 15$^{th}$ specific embodiment is represented by the following formula:

—$NR^e$—[$CR_{1''}R_{2''}$]$_a$—S—[$CR_{3''}R_{4''}$]$_b$—C(=O)—.

In certain embodiments, such as in the 14$^{th}$ to 15$^{th}$ specific embodiments, L' in formula (VAb), (VIAb) or (VIIAb), or one of $Q_2$ and $Q_2$' in formula (VIIA2b) is conjugated to the CBA as L'-CBA with the following structure:

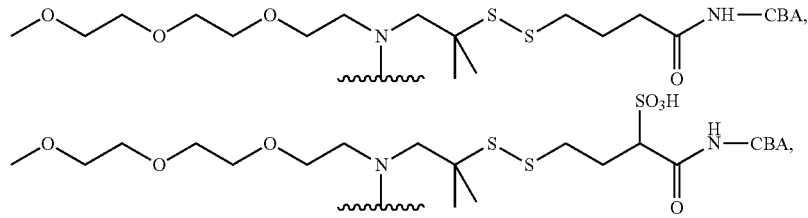

or wherein Y is —H or —$SO_3M$ (e.g., Y is —$SO_3M$), and M is —H or a pharmaceutically acceptable cation.

In certain embodiments, such as in the 14$^{th}$ to 16$^{th}$ specific embodiments, the antibody is huMy9-6.

In a 17$^{th}$ specific embodiment, L' in the 14$^{th}$ or the 15$^{th}$ specific embodiment is represented by the following formula:

—$NR^e$—[$CR_{1''}R_{2''}$]$_a$—S-Cy-[$CR_{3''}R_{4''}$]$_b$—C(=O)—.

In certain embodiments, such as in the 14$^{th}$, 15$^{th}$, and the 17$^{th}$ specific embodiments, L' in formula (VAb), (VIAb) or (VIIAb), or one of $Q_2$ and $Q_2$' in formula (VIIA2b) is conjugated to the CBA through the following structure:

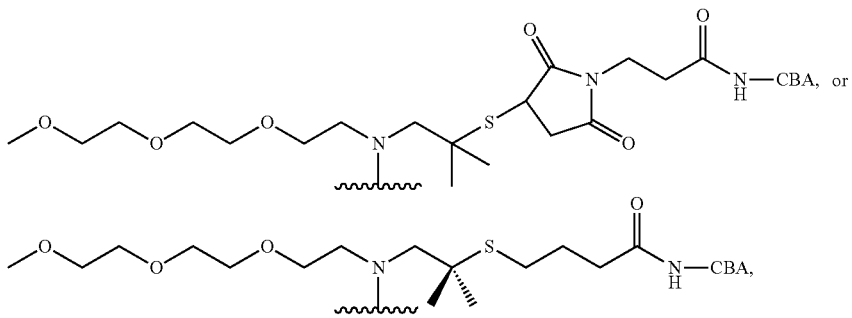

wherein Y is —H or —SO₃M (e.g., Y is —SO₃M), and M is —H or a pharmaceutically acceptable cation.

In certain embodiments, such as in the 14$^{th}$, 15$^{th}$, and the 17$^{th}$ specific embodiments, the antibody is huMy9-6.

In a 18$^{th}$ specific embodiment, L' in formula (VAb), (VIAb) or (VIIAb), or one of Q₂ and Q₂' in formula (VIIA2b) is represented by the following formula:

—W'—R$^x$—S—Z$^s$ wherein:
W' is absent, or selected from —O—, —N(R$^e$)—, —N(R$^e$)—C(=O)—, —N(C(=O)R$^e$)—, —S—, —CH₂—S—, or —CH₂NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH₂—CH₂—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

Z$^s$ is linked to the CBA, and is either a bond, or —SR$^m$—;

R$^m$ is R$^d$ or a substituted linear or branched alkyl having 1 to 4 carbon atoms bearing a reactive ester, selected from N-hydroxysuccinimide esters, N-hydroxyphtalimide esters, N-hydroxy sulfo-succinimide esters, para-nitrophenyl esters, dinitrophenyl esters, and pentafluorophenyl esters;

R$^d$ is selected from phenyl, nitrophenyl, dinitrophenyl, carboxynitrophenyl, pyridyl or nitropyridyl; and n is an integer from 1 to 24; and the remainder of the variables are as described above in the eighth or the fifteenth specific embodiment.

In a 19$^{th}$ specific embodiment, L' in formula (VAb), (VIAb) or (VIIAb), or one of Q₂ and Q₂' in formula (VIIA2b) is represented by the following formula:

—W'—R$^x$—S—Z$^s$ wherein:
W' is absent, or selected from —O—, —N(R$^e$)—, —N(R$^e$)—C(=O)—, —N(C(=O)R$^e$)—, —S—, —CH₂—S—, or —CH₂NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH₂—CH₂—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

n is an integer from 2 to 6;

Z$^s$ is linked to the CBA, and is selected from:
a bond;

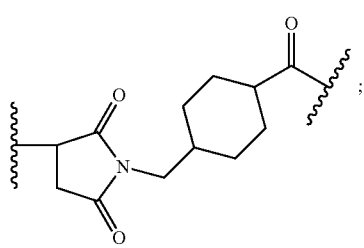
(b1)

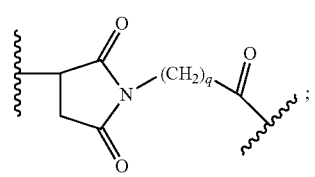
(b2)

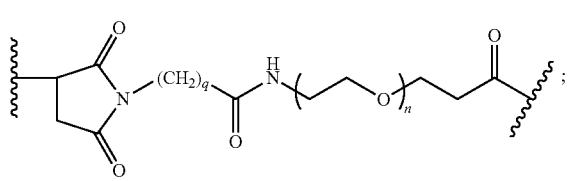
(b3)

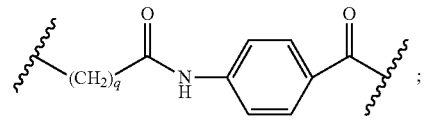
(b4)

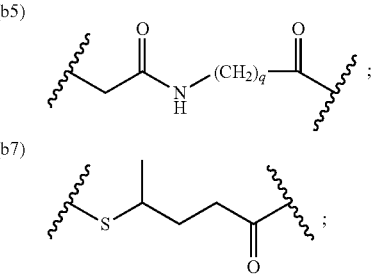(b5)

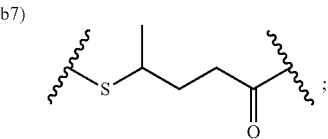(b6)

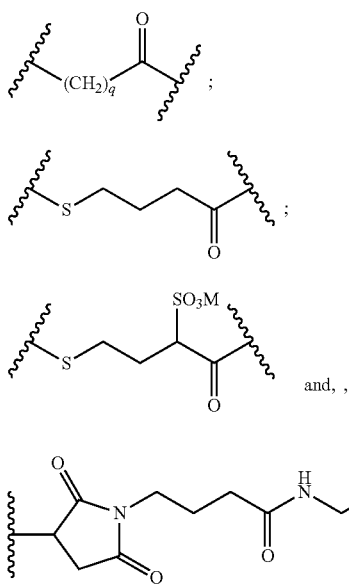(b7)

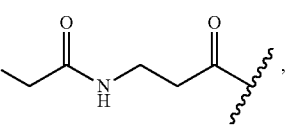(b8)

(b9)

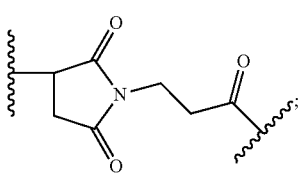 and, (b10)

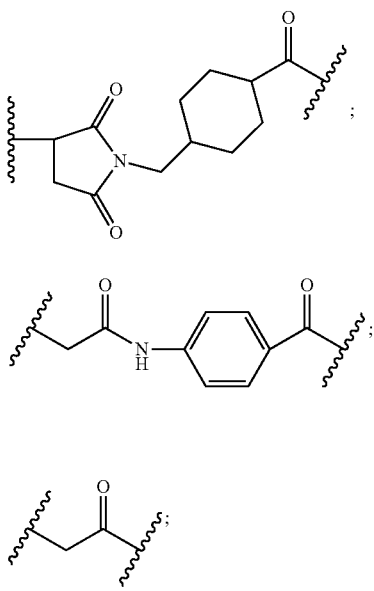

wherein:

q is an integer from 1 to 5; and,

M is —H or a pharmaceutically acceptable cation, such as Na⁺ or K⁺.

In certain embodiments, $Z^s$ is represented by any one of the following formulas:

(b1)

(b4')

(b5')

(b12)

(b13)

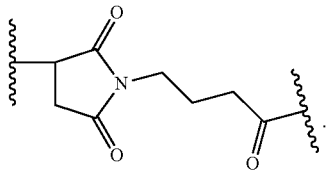

In certain embodiments, W' is —N($R^e$)—.

In certain embodiments, $R^e$ is —($CH_2$—$CH_2$—O)$_n$—$R^k$, wherein $R^k$ is a —H, a linear, branched cyclic alkyl having 1 to 6 carbon atoms.

In certain embodiments, $R^k$ is —H or -Me, n is 4, and q is 2.

In certain embodiments, $R^x$ is a linear or branched alkyl having 1 to 6 carbon atoms.

In certain embodiments, $R^x$ is —($CH_2$)$_p$—(CR$^f$R$^g$)—, wherein $R^f$ and $R^g$ are each independently selected from H or a linear or branched alkyl having 1 to 4 carbon atoms; and p is 0, 1, 2 or 3.

In certain embodiments, $R^f$ and $R^g$ are the same or different, and are selected from —H and -Me; and p is 1.

In a 20$^{th}$ specific embodiment, the conjugate of formula (VAb), (VIAb), (VIIAb), or (VIIA2b) described in the 19$^{th}$ specific embodiment, the variables are as described below:

the double line ═ between N and C represents a single bond or a double bond, provided that when it is a double bond X is absent and Y is —H, and when it is a single bond, X is —H; Y is —H, —OH or —$SO_3$M (e.g., Y is —OH or —$SO_3$M);

M is —H or a pharmaceutically acceptable cation (e.g., Na⁺);

X' and Y' are both —H;

A and A' are both —O—;

$R_6$ is —OMe; and $R^x$ is a linear or branched alkyl having 1 to 6 carbon atoms.

In a 21$^{st}$ specific embodiment, for compounds of formula (VAb), (VIAb), (VIIAb), or (VIIA2b) described in the twentieth specific embodiment, the variables are as described below:

the double line ⚌ between N and C represents a single bond or a double bond, provided that when it is a double bond X is absent and Y is —H, and when it is a single bond, X is —H; Y is —H, —OH or —SO$_3$M (e.g., Y is —OH or —SO$_3$M);

M is —H or Na$^+$;

X' and Y' are both —H;

A and A' are both —O—;

R$_6$ is —OMe;

R$^x$ is a linear or branched alkyl having 1 to 6 carbon atoms.

Preferably, R$^x$ is —(CH$_2$)$_p$—(CR$^f$R$^g$)—, wherein R$^f$ and R$^g$ are each independently selected from —H or a linear or branched alkyl having 1 to 4 carbon atoms; p is 0, 1, 2 or 3. More preferably, R$^f$ and R$^g$ are the same or different, and are selected from —H and -Me; and p is 1.

In any of the specific embodiments, for the conjugate of the invention above, such as the 12$^{th}$ to the 21$^{st}$ specific embodiments, the double line ⚌ between N and C may represent a double bond.

In any of the specific embodiments for the conjugate of the invention above, such as the 12$^{th}$ to the 21$^{st}$ specific embodiments, the double line ⚌ between N and C may represent a single bond, X is —H, the linking group, or an amine protecting group (e.g., X is —H); and Y is —H or selected from —OR, —OCOR', —SR, —NR'R", an optionally substituted 5- or 6-membered nitrogen-containing heterocycle, —SO$_3$M, —SO$_2$M and a sulfate —OSO$_3$M. In certain embodiments, Y is not —H. In certain embodiments, Y is selected from —H, —SO$_3$M, —OH, —OMe, —OEt or —NHOH (e.g., Y is —SO$_3$M, —OH, —OMe, —OEt or —NHOH). In certain embodiments, Y is —H, —SO$_3$M or —OH (e.g., Y is —SO$_3$M or —OH). In certain embodiments, M is —H, Na$^+$ or K$^+$.

In any of the specific embodiments for the conjugate of the invention above, such as the 12$^{th}$ to the 21$^{st}$ specific embodiments, W, when present, is C=O.

In any of the specific embodiments for the conjugate of the invention above, such as the 12$^{th}$ to the 21$^{st}$ specific embodiments, X' is selected from the group consisting of —H, —OH, an optionally substituted linear, branched or cyclic alkyl, alkenyl or alkynyl having from 1 to 10 carbon atoms, phenyl, the linking group, and an amine-protecting group. In certain embodiments, X' is —H, —OH, -Me or the linking group. In certain embodiments, X' is —H.

In any of the specific embodiments for the conjugate of the invention above, such as the 12$^{th}$ to the 21$^{st}$ specific embodiments, Y' is selected from the group consisting of —H, an oxo group, a substituted or unsubstituted linear, branched or cyclic alkyl, alkenyl or alkynyl having from 1 to 10 carbon atoms. In certain embodiments, Y' is —H or oxo. In certain embodiments, Y' is —H.

In any of the specific embodiments for the conjugate of the invention above, such as the 12$^{th}$ to the 21$^{st}$ specific embodiments, A and A' are the same or different, and are selected from —O—, —S—, —N(R$_5$)—, and oxo (C=O). In certain embodiments, A and A' are the same or different, and are selected from —O— and —S—. In certain embodiments, A and A' are —O—.

In any of the specific embodiments for the conjugate of the invention above, such as the 12$^{th}$ to the 21$^{st}$ specific embodiments, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. In certain embodiments, D and D' are linear or branched alkyl bearing 1 to 4 carbon atoms.

In a 22$^{nd}$ specific embodiment, the conjugate of the present invention as described in the 12$^{th}$, 13$^{th}$, or the 19$^{th}$ specific embodiment is represented by the following:

the double line ⚌ between N and C represents a double bond;

Y is —H;

W is C=O;

R$_6$ is —OMe;

X' is —H;

Y' is —H; and

A and A' are —O—.

The invention also provides a conjugate having formula Ia'

or a pharmaceutically acceptable salt or solvate thereof; wherein L$_{10}$ is a Ligand unit, LU is a Linker unit, p' is 1 to 20; and D$_{10}$ is a Drug unit comprising a PBD dimer having the following formula Ia:

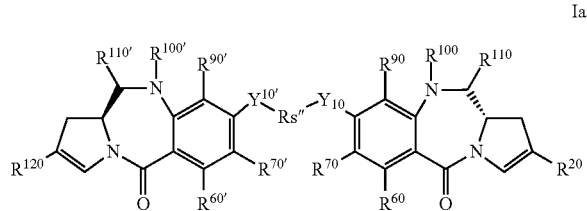

wherein:

R$^{20}$ is of formula IIa':

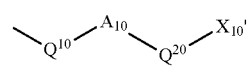

where A$_{10}$ is a C$_{5-7}$ aryl group, X$_{10}$ is selected from the group consisting of —O—, —S—, —C(O)O—, —C(O)—, —NH(C=O)—, —N(R$^N$)—, wherein R$^N$ is selected from the group consisting of H, C$_{1-4}$ alkyl and (C$_2$H$_4$O)$_m$CH$_3$, where m is 1 to 3, and either:

(i) Q$^{10}$ is a single bond, and Q$^{20}$ is selected from a single bond and —Z—(CH$_2$)$_n$—, where Z is selected from a single bond, O, S, and NH and n' is from 1 to 3; or (ii) Q$^{10}$ is —CH=CH—, and Q$^{20}$ is a single bond;

R$^{120}$ is a C$_{5-10}$ aryl group, optionally substituted by one or more substituents selected from the group comprising: halo, nitro, cyano, ether, C$_{1-7}$ alkyl, C$_{3-7}$ heterocyclyl, dimethyl-aminopropyloxy, piperazinyl and bis-oxy-C$_{1-3}$ alkylene;

R$^{60}$ and R$^{90}$ are independently selected from H, R$_{10}$, OH, OR$_{10}$, SH, SR$_{10}$, NH$_2$, NHR$_{10}$, NR$_{10}$R$_{10}$', nitro, Me$_3$Sn and halo; where R$_{10}$ and R$_{10}$' are independently selected from optionally substituted $C_{1-12}$ alkyl, $C_{3-20}$ heterocyclyl, and $C_{5-20}$ aryl groups;

$R^{70}$ is selected from H, $R_{10}$, OH, $OR_{10}$, SH, $SR_{10}$, $NH_2$, $NHR_{10}$, $NR_{10}R_{10}'$, nitro, $Me_3Sn$, and halo;

either:
(a) $R^{100'}$ is selected from —H, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P; and $R^{110'}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

when the nitrogen and carbon atoms to which $R^{100}$ and $R^{110}$ are bound, form a nitrogen-carbon double bond; $R^{100}$ is absent; $R^{110}$ is —H, or a linear or branched alkyl having 1 to 4 carbon atoms; or when the nitrogen and carbon atoms to which $R^{100}$ and $R^{110}$ are bound, form a nitrogen-carbon single bond; $R^{100}$ is H or an amine-protecting group, and $R^{110}$ is —H, an oxo group, O-Prot$^o$, wherein Prot$^o$ is an oxygen protecting group, or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or $R^{110}$ is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^kC(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; or (b) $R^{100}$ is selected from —H, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P; and $R^{110}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

when the nitrogen and carbon atoms to which $R^{100}$ and $R^{110'}$ are bound, form a nitrogen-carbon double bond; $R^{100'}$ is absent; $R^{110'}$ is —H, or a linear or branched alkyl having 1 to 4 carbon atoms; or when the nitrogen and carbon atoms to which $R^{100'}$ and $R^{110'}$ are bound, form a nitrogen-carbon single bond; $R^{100'}$ is H or an amine-protecting group, and $R^{110'}$ is —H, an oxo group, O-Prot$^o$, wherein Prot$^o$ is an oxygen protecting group, or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc.), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or $R^{110'}$ is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^kC(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —N(R)$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms;

n is an integer from 1 to 24;

R" is a C$_{3-12}$ alkylene group, which chain may be interrupted by one or more heteroatoms, selected from the group consisting of O, S, NH, and an aromatic ring;

Y is selected from O, S, or NH;

R$^6$, R$^7$, R$^9$ are selected from the same groups as R$^6$, R$^7$, and R$^9$ respectively.

The synthesis of such conjugates and the corresponding cytotoxic compounds can be based on the methods/schemes described herein, and methods/schemes essentially identical to those in WO 2001/130613 A1 and WO 2001/130616 A1 (both incorporated herein by reference).

In certain embodiments, (a) when the nitrogen and carbon atoms to which R$^{100}$ and R$^{110}$ are bound, form a nitrogen-carbon double bond; R$^{100}$ is absent; and R$^{110}$ is —H; or when the nitrogen and carbon atoms to which R$^{100}$ and R$^{110}$ are bound, form a nitrogen-carbon single bond;

(a)(i) R$^{100}$ is H and R$^{110}$ is OH, OR$^A$, or SO$_z$M, where R$^A$ is C$_{1-4}$ alkyl; z is 2 or 3; and M is a monovalent pharmaceutically acceptable cation;

(a)(ii) R$^{100}$ is carbamate nitrogen protecting group, and R$^{110}$ is O-Prot$^o$, wherein Prot$^o$ is an oxygen protecting group; or (a)(iii) R$^{100}$ is a hemi-aminal nitrogen protecting group and R$^{110}$ is an oxo group;

or (b) when the nitrogen and carbon atoms to which R$^{100'}$ and R$^{110'}$ are bound, form a nitrogen-carbon double bond; R$^{100'}$ is absent; and R$^{110'}$ is —H; or when the nitrogen and carbon atoms to which R$^{100'}$ and R$^{110'}$ are bound, form a nitrogen-carbon single bond;

(b)(i) R$^{100'}$ is H, and R$^{110'}$ is OH, OR$^A$, or SO$_z$M, where R$^A$ is C$_{1-4}$ alkyl; z is 2 or 3; and M is a monovalent pharmaceutically acceptable cation;

(b)(ii) R$^{100'}$ is carbamate nitrogen protecting group, and R$^{110'}$ is O-Prot$^o$, wherein Prot$^o$ is an oxygen protecting group; or (b)(iii) R$^{100'}$ is a hemi-aminal nitrogen protecting group and R$^{110'}$ is an oxo group.

In certain embodiments, under condition (a), R$^{100'}$ is selected from the group consisting of —H, —OH, a linear, branched or cyclic alkyl, alkenyl or alkynyl having from 1 to 10 carbon atoms, phenyl, and an amine-protecting group. R$^{110'}$ is selected from the group consisting of —H, an oxo group, a linear, branched or cyclic alkyl, alkenyl or alkynyl having from 1 to 10 carbon atoms; or under condition (b), R$^{100}$ is selected from the group consisting of —H, —OH, a linear, branched or cyclic alkyl, alkenyl or alkynyl having from 1 to 10 carbon atoms, phenyl, and an amine-protecting group. R$^{110}$ is selected from the group consisting of —H, an oxo group, a linear, branched or cyclic alkyl, alkenyl or alkynyl having from 1 to 10 carbon atoms.

In certain embodiments, R$^{70}$ is selected from H, OH, and OR. Preferably, R$^{70}$ is a C$_{1-4}$ alkyloxy group.

In certain embodiments, Y$_{10}$ is O.

In certain embodiments, R$_s$" is C$_{3-7}$ alkylene.

In certain embodiments, R$^{90}$ is H.

In certain embodiments, R$^{60}$ is selected from H and halo.

In certain embodiments, A$_{10}$ is phenyl.

In certain embodiments, X$_{10}$ is selected from —O—, —S—, or —NH—.

In certain embodiments, Q$^{10}$ is a single bond.

In certain embodiments, Q$^{20}$ is a single bond. In certain embodiments, Q$^{20}$ is —Z—(CH$_2$)$_{n'}$—, Z is O or S and n' is 1 or 2.

In certain embodiments, Q$^{10}$ is —CH═CH—.

In certain embodiments, R$^{120}$ is a C$_{5-7}$ aryl group. Preferably, R$^{120}$ is phenyl.

In certain embodiments, R$^{120}$ is a C$_{8-10}$ aryl group.

In certain embodiments, R$^{120}$ is bears one to three substituent groups.

In certain embodiments, the nitrogen and carbon atoms to which R$^{100}$ and R$^{110}$ are bound, form a nitrogen-carbon double bond; R$^{100}$ is absent; and R$^{110}$ is H; or the nitrogen and carbon atoms to which R$^{100'}$ and R$^{110'}$ are bound, form a nitrogen-carbon double bond; R$^{100'}$ is absent; and R$^{110'}$ is —H.

In certain embodiments, R$^{60'}$, R$^{70'}$, R$^{90'}$, and Y$_{10}$' are the same as R$^{60}$, R$^{70}$, R$^{90}$, and Y$_{10}$ respectively.

In certain embodiments, the Linker unit (LU) has the formula Ia or Ib:

(1a)

wherein:

A$^1$ is a Stretcher unit, a is 1 or 2,

L$^1$ is a Specificity unit, s is an integer ranging from 0 to 12,

L$^2$ is a Spacer unit, and y is 0, 1, or 2, or

(1b)

wherein:

A$^1$ is a Stretcher unit linked to a Spacer unit (L$^2$), a is 1 or 2,

L$^1$ is a Specificity unit linked to a Spacer unit (L$^2$), s is an integer ranging from 1 to 12, L$^2$ is a Spacer unit, y is 1 ort.

In certain embodiments, the Linker unit (LU) has formula 1a.

In certain embodiments, $A^1$ is selected from:

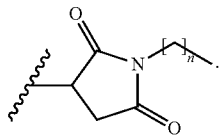

where the asterisk indicates the point of attachment to $L^1$, the wavy line indicates the point of attachment to the Ligand unit, and n is 0 to 6;

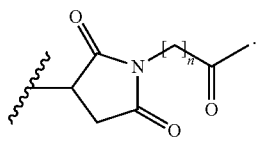

where the asterisk indicates the point of attachment to $L^1$, the wavy line indicates the point of attachment to the Ligand unit, and n is 0 to 6;

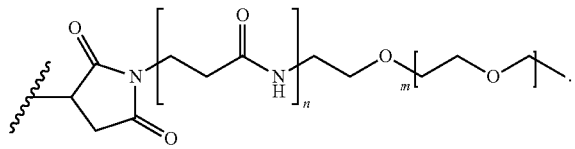

where the asterisk indicates the point of attachment to $L^1$, the wavy line indicates the point of attachment to the Ligand unit, n is 0 or 1, and m is 0 to 30; or

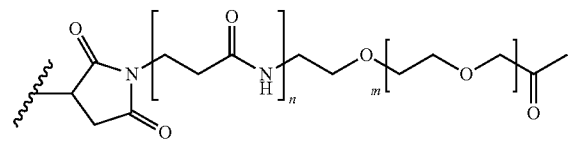

where the asterisk indicates the point of attachment to $L^1$, the wavy line indicates the point of attachment to the Ligand unit, n is 0 or 1, and m is 0 to 30.

In certain embodiments, $A^1$ is:

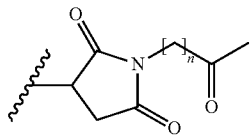

where the asterisk indicates the point of attachment to $L^1$, the wavy line indicates the point of attachment to the Ligand unit, and n is 0 to 6. Preferably, n is 5.

In certain embodiments, $L^1$ comprises an amino acid sequence. Preferably, $L^1$ is a dipeptide. More preferably, $L^1$ is selected from the group consisting of valine-alanine, valine-citrulline and phenylalanine-lysine.

In certain embodiments, y is 0.

In certain embodiments, y is 1 or 2. $L^2$ is:

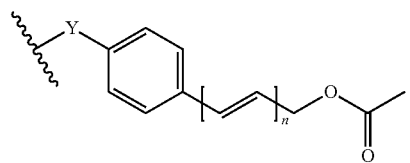

where the asterisk indicates the point of attachment to the Drug unit, the wavy line indicates the point of attachment to the $L^1$, Y is —N(H)—, —O—, —C(=O)N(H)— or —C(=O)O—, and n is 0 to 3. Preferably, $L^2$ is:

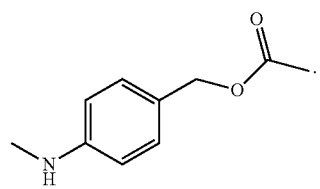

The invention further provides the use of a Conjugate of the invention, or a pharmaceutically acceptable salt or solvate thereof, in the manufacture of a medicament for treating a proliferative disease or an autoimmune disease.

The invention additionally provides the use of a Conjugate of the invention, or a pharmaceutically acceptable salt or solvate thereof, for treating a proliferative disease or an autoimmune disease.

The invention additionally provides the use of a compound according to any one of claims 1 to 31 in the manufacture of a medicament for treating a proliferative disease.

The invention additionally provides a compound as described herein above for use in the treatment of a proliferative disease.

Figures 1, 42:
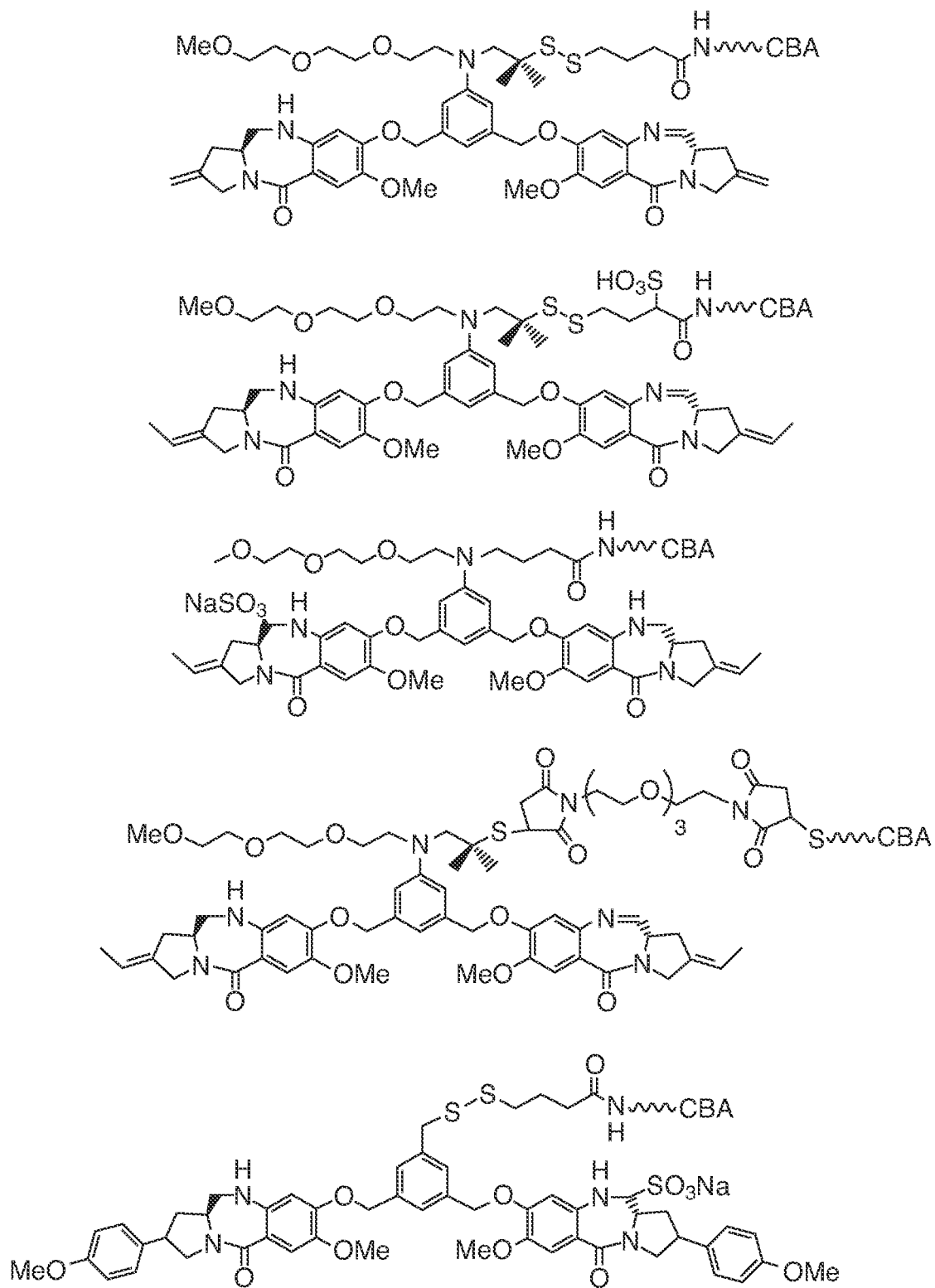
FIG. 42 shows certain preferred conjugates of the invention, which may be produced by the methods of the invention.
Figures 2, 42:
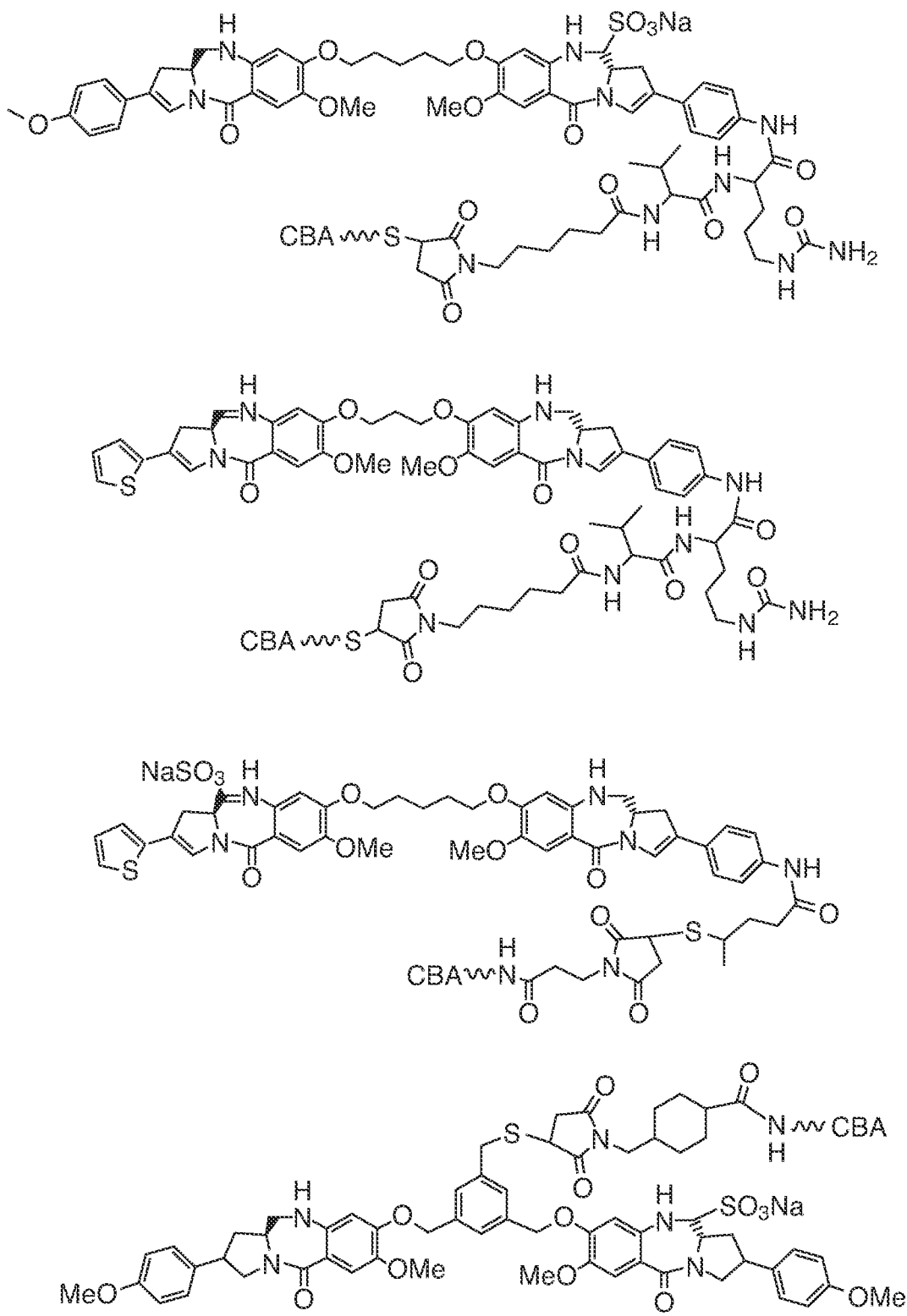

Certain preferred conjugates of the invention, or conjugates that can be produced by the methods of the invention, are represented in FIG. 42.

In certain embodiments, the conjugate of any one of the described embodiments, such as the $12^{th}$ to the $22^{nd}$ specific embodiments, may comprise 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In certain embodiments, the conjugate of any one of the described embodiments, such as the $12^{th}$ to the $22^{nd}$ specific embodiments, may comprise 1-10 modified cytotoxic compounds, 2-9 modified cytotoxic compounds, 3-8 modified cytotoxic compounds, 4-7 modified cytotoxic compounds, or 5-6 modified cytotoxic compounds, each modified cytotoxic compound comprising the linking group linking the modified cytotoxic compound to the CBA, and each modified cytotoxic compound on the conjugate is the same.

In certain embodiments, the conjugate of any one of the described embodiments, such as the $12^{th}$ to the $22^{nd}$ specific embodiments, may comprise 1-10 total modified and unmodified cytotoxic compounds (those cytotoxic compounds with the imine group intact), 2-9 total modified and unmodified cytotoxic compounds, 3-8 total modified and unmodified cytotoxic compounds, 4-7 total modified and unmodified cytotoxic compounds, or 5-6 total modified and unmodified cytotoxic compounds, each modified or unmodified cytotoxic compound comprising the linking group linking the modified or unmodified cytotoxic compound to the CBA, and each modified or unmodified cytotoxic compound on the conjugate is the same (except for the (bisulfite) modification).

In any of the conjugates embodiments, such as the $12^{th}$ to the $22^{nd}$ specific embodiments, the cell-binding agent may bind to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

In any of the conjugates embodiments, such as the $12^{th}$ to the $22^{nd}$ specific embodiments, the cell-binding agent may be an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

The antibody may be a resurfaced antibody, a resurfaced single chain antibody, or a resurfaced antibody fragment.

The antibody may be a monoclonal antibody, a single chain monoclonal antibody, or a monoclonal antibody fragment thereof.

The antibody may be a humanized antibody, a humanized single chain antibody, or a humanized antibody fragment.

The invention further provides a pharmaceutical composition comprising any of the conjugates described herein, and a pharmaceutically acceptable carrier.

The invention further provides a drug-linker compound comprising any of the subject compound covalently linked to a bifunctional linker.

The invention additional provides a conjugate comprising any of the subject compounds, or the subject drug-linker compounds, linked to a cell-binding agent.

The invention further provides a method of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal comprising administering to the mammal a therapeutically effective amount of any of the compounds (with or without any linker group) or conjugates of the invention, and, optionally, a second chemotherapeutic agent.

In certain embodiments, the second chemotherapeutic agent is administered to the mammal sequentially or consecutively.

In certain embodiments, the method is for treating a condition selected from cancer, rheumatoid arthritis, multiple sclerosis, graft versus host disease (GVHD), transplant rejection, lupus, myositis, infection, and immune deficiency.

In certain embodiments, the method or conjugate is for treating a cancer.

In certain embodiments, the cancer is selected from breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, non small-cell lung cancer, testicular cancer, Merkel cell carcinoma, glioblastoma, neuroblastoma, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

Production of Cell-Binding Agent-Drug Conjugates

In order to link the cytotoxic compounds or derivative thereof of the present invention to the cell-binding agent, the cytotoxic compound may comprise a linking moiety with a reactive group bonded thereto. In one embodiment, a bifunctional crosslinking reagent can be first reacted with the cytotoxic compound to provide the compound bearing a linking moiety with one reactive group bonded thereto (i.e., drug-linker compound), which can then react with a cell binding agent. Alternatively, one end of the bifunctional crosslinking reagent can first react with the cell binding agent to provide the cell binding agent bearing a linking moiety with one reactive group bonded thereto, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 2005/0169933, or charged linkers or hydrophilic linkers and are described in US 2009/

0274713, US 2010/01293140 and WO 2009/134976, each of which is expressly incorporated herein by reference, each of which is expressly incorporated herein by reference.

The compounds of the invention, such as those in formulas (V)-(VII), (Va)-(VIIa), (VAa)-(VIIAa) and (VIIA2a), and (VBa)-(VIIBa) and (VIIB2a) can be linked through L, L', L", L'", X (when present), Y, X', Y', $R_6$, $Q_2$ or $Q_2$'. Of these, preferred linkable groups are L', L", L'" and $Q_2$ or $Q_2$', and most preferred linkable groups are L' and $Q_2$ or $Q_2$'.

In one embodiment, a solution of an antibody in aqueous buffer may be incubated with a molar excess of an antibody modifying agent such as N-succinimidyl-3-(2-pyridyldithio) propionate (SPDP) or with N-succinimidyl-4-(2-pyridyldithio)butanoate (SPDB) to introduce dithiopyridyl groups. The modified antibody is then reacted with the thiol-containing cytotoxic compound to produce a disulfide-linked antibody-benzodiazepine dimer conjugate. The cell binding agent-drug conjugate may then be purified using any purification methods known in the art, such as those described in U.S. Pat. No. 7,811,572 and US Publication No. 2006/0182750, both of which are incorporated herein by reference. For example, the cell-binding agent-drug conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Alternatively, the antibody may be incubated with a molar excess of an antibody modifying agent such as 2-iminothiolane, L-homocysteine thiolactone (or derivatives), or N-succinimidyl-5-acetylthioacetate (SATA) to introduce sulfhydryl groups. The modified antibody is then reacted with the appropriate disulfide-containing cytotoxic agent, to produce a disulfide-linked antibody-cytotoxic agent conjugate. The antibody-cytotoxic agent conjugate may then be purified by methods described above. The cell binding may also be engineered to introduce thiol moieties, such as cysteine-engineered antibodies disclosed in U.S. Pat. Nos. 7,772,485 and 7,855,275.

In another embodiment, a solution of an antibody in aqueous buffer may be incubated with a molar excess of an antibody-modifying agent such as N-succinimidyl-4-(N-maleimidomethyl)-cyclohexane-1-carboxylate to introduce maleimido groups, or with N-succinimidyl-4-(iodoacetyl)-aminobenzoate (SIAB) to introduce iodoacetyl groups. The modified antibody is then reacted with the thiol-containing cytotoxic agent to produce a thioether-linked antibody-cytotoxic conjugate. The antibody-cytotoxic conjugate may then be purified by methods described above.

The number of cytotoxic molecules bound per antibody molecule can be determined spectrophotometrically by measuring the ratio of the absorbance at 280 nm and 330 nm. An average of 1-10 cytotoxic compounds/antibody molecule(s) can be linked by the methods described herein. The preferred average number of linked cytotoxic compounds per antibody molecule is 2-5, and the most preferred is 2.5-4.0.

Cytotoxic agents containing linkers terminating in an N-hydroxy succinimidyl (NHS) ester can react with the antibody to produce direct amide linked conjugates. The antibody-cytotoxic agent conjugate may then be purified by gel-filtration by any methods described above.

Figure 30:
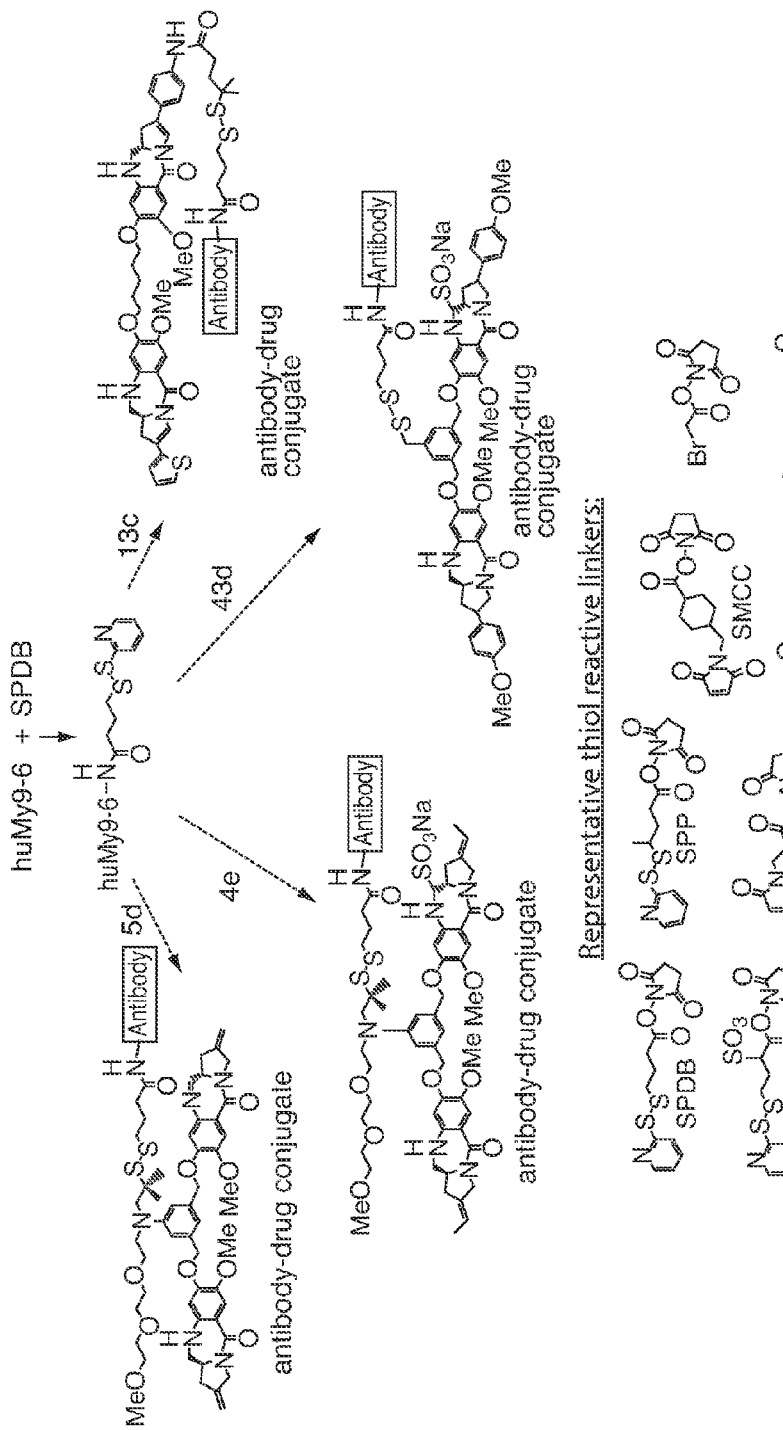
Figure 31A:
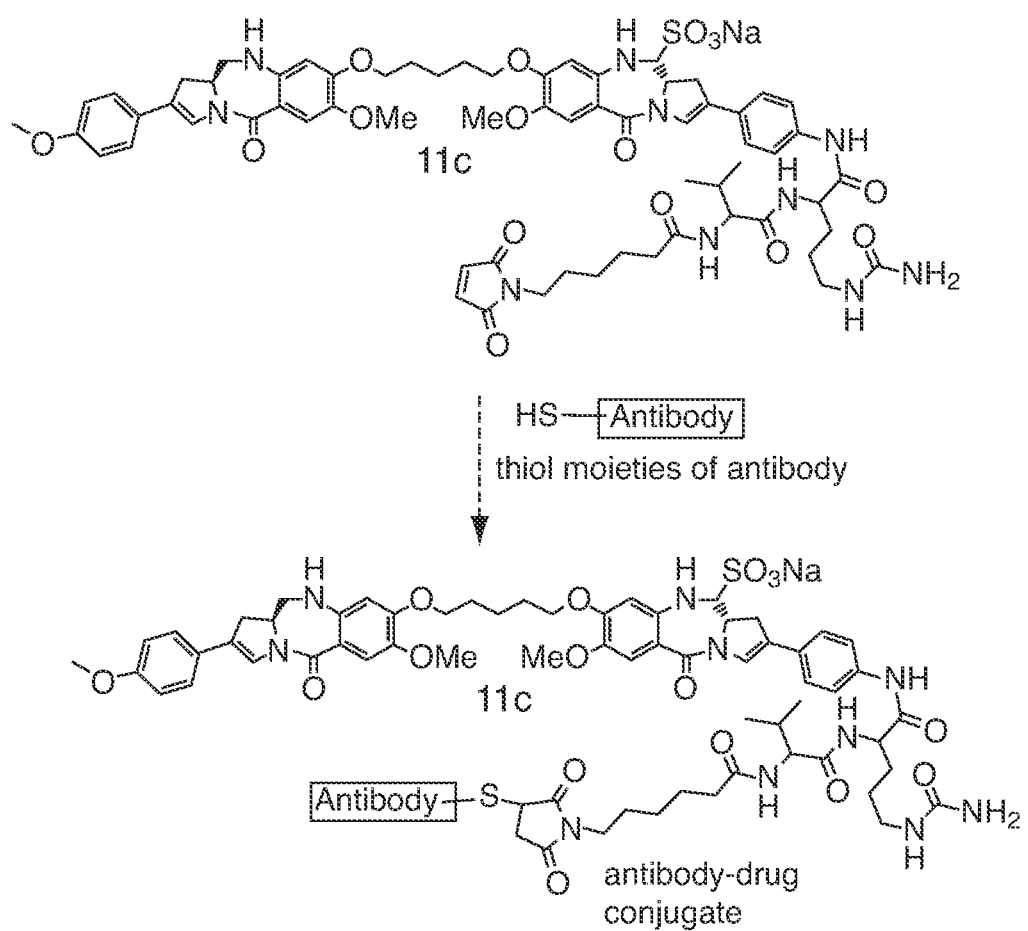
Figure 31B:
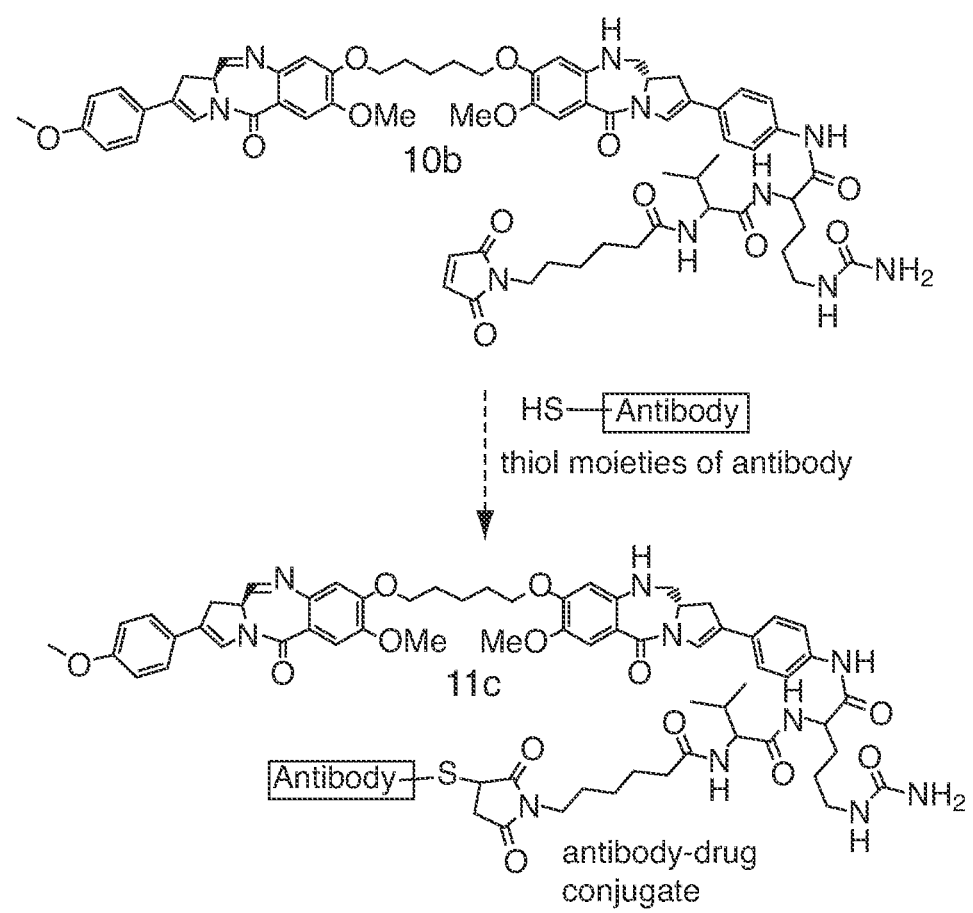
Figure 31C:
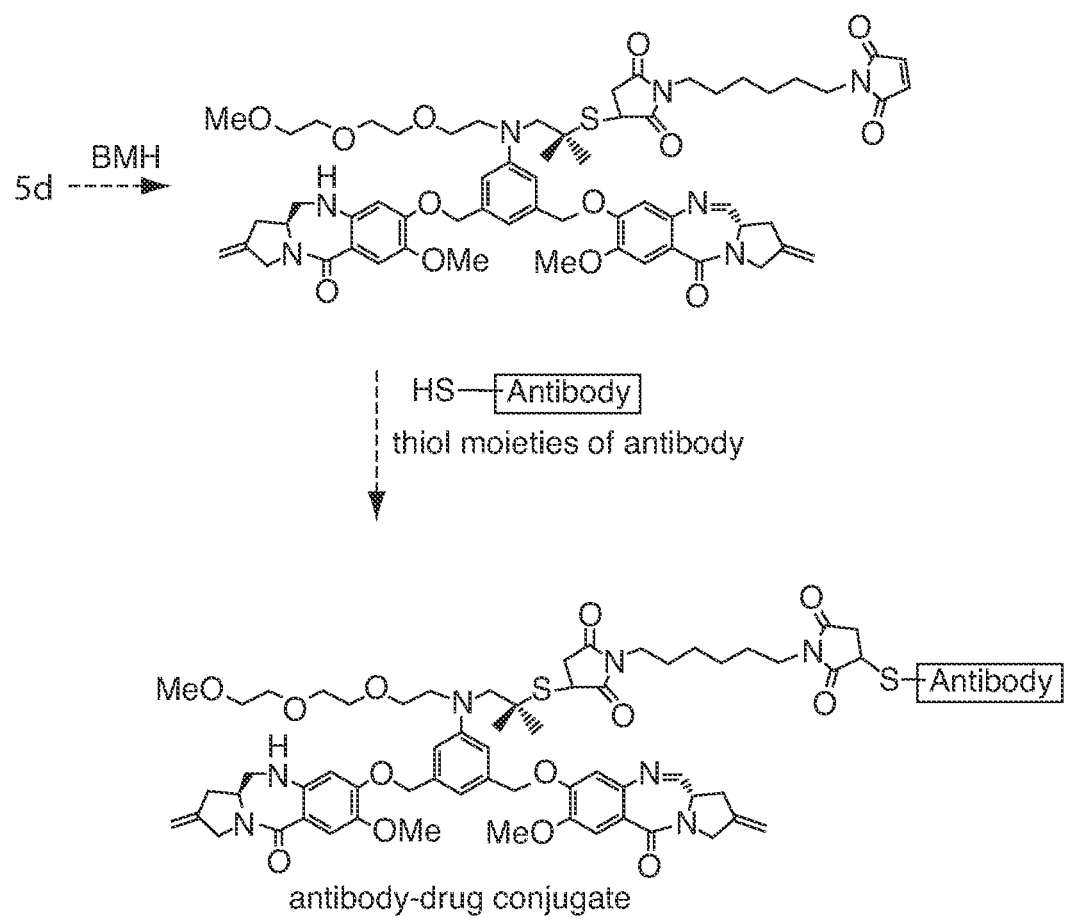
Figure 31D:
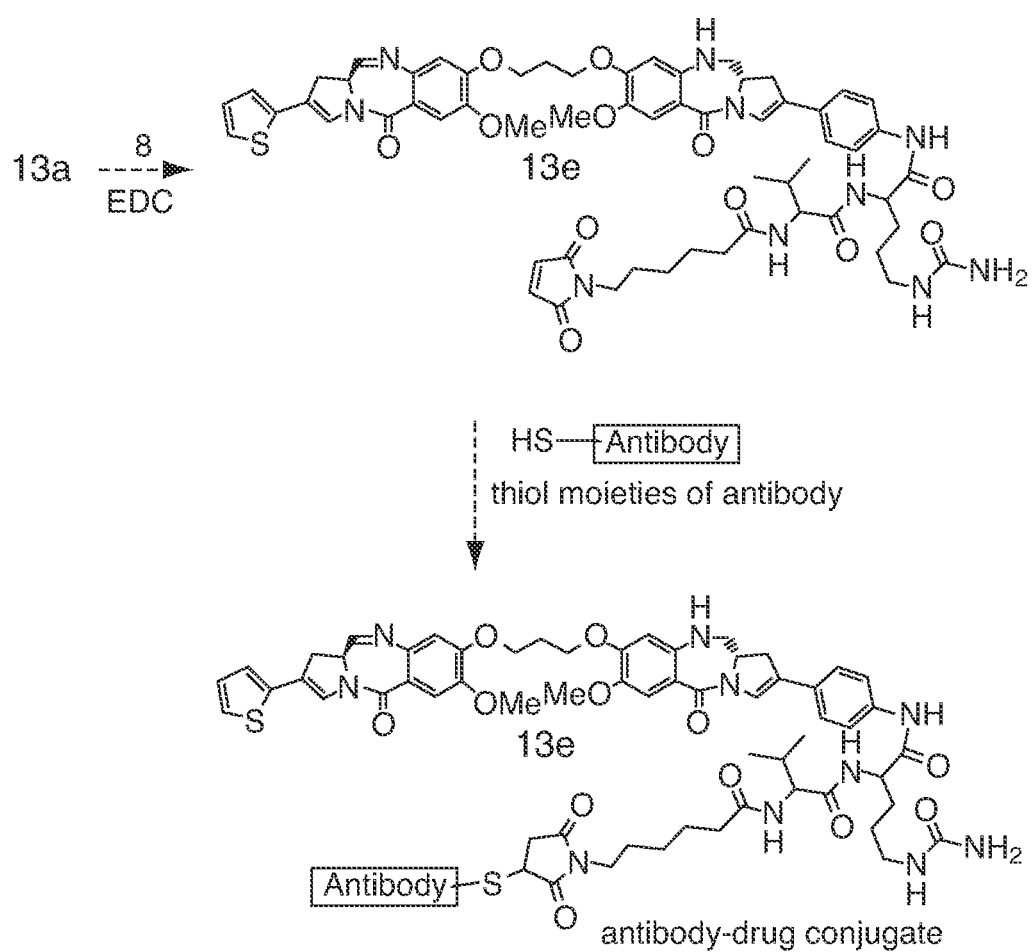
Figure 31E:
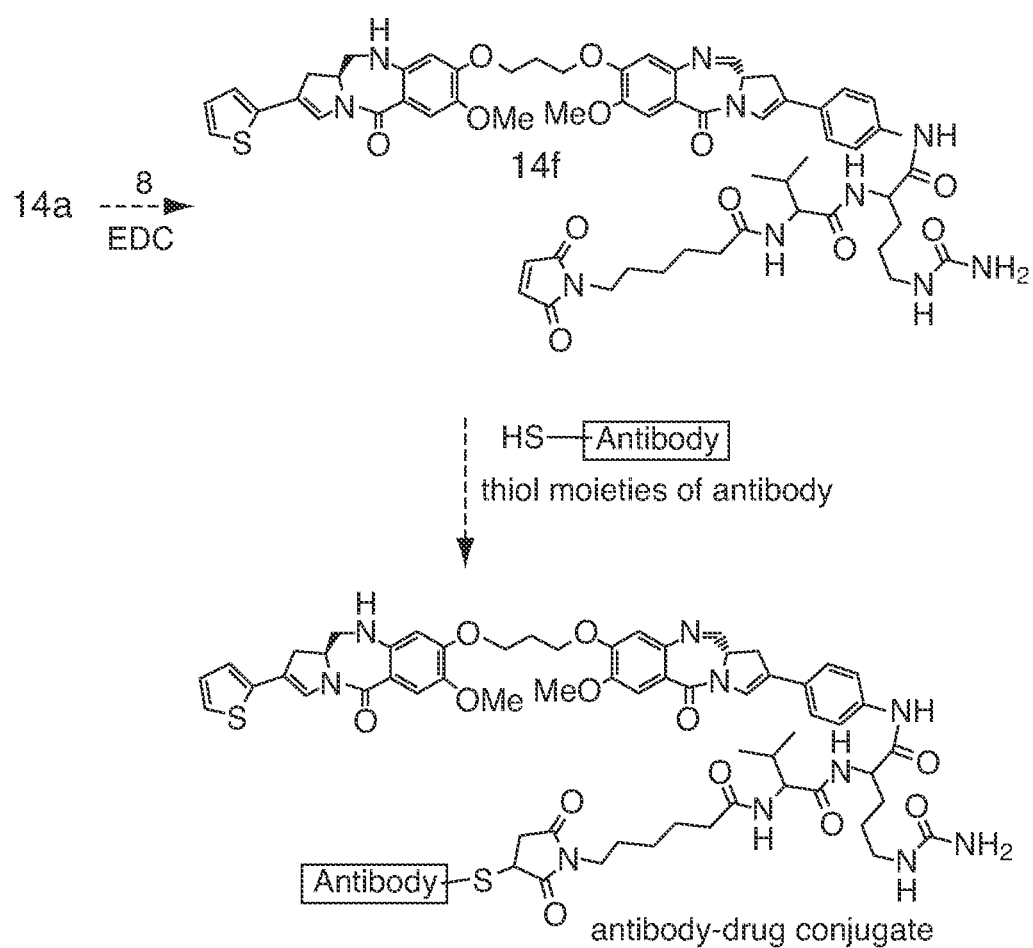
Figure 31F:
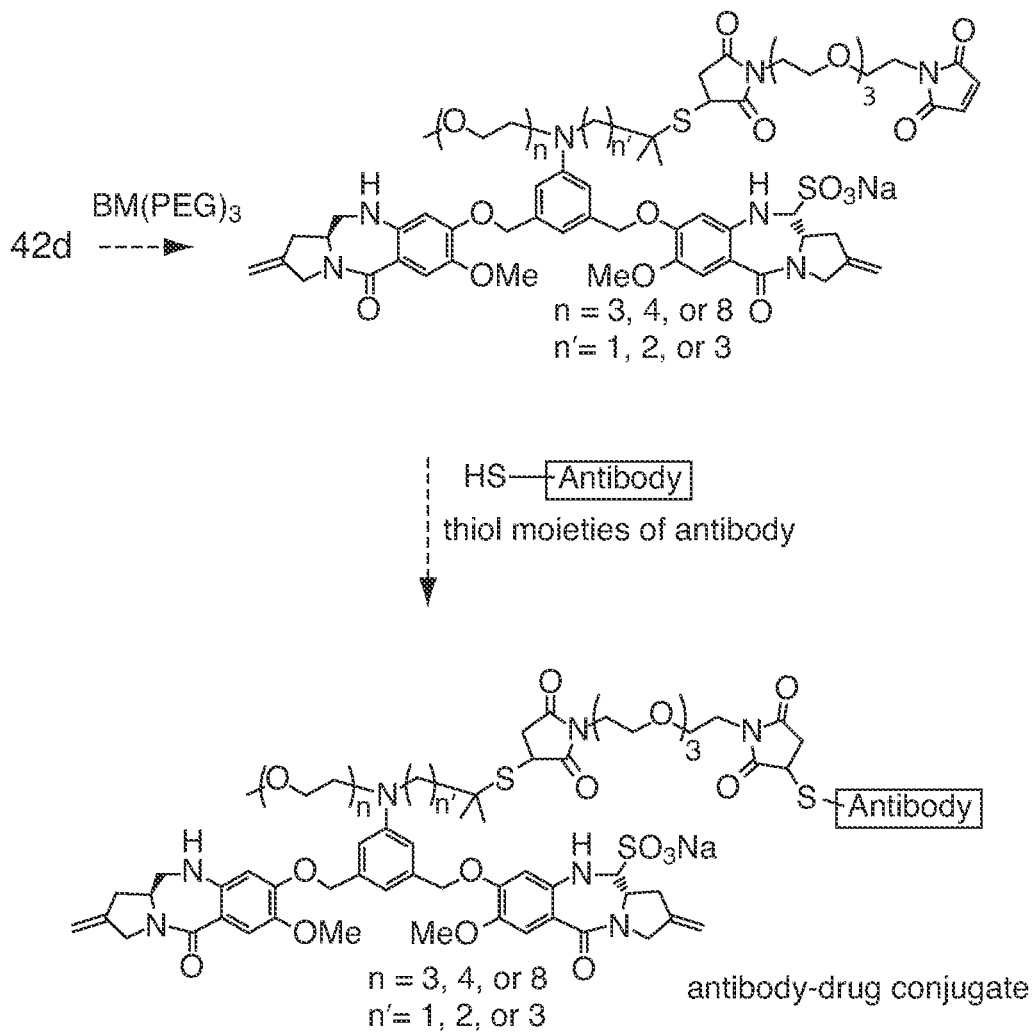

Representative processes for preparing the cell-binding agent-drug conjugates of the present invention are shown in FIGS. 29 and 30. A cytotoxic dimer compound of the present invention can be conjugated with a cell binding agent through either a one-step or a two-step conjugation method. In FIGS. 29a and 29b, representative examples are described, wherein a dimer compound that possesses a linker such as an N-hydroxysuccinimide ester is reacted directly with a cell binding agent, such as an antibody, generating the desired conjugate. In FIG. 29b linkable dimer 13f was first treated with sodium bisulfate to provide a modified dimer compound before adding antibody to form the conjugate of the present invention.

A representative example of a two-step conjugation method is described in FIG. 30, wherein an antibody is first modified with a bifunctional crosslinking agent resulting in an antibody that possesses a desired number of linkers suitable for reaction with a dimer compound having a free thiol moiety. In this example the antibody huMy9-6 was first modified with SPDB to give an antibody with linkers containing the dithiopyridyl moiety. The modified antibody was then exposed to a free thiol, such as 5d, generating the desired conjugate huMy9-6-SPDB-5d.

Processes for synthesizing the drug-linker compounds and conjugates of the invention are also described in further details below.

Methods of the Present Invention

In a first aspect, the present invention is directed to a method for preparing a conjugate comprising a cell-binding agent (CBA) conjugated to a cytotoxic compound with a linking group, the method comprising reacting a modified cytotoxic compound with a modified CBA at a pH of about 4 to about 9, wherein:

a) the modified CBA comprises a residue of a bifunctional crosslinking agent bonded to the CBA, and the residue comprises the linking group and a thiol-reactive group; and b) the modified cytotoxic compound comprises a thiol group, and a group represented by:

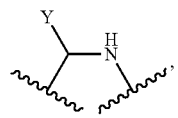

wherein:

(1) the modified cytotoxic compound is represented by one of the following formulae, or a pharmaceutically acceptable salt thereof:

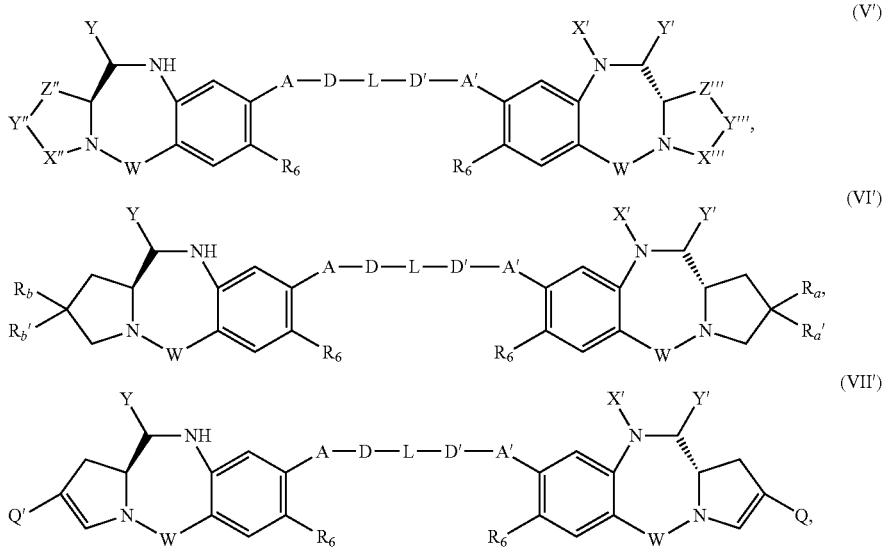

(V')

(VI')

(VII')

and,
(2) the modified cytotoxic compound and the linking group portion of the conjugate is represented by one of the following formulae:

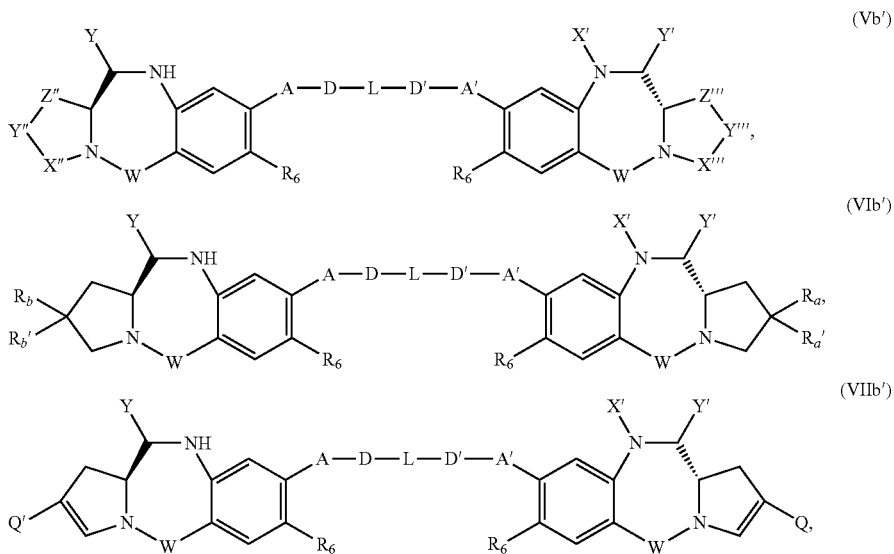

(Vb')

(VIb')

(VIIb')

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$ $PO_2S_2^{3-}$ $POS_3^{3-}$ or $PS_4^{3-}$ formed with a cation), thio phosphate ester $(R^iO)_2PS(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; RR is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from $-H$, an amine-protecting group, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

$R^c$ is —H or a substituted or unsubstituted linear or branched alkyl having 1 to 4 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3-18-membered heterocyclic ring having 1 to 6 heteroatoms independently selected from O, S, N and P;

n is an integer from 1 to 24;

W is selected from C=O, C=S, $CH_2$, BH, SO and $SO_2$;

$R_6$ is —H, —R, —OR, —SR, —NR'R", —$NO_2$, or halogen;

A and A' are the same or different, and are independently selected from —O—, oxo (—C(=O)—), —CRR'O—, —CRR'—, —S—, —CRR'S—, —N($R_5$)— and —CRR'N($R_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2)_n$—;

L is absent, or when present, comprises the thiol group, or is a polyethylene glycol unit (—$OCH_2CH_2)_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X" and X' are the same or different, and are independently selected from —$(CH_2)_{n'}$—, —NR'—, —CO—, —BH—, —SO— or —$SO_2$—;

Y" and Y'" are the same or different, and are independently selected from —O—, —$(CH_2)_{n'}$—, —NR'— or —S—;

Z" and Z'" are the same or different, and are independently selected from —$(CH_2)_{n'}$—, —$CR_7R_8$—, —$NR_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH unit;

Ar and Ar' are each independently absent or represent an aryl group;

$Q_2$ and $Q_2'$ are each independently selected from —H, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)$NH_2$], —OR, —NR'R", —$NO_2$, —NCO, —NR'COR", —SR, a sulfoxide represented by —SOR', a sulfone represented by —$SO_2R'$, a sulfonate —$SO_3M$, a sulfate —$OSO_3M$, a sulfonamide represented by $SO_2NR'R"$, cyano, an azido, —COR', —OCOR' or —OCONR'R";

$R^{c'}$ is absent or selected from linear or branched alkyl, alkenyl or alkynyl having 1 to 5 carbon atoms; and wherein at least one of X', Y', $R_6$, $R^c$, L (e.g., through an optionally substituted group), Q, Q', $Q_2$ or $Q_2'$ is bonded to the linking group in formulas (Vb'), (VIb'), or (VIIb').

In certain embodiments, the modified cytotoxic compound is produced by reacting an imine reactive reagent with an imine-containing cytotoxic compound bearing the thiol group having one of the following formulas, or a pharmaceutically acceptable salt thereof:

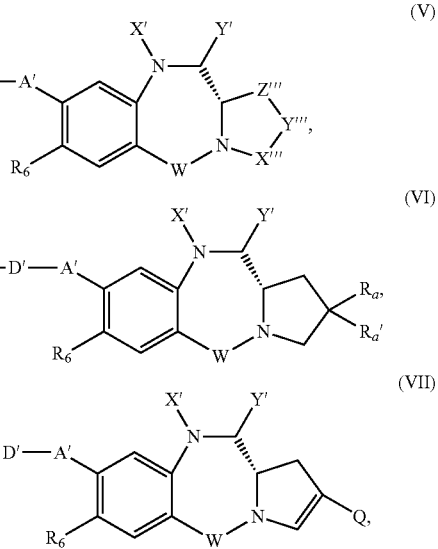

(V)

(VI)

(VII)

In certain embodiments, the method may further comprises purifying the modified cytotoxic compound prior to reacting with the modified CBA.

In certain embodiments, the modified CBA is prepared by reacting the CBA with the bifunctional crosslinking agent, said bifunctional crosslinking agent comprising the thiol-reactive group and a group reactive with the CBA, both bonded to the linking group.

In certain embodiments, the group reactive with the CBA reacts with an amino group of the CBA (such as the amino group of a Lys sidechain), or with a thiol group of the CBA (such as the thiol group of a Cys sidechain).

In certain embodiments, the thiol-reactive group is selected from the group consisting of maleimido, vinylpyridine, vinyl sulfone, vinyl sulfonamide, a haloacetyl-based group and a disulfide group.

alternatively, the thiol-reactive group may be maleimido, haloacetamido or —SSR$^d$, wherein R$^d$ is a linear or branched alkyl having 1 to 4 carbon atoms, phenyl, nitrophenyl, dinitrophenyl, carboxynitrophenyl, pyridyl, 2-nitropyridyl, 4-nitropyridyl, or 3-carboxy-4-nitropyridyl.

In certain embodiments, the modified CBA is:

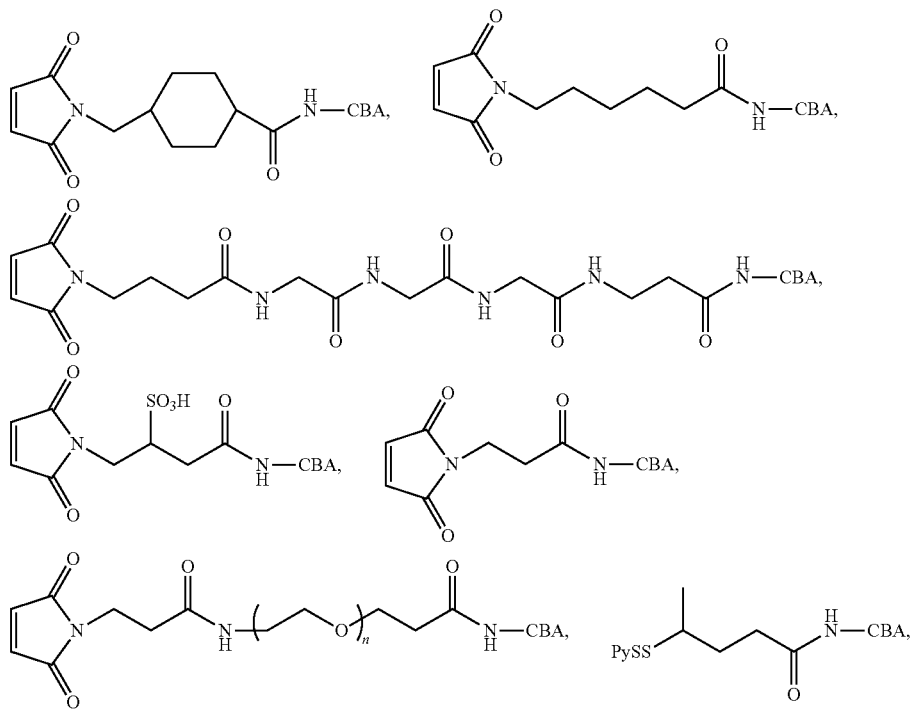

n = 2-20 (e.g., 2, 4, 6, 8, 10)

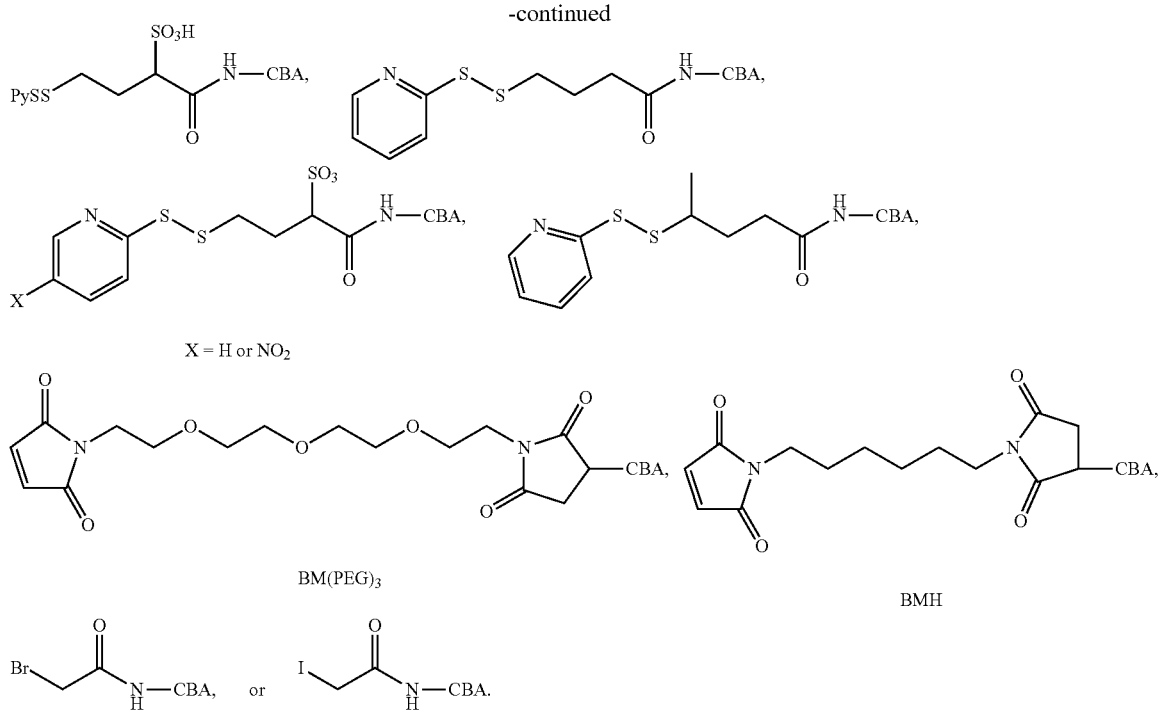

Figure 38:
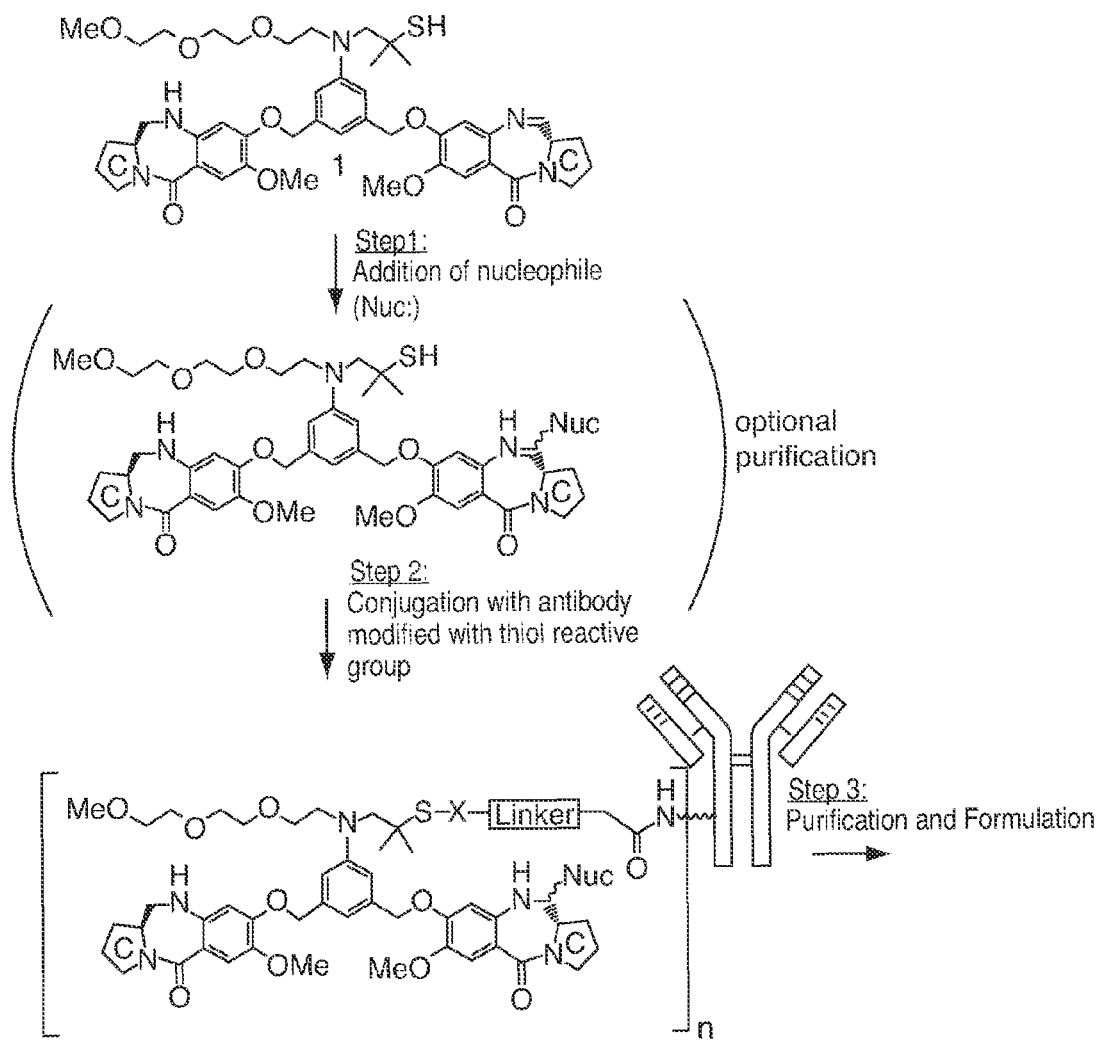

An exemplary reaction scheme is shown in FIG. 38, in which in "step one," an imine reactive reagent (shown in the reaction scheme as a nucleophile (Nuc:)) is added to a drug containing a thiol and allowed to react and form a modified drug bearing the thiol group. The modified drug is optionally purified to remove excess imine reactive reagent. In "step two," the antibody is modified with a linker containing a thiol reactive group X (maleimide, SSPy, vinyl sulfone, etc), and reacted with the modified drug bearing the thiol group at pH 6-9 to generate a stable disulfide or thioether bond between the drug and the antibody. In "step three," the side products (such as excess imine reactive reagent, the modified drug that does not react with the antibody, etc.) are removed and the conjugate is formulated. The number of the drug molecules conjugated to the antibody is equal to n, which can be from, for example, 1-10. The scheme is generally expected to apply to all compounds of formulas (V)-(VII).

A representative example of a two-step conjugation method is described in FIG. 30, wherein an antibody is first modified with a bifunctional crosslinking agent resulting in an antibody that possesses a desired number of linkers suitable for reaction with a dimer compound having a free thiol moiety. In this example the antibody huMy9-6 was first modified with SPDB to give an antibody with linkers containing the dithiopyridyl moiety. The modified antibody was then exposed to a free thiol, such as 5d, generating the desired conjugate huMy9-6-SPDB-5d. Additional suitable thiol reactive linkers that may be used in similar reactions are included in FIG. 30. The scheme is generally expected to apply to all compounds of formulas (V)-(VII).

The imine reactive reagent can be mixed with the drug bearing a thiol group in organic solvent (e.g., dimethylacetamide, dimethylformamide, dimethylsulfoxide, acetonitrile, ethanol, methanol, methylene chloride, chloroform, dioxane, or a mixture thereof) or a mixture of water (e.g., deionized water) and one or more organic solvents. When only organic solvent is used, the imine reactive reagent can be mixed with the drug at room temperature for 30 min or longer (for example, about 1 hour, about 2 hours, about 3 hours, about 4 hours, about 5 hours, about 10 hours, about 24 hours or until the reaction is complete). Preferably, the incubation/reaction time is about 0-4 hrs, or 1-3 hrs. The resulting mixture can be used immediately to react with the cell-binding agent (e.g., antibody) modified with a thiol-reactive group buffered at pH about 4 to about 9, preferably about 6 to about 9. Alternatively, the mixture can be frozen and stored, for example, at −20° C. or −80° C., and used later while maintaining its reactivity with the cell-binding agent (e.g., antibody). If a mixture of water and organic solvent(s) is used as a miscible co-solvent system (e.g., water and dimethylacetamide), the reaction mixture of drug and imine reactive reagent is used immediately or kept frozen until use after mixing to react with the cell-binding agent bearing a thiol-reactive group. If a mixture of water and organic solvent(s) is used as a non-miscible co-solvent system (e.g., water and methylene chloride), the drug and the imine reactive reagent are mixed for 10 min or longer (for example, about 30 mins, about 1 hour, about 2 hours, about 5 hours, about 10 hours, about 24 hours or until the reaction is complete), and the aqueous layer is collected, quantified for the drug and reactive thiol (e.g., by UV spectroscopy and Ellman's assay with DTNB (5,5'-dithiobis-(2-nitrobenzoic acid)) reagent) and added to the cell-binding agent (e.g., antibody) bearing a thiol-reactive group buffered at pH of about 4 to about 9, preferably about 6 to about 9.

In a second aspect, the present invention provides a method for preparing a conjugate comprising a cell-binding agent (CBA) conjugated to a cytotoxic compound with a linking group, the method comprising reacting the CBA with an imine-containing cytotoxic compound, an imine reactive reagent, and a bifunctional crosslinking agent comprising the linking group to form the conjugate, wherein:
the imine-containing cytotoxic compound is represented by one of the following formulae, or a pharmaceutically acceptable salt thereof:

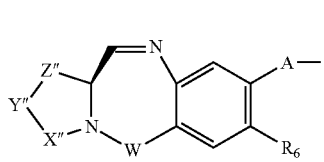 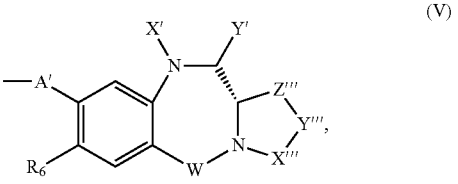

(V)

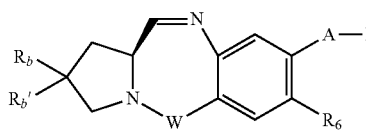 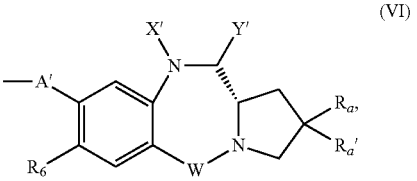

(VI)

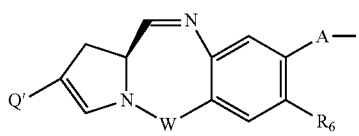 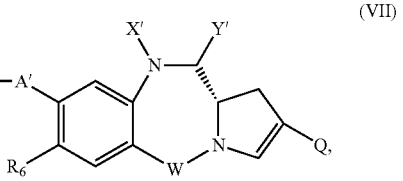

(VII)

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$^c$ is —H or a substituted or unsubstituted linear or branched alkyl having 1 to 4 carbon atoms;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, or halogen;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O, —(CH$_2$)$_{n'}$—, —NR'— or —S—;

Z" and Z'" are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R'', —NO$_2$, —NCO, —NR'COR'', —SR, a sulfoxide represented by —SOR', a sulfone represented by —SO$_2$R', a sulfonate —SO$_3$M, a sulfate —OSO$_3$M, a sulfonamide represented by SO$_2$NR'R'', cyano, an azido, —COR', —OCOR' or —OCONR'R'';

R$^{c'}$ is absent or selected from linear or branched alkyl, alkenyl or alkynyl having 1 to 5 carbon atoms; and wherein at least one of X', Y', R$_6$, R$^c$, L (e.g., through an optionally substituted group), Q, Q', Q$_2$ or Q$_2$' is bonded to the linking group in the conjugate.

In certain embodiments, the cell-binding agent (e.g., antibody) is contacted with a drug (e.g., the imine-containing cytotoxic compound) and an imine reactive reagent to form a first mixture; and the first mixture is then contacted with a bifunctional crosslinking agent to form the cell-binding agent-drug conjugate. Preferably, the bifunctional crosslinking agent is contacted with the first mixture immediately after the formation of the first mixture. Alternatively, the first mixture was held for a time interval (e.g., about 1-10 mins, about 10-30 mins, about 30 mins to 1 hr, about 1 to 5 hrs, about 5 to 24 hrs, or about 1 to 2 days) before it is contacted with a bifunctional crosslinking agent.

In certain embodiments, the method may further comprises purifying the conjugate.

Figure 40:
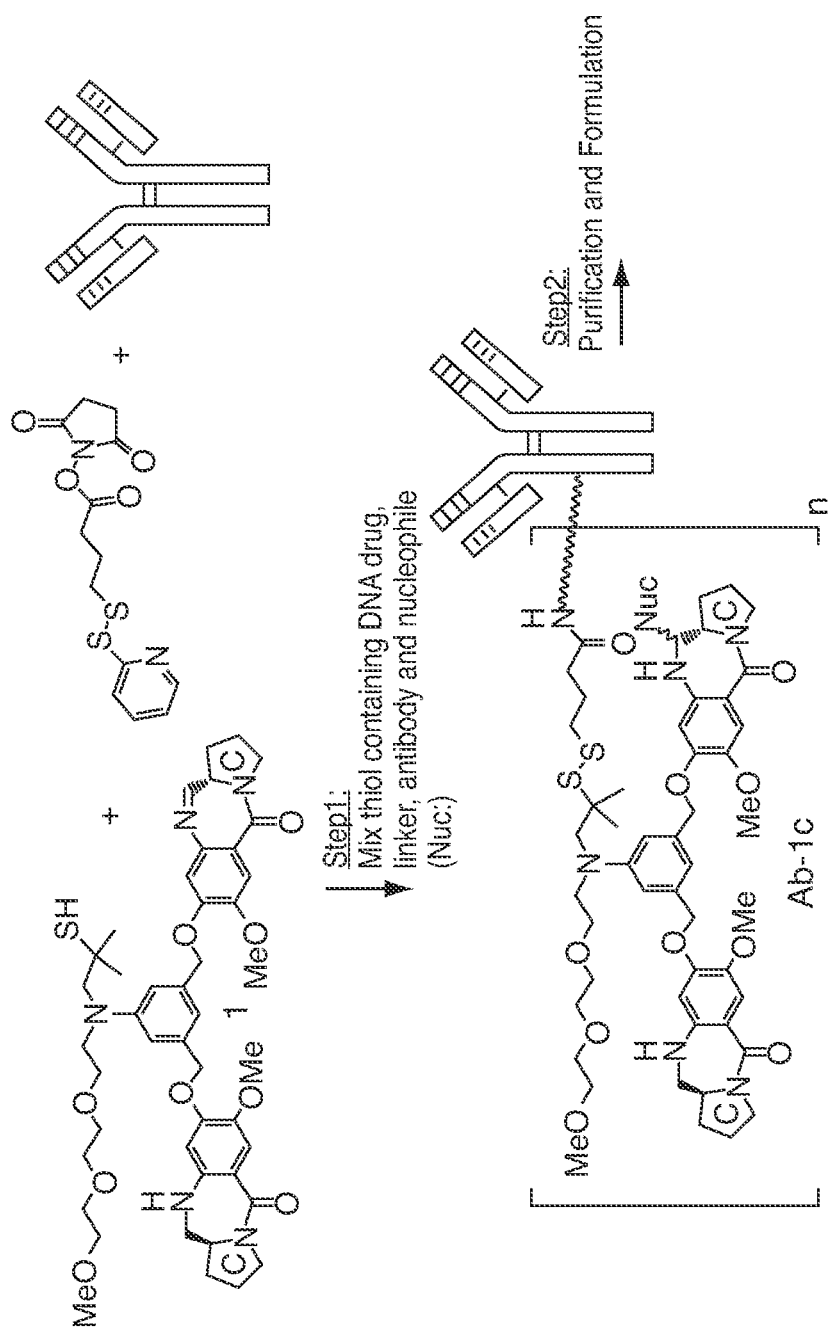

An exemplary reaction scheme is shown in FIG. 40, in which in "step 1," an imine reactive reagent (shown in the reaction scheme as a nucleophile (Nuc:)) is added to the CBA (e.g., an antibody), a drug containing a thiol, a bifunctional crosslinking agent containing both a thiol reactive group X (maleimide, SSPy, vinyl sulfone, etc) and a reactive ester group, and allow the reaction to proceed at pH 6-9 to generate a stable drug-antibody conjugate. In "step two," the side products (such as excess imine reactive reagent, the modified drug that does not react with the antibody, etc.) are removed and the conjugate is formulated. The number of the drug molecules conjugated to the antibody is equal to n, which can be from, for example, 1-10. The scheme is generally expected to apply to all compounds of formulas (V)-(VII).

In a third aspect, the present invention provides a method for preparing a conjugate comprising a cell-binding agent (CBA) conjugated to a cytotoxic compound with a linking group, the method comprising:

a) reacting a modified cytotoxic compound with a bifunctional crosslinking agent comprising the linking group, a group reactive with the CBA (such as a thiol group, a maleimide group, a haloacetamide group, or an amine group), and a group reactive with the modified cytotoxic compound, to form a second modified cytotoxic compound covalently bonded to a residue of the bifunctional crosslinking agent, wherein the residue comprises the linking group and the group reactive with the CBA;

wherein the modified cytotoxic compound is represented by one of the following formulas, or a pharmaceutically acceptable salt thereof:

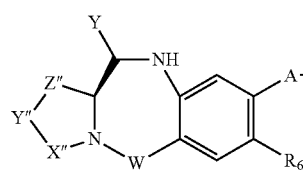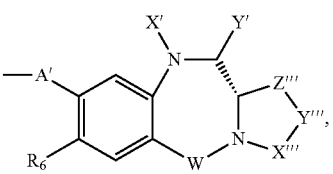

(V')

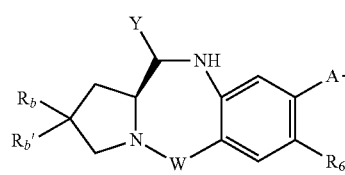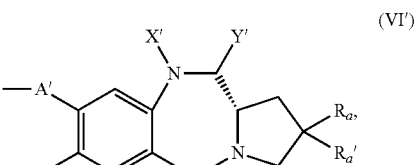

(VI')

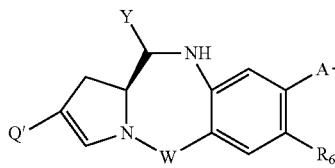
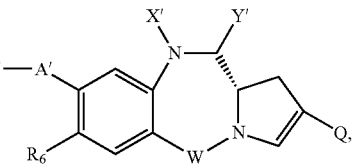

(VII')

wherein:
Y is a leaving group, and is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;
X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;
Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;
R$^c$ is —H or a substituted or unsubstituted linear or branched alkyl having 1 to 4 carbon atoms;
R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;
R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;
n is an integer from 1 to 24;
W is selected from C=O, C=S, CH$_2$, BH, SO and SO$_2$;
R$_6$ is —H, —R, —OR, —SR, —NR'R", —NO$_2$, or halogen;
A and A' are the same or different, and are independently selected from —O—, oxo (—C(=O)—), —CRR'O—, —CRR'—, —S—, —CRR'S—, —N(R$_5$)— and —CRR'N(R$_5$)—,
R$_5$ for each occurrence is independently —H or an optionally substituted linear or branched alkyl having 1 to 10 carbon atoms;
D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;
L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;
X" and X'" are the same or different, and are independently selected from —(CH$_2$)$_{n'}$—, —NR'—, —CO—, —BH—, —SO— or —SO$_2$—;
Y" and Y'" the same or different, and are independently selected from —O—, —(CH$_2$)$_{n'}$—, —NR'— or —S—;
Z" and Z'" are the same or different, and are independently selected from —(CH$_2$)$_{n'}$—, —CR$_7$R$_8$—, —NR$_9$—, —O—, and —S—;
n' is selected from 0, 1, 2 and 3;
R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;
R$_9$ is independently selected from —H, an optionally substituted linear, branched or cyclic alkyl having from 1 to 10 carbon atoms, a polyethylene glycol unit —(OCH$_2$CH$_2$)$_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$, and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH— unit;

Ar and Ar' are each independently absent or represent an aryl group;

$Q_2$ and $Q_2'$ are each independently selected from —H, a substituted or unsubstituted linear, branched or cyclic alkyl, alkenyl or alkynyl having from 1 to 10 carbon atoms, a polyethylene glycol unit —$R^c$—(OCH$_2$CH$_2$)$_n$—$R^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R";

$R^{c'}$ is absent or selected from linear or branched alkyl, alkenyl or alkynyl having 1 to 5 carbon atoms; and b) reacting the second modified cytotoxic compound with the CBA through the group reactive with the CBA, at a pH of about 4 to about 9, to form the conjugate, wherein at least one of X', Y', $R_6$, $R^c$, L (e.g., through an optionally substituted group), Q, Q', $Q_2$ or $Q_2'$ is bonded to the linking group in the conjugate.

In certain embodiments, the group reactive with the CBA is a thiol group, a maleimide group, a haloacetamide group, or an amine group.

In certain embodiments, the modified cytotoxic compound comprises a thiol group, and the group reactive with the modified cytotoxic compound is a thiol-reactive group.

In certain embodiments, the modified cytotoxic compound is produced by reacting an imine reactive reagent with an imine-containing cytotoxic compound in a reaction mixture, wherein the imine-containing cytotoxic compound comprises the thiol group and has one of the following formulas:

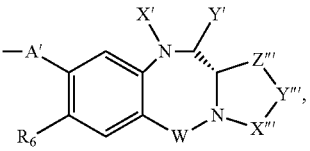
(V)

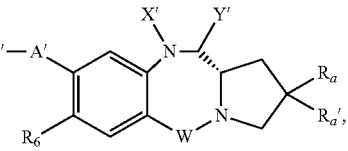
(VI)

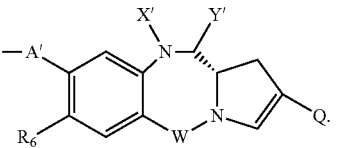
(VII)

In certain embodiments, the method may further comprises purifying the modified cytotoxic compound prior to step a).

In certain embodiments, the method may further comprises purifying the second modified cytotoxic compound prior to step b).

In certain embodiments, the reaction mixture is stored frozen before the frozen mixture is thawed and step a) is carried out.

In certain embodiments, the method may further comprises storing the reaction mixture of step a) frozen before thawing and before step b) is carried out.

In certain embodiments, the bifunctional crosslinking agent is bis-maleimidohexane or BMPEO.

Figure 41:
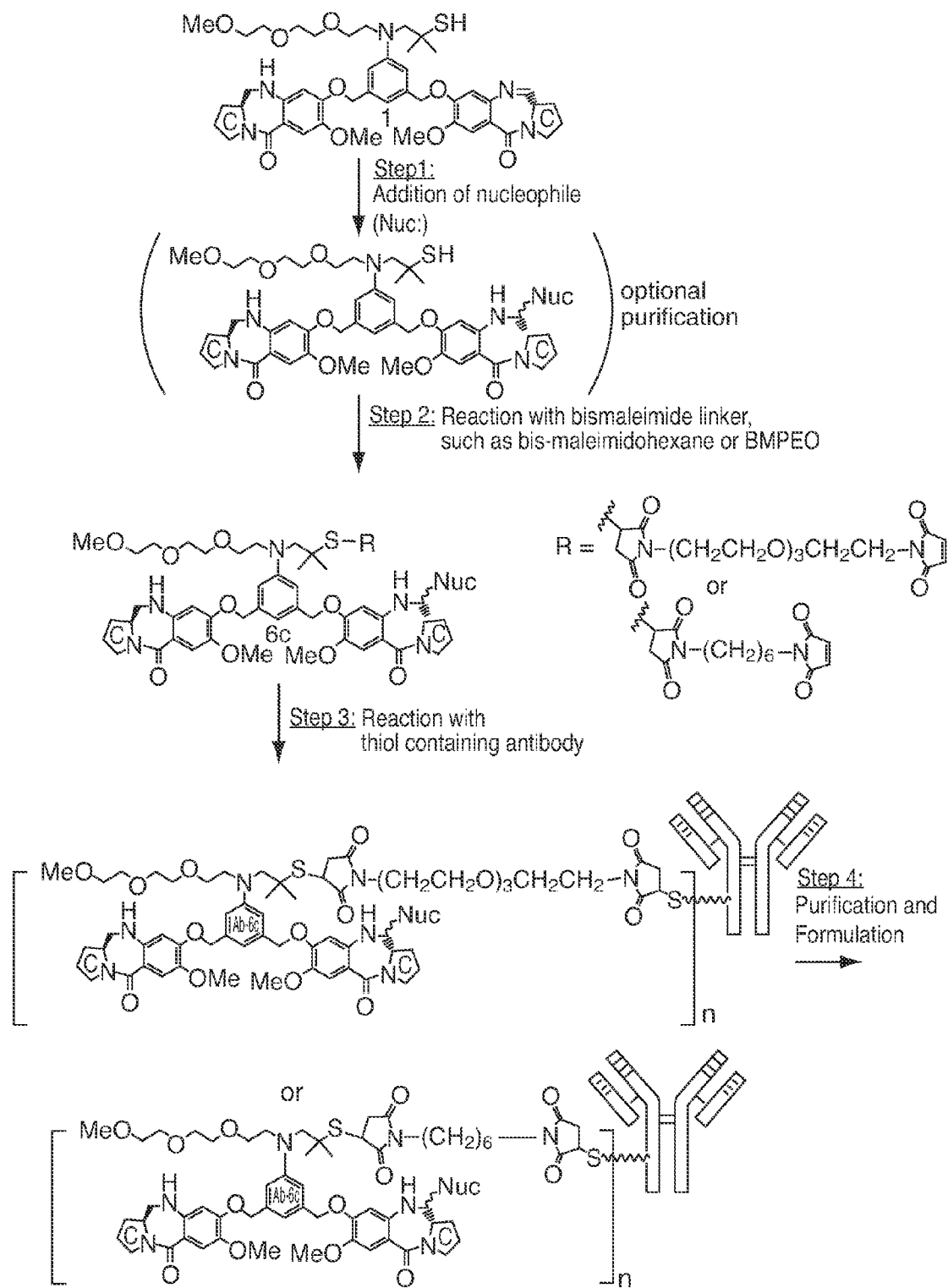

An exemplary reaction scheme is shown in FIG. 41, in which in "step 1," an imine reactive reagent (shown in the reaction scheme as a nucleophile (Nuc:)) is added to a cytotoxic compound containing a thiol. The resulting modified cytotoxic compound is optionally purified, before the modified cytotoxic compound is reacted in "step two" with a bifunctional crosslinking agent (such as a bismaleimidohexane or BMPEO) to produce a second modified drug bearing a thiol-reacting group. Then in "step three," a thiol-containing CBA (such as antibody) is added, and the reaction is allowed to proceed (at pH 6-9) to generate a stable drug-antibody conjugate. In "step four," the side products (such as excess imine reactive reagent, the modified drug that does not react with the antibody, etc.) are removed and the conjugate is formulated. The number of the drug molecules conjugated to the antibody is equal to n, which can be from, for example, 1-10. The scheme is generally expected to apply to all compounds of formulas (V)-(VII).

The imine reactive reagent can be mixed with the drug bearing a thiol-reactive group in organic solvent (e.g., dimethylacetamide, dimethylformamide, dimethylsulfoxide, acetonitrile, ethanol, methanol, methylene chloride, chloroform, dioxane, or a mixture thereof) or a mixture of water (e.g., deionized water) and one or more organic solvents. When only organic solvent is used, the imine reactive reagent can be mixed with the drug at room temperature for 30 min or longer (for example, about 1 hour, about 2 hours, about 3 hours, about 4 hours, about 5 hours, about 10 hours, about 24 hours or until the reaction is complete). Preferrably, the incubation/reaction time is about 0-4 hrs, or 1-3 hrs. The resulting mixture can be used immediately to react with the cell-binding agent (e.g., antibody) modified with a thiol-reactive group buffered at pH about 4 to about 9, preferably about 6 to about 9. Alternatively, the mixture can be frozen and stored, for example, at −20° C. or −80° C., and used later while maintaining its reactivity with the cell-binding agent (e.g., antibody). If a mixture of water and organic solvent(s) is used as a miscible co-solvent system (e.g., water and dimethylacetamide), the reaction mixture of the drug and the imine reactive reagent is used immediately after mixing or kept frozen until use to react with the cell-binding agent bearing a thiol-reactive group. If a mixture of water and organic solvent(s) is used as a non-miscible co-solvent system (e.g., water and methylene chloride), the drug and the imine reactive reagent are mixed for 10 min or longer (for example, about 30 mins, about 1 hour, about 2 hours, about 5 hours, about 10 hours, about 24 hours or until the reaction is complete), and the aqueous layer is collected, quantified for the drug (e.g., by UV spectroscopy) and added to the cell-binding agent (e.g., antibody) bearing a thiol group buffered at pH of about 4 to about 9, preferably about 6 to about 9.

In a fourth aspect, the present invention is directed to a method for preparing a conjugate comprising a cell-binding agent (CBA) conjugated to a cytotoxic compound with a linking group, the method comprising reacting a second modified cytotoxic compound with the CBA at a pH of about 4 to about 9, wherein the second modified cytotoxic compound has the structure of one of the following formulas, or a pharmaceutically acceptable salt thereof:

b) a group represented by:

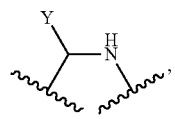

wherein:
Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester ($R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(\!=\!S)(OR^{k'})(S)(OH)$ or a salt thereof formed with a cation), hydroxamic acid ($R^{k'}C(\!=\!O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;
X' is selected from —H, an amine-protecting group, the linking group with the reactive group bonded thereto,

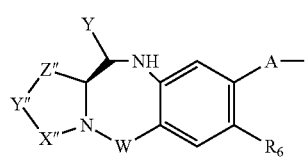 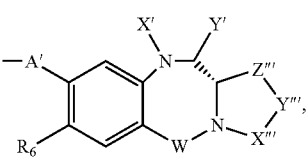 (Va')

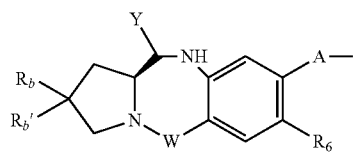 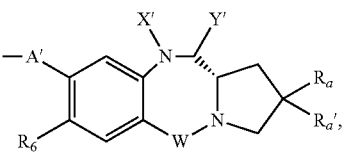 (VIa')

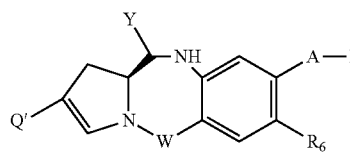 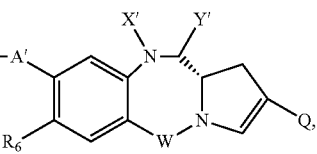 (VIIa')

said second modified cytotoxic compound comprising:
a) a residue of a bifunctional crosslinking agent bonded to the cytotoxic compound, and the residue comprises the linking group and a reactive group selected from a reactive ester and a thiol-reactive group, and, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group with the reactive group bonded thereto;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3- to 18-membered heterocyclic ring having 1 to 6 heteroatoms independently selected from O, S, N and P;

n is an integer from 1 to 24;

W is selected from C=O, C=S, $CH_2$, BH, SO and $SO_2$;

$R_6$ is —H, —R, —OR, —SR, —NR'R", —$NO_2$, halogen or the linking group with the reactive group bonded thereto;

A and A' are the same or different, and are independently selected from —O—, oxo (—C(=O)—), —CRR'O—, —CRR'—, —S—, —CRR'S—, —$NR_5$ and —CRR'N($R_5$)—;

$R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2$)$_n$—;

L is absent, the linking group with the reactive group bonded thereto, a polyethylene glycol unit (—$OCH_2CH_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto;

X" and X''' are the same or different, and are independently selected from —$(CH_2)_{n'}$—, —NR'—, —CO—, —BH—, —SO— or —$SO_2$—;

Y" and Y''' are the same or different, and are independently selected from —O—, —$(CH_2)_{n'}$—, —NR'— or —S—;

Z" and Z''' are the same or different, and are independently selected from —$(CH_2)_{n'}$—, —$CR_7R_8$—, —$NR_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1$'-Ar'-$Q_2$';

$Q_1$ and $Q_1$' are each independently absent, a linear, branched or cyclic alkyl from 1 to 6 carbon atoms or a —CH=CH unit;

Ar and Ar' are each independently absent, or represent an aryl group;

$Q_2$ and $Q_2$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)$NH_2$], —OR, —NR'R", —$NO_2$, —NCO, —NR'COR", —SR, a sulfoxide represented by —SOR', a sulfone represented by —$SO_2$R', a sulfonate —$SO_3$M, a sulfate —$OSO_3$M, a sulfonamide represented by $SO_2$NR'R", cyano, an azido, —COR', —OCOR' or —OCONR'R"; and $R^{c'}$ is absent or selected from linear or branched alkyl, alkenyl or alkynyl having 1 to 5 carbon atoms.

In certain embodiments, the second modified cytotoxic compound is produced by reacting an imine reactive reagent with an imine-containing cytotoxic compound bearing the linking group and the reactive group having the following structure:

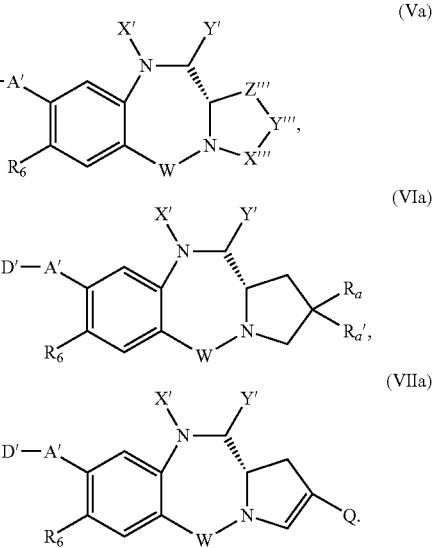

(Va)

(VIa)

(VIIa)

In certain embodiments, the method may further comprises purifying the second modified cytotoxic compound prior to reacting with the CBA.

In certain embodiments, the reactive ester may be selected from the group consisting of N-hydroxysuccinimide ester, N-hydroxy sulfosuccinimide ester, nitrophenyl ester, dinitrophenyl ester, tetrafluorophenyl ester, sulfo-tetrafluorophenyl ester, and pentafluorophenyl ester. Preferably, the reactive ester is N-hydroxysuccinimide ester.

In certain embodiments, the thiol-reactive group may be selected from the group consisting of maleimido, vinylpyridine, vinyl sulfone, vinyl sulfonamide, a haloacetyl-based group and a disulfide group.

In certain embodiments, the thiol-reactive group may be maleimido, haloacetamido or —$SSR^d$, wherein $R^d$ is a linear or branched alkyl having 1 to 4 carbon atoms, phenyl, nitrophenyl, dinitrophenyl, carboxynitrophenyl, pyridyl, 2-nitropyridyl, 4-nitropyridyl, or 3-carboxy-4-nitropyridyl.

Figure 37:
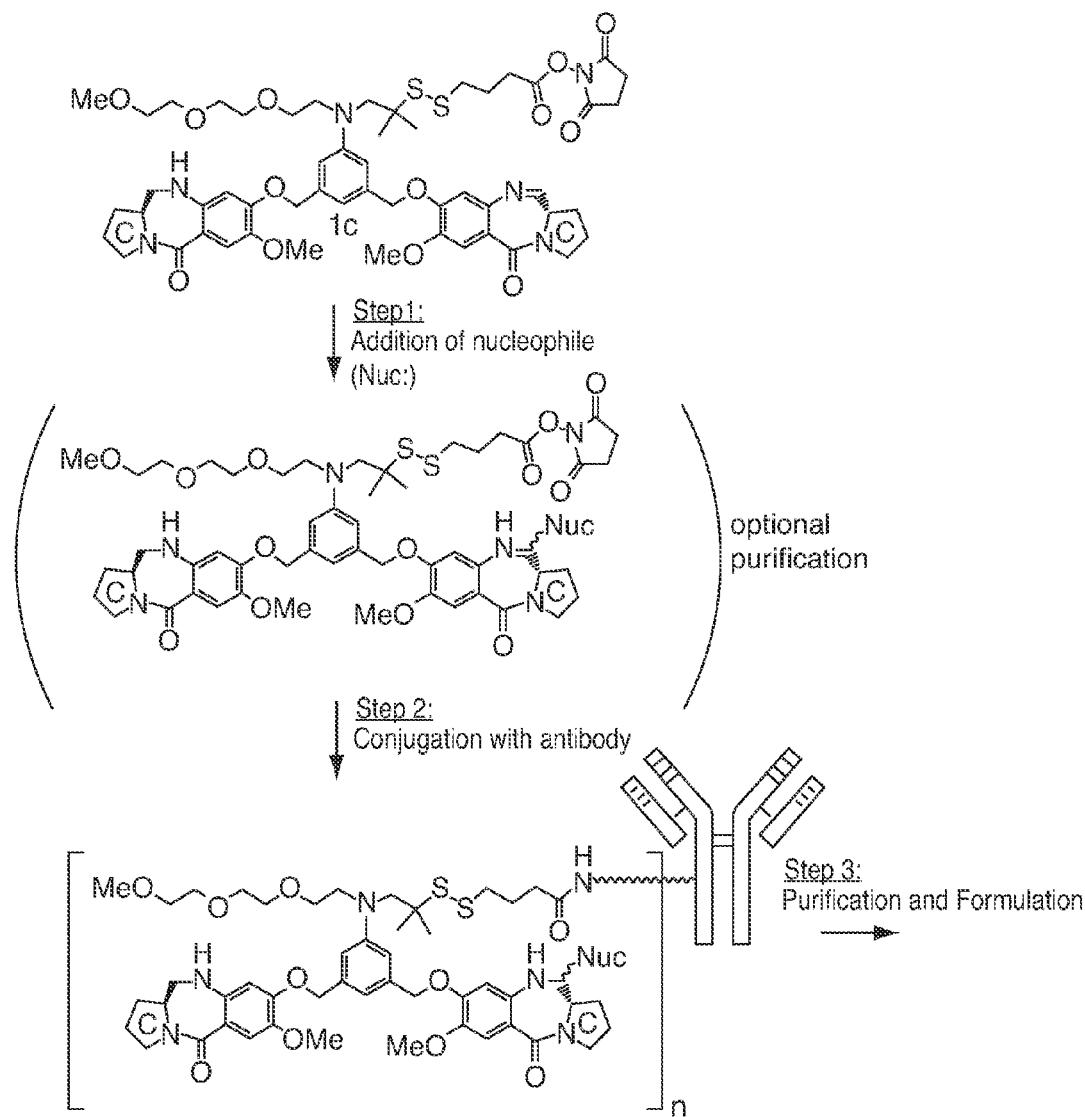
FIGS. 37-41 show exemplary methods of the present invention for preparing a cell-binding agent-drug conjugate. The "C" ring generically representing the common structures of formulas (V)-(VII).

An exemplary reaction scheme is shown in FIG. 37, in which in "step one," an imine reactive reagent (shown in the reaction scheme as a nucleophile (Nuc:)) is added to the drug containing an reactive ester (1c) and allowed to react to form a modified drug. The modified drug can be optionally purified to remove excess imine reactive reagent. In "step two," the modified drug with a reactive ester is reacted with an antibody buffered at pH 6-9. In "step three," the side products (such as excess imine reactive reagent, modified drug that does not react with the antibody, etc.) are removed, and the conjugate is formulated. The number of the drug molecules conjugated to the antibody is equal to n, which can be from, for example, 1 to 10. The scheme is generally expected to apply to all compounds of formulas (V)-(VII).

Figure 39:
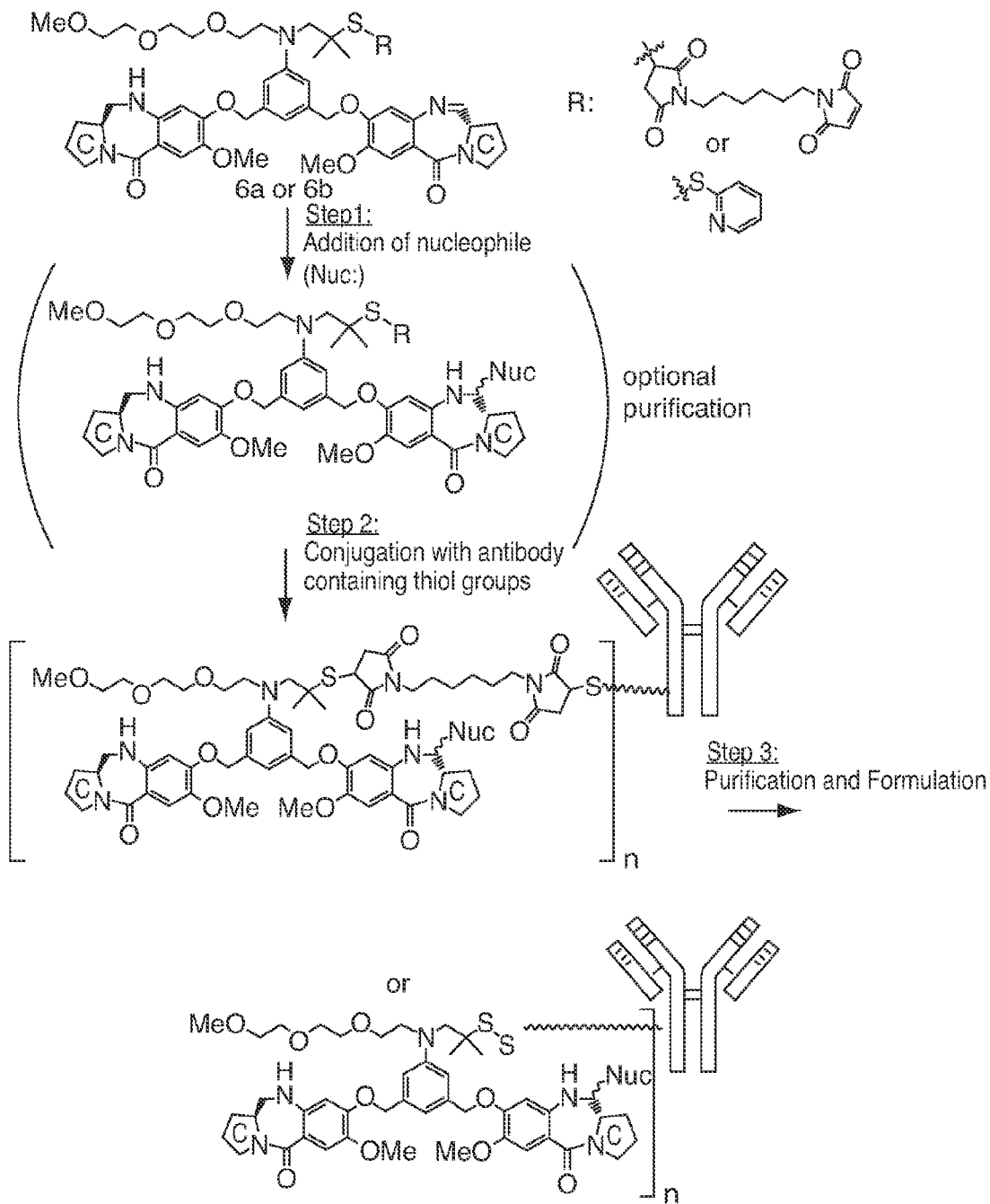

Another reaction scheme depicting an exemplary method of the present invention is shown in FIG. 39. In "step one," an imine reactive regent is added to the drug containing a thiol-reactive group (where R is maleimide group, SSPy, etc.) and allowed to react and form a modified drug. The modified drug is optionally purified to remove excess imine reactive reagent. In "step two," the modified drug is reacted with an antibody containing a reactive thiol to form an antibody-drug conjugate having antibody covalently linked to the drug through a stable disulfide or thioether bond.

Antibodies with reactive thiol group can be generated by methods described herein, for example, by reducing interchain disulfides, genetically encoding cysteine, or modifying antibody with linkers containing thiols or chemically masked thiols. In "step three," the drug which does not react with the antibody is removed and the conjugate is formulated. The number of the drug molecules conjugated to the antibody is equal to n, which can be from, for example, 1-10. The scheme is generally expected to apply to all compounds of formulas (V)-(VII).

The imine reactive reagent can be mixed with the drug bearing an activated ester (e.g., N-hydroxysuccinimidyl ester, pentafluorophenol ester, sulfo N-hydroxysuccinimidyl ester) in an organic solvent (e.g., dimethyl acetamide, ethanol, methylene chloride, chloroform, dioxane, or a mixture thereof) or a mixture of water (e.g., deionized water) and one or more organic solvents. When only organic solvent is used, the imine reactive reagent can be mixed with the drug at a temperature of 0 to 100° C., preferably at a temperature of 0 to 30° C., more preferably at room temperature for 5 min or longer (for example, about 30 min, 1 hour, about 2 hours, about 3 hours, about 4 hours, about 5 hours, about 10 hours, about 24 hours or until the reaction is complete). Preferably, the incubation/reaction time is about 0-4 hrs, or 1-3 hrs. The resulting reaction mixture can be used immediately to react with the cell-binding agent (e.g., antibody) buffered in pH of about 4 to about 9, preferably about 6 to about 9. Alternatively, the reaction mixture can be frozen and stored, for example, at about −20° C. or −80° C. and used later while maintaining its reactivity with the antibody. Preferably, no purification of intermediate products is required. When a mixture of water and organic solvent is used as a miscible co-solvent system (e.g., water and dimethylacetamide), the drug and imine reaction mixture is used immediately after mixing, or kept frozen until use, to react with the cell-binding agent (e.g., antibody). When a mixture of water and organic solvent is used as a non-miscible co-solvent system (e.g., water and methylene chloride), the drug and the imine reactive reagent are mixed for 10 min or longer, and the aqueous layer is collected, quantified for the drug and added to the cell-binding agent (e.g., antibody) buffered at pH about 4 to about 9, preferably about 6 to about 9.

In any of the above aspects, a suitable amount of the imine reactive reagent can be used. For example, about 0.1 to about 30 molar equivalents of the imine reactive reagent to the drug can be used. Preferably, about 1 to about 10 molar equivalents, more preferably, about 1 to about 5 molar equivalents, and even more preferably about 3 to about 5 molar equivalents of the imine reactive reagent can be used.

Using this general procedure, in any of the above aspects, any of the following imine reactive reagent can be used: sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxylamine e.g., $NH_2OH$), hydrazine (e.g., $NH_2NH_2$), $NH_2O-R^i$, $R^{i'}NH-R^i$, $NH_2-R^i$), $NH_2-CO-NH_2$, $NH_2-C(=S)-NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate ($P(=S)(OR^k)(SH)(OH)$ or a salt thereof formed with a cation), hydroxamic acid ($R^kC(=O)NHOH$ or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-Na^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from $-N(R^j)_2$, $-CO_2H$, $-SO_3H$, and $-PO_3H$; $R^i$ and can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as $Na^+$ or $K^+$.

Preferably, the imine reactive reagent is selected from sulfites (e.g., $NaHSO_3$ or $KHSO_3$), hydroxylamine, hydrazine and urea. More preferably, the imine reactive reagent is $NaHSO_3$ or $KHSO_3$.

In one embodiment, the modified drugs described in any of the above aspects are purified before reacting with a cell-binding agent. Any suitable methods known in the art can be used for purifying the modified drug. For example, the modified drug can be purified by column chromatography (e.g., silica gel chromatography) or HPLC.

In another embodiment, the cell-binding agent-drug conjugate prepared according to any of the aspects above is purified by tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Any suitable TFF systems may be utilized, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized. Preferred adsorptive chromatography resins include resins for hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.), where the cell binding agent is an antibody, and lectin affinity resins, e.g. Lentil Lectin Sepharose resin (GE Healthcare, Piscataway, N.J.), where the cell binding agent bears appropriate lectin binding sites. Alternatively an antibody specific to the cell binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-absorptive chromatography resins can be used in the methods of the present invention. Examples of suitable chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Cytotoxic Compounds (Drugs) for Producing CBA-Drug Conjugates Using the Methods of the Invention Drugs Bearing a Linking Moiety Drugs that can be used in the present methods include compounds described in US2010/0316656, US 2010/003641, US2010/0203007, all of which are incorporated herein by reference.

In certain other embodiments, cytotoxic compounds that can be conjugated with cell-binding agents via a linking group do not comprise the linking group. Instead, a bifunctional cross-linking reagent (comprising the linking group) may be required to conjugate the linkerless cytotoxic compound with the CBA through the linker group.

Thus in the alternative first specific embodiment, a drug covalently connected to a linking group with a reactive group bonded thereto, which can be used in the methods of the present invention (such as in the 1-step reagent method as described in the fourth aspect of the invention above), or which may be an intermediate product of the methods of the invention (such as the method described in the third aspect of the invention), is a cytotoxic compound bearing a reactive group, such as a reactive ester or a thiol-reactive group (collectively "the reactive group"), comprising a linking group with the reactive group bonded thereto, capable of covalently linking the cytotoxic compound to the CBA, wherein the cytotoxic compound is represented by any one of the following formulas:

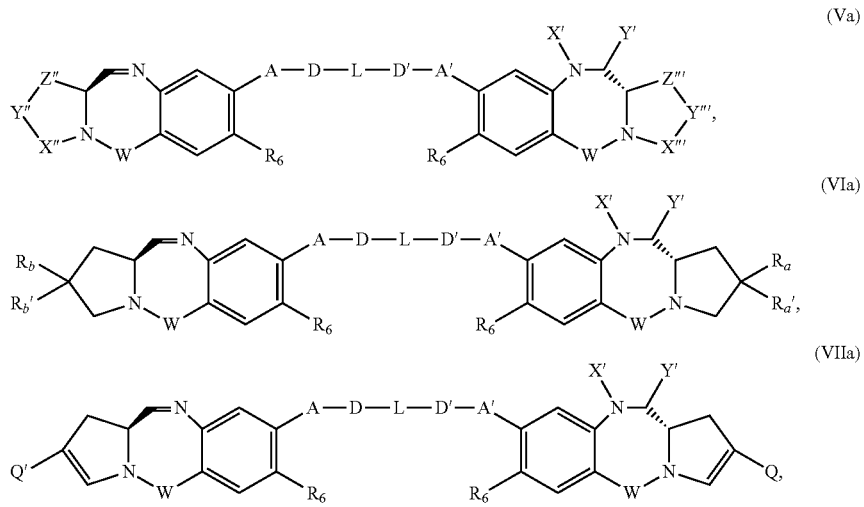

(Va)

(VIa)

(VIIa)

or a pharmaceutically acceptable salt thereof. Upon reacting with the imine reactive reagent, the cytotoxic compounds may be represented by any one of the following formulas, or a pharmaceutically acceptable salt thereof:

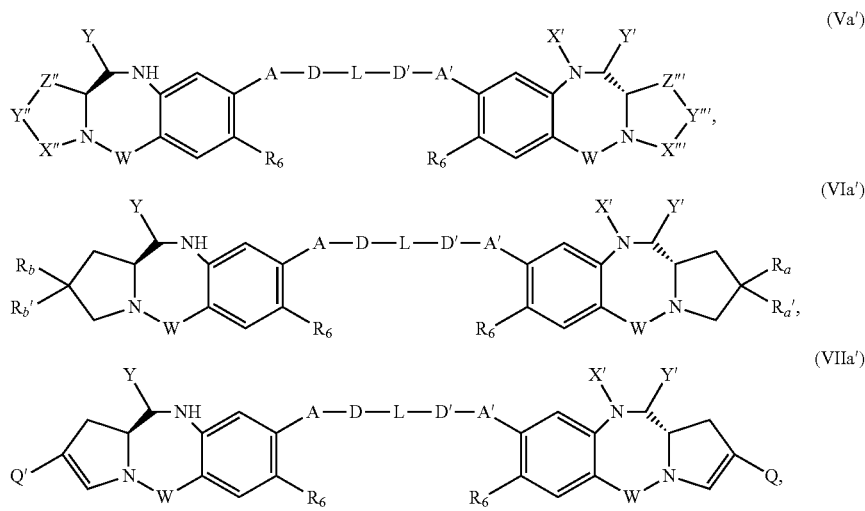

(Va')

(VIa')

(VIIa')

wherein:
Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri- and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS$ $(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from $-H$, $-OH$, an amine-protecting group, the linking group with the reactive group bonded thereto, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group with the reactive group bonded thereto;

$R_6$ is —H, —R, —OR, —SR, —NR'R", —NO$_2$, halogen or the linking group with the reactive group bonded thereto;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

n is an integer from 1 to 24;

W is selected from C=O, C=S, CH$_2$, BH, SO and SO$_2$;

A and A' are the same or different, and are independently selected from —O—, oxo (—C(=O)—), —CRR'O—, —CRR'—, —S—, —CRR'S—, —NR$_5$ and —CRR'N(R$_5$)—;

$R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O, —(CH$_2$)$_{n'}$—, —NR'— or —S—;

Z" and Z'" are the same or different, and are independently selected from —(CH$_2$)$_{n'}$—, —CR$_7$R$_8$—, —NR$_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —(OCH$_2$CH$_2$)$_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent, or represent an aryl group;

Q$_2$ and Q$_2$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and $R^{c'}$ is absent or selected from linear or branched alkyl, alkenyl or alkynyl having 1 to 5 carbon atoms.

In certain embodiments,

X' is selected from the group consisting of —H, —OH, an optionally substituted linear, branched or cyclic alkyl, alkenyl or alkynyl having from 1 to 10 carbon atoms, phenyl, the linking group with the reactive group bonded thereto, and an amine-protecting group. Preferably, X' is —H, —OH, -Me or the linking group with the reactive group bonded thereto. More preferably, X' is —H;

Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or oxo.

More preferably, Y' is —H;
W is C=O;
$R_6$ is —OR$^c$ or —SR$^c$, wherein R$^c$ is —H, a linear or branched alkyl having 1 to 4 carbon atoms. Preferably, $R_6$ is —OMe or —SMe. Even more preferably, $R_6$ is —OMe;
R, for each occurrence, is independently selected from the group consisting of —H, an optionally substituted linear, branched or cyclic alkyl, alkenyl or alkynyl having from 1 to 10 carbon atoms or phenyl;
R' and R" are the same or different, and are independently selected from —H, —OH, —OR, an optionally substituted linear, branched or cyclic alkyl, alkenyl or alkynyl having from 1 to 10 carbon atoms or phenyl;
A and A' are the same or different, and are selected from —O—, —S—, —NR$_5$ and oxo (C=O). Preferably, A and A' are the same or different, and are selected from —O— and —S—. More preferably, A and A' are —O—;
D and D' are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more (e.g., 2, 3, 4, 5, 6 or more) substituents independently selected from the group consisting of halogen, —OR, —NR'COR", —SR, and —COR';

Preferably, D and D' are the same or different, and are independently selected from linear, branched or cyclic alkyl, alkenyl or alkynyl having from 1 to 10 carbon atoms. More preferably, D and D' are linear or branched alkyl bearing 1 to 4 carbon atoms. Still more preferably, D and D' are the same or different, and are selected from a linear alkyl having 1 to 4 carbon atoms;
L is absent, or is selected from an optionally substituted phenyl group and an optionally substituted pyridyl group, wherein the phenyl and the pyridyl group bears the linking group with the reactive group bonded thereto, or L is an amine group bearing the linking group with the reactive group bonded thereto (i.e., —N(linking group)-), or L is a linear; branched or cyclic alkyl or alkenyl having 1 to 6 carbon atoms and bearing the linking group with the reactive group bonded thereto.

In an alternative second specific embodiment, for cytotoxic dimers (Va')-(VIIa'), the variables are as described below:
W is C=O;
$R_6$ is —OMe;
X' is —H;
Y' is —H;
A and A' are —O—; and the remainder of the variables are as described in the alternative first specific embodiment.

In an alternative third specific embodiment, the cytotoxic dimers (bonded to the linking group with the reactive group attached thereto) are represented by the following formulas:

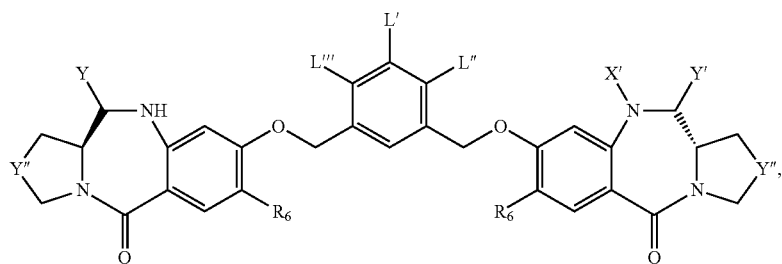

(VAa')

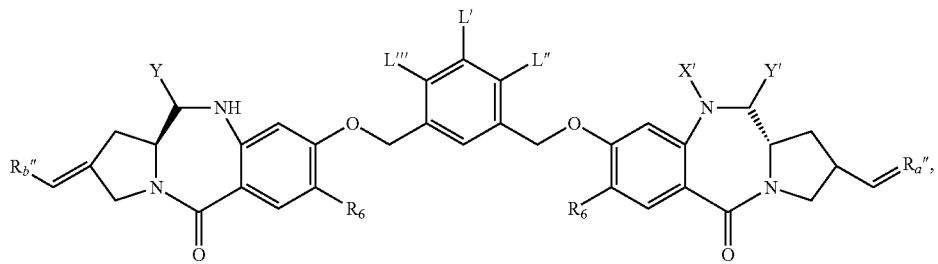

(VIAa')

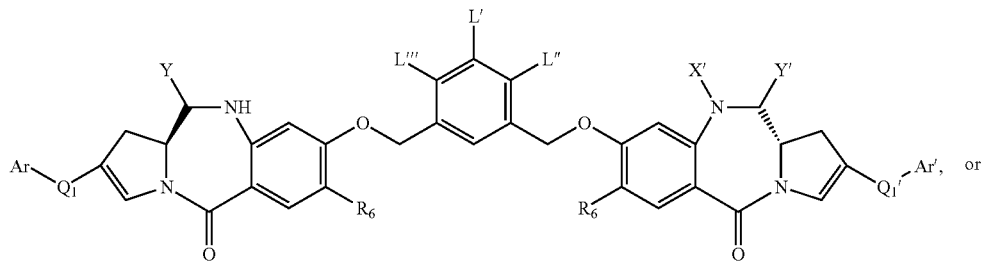

(VIIAa')

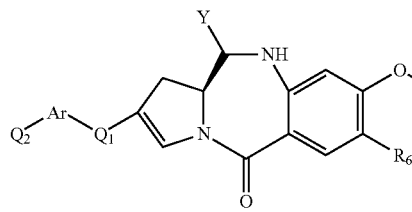 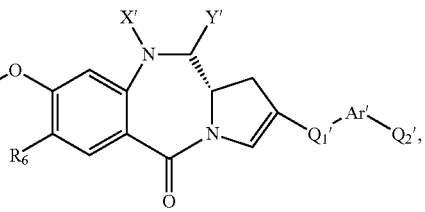

(VIIA2a')

wherein:
L', L", and L'" are the same or different, and are independently selected from —H, an optionally substituted linear, branched or cyclic alkyl, alkenyl or alkynyl having from 1 to 10 carbon atoms, a polyethylene glycol unit —$(OCH_2CH_2)_n$—$R^c$, halogen, guanidinium [—$NH(C=NH)NH_2$], —OR, —NR'R", —$NO_2$, —NR'COR", —SR, a sulfoxide represented by —SOR', a sulfone represented by —$SO_2R'$, a sulfonate —$SO_3^-M^+$, a sulfate —$OSO_3^+M^-$, a sulfonamide represented by —$SO_2NR'R$", cyano, an azido, —COR', —OCOR', —OCONR'R" and the linking group with the reactive group bonded thereto, provided only one of L', L" and L'" is the linking group with the reactive group bonded thereto; preferably, L' is the linking group with the reactive group bonded thereto. Alternatively, one of L', L", or L'" is the linking group with the reactive group bonded thereto, while the others are —H. More preferably, L' is the linking group with the reactive group bonded thereto, and L" and L'" are —H;

$R_a$" and $R_b$" are the same or different, and are selected from —H and -Me;

M is —H or a pharmaceutically acceptable cation;

Y" is O, S or NR'; preferably, Y" is O; and, one of $Q_2$ and $Q_2'$ is selected from —H, —R, —OR, —NR'R", —NR'(C=O)OR", —SR, and —$NO_2$, the other is the linking group with the reactive group bonded thereto.

In certain embodiments,

X' is selected from the group consisting of —H, —OH, a substituted or unsubstituted linear, branched or cyclic alkyl, alkenyl or alkynyl having from 1 to 10 carbon atoms, phenyl, and an amine-protecting group. Preferably, X' is —H, —OH or -Me. More preferably, X' is —H;

Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or -Me. More preferably Y' is —H;

$R_6$ is —$OR^c$ or —$SR^c$. Preferably, $R_6$ is —OMe or —SMe. Even more preferably, $R_6$ is —OMe;

A and A' are selected from —O— and —S—. Preferably, A and A' are —O—;

R is —H, an optionally substituted linear, branched or cyclic alkyl, alkenyl or alkynyl having from 1 to 10 carbon atoms or a PEG group $(CH_2CH_2O)_n$—$R^c$;

n is an integer from 1 to 24; and, $R^c$ is a linear or branched alkyl having 1 to 4 carbon atoms;

R' and R" are the same or different, and are selected from —H, —OH, —OR, —$NRR^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —$(CH_2CH_2O)_n$—$R^c$, wherein n is an integer from 1 to 24, preferably n is 2, 4 or 8; and $R^{g'}$ is —H, an optionally substituted linear, branched or cyclic alkyl, alkenyl or alkynyl having from 1 to 10 carbon atoms or a PEG group $(CH_2CH_2O)_n$—$R^c$, and the remainder of the variables are as described in the alternative first specific embodiment.

In certain embodiments, $Q_1$ and $Q_1'$ are absent; Ar and Ar' are an optionally substituted phenyl.

In certain embodiments, $R_a$" and $R_b$" are both —H or both Me.

In an alternative fourth specific embodiment, L' in formula (VAa'), (VIAa') or (VIIAa'), or one of $Q_2$ and $Q_2'$ in formula (VIIA2a') is represented by the following formula:

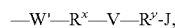

wherein:

W' and V are the same or different, and are each independently absent, or selected from —$CR^eR^{e'}$—, —O—, —O—C(=O)—, —C(=O)—O—, —S—, —SO—, —$SO_2$—, —$CH_2$—S—, —$CH_2O$—, —$CH_2NR^e$—, —O—(C=O)O—, —O—(C=O)N($R^e$)—, —N($R^e$)—, —N($R^e$)—C(=O)—, —C(=O)—N($R^e$)—, —N($R^e$)—C(=O)O—, —N(C(=O)$R^e$)C(=O)—, —N(C(=O)$R^e$)—, —(O—$CH_2$—$CH_2$)$_n$—, —SS—, or —C(=O)—, or an amino acid, or a peptide having 2 to 8 amino acids;

$R^x$ and $R^y$ are the same or different, and are each independently absent or an optionally substituted linear, branched or cyclic alkyl, alkenyl or alkynyl having 1 to 10 carbon atoms, an aryl bearing 6 to 10 carbon atoms or a 3- to 8-membered heterocyclic ring bearing 1 to 3 heteroatoms selected from O, N or S;

$R^e$ and $R^{e'}$ are the same or different, and are selected from —H, a linear, branched or cyclic alkyl, alkenyl or alkynyl having 1 to 10 carbon atoms or —$(CH_2$—$CH_2$—$O)_n$—$R^k$, wherein $R^k$ is a —H, a linear, branched cyclic alkyl having 1 to 6 carbon atoms, optionally bearing a secondary amino (e.g., —$NHR^{101}$) or tertiary amino (—$NR^{101}R^{102}$) group or a 5- or 6-membered nitrogen containing heterocycle, such as piperidine or morpholine, wherein $R^{101}$ and $R^{102}$ are each independently a linear, branched, or cyclic alkyl, alkenyl or alkynyl having 1 to 10 carbon atoms; preferably, $R^{101}$ and $R^{102}$ are each independently a linear or branched alkyl having 1 to 6 carbon atoms;

n is an integer from 1 to 24;

J comprises the reactive group bonded thereto, and is selected from a maleimide, a haloacetamido, —SH, —$SSR^d$, —$CH_2SH$, —CH(Me)SH, —$C(Me)_2SH$, and —COE, wherein —COE represents a reactive ester selected from, but not limited to, N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester, and wherein $R^{c1}$ is —H or a substituted or unsubstituted linear or branched alkyl having 1 to 4 carbon atoms, and, $R^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl).

Preferably, J is —SH, —SSR$^d$, a maleimide, or a N-hydroxysuccinimide ester.

Preferably, $R^{e'}$ is —H or -Me; $R^e$ is a linear or branched alkyl having 1 to 6 carbon atoms or —(CH$_2$—CH$_2$—O)$_n$—R$^k$; n is an integer from 2 to 8; preferably $R^k$ is —H, -Me or —CH$_2$CH$_2$—NMe$_2$, and the remainder of the variables are as described above in the alternative third specific embodiment.

In another preferred embodiment, V is an amino acid or a peptide having 2 to 8 amino acids. More preferably, V is valine-citrulline, gly-gly-gly or ala-leu-ala-leu.

In another preferred embodiment,
W' is absent, —CR$^e$R$^{e'}$—, —O—, —O—C(=O)—, —S—, —CH$_2$—S—, —O—(C=O)O—, —O—(C=O)N(R$^e$)—, —N(R$^e$)—, —N(R$^e$)—C(=O)—, —N(R$^e$)—C(=O)O—, or —C(=O)—;

$R^{e'}$ is —H or a linear or branched alkyl having 1 to 4 carbon atoms;

$R^e$ is H, a linear, branched or cyclic alkyl, alkenyl or alkynyl having 1 to 10 carbon atoms or —(CH$_2$—CH$_2$—O)$_n$—R$^c$;

$R^x$ is absent or an optionally substituted linear, branched or cyclic alkyl, alkenyl or alkynyl having 1 to 10 carbon atoms;

V is absent, —(CH$_2$—CH$_2$—O)$_n$—, —O—, —O—C(=O)—, —S—, —O—(C=O)O—, —O—(C=O)N(R$^e$)—, —N(R$^e$)—, —N(R$^e$)—C(=O)—, —N(R$^e$)—C(=O)O—, —C(=O)—, an amino acid, or a peptide having 2 to 8 amino acids;

$R^y$ is absent or a linear, branched or cyclic alkyl having 1 to 10 carbon atoms;

n is an integer from 1 to 24.

In another preferred embodiment, W' is —O—, —N(R$^e$)— or —N(R$^e$)—C(=O)—; $R^e$ is —H, a linear or branched alkyl having 1 to 4 carbon atoms, or —(CH$_2$—CH$_2$—O)$_n$—R$^k$; $R^x$ is a linear or branched alkyl having 1 to 6 carbon atoms; V is absent, —(O—CH$_2$—CH$_2$)$_n$—, —C(=O)—NH—, —S—, —NH—C(=O)—; $R^y$ is absent or a linear or branched alkyl having 1 to 4 carbon atoms; and J is —SH, —SSR$^d$ or —COE (preferably, N-hydroxysuccinimide ester). The remainder of the variables is as described in the alternative fourth specific embodiment.

In another preferred embodiment, W' is —O—, —N(R$^e$)— or —N(R$^e$)—C(=O)—; $R^e$ is H, -Me, or —(CH$_2$—CH$_2$—O)$_n$-Me; n is an integer from 2 to 6; $R^x$ is linear or branched alkyl bearing 1 to 6 carbon atoms; V and $R^y$ are absent; and J is —COE, preferably N-hydroxysuccinimide ester.

In an alternative fifth specific embodiment, L' in formula (VAa'), (VIAa') or (VIIAa'), or one of Q$_2$ and Q$_2$' in formula (VIIA2a') is represented by the following formula:

—W'—[CR$_{1''}$R$_{2''}$]$_a$—V—[Cy]$_{0-1}$—[CR$_{3''}$R$_{4''}$]$_b$—COE, wherein:

R$_{1''}$, R$_{2''}$, and R$_{3''}$ are each independently —H or -Me;

R$_{4''}$ is —H, -Me, —SO$_3$H, or —SO$_3$$^-$M$^+$, wherein M$^+$ is a pharmaceutically acceptable cation;

a is an integers from 0-2, b is an integer from 0-3; and,

Cy is an optionally substituted 5-membered heterocyclic ring bearing an N heteroatom, preferably Cy is

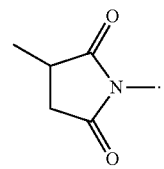

In certain embodiments, such as in the alternative fourth or the alternative fifth specific embodiments, W' is —N(R$^e$)—.

In certain embodiments, such as in the alternative fourth or the alternative fifth specific embodiments, $R^e$ is —(CH$_2$—CH$_2$—O)$_{2-6}$—R$^k$, wherein $R^k$ is a —H, a linear, branched cyclic alkyl having 1 to 6 carbon atoms.

In certain embodiments, such as in the alternative fourth or the alternative fifth specific embodiments, V is —S— or —SS—.

In an alternative sixth specific embodiment, L' in formula (VAa'), (VIAa') or (VIIAa'), or one of Q$_2$ and Q$_2$' in formula (VIIA2a'), such as in the alternative fourth and alternative fifth specific embodiment, is represented by the following formula:

—NR$^e$—[CR$_{1''}$R$_{2''}$]$_a$—S—[CR$_{3''}$R$_{4''}$]$_b$—COE.

In certain embodiments, the cytotoxic compound bonded to the linking group with the reactive group attached thereto, as in the alternative 4th, 5th, and 6th specific embodiments, is:

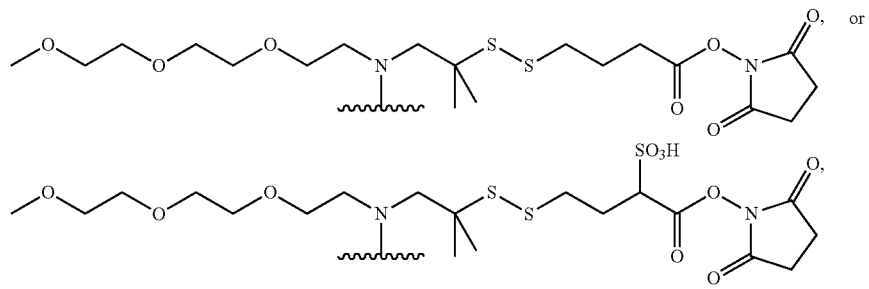

wherein Y is —H or —SO$_3$M (e.g., Y is —SO$_3$M), and M is —H or a pharmaceutically acceptable cation.

In an alternative seventh specific embodiment, L' in formula (VAa'), (VIAa') or (VIIAa'), or one of Q$_2$ and Q$_2$' in formula (VIIA2a'), such as in the alternative fourth, fifth, or sixth specific embodiments, is represented by the following formula:

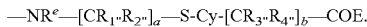
—NR$^e$—[CR$_1$"R$_2$"]$_a$—S-Cy-[CR$_3$"R$_4$"]$_b$—COE.

In certain embodiments, L' in formula (VAa'), (VIAa') or (VIIAa'), or one of Q$_2$ and Q$_2$' in formula (VIIA2a'), as in the alternative 4th, 5th, and 7th specific embodiments, is:

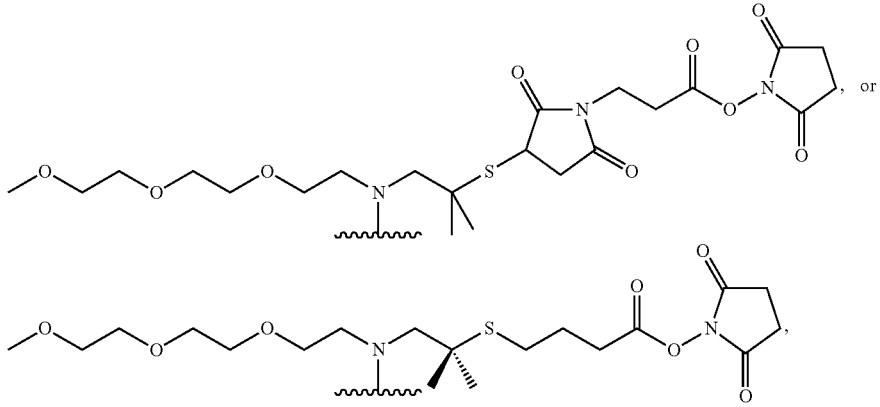

wherein Y is —H or —SO$_3$M (e.g., Y is —SO$_3$M), and M is —H or a pharmaceutically acceptable cation.

In an alternative eighth specific embodiment, L' in formula (VAa'), (VIAa') or (VIIAa'), or one of Q$_2$ and Q$_2$' in formula (VIIA2a') is represented by the following formula:

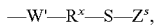
—W'—R$^x$—S—Z$^s$, wherein:
W' is absent, or selected from —O—, —N(R$^e$)—, —N(R$^e$)—C(=O)—, —N(C(=O)R$^e$)—, —S— or —CH$_2$—S—, —CH$_2$NR$^e$—;
R$^x$ is absent or selected from a linear, branched or cyclic alkyl having 1 to 10 carbon atoms;
R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms. Preferably, R$^{101}$ and R$^{102}$ are each independently a linear or branched alkyl having 1 to 6 carbon atoms;
Z$^s$ is —H, —SR$^m$;
R$^m$ is R$^d$ or a substituted or unsubstituted linear or branched alkyl having 1 to 4 carbon atoms bearing a reactive ester, selected from N-hydroxysuccinimide esters, N-hydroxyphtalimide esters, N-hydroxy sulfo-succinimide esters, para-nitrophenyl esters, dinitrophenyl esters, pentafluorophenyl esters;
R$^d$ is selected from phenyl, nitrophenyl, dinitrophenyl, carboxynitrophenyl, pyridyl or nitropyridyl;
n is an integer from 1 to 24; and the remainder of the variables are as described above in the alternative fourth specific embodiment.
Preferably, R$^k$ is —H or -Me and n is an integer from 2 to 8. Preferably, R$^x$ is a linear or branched alkyl having 1 to 6 carbon atoms; and the remainder of the variables is as described above in the alternative fifth specific embodiment.

In certain embodiments, for compounds described in the alternative eighth specific embodiment, the variables are as described below:
X' and Y' are both —H;
A and A' are both —O—;
R$_6$ is —OMe;

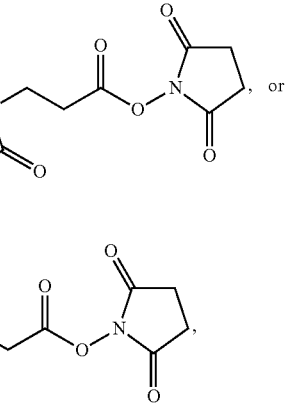

R$^x$ is a linear or branched alkyl having 1 to 6 carbon atoms; and the remainder of the variables is as described above in the alternative eighth specific embodiment.

Preferably, R$^x$ is —(CH$_2$)$_p$—(CR$^f$R$^g$)—, wherein R$^f$ and R$^g$ are each independently selected from H or a linear or branched alkyl having 1 to 4 carbon atoms; p is 0, 1, 2 or 3. More preferably, R$^f$ and R$^g$ are the same or different and are selected from —H and -Me; and p is 1.

In an alternative ninth specific embodiment, L' in formula (VAa'), (VIAa') or (VIIAa'), or one of Q$_2$ and Q$_2$' in formula (VIIA2a') is represented by the following formula:

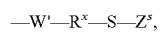
—W'—R$^x$—S—Z$^s$, wherein:
Y is selected from —SO$_3$M, —SO$_2$M or —OSO$_3$M;
M is —H or a pharmaceutically acceptable cation such as Na$^+$ or K$^+$;
R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;
R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;
X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N(R$^e$)—, —N(R$^e$)—C(=O)—, —N(C(=O)R$^e$)—, —S— or —CH$_2$—S—, —CH$_2$NR$^e$—;

cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

Z$^s$ is —H, or is selected from any one of the following formulas:

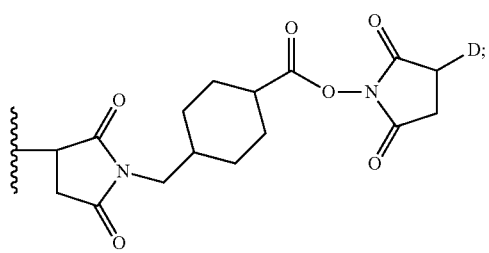
(a1)

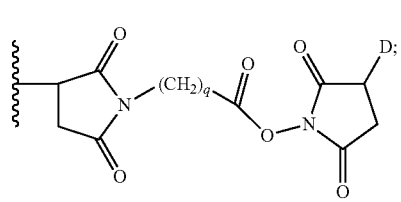
(a2)

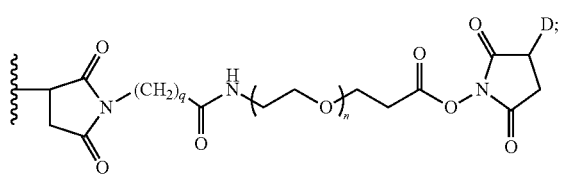
(a3)

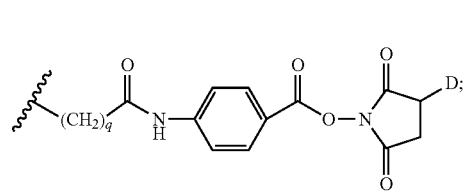
(a4)

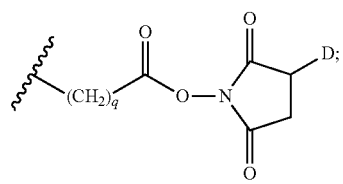
(a5)

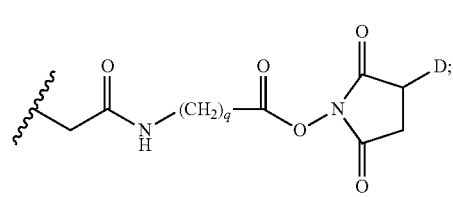
(a6)

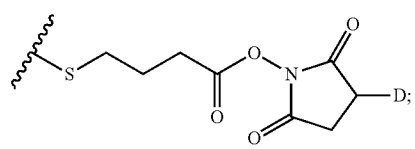
(a7)

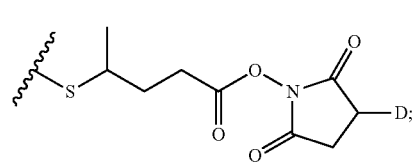
(a8)

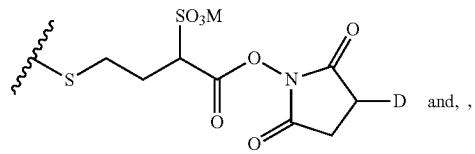
(a9)

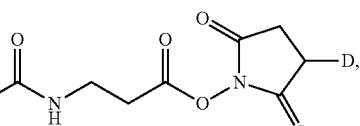
and, ,

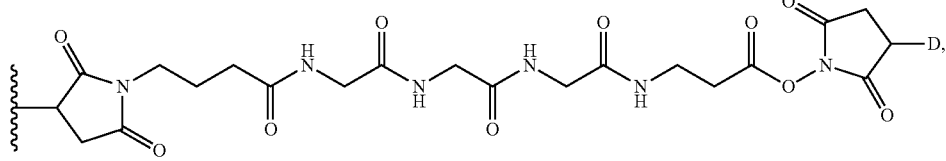
(a10)

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched wherein:

q is an integer from 1 to 5; preferably q is 2;

n is an integer from 2 to 6; preferably n is 4;

D is —H or —SO$_3$M;

M is —H or a pharmaceutically acceptable cation, such as Na⁺ or K⁺.

In certain embodiments, $Z^s$ is represented by any one of the following formulas:

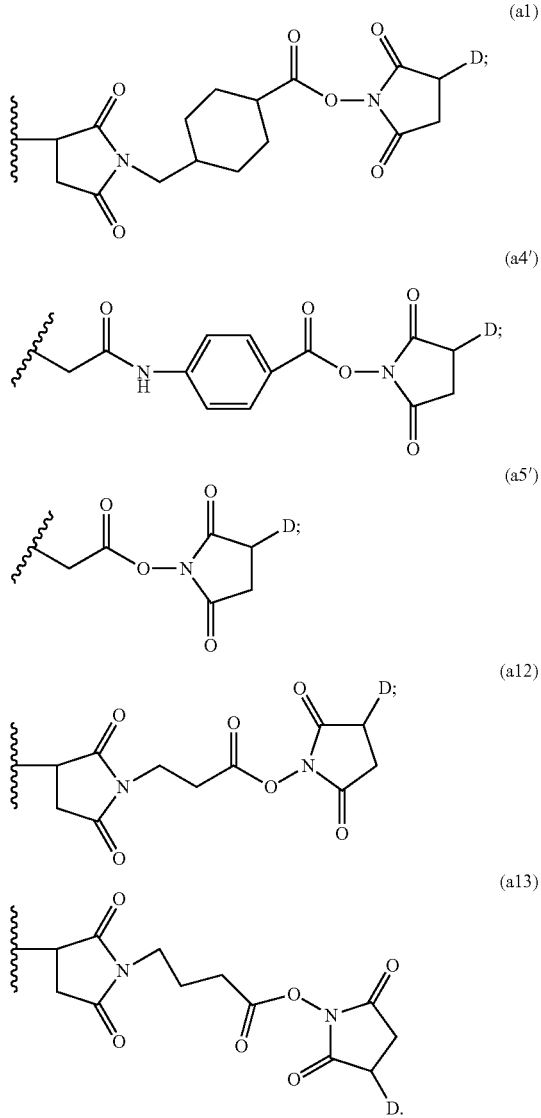

In certain embodiments, such as the alternative ninth specific embodiment, W' is —N(R$^e$)—.

In certain embodiments, R$^e$ is —(CH$_2$—CH$_2$—O)$_n$—R$^k$, wherein R$^k$ is a —H, a linear, branched cyclic alkyl having 1 to 6 carbon atoms.

In certain embodiments, R$^k$ is —H or -Me, n is 4, and q is 2.

In certain embodiments, R$^x$ is a linear or branched alkyl having 1 to 6 carbon atoms.

In certain embodiments, R$^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3.

In certain embodiments, R$^f$ and R$^g$ are the same or different, and are selected from —H and -Me; and p is 1.

In an alternative tenth specific embodiment, the variables of the alternative ninth specific embodiment are represented below: Y is —SO$_3$M; M is —H or a pharmaceutically acceptable cation (e.g., Na⁺); X' and Y' are both —H; A and A' are both —O—; R$_6$ is —OMe; and R$^x$ is a linear or branched alkyl having 1 to 6 carbon atoms.

In any of the embodiments above, such as the alternative 1$^{st}$ through the alternative 9$^{th}$ specific embodiments, Y is selected from —SO$_3$M, —SO$_2$M and a sulfate —OSO$_3$M. Preferably, Y is —SO$_3$M, wherein M is preferably —H, Na⁺ or K⁺.

In any of the embodiments above, such as the alternative 1$^{st}$ through the alternative 10$^{th}$ specific embodiments, W, when present, is C═O.

In any of the embodiments above, such as the alternative 1$^{st}$ through the alternative 10$^{th}$ specific embodiments, X' is selected from the group consisting of —H, —OH, an optionally substituted linear, branched or cyclic alkyl, alkenyl or alkynyl having from 1 to 10 carbon atoms, phenyl, the linking group with the reactive group bonded thereto, and an amine-protecting group. Preferably, X' is —H, —OH, -Me or the linking group with the reactive group bonded thereto. More preferably, X' is —H.

In any of the embodiments above, such as the alternative 1$^{st}$ through the alternative 10$^{th}$ specific embodiments, Y' is selected from the group consisting of —H, an oxo group, a substituted or unsubstituted linear, branched or cyclic alkyl, alkenyl or alkynyl having from 1 to 10 carbon atoms. Preferably, Y' is —H or oxo. More preferably, Y' is —H.

In any of the embodiments above, such as the alternative 1$^{st}$ through the alternative 10$^{th}$ specific embodiments, A and A' are the same or different, and are selected from —O—, —S—, —NR$_5$—, and oxo —(C═O)—. Preferably, A and A' are the same or different, and are selected from —O— and —S—. More preferably, A and A' are —O—.

In any of the embodiments above, such as the alternative 1$^{st}$ through the alternative 10$^{th}$ specific embodiments, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. Preferably, D and D' are linear or branched alkyl bearing 1 to 4 carbon atoms.

In an alternative eleventh specific embodiment, the various groups of the cytotoxic compounds of the alternative first, third, and ninth specific embodiments, are represented below: W is C═O; R$_6$ is —OMe; X' is —H; Y' is —H; and A and A' are —O—.

In another embodiment, the linking group with the reactive group attached thereto as in any of the alternative specific embodiment above is any one of those listed in List 1.

Drugs without a Linking Moiety (Imine-Containing Cytotoxic Compounds)

In another embodiment, cytoxic dimers without a linker moieties (such as the linker moieties described above) attached thereto may further react with a bifunctional crosslinking reagent to form a drug bearing a linking moiety with a reactive group attached thereto, in order to be used in the methods of the present invention (e.g., to further react with a cell-binding agent to form the drug-CBA conjugate). Alternatively, cytoxic dimers without a linker moieties (such as the linker moieties described above) attached thereto may further react with a bifunctional crosslinking reagent and a cell-binding reagent in a one-step reaction to directly form the drug-CBA conjugate. In either case, an imine-reactive reagent may be added to the reaction mixture to form a drug-imine reactive reagent adduct (such as a bisulfite adduct) prior to the reaction to create the drug-CBA conjugate. Preferably, the cytoxic dimers without a linker moieties (such as the linker moieties described above) attached thereto may be first pre-incubated with the imine reactive reagent to form the adduct, before the reaction mixture is used in the subsequent reactions to form the drug-CBA conjugate.

Thus in an alternative twelfth specific embodiment, the imine-containing cytotoxic compound is represented by any one of the following formulas, or a pharmaceutically acceptable salt thereof:

wherein:

Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester ($R^iO)_2PS(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of

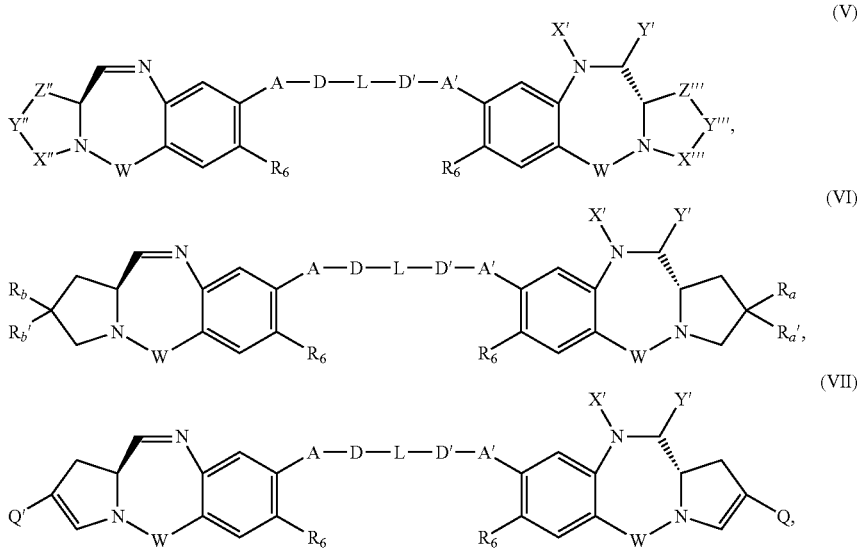

and, after reacting with the imine reactive reagent, the modified cytotoxic compound is represented by the following formula, or a pharmaceutically acceptable salt thereof:

$HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected

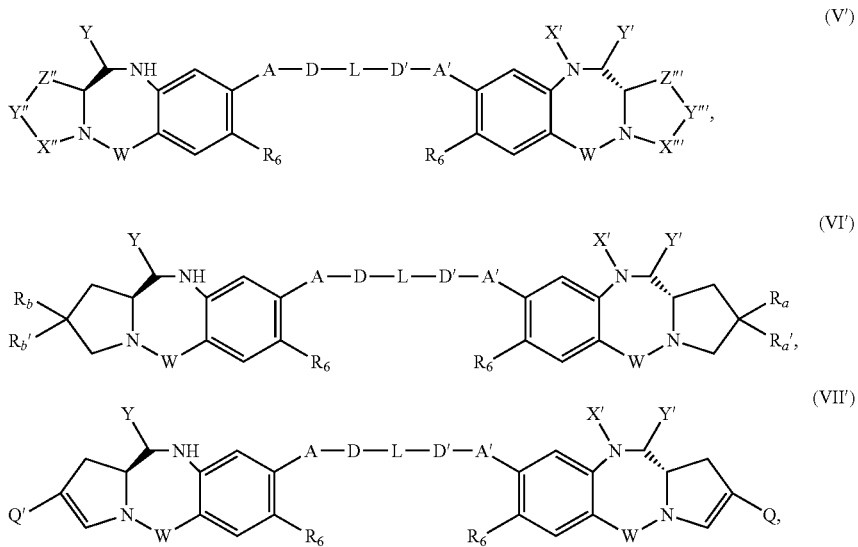

from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

X' is selected from —H, —OH, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms (e.g., phenyl), an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P. Preferably, X' is —H, —OH, or -Me. More preferably, X' is —H;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms. Preferably, Y' is selected from —H or oxo. More preferably, Y' is —H;

R$^c$ is —H or a substituted or unsubstituted linear or branched alkyl having 1 to 4 carbon atoms;

M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are the same or different, and are independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

n is an integer from 1 to 24;

W is selected from C=O, C=S, CH$_2$, BH, SO, and SO$_2$;

R$_6$ is —H, —R, —OR, —SR, —NR'R", —NO$_2$, halogen, —OR$^c$ or —SR$^c$; preferably, R$_6$ is —OMe or —SMe. Even more preferably, R$_6$ is —OMe;

A and A' are the same or different, and are independently selected from —O—, oxo (—C(=O)—), —CRR'O—, —CRR'—, —S—, —CRR'S—, —N(R$_5$)— and —CRR'N(R$_5$)—. Preferably, A and A' are the same or different, and are selected from —O— and —S—. More preferably, A and A' are —O—;

R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, and is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

X" and X"' are the same or different, and are independently selected from —(CH$_2$)$_{n'}$—, —NR'—, —CO—, —BH—, —SO— or —SO$_2$—;

Y" and Y"' are the same or different, and are independently selected from —O—, —(CH$_2$)$_{n'}$—, —NR'— or —S—;

Z" and Z"' are the same or different, and are independently selected from —(CH$_2$)$_{n'}$—, —CR$_7$R$_8$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and R$^{c'}$ is absent or selected from linear or branched alkyl, alkenyl or alkynyl having 1 to 5 carbon atoms.

In certain embodiments,
W is C=O;
A and A' are both —O—;
W is —(C=O)—;
R₆ is —H, or optionally substituted C1-C10 linear, C1-C10 branched, or C3-C7 cyclic alkyl, —O-alkyl, or —O-halo-alkyl, such as —OMe;
X' is selected from the group consisting of —H, —OH, a substituted or unsubstituted linear, branched or cyclic alkyl, alkenyl or alkynyl having from 1 to 10 carbon atoms, phenyl, and an amine-protecting group; and
Y' is selected from the group consisting of —H, an oxo group, a substituted or unsubstituted linear, branched or cyclic alkyl, alkenyl or alkynyl having from 1 to 10 carbon atoms.

Preferably, Y is selected from —SO₃M, —SO₂M, or —OSO₃M, and wherein M is —H or a pharmaceutically acceptable cation such as Na⁺ or K⁺.

Preferably, Y is —SO₃M; M is —H or Na⁺.

In certain embodiments, the imine-containing cytotoxic compound is represented by any one of the following formulas:

wherein:
L', L", and L''' are the same or different, and are independently selected from —H, an optionally substituted linear, branched or cyclic alkyl, alkenyl or alkynyl having from 1 to 10 carbon atoms, a polyethylene glycol unit —(OCH₂CH₂)ₙ—Rᶜ, halogen, guanidinium [—NH(C=NH)NH₂], —OR, —NR'R", —NO₂, —NR'COR", —SR, a sulfoxide represented by —SOR', a sulfone represented by —SO₂R', a sulfonate —SO₃M, a sulfate —OSO₃M, a sulfonamide represented by —SO₂NR'R", cyano, an azido, —COR', —OCOR', —OCONR'R";
M is —H or a pharmaceutically acceptable cation;
Rₐ" and R_b" are the same or different, and are selected from —H and -Me;
Y" is O, S or NR'; preferably, Y" is O;
Q₂ and Q₂' are independently selected from —H, —R, —OR, —NR'R", —NR'(C=O)OR", —SR, and —NO₂.

In certain embodiments, the modified cytotoxic compound, when present, is represented by one of the following formulas, or a pharmaceutically acceptable salt thereof:

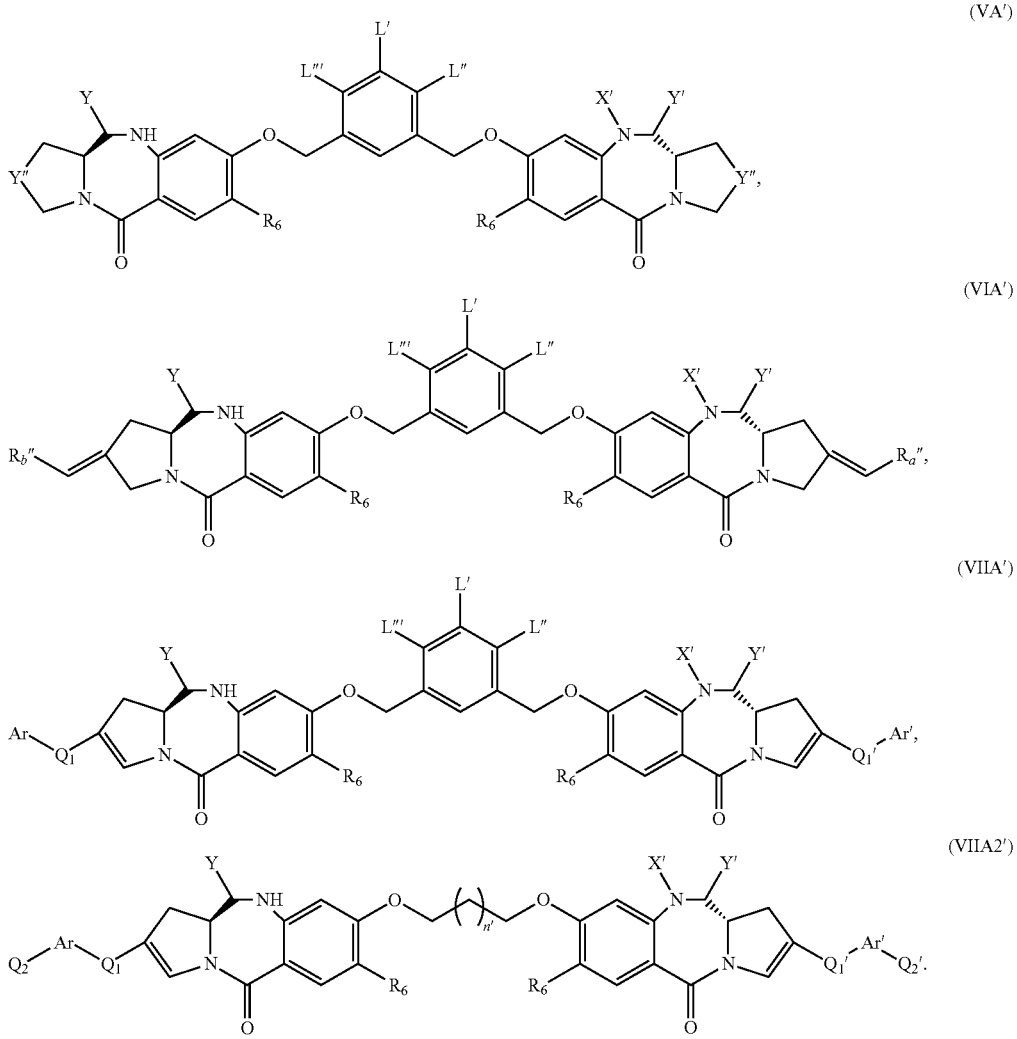

In certain embodiments, $Q_1$ and $Q_1'$ are absent; Ar and Ar' are an optionally substituted phenyl.

In certain embodiments, $R_a''$ and $R_b''$ are both —H or both Me.

In certain embodiments, one of L', L", or L'" bears the thiol group, while the others are —H. Preferably, L' bears the thiol group, and L" and L'" are —H.

In certain embodiments, A and A' are both —O—; $R_6$ is —OMe.

In certain embodiments, L' in formula (VA), (VIA) or (VIIA), or one of $Q_2$ and $Q_2'$ in formula (VIIA2) is represented by the following formula:

—W'—R$^x$—SH, wherein:

W' is absent, or when present, is selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ is absent, or when present, is an optionally substituted linear, branched or cyclic alkyl, alkenyl or alkynyl having 1 to 10 carbon atoms, an aryl bearing 6 to 10 carbon atoms or a 3- to 8-membered hetereocyclic ring bearing 1 to 3 heteroatoms selected from O, N or S;

R$^e$ and R$^{e'}$ are the same or different, and are selected from —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24.

In certain embodiments,

Y is selected from —SO$_3$M, —SO$_2$M or —OSO$_3$M;

M is —H or a pharmaceutically acceptable cation such as Na$^+$ or K$^+$;

X' is selected from the group consisting of —H, —OH, a substituted or unsubstituted linear, branched or cyclic alkyl, alkenyl or alkynyl having from 1 to 10 carbon atoms, phenyl, and an amine-protecting group;

Y' is selected from the group consisting of —H, an oxo group, a substituted or unsubstituted linear, branched or cyclic alkyl, alkenyl or alkynyl having from 1 to 10 carbon atoms;

A and A' are selected from —O— and —S—;

W' is absent, or selected from —O—, —N($R^e$)—, —N($R^e$)—C(=O)—, —N(C(=O)$R^e$)—, —S— or —CH$_2$—S—, —CH$_2$N$R^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms.

In certain embodiments, W' is —N($R^e$)—.

In certain embodiments, $R^e$ is —(CH$_2$—CH$_2$—O)$_n$—$R^k$, wherein $R^k$ is a —H, a linear, branched cyclic alkyl having 1 to 6 carbon atoms.

In certain embodiments, $R^k$ is —H or -Me, n is 4, and q is 2.

In certain embodiments, $R^x$ is a linear or branched alkyl having 1 to 6 carbon atoms.

In certain embodiments, $R^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3.

In certain embodiments, R$^f$ and R$^g$ are the same or different, and are selected from —H and -Me; and p is 1.

In certain embodiments,

Y is —SO$_3$M, —SON, or a sulfate —OSO$_3$M; preferably —SO$_3$M;

M is —H or a pharmaceutically acceptable cation (e.g., Na$^+$);

X' and Y' are both —H;

A and A' are both —O—;

R$_6$ is —OMe; and $R^x$ is a linear or branched alkyl having 1 to 6 carbon atoms.

In certain embodiments, the bifunctional crosslinking agent is: a maleimido-based moiety selected from: N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), N-(p-maleimidophenyl)isocyanate (PMPI); or, a haloacetyl-based moiety selected from: N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-(β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl) cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-κ-maleimidoundecanoyloxy) sulfosuccinimide ester (sulfo-KMUS), sulfosuccinimidyl 4-(p-maleimidophenyl)butyrate (sulfo-SMPB), CX1-1, sulfo-Mal and PEG$_n$-Mal.

In certain embodiments, the bifunctional crosslinking agent is selected from the group consisting of SMCC, Sulfo-SMCC, BMPS, GMBS, SIA, SIAB, N-succinimidyl-, 4-(4-nitropyridyl-2-dithio)butanoate, bis-maleimidohexane or BMPEO.

In certain embodiments, the modified CBA, when present, is:

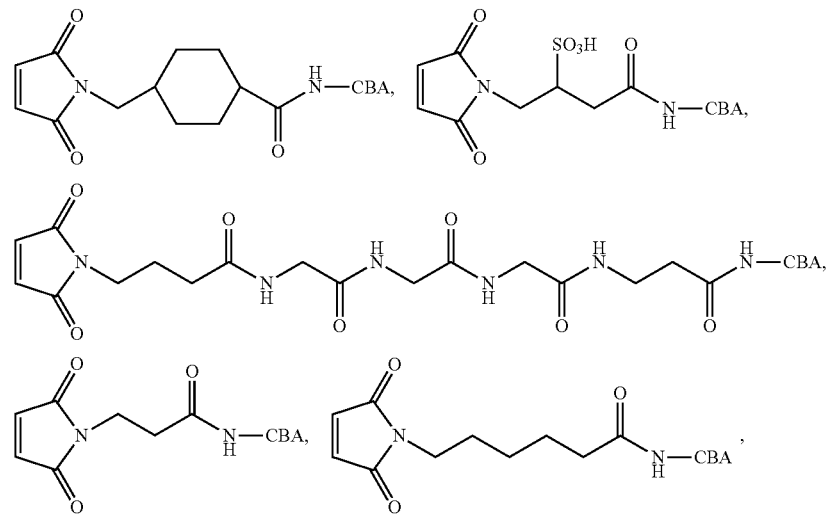

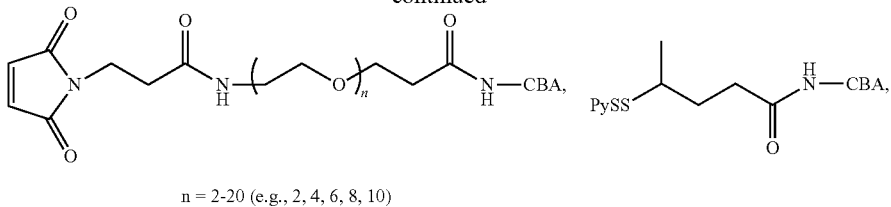

n = 2-20 (e.g., 2, 4, 6, 8, 10)

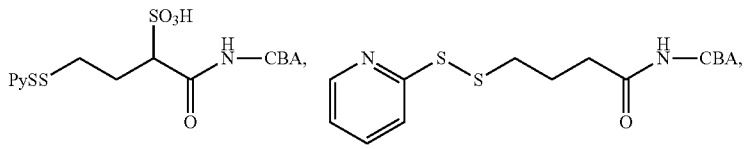

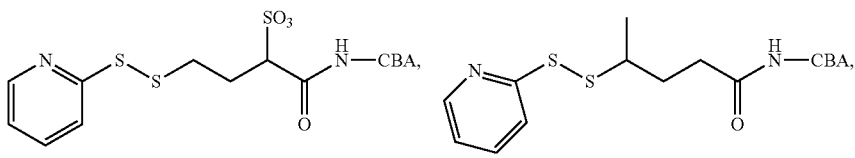

BM(PEG)₃

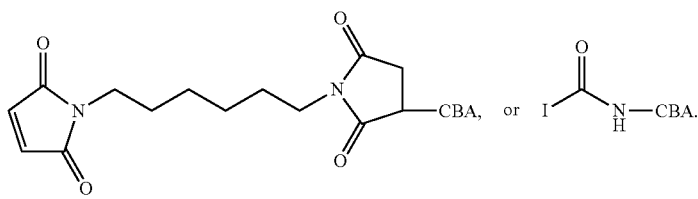

BMH

Conjugates Produced by the Methods of the Invention

The present invention provides improved methods to produce cell-binding agent-drug conjugates, comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers.

Representative conjugates that can be made using the methods of the invention include antibody/cytotoxic compound, antibody fragment/cytotoxic compound, epidermal growth factor (EGF)/cytotoxic compound, melanocyte stimulating hormone (MSH)/cytotoxic compound, thyroid stimulating hormone (TSH)/cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound. A representative folate/cytotoxic compound conjugate is depicted below, with the optional —SO₃Na adduct on the imine bond of one of the two drug monomers. A representative synthesis scheme for this conjugate is shown in FIG. 36.

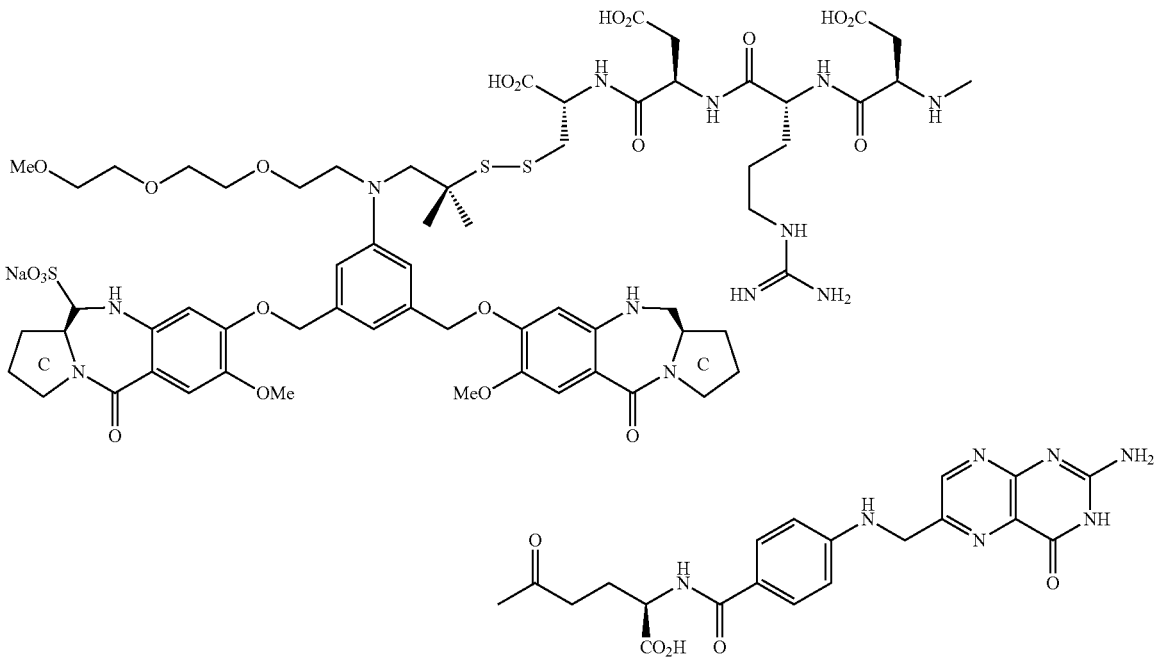

folate/cytotoxic compound conjugate

In a preferred embodiment, the present invention provides methods for producing conjugates comprising a pyrrolobenzodiazepine dimer compound (e.g., formulas (Vb'), (VIb'), (VIIb'), (VAb'), (VIAb'), (VIIAb'), etc.) and the cell-binding agent linked through a covalent bond. The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

In a preferred aspect, representative cytotoxic conjugates that can be produced by the methods of the invention are antibody/pyrrolobenzodiazepine dimer compound, antibody fragment/pyrrolobenzodiazepine dimer compound, epidermal growth factor (EGF)/pyrrolobenzodiazepine dimer compound, melanocyte stimulating hormone (MSH)/pyrrolobenzodiazepine dimer compound, thyroid stimulating hormone (TSH)/pyrrolobenzodiazepine dimer compound, somatostatin/pyrrolobenzodiazepine dimer compound, folate/pyrrolobenzodiazepine dimer compound, estrogen/pyrrolobenzodiazepine dimer compound, estrogen analogue/pyrrolobenzodiazepine dimer compound, prostate specific membrane antigen (PSMA) inhibitor/pyrrolobenzodiazepine dimer compound, matriptase inhibitor/pyrrolobenzodiazepine dimer compound, designed ankyrin repeat proteins (DARPins)/pyrrolobenzodiazepine dimer compound, androgen/pyrrolobenzodiazepine dimer compound, and androgen analogue/pyrrolobenzodiazepine dimer compound.

Thus in the alternative fourteenth specific embodiment, the methods of the invention produce a conjugate comprising: a cytotoxic compound and a cell binding agent (CBA), wherein the cytotoxic compound is covalently linked to the CBA through a linking group, and wherein the cytotoxic compound and the linking group portion of the conjugate is represented by any one of the following formulas:

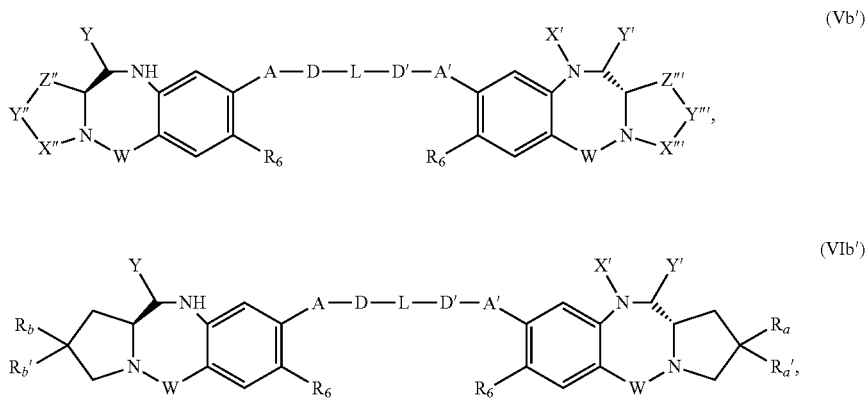

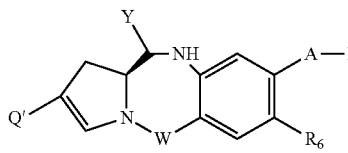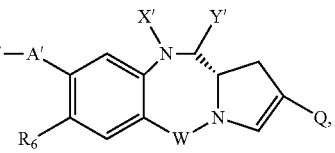

(VIIb')

or a pharmaceutically acceptable salt thereof, wherein:

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^kC(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt);

M is —H or a pharmaceutically acceptable cation, such as $Na^+$;

X' is selected from —H, an amine-protecting group, the linking group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3-18-membered heterocyclic ring having 1 to 6 heteroatoms independently selected from O, S, N and P;

n is an integer from 1 to 24;

W is selected from C=O, C=S, $CH_2$, BH, SO and $SO_2$;

$R_6$ is —H, —R, —OR, —SR, —NR'R", —$NO_2$, halogen or the linking group;

A and A' are the same or different, and are independently selected from —O—, oxo (—C(=O)—), —CRR'O—, —CRR'—, —S—, —CRR'S—, —$N(R_5)$— and —CRR'$N(R_5)$—;

$R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2)_n$—;

L is absent, the linking group, a polyethylene glycol unit (—$OCH_2CH_2)_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; the phenyl or heterocyclic or heteroaryl ring can be optionally substituted, wherein the substituent can comprise the linking group;

X" and X'" are the same or different, and are independently selected from —$(CH_2)_{n'}$—, —NR'—, —CO—, —BH—, —SO— or —$SO_2$—;

Y" and Y'" are the same or different, and are independently selected from —O, —$(CH_2)_{n'}$—, —NR'— or —S—;

Z" and Z'" are the same or different, and are independently selected from —$(CH_2)_{n'}$—, —$CR_7R_8$—, —$NR_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a —CH=CH unit;

Ar and Ar' are each independently absent or represent an aryl group;

$Q_2$ and $Q_2'$ are each independently selected from —H, the linking group, a substituted or unsubstituted linear, branched or cyclic alkyl, alkenyl or alkynyl having from 1 to 10 carbon atoms, a polyethylene glycol unit —$R^{c'}$—$(OCH_2CH_2)_n$—$R^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and $R^{c'}$ is absent or selected from linear or branched alkyl, alkenyl or alkynyl having 1 to 5 carbon atoms.

In certain embodiments, Y is —SO$_2$M, —SO$_3$M, or —OSO$_3$M.

In certain embodiments, L is absent, or is selected from an optionally substituted phenyl group and an optionally substituted pyridyl group, wherein the phenyl and the pyridyl group bears the linking group, or L is an amine group bearing the linking group (i.e., —N(linking group)-), or L is a linear, branched or cyclic alkyl or alkenyl having from 1 to 6 carbon atoms and bearing the linking group.

In the alternative fifteenth specific embodiment, the cytotoxic compound bonded to the linking group is represented by any one of the following formulas:

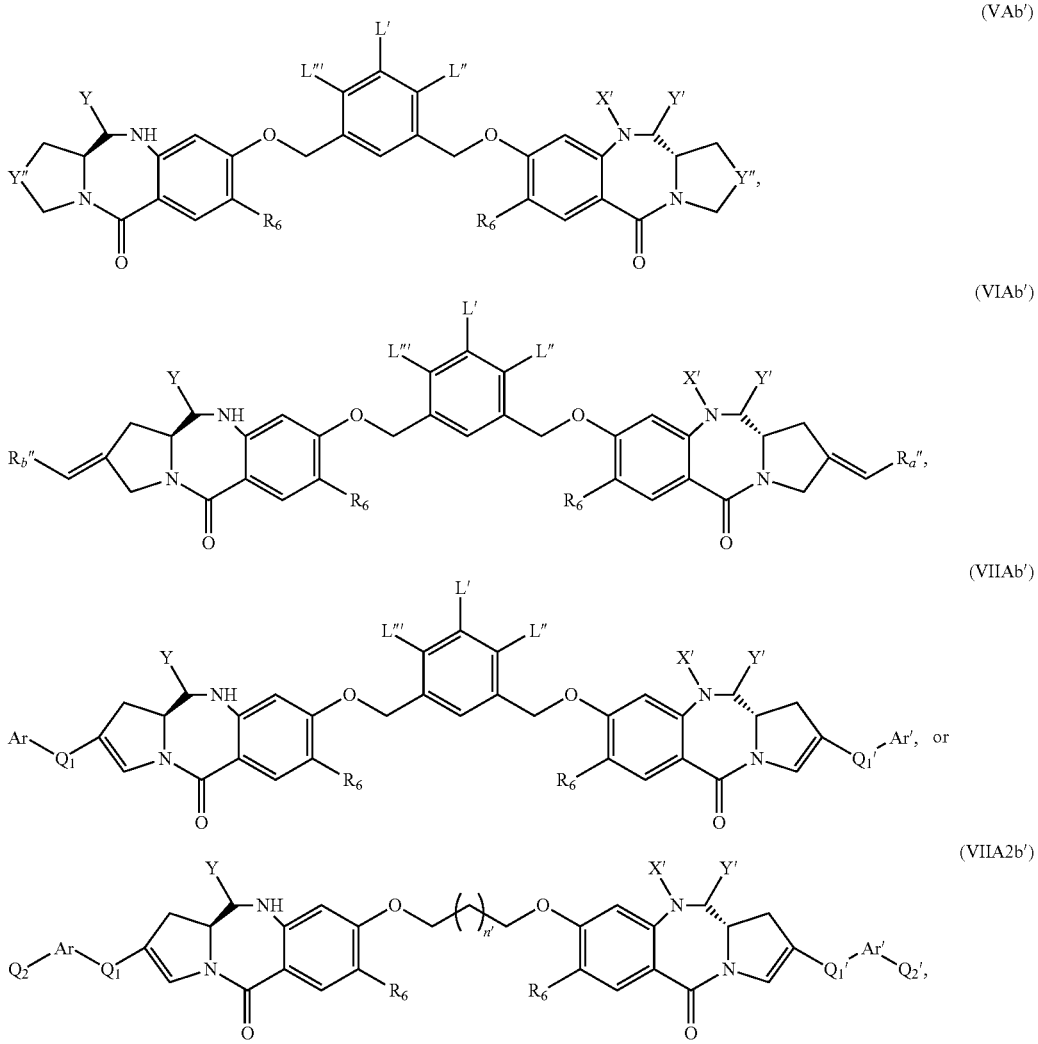

wherein:

$R_a''$ and $R_b''$ are the same or different and are selected from —H and -Me; one of $Q_2$ and $Q_2'$ is selected from —H, —R, —OR, —NR'R", —NR'(C=O)OR", —SR, and —NO$_2$, the other is the linking group.

L', L", and L'" are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, an azido, —COR', —OCOR', —OCONR'R" and the linking group, provided only one of L', L", and L'" is the linking group; and the remaining groups are as described in the alternative fourteenth specific embodiment above.

In certain embodiments, $Q_1$ and $Q_1'$ are absent; Ar and Ar' are an optionally substituted phenyl.

In certain embodiments, $R_a''$ and $R_b''$ are both —H or both Me.

In certain embodiments, one of L', L", or L'" is the linking group, while the others are —H. Preferably, L' is the linking group, and L" and L'" are —H.

In certain embodiments, A and A' are both —O—, $R_6$ is —OMe.

In an alternative sixteenth specific embodiment, L' in formula (Vab'), (VIAb') or (VIIAb'), or one of $Q_2$ and $Q_2'$ in formula (VIIA2b') is represented by the following formula:

—W'—R$^x$—V—R$^y$-J, wherein:

W' and V are the same or different, and are each independently absent, or selected from —CR$^e$R$^{e'}$, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

$R^x$ and $R^y$ are the same or different, and are each independently absent or an optionally substituted linear, branched or cyclic alkyl, alkenyl, or alkynyl having 1 to 10 carbon atoms, an aryl bearing 6 to 10 carbon atoms or a 3- to 8-membered hetereocyclic ring bearing 1 to 3 heteroatoms selected from O, N or S;

$R^e$ and $R^{e'}$ are the same or different, and are selected from —H, a linear, branched or cyclic alkyl, alkenyl, or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24; and

J is covalently linked to the CBA, and is selected from a succinimide, a acetamido, —S—, —SS—, —CH$_2$S—, —CH(Me)S—, —C(Me)$_2$S—, —NR$^{c1}$—, —CH$_2$NR$^{c1}$—, —NR$^{c1}$N—, and —C(=O)—, wherein R$^{c1}$ is —H or a substituted or unsubstituted linear or branched alkyl having 1 to 4 carbon atoms.

In certain embodiments, J is —S—, —SS—, a succinimide, or —C(=O)—.

In certain embodiments, $R^{e'}$ is —H or -Me; $R^e$ is a linear or branched alkyl having 1 to 6 carbon atoms or —(CH$_2$—CH$_2$—O)$_n$—R$^k$; n is an integer from 2 to 8; and $R^k$ is —H, -Me or —CH$_2$CH$_2$—NMe$_2$, and the remainder of the variables are as described above in the alternative fifteenth specific embodiment.

In certain embodiments, V is an amino acid or a peptide having 2 to 8 amino acids. In certain embodiments, V is valine-citrulline, gly-gly-gly, or ala-leu-ala-leu.

In certain embodiment,

W' is absent, —CR$^e$R$^{e'}$—, —O—, —O—C(=O)—, —S—, —O—(C=O)O—, —O—(C=O)N(R$^e$)—, —N(R$^e$)—C(=O)—, —N(R$^e$)—C(=O)O—, or —C(=O)—;

$R^{e'}$ is —H or a linear or branched alkyl having 1 to 4 carbon atoms;

$R^e$ is H, a linear, branched or cyclic alkyl, alkenyl or alkynyl having 1 to 10 carbon atoms or —(CH$_2$—CH$_2$—O)$_n$—R$^c$;

$R^x$ is absent or an optionally substituted linear, branched or cyclic alkyl, alkenyl or alkynyl having 1 to 10 carbon atoms;

V is absent, —(CH$_2$—CH$_2$—O)$_n$—, —O—, —O—C(=O)—, —S—, —O—(C=O)O—, —O—(C=O)N(R$^e$)—, —N(R$^e$)—, —N(R$^e$)—C(=O)—, —N(R$^e$)—C(=O)O—, —C(=O)—, an amino acid, or a peptide having 2 to 8 amino acids;

$R^y$ is absent or a linear, branched or cyclic alkyl having 1 to 10 carbon atoms;

n is an integer from 1 to 24.

In certain embodiments,

W' is —O—, —N(R$^e$)— or —N(R$^e$)—C(=O)—;

$R^e$ is H, a linear or branched alkyl having 1 to 4 carbon atoms, or —(CH$_2$—CH$_2$—O)$_n$—R$^k$;

$R^x$ is a linear or branched alkyl having 1 to 6 carbon atoms;

V is absent, —(O—CH$_2$—CH$_2$)$_n$—, —C(=O)—NH—, —S—, —NH—C(=O)—;

$R^y$ is absent or a linear or branched alkyl having 1 to 4 carbon atoms; and

J is —S—, —SS—, or —C(=O)—, and the remaining groups are as defined in the alternative sixteenth specific embodiment.

In certain embodiments,

W' is —O—, —N(R$^e$)— or —N(R$^e$)—C(=O)—;

$R^e$ is —H, -Me, or —(CH$_2$—CH$_2$—O)$_n$-Me;

n is an integer from 2 to 6;

$R^x$ is linear or branched alkyl bearing 1 to 6 carbon atoms;

V and $R^y$ are absent; and

J is —C(=O)—. The remaining groups are as defined in the alternative sixteenth specific embodiment.

In an alternative seventeenth specific embodiment, L' in formula (Vab'), (VIAb') or (VIIAb'), or one of $Q_2$ and $Q_2'$ in formula (VIIA2b'), such as in the alternative sixteenth specific embodiment, is represented by the following formula:

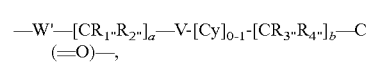

—W'—[CR$_1''$R$_2''$]$_a$—V—[Cy]$_{0-1}$—[CR$_3''$R$_4''$]$_b$—C(=O)—, wherein:
R$_{1''}$, R$_{2'''}$, and R$_{3''}$ are each independently —H or a linear or branched alkyl bearing 1 to 4 carbon atoms, preferably -Me;
R$_{4''}$ is —H, a linear or branched alkyl bearing 1 to 4 carbon atoms (preferably -Me), —SO$_3$H, or —SO$_3^-$ M$^+$, wherein M$^+$ is a pharmaceutically acceptable cation;
a is an integers from 0-5 (e.g., from 0 to 2, 3, 4, or 5), and b is an integer from 0-6 (e.g., from 0 to 3, 4, 5, or 6); and,
Cy is an optionally substituted 5-membered heterocyclic ring bearing an N heteroatom, preferably Cy is

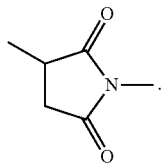

In certain embodiments, such as in the alternative sixteenth or the alternative seventeenth specific embodiment, W' is —N(R$^e$)—.

In certain embodiments, such as in the alternative sixteenth or the alternative seventeenth specific embodiment, R$^e$ is —(CH$_2$—CH$_2$—O)$_{2-6}$—R$^k$, wherein R$^k$ is a linear or branched alkyl having 1 to 6 carbon atoms.

In certain embodiments, such as in the alternative sixteenth or the alternative seventeenth specific embodiment, V is —S— or —SS—.

In an alternative eighteenth specific embodiment, L' in formula (Vab'), (VIAb') or (VIIAb'), or one of Q$_2$ and Q$_2$' in formula (VIIA2b'), such as in the alternative sixteenth or the alternative seventeenth specific embodiment, is represented by the following formula:

—NR$^e$—[CR$_{1''}$R$_{2''}$]$_a$—S—[CR$_{3''}$R$_{4''}$]$_b$—C(=O)—.

In certain embodiments, L' in formula (Vab'), (VIAb') or (VIIAb'), or one of Q$_2$ and Q$_2$' in formula (VIIA2b'), such as in the alternative sixteenth or the alternative seventeenth specific embodiment, is connected to the CBA as L'-CBA with the following structure:

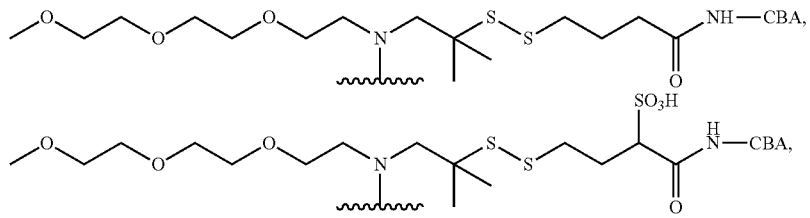

or
wherein Y is —H or —SO$_3$M (e.g., Y is —SO$_3$M), and M is —H or a pharmaceutically acceptable cation.

In certain embodiments, such as in the alternative sixteenth to alternative eighteenth specific embodiments, the antibody is huMy9-6.

In an alternative nineteenth specific embodiment, L' in formula (VAb'), (VIAb') or (VIIAb'), or one of Q$_2$ and Q$_2$' in formula (VIIA2b'), such as in the alternative sixteenth or the alternative seventeenth specific embodiment, is represented by the following formula:

—NR$^e$—[CR$_{1''}$R$_{2''}$]$_a$—S-Cy-[CR$_{3''}$R$_{4''}$]$_b$—C(=O)—.

In certain embodiments, L' in formula (VAb'), (VIAb') or (VIIAb'), or one of Q$_2$ and Q$_2$' in formula (VIIA2b'), such as in the alternative sixteenth, seventeenth, and the nineteenth specific embodiments, is connected to the CBA as L'-CBA with the following structure:

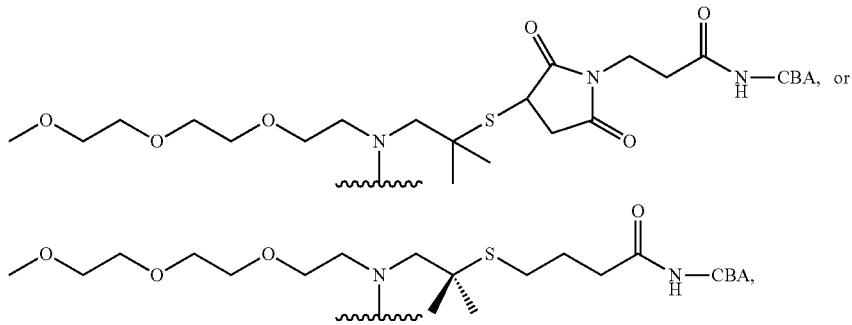

wherein Y is —H or —SO₃M (e.g., Y is —SO₃M), and M is —H or a pharmaceutically acceptable cation.

In certain embodiments, such as in the alternative sixteenth, seventeenth, and the nineteenth specific embodiments, the antibody is huMy9-6.

In an alternative twentieth specific embodiment, L' in formula (VAb), (VIAb) or (VIIAb), or one of $Q_2$ and $Q_2'$ in formula (VIIA2b), is represented by the following formula:

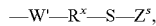

wherein:

W' is absent, or selected from —O—, —N($R^e$)—, —N($R^e$)—C(=O)—, —N(C(=O)$R^e$)—, —S—, —CH₂—S—, or —CH₂N$R^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH₂—CH₂—O)$_n$—$R^k$, wherein $R^k$ is a —H, a linear, branched cyclic alkyl having 1 to 6 carbon atoms, optionally bearing a secondary amino (e.g., —NH$R^{101}$) or tertiary amino (—N$R^{101}R^{102}$) group or a 5 or 6-membered nitrogen containing heterocycle, such as piperidine or morpholine, wherein $R^{101}$ and $R^{102}$ are each independently a linear, branched, or cyclic alkyl, alkenyl or alkynyl having 1 to 10 carbon atoms;

$Z^s$ is linked to the CBA, and is either a bond, or —S$R^m$—;

$R^m$ is $R^d$ or a substituted linear or branched alkyl having 1 to 4 carbon atoms bearing a reactive ester, selected from N-hydroxysuccinimide esters, N-hydroxyphtalimide esters, N-hydroxy sulfo-succinimide esters, para-nitrophenyl esters, dinitrophenyl esters, and pentafluorophenyl esters;

$R^d$ is selected from phenyl, nitrophenyl, dinitrophenyl, carboxynitrophenyl, pyridyl or nitropyridyl; and n is an integer from 1 to 24; and the remainder of the variables are as described above in the alternative eighth or the alternative fifteenth specific embodiment.

In an alternative twenty-first specific embodiment, L' in formula (VAb'), (VIAb') or (VIIAb'), or one of $Q_2$ and $Q_2'$ in formula (VIIA2b'), is represented by the following formula:

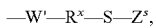

wherein:

W' is absent, or selected from —O—, —N($R^e$)—, —N($R^e$)—C(=O)—, —N(C(=O)$R^e$)—, —S—, —CH₂—S—, or —CH₂N$R^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH₂—CH₂—O)$_n$—$R^k$, wherein $R^k$ is a —H, a linear, branched cyclic alkyl having 1 to 6 carbon atoms, optionally bearing a secondary amino (e.g., —NH$R^{101}$) or tertiary amino (—N$R^{101}R^{102}$) group or a 5 or 6-membered nitrogen containing heterocycle, such as piperidine or morpholine, wherein $R^{101}$ and $R^{102}$ are each independently a linear, branched, or cyclic alkyl, alkenyl or alkynyl having 1 to 10 carbon atoms;

n is an integer from 2 to 6;

$Z^s$ is linked to the CBA, and is selected from:

a bond;

(b1) 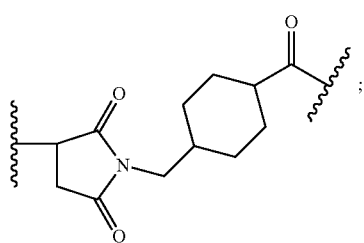

(b2) 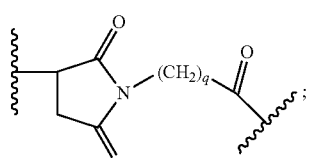

(b3) 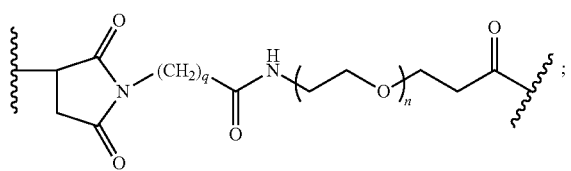

(b4) 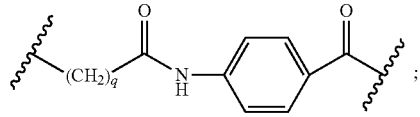

(b5) 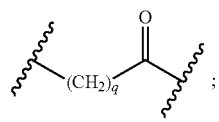

(b6) 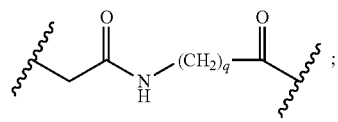

(b7) 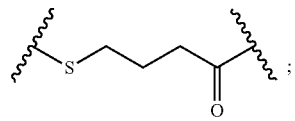

(b8) 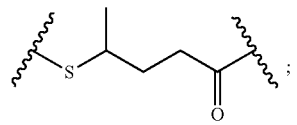

-continued

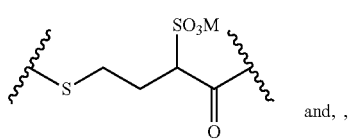
and, ,
(b9)

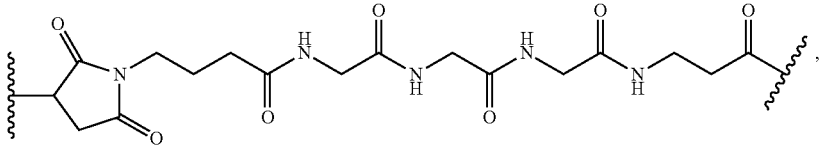
(b10)

wherein:
q is an integer from 1 to 5; and,
M is —H or a pharmaceutically acceptable cation, such as Na⁺ or K⁺.

In certain embodiments, $Z^s$ is represented by any one of the following formulas:

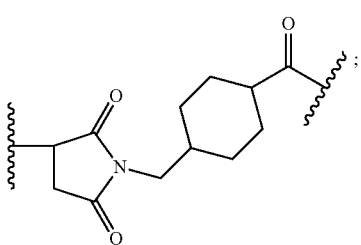
(b1)

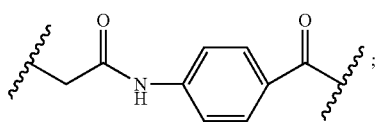
(b4')

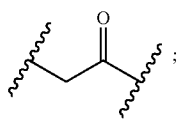
(b5')

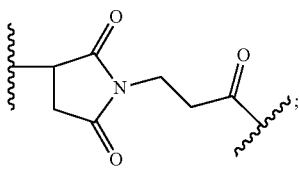
(b12)

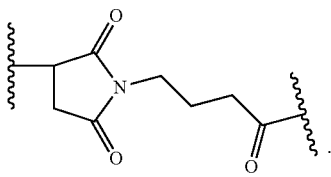
(b13)

In certain embodiments, such as the alternative 21st specific embodiment, W' is —N(R$^e$)—.

In certain embodiments, such as the alternative 21st specific embodiment, R$^e$ is —(CH$_2$—CH$_2$—O)$_n$—R$^k$, wherein R$^k$ is a —H, a linear, branched cyclic alkyl having 1 to 6 carbon atoms.

In certain embodiments, such as the alternative 21st specific embodiment, R$^k$ is —H or -Me, n is 4, and q is 2.

In certain embodiments, such as the alternative 21st specific embodiment, R$^x$ is a linear or branched alkyl having 1 to 6 carbon atoms.

In certain embodiments, such as the alternative 21st specific embodiment, R" is —(CH$_2$)$_p$—(CR$^f$R$^g$)—, wherein R$^f$ and R$^g$ are each independently selected from H or a linear or branched alkyl having 1 to 4 carbon atoms; and p is 0, 1, 2 or 3.

In certain embodiments, such as the alternative 21st specific embodiment, R$^f$ and R$^g$ are the same or different, and are selected from —H and -Me; and p is 1.

In an alternative twenty-second specific embodiment, for the conjugate described in the alternative twenty-first specific embodiment, the variables are as described below:
Y is —SO$_3$M;
M is —H or a pharmaceutically acceptable cation (e.g., Na⁺);
X' and Y' are both —H;
A and A' are both —O—;
R$_6$ is —OMe; and
R$^x$ is a linear or branched alkyl having 1 to 6 carbon atoms.

In certain embodiments, such as the alternative 14th to the alternative 21st specific embodiment, Y is selected from —SO$_3$M, —SO$_2$M and a sulfate —OSO$_3$M. Preferably, Y is —SO$_3$M. Preferably, M is —H, Na⁺ or K⁺.

In certain embodiments, such as the alternative 14th to the alternative 22nd specific embodiment, W, when present, is C═O.

In certain embodiments, such as the alternative 14th to the alternative 22nd specific embodiment, X' is selected from the group consisting of —H, —OH, an optionally substituted linear, branched or cyclic alkyl, alkenyl or alkynyl having from 1 to 10 carbon atoms, phenyl, the linking group, and an amine-protecting group. In certain embodiments, X' is —H, —OH, -Me or the linking group. Preferably, X' is —H.

In certain embodiments, such as the alternative 14th to the alternative 22nd specific embodiment, Y' is selected from the group consisting of —H, an oxo group, a substituted or unsubstituted linear, branched or cyclic alkyl, alkenyl or alkynyl having from 1 to 10 carbon atoms. Preferably, Y' is —H or oxo. More preferably, —H.

In certain embodiments, such as the alternative 14th to the alternative 22nd specific embodiment, A and A' are the same or different, and are selected from —O—, —S—, —N(R$_5$)—, and oxo, (C═O). Preferably, A and A' are the same or different, and are selected from —O— and —S—. More preferably, A and A' are —O—.

In certain embodiments, such as the alternative 14th to the alternative 22nd specific embodiment, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. Preferably, D and D' are linear or branched alkyl bearing 1 to 4 carbon atoms.

In an alternative twenty-third specific embodiment, for compounds of formula (IBb') or (IIBb'), described in the alternative twentieth specific embodiment, the variables are as described below:

Y is —SO$_3$M;
M is —H or Na$^+$;
X' and Y' are both —H;
A and A' are both —O—;
R$_6$ is —OMe;
R$^x$ is a linear or branched alkyl having 1 to 6 carbon atoms.
Preferably, R$^x$ is —(CH$_2$)$_p$—(CR$^f$R$^g$)—, wherein R$^f$ and R$^g$ are each independently selected from —H or a linear or branched alkyl having 1 to 4 carbon atoms; p is 0, 1, 2 or 3. More preferably, R$^f$ and R$^g$ are the same or different, and are selected from —H and -Me; and p is 1.

In an alternative twenty-fourth specific embodiment, the conjugate of the present invention as described in the alternative fourteenth, fifteenth, or the twenty-first specific embodiment is represented by the following:

Y is —SO$_3$M, wherein M is —H or a pharmaceutically acceptable cation (e.g., Na$^+$);
W is C=O;
R$_6$ is —OMe;
Z and Z' are —CH$_2$;
X' is —H;
Y' is —H; and
A and A' are —O—.

In any of the alternative specific embodiments for the conjugate of the invention above, such as the alternative 14$^{th}$ to the alternative 24$^{th}$ specific embodiments, Y is selected from —SO$_3$M, —SO$_2$M and a sulfate —OSO$_3$M. Preferably, Y is —SO$_3$M.

In certain embodiments, such as the alternative 14$^{th}$ to the alternative 24$^{th}$ specific embodiment, M is —H, Na$^+$ or K$^+$.

In any of the alternative specific embodiments for the conjugate of the invention above, such as the alternative 14$^{th}$ to the alternative 24th specific embodiments, W, when present, is C=O.

In any of the alternative specific embodiments for the conjugate of the invention above, such as the alternative 14$^{th}$ to the alternative 24$^{th}$ specific embodiments, X' is selected from the group consisting of —H, —OH, an optionally substituted linear, branched or cyclic alkyl, alkenyl or alkynyl having from 1 to 10 carbon atoms, phenyl, the linking group, and an amine-protecting group. In certain embodiments, X' is —H, —OH, -Me or the linking group. In certain embodiments, X' is —H.

In any of the alternative specific embodiments for the conjugate of the invention above, such as the alternative 14$^{th}$ to the alternative 24$^{th}$ specific embodiments, Y' is selected from the group consisting of —H, an oxo group, a substituted or unsubstituted linear, branched or cyclic alkyl, alkenyl or alkynyl having from 1 to 10 carbon atoms. In certain embodiments, Y' is —H or oxo. In certain embodiments, Y' is —H.

In any of the alternative specific embodiments for the conjugate of the invention above, such as the alternative 14$^{th}$ to the alternative 24$^{th}$ specific embodiments, A and A' are the same or different, and are selected from —O—, —S—, —N(R$_5$)—, and oxo (C=O). In certain embodiments, A and A' are the same or different, and are selected from —O— and —S—. In certain embodiments, A and A' are —O—.

In any of the alternative specific embodiments for the conjugate of the invention above, such as the alternative 14$^{th}$ to the alternative 24$^{th}$ specific embodiments, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. In certain embodiments, D and D' are linear or branched alkyl bearing 1 to 4 carbon atoms.

In certain embodiments, the conjugate of any one of the described embodiments, such as the alternative 14$^{th}$ to the alternative 24$^{th}$ specific embodiments, may comprise 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In certain embodiments, the conjugate of any one of the described embodiments, such as the alternative 14$^{th}$ to the alternative 24$^{th}$ specific embodiments, may comprise 1-10 modified cytotoxic compounds, 2-9 modified cytotoxic compounds, 3-8 modified cytotoxic compounds, 4-7 modified cytotoxic compounds, or 5-6 modified cytotoxic compounds, each modified cytotoxic compound comprising the linking group linking the modified cytotoxic compound to the CBA, and each modified cytotoxic compound on the conjugate is the same.

In certain embodiments, the conjugate of any one of the described embodiments, such as the alternative 14$^{th}$ to the alternative 24$^{th}$ specific embodiments, may comprise 1-10 total modified and unmodified cytotoxic compounds, 2-9 total modified and unmodified cytotoxic compounds, 3-8 total modified and unmodified cytotoxic compounds, 4-7 total modified and unmodified cytotoxic compounds, or 5-6 total modified and unmodified cytotoxic compounds, each modified or unmodified cytotoxic compound comprising the linking group linking the modified or unmodified cytotoxic compound to the CBA, and each modified or unmodified cytotoxic compound on the conjugate is the same (except for the (bisulfite) modification).

In any of the conjugates embodiments, such as the alternative 14$^{th}$ to the alternative 24$^{th}$ specific embodiments, the cell-binding agent may bind to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

In any of the conjugates embodiments, such as the alternative 14$^{th}$ to the alternative 24$^{th}$ specific embodiments, the cell-binding agent may be an antibody, a single chain antibody, an antibody fragment that specifically binds to the target cell, a monoclonal antibody, a single chain monoclonal antibody, or a monoclonal antibody fragment that specifically binds the a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

The antibody may be a resurfaced antibody, a resurfaced single chain antibody, or a resurfaced antibody fragment.

The antibody may be a monoclonal antibody, a single chain monoclonal antibody, or a monoclonal antibody fragment thereof.

The antibody may be a humanized antibody, a humanized single chain antibody, or a humanized antibody fragment.

In any one of the alternative specific embodiment herein, such as the alternative $1^{st}$-$24^{th}$ specific embodiments, the imine reactive reagent is selected from the group consisting of sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxylamine (e.g., $NH_2OH$), hydrazine (e.g., $NH_2NH_2$), $NH_2O$—$R^i$, $R^{i'}NH$—$R^i$, $NH_2$—$R^i$), $NH_2$—CO—$NH_2$, $NH_2$—C(=S)—$NH_2'$ thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)($OR^k$)(SH)(OH) or a salt thereof formed with a cation), hydroxamic acid ($R^kC$(=O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-Na^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —$N(R^j)_2$, —$CO_2H$, —$SO_3H$, and —$PO_3H$; $R^i$ and $R^{i'}$ can be further optionally substituted with a substituent for an alkyl described herein; $R^j$ is a linear or branched alkyl having 1 to 6 carbon atoms; $R^k$ is a linear, branched or cyclic alkyl, alkenyl or alkynyl having 1 to 10 carbon atoms, aryl, heterocyclyl or heteroaryl.

Preferably, the imine reactive reagent is selected from sulfites, hydroxylamine, hydrazine and urea. More preferably, the imine reactive reagent is $NaHSO_3$ or $KHSO_3$.

In any one of the alternative specific embodiment herein, such as the alternative 1-$24^{th}$ specific embodiments, about 0.1 to about 30 molar equivalents of the imine reactive reagent to the imine-containing cytotoxic compound is used. In certain embodiments, about 1 to about 10 molar equivalents of the imine reactive reagent to the imine-containing cytotoxic compound is used. In certain embodiments, about 3 to about 5 molar equivalents of the imine reactive reagent to the imine-containing cytotoxic compound is used.

In any one of the alternative specific embodiment herein, such as the alternative $1^{st}$-$24^{th}$ specific embodiments, the bifunctional crosslinking agent links the cytotoxic agent to the cell-binding agent through a thioether bond, and may have a maleimido- or haloacetyl-based moiety, wherein the bifunctional crosslinking agent having the maleimido-based moiety is selected from: N-succinimidyl 4-(maleimidomethyl)cyclohexanecarboxylate (SMCC), N-succinimidyl-4-(N-maleimidomethyl)-cyclohexane-1-carboxy-(6-amido-caproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), N-(p-maleimidophenyl)isocyanate (PMPI), N-succinimidyl-4-(4-nitropyridyl-2-dithio)butanoate; and, wherein the bifunctional crosslinking agent having the haloacetyl-based moiety is selected from: N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-(β-maleimidopropyloxy)succinimide ester (BMPS), 5-maleimidovaleric acid NHS, HBVS, 4-(4-N-maleimidophenyl)-butyric acid hydrazide.HCl(MPBH), Succinimidyl-(4-vinylsulfonyl)benzoate (SVSB), dithiobis-maleimidoethane (DIME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutyryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal.

In certain embodiments, the bifunctional crosslinking agent is selected from the group consisting of SMCC, Sulfo-SMCC, BMPS, GMBS, SIA, SIAB, N-succinimidyl-4-(4-nitropyridyl-2-dithio)butanoate, bis-maleimidohexane or BMPEO.

In any of the embodiments, such as the alternative $1^{st}$-$24^{th}$ specific embodiments, the conjugate is purified by tangential flow filtration, adsorptive chromatography, adsorptive filtration, selective precipitation, non-absorptive filtration or combination thereof. Preferably, the conjugate is purified by tangential flow filtration and/or adsorptive chromatography.

In certain embodiments, such as the alternative $1^{st}$-$24^{th}$ specific embodiments, the cell-binding agent (CBA) bearing the thiol-reactive group is:

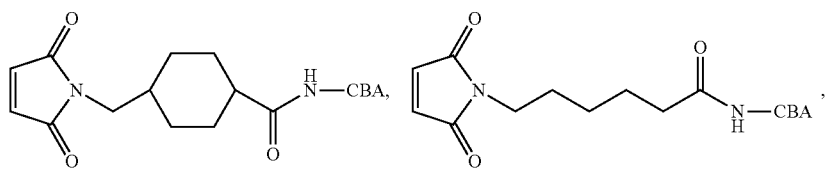

-continued
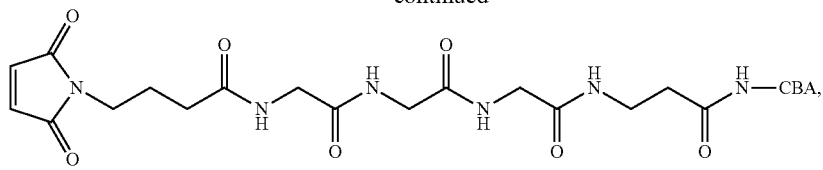
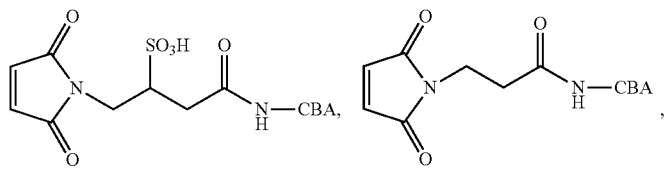
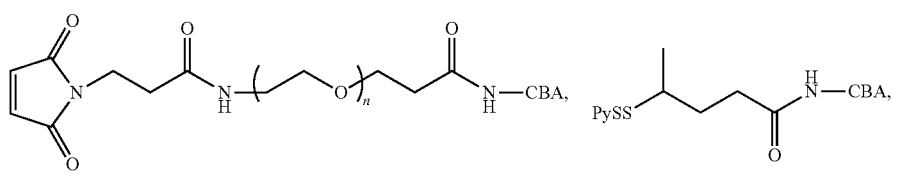
n = 2-20 (e.g., 2, 4, 6, 8, 10)
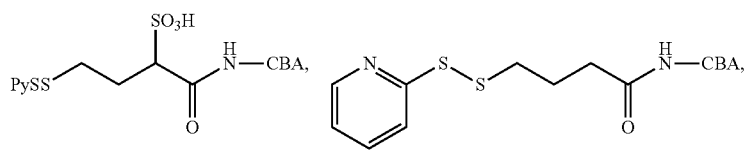
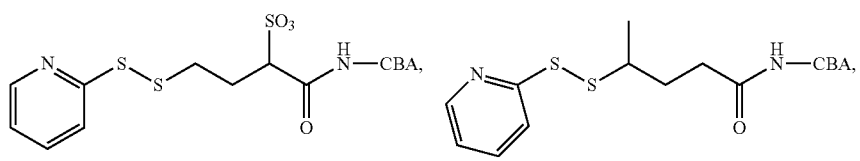
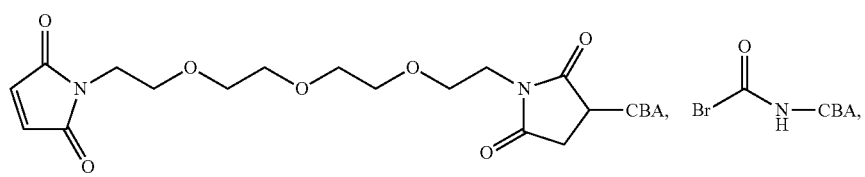
BM(PEG)₃
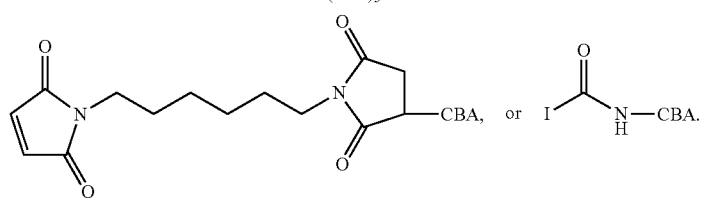
BMH In an alternative 25th specific embodiment, the invention provides a method for preparing a conjugate of the following formula:
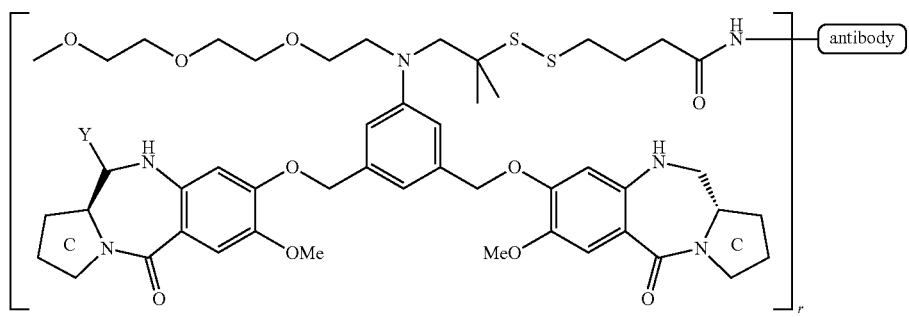
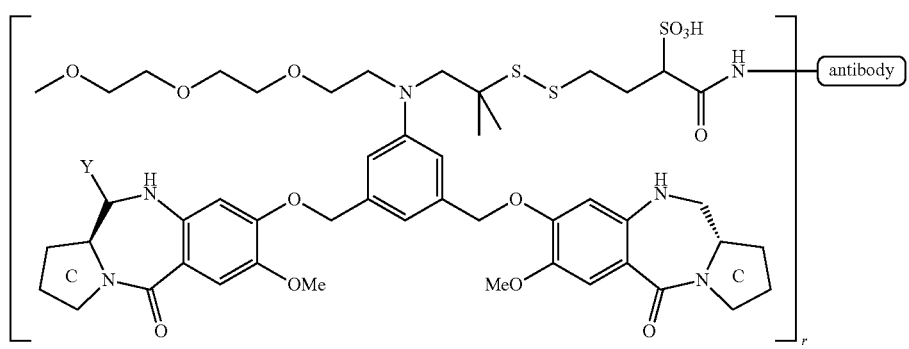
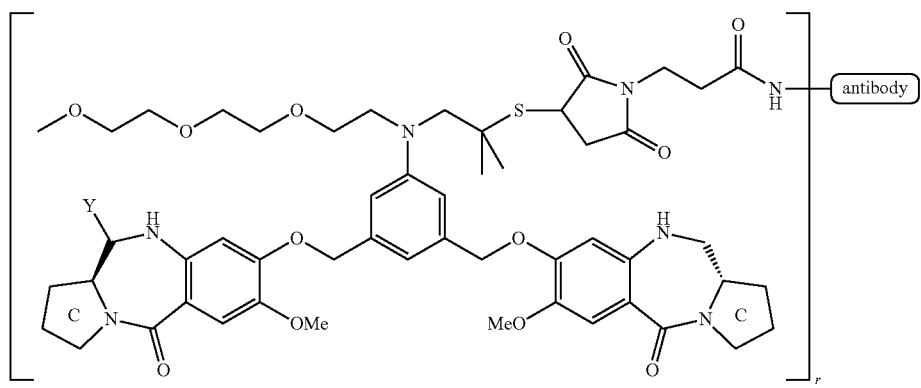
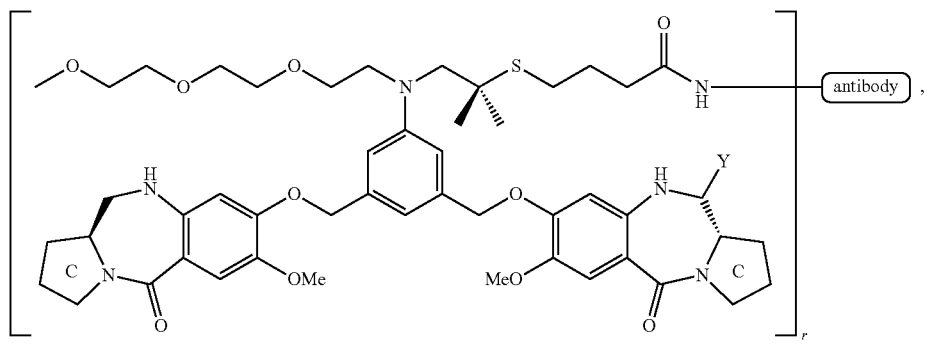
or
the method comprising reacting a modified cytotoxic compound of the following formula,

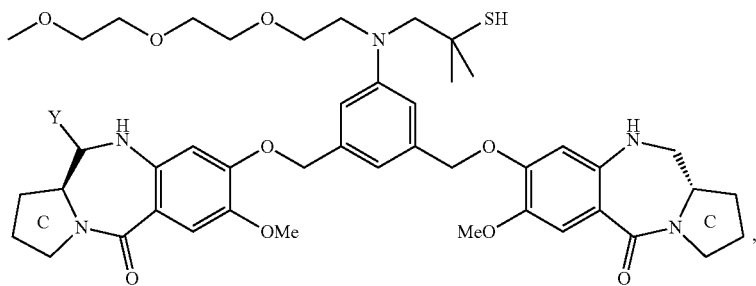

with a modified CBA of the following formula, respectively, at a pH of about 4 to about 9,

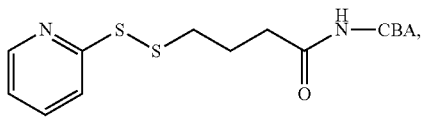

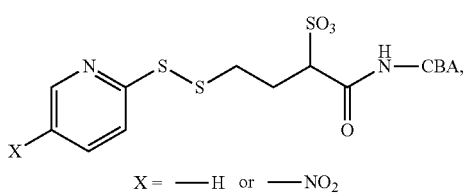

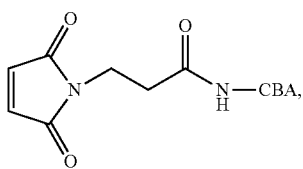

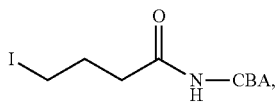

wherein:

the compound monomer with a C ring represents any monomer in formula (Vb'), (VIb'), or (VIIb');

r is an integer from 1 to 10;

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester ($R^iO)_2PS(OR^i$), $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; preferably Y is —$SO_3M$; and M is —H or a pharmaceutically acceptable cation.

In certain embodiments, Y is —$SO_3M$; and M is —H or a pharmaceutically acceptable cation. In certain embodiments, the CBA is huMy9-6.

In certain embodiments, the modified cytotoxic compound is produced by reacting an imine reactive reagent with an imine-containing cytotoxic compound of the following formula:

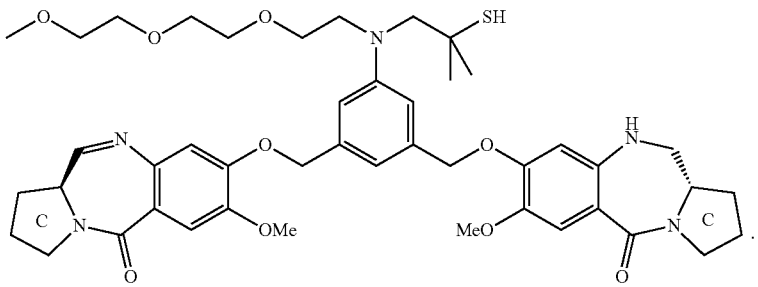

In certain embodiments, the CBA is huMy9-6.

In an alternative 26$^{th}$ specific embodiment, the invention provides a method for preparing a conjugate of the following formula:

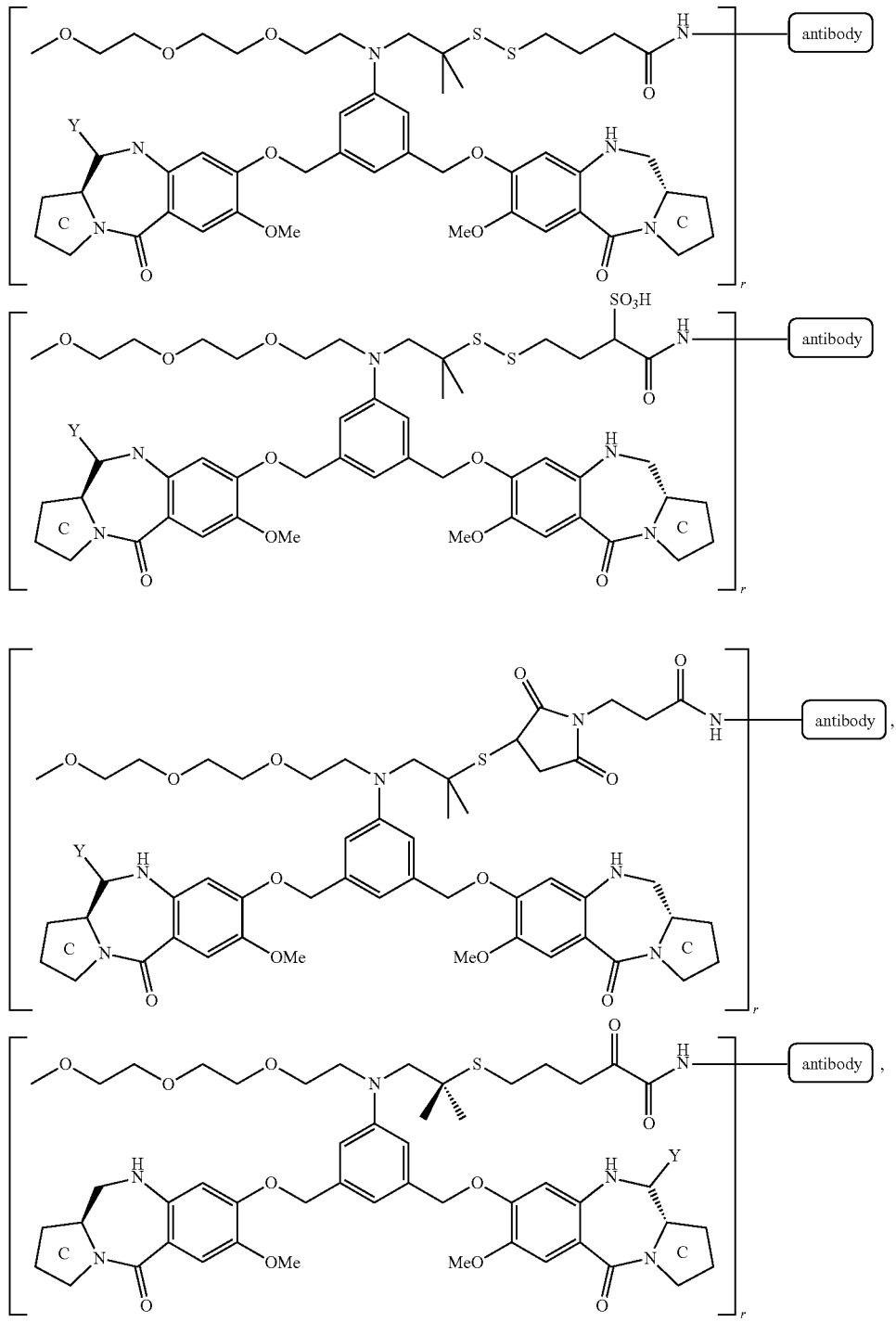

or the method comprising reacting the CBA with an imine-containing cytotoxic compound, an imine reactive reagent, and a bifunctional crosslinking agent comprising the linking group to form the conjugate, wherein:
the compound monomer with a C ring represents any monomer in formula (Vb'), (VIb'), or (VIIb');
the imine-containing cytotoxic compound is:

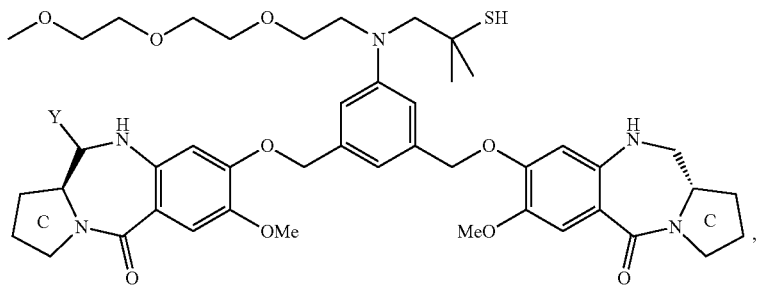

the bifunctional crosslinking agent is:

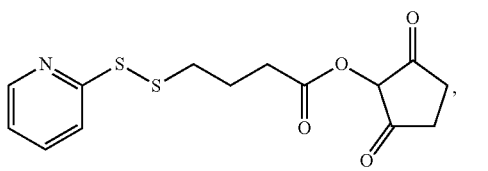

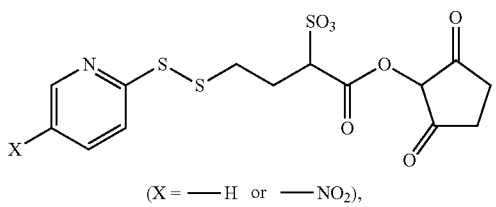

(X = —H or —NO$_2$),

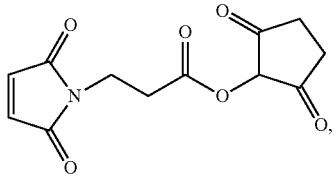

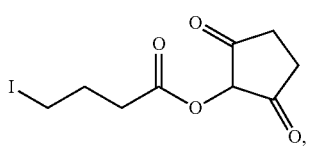

respectively, and,
the imine reactive reagent is selected from: sulfites (H$_2$SO$_3$, H$_2$SO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono, di, tri, and tetra-thiophosphates (PO$_3$SH$_3$, PO$_2$S$_2$H$_3$, POS$_3$H$_3$, PS$_4$H$_3$ or a salt of PO$_3$S$^{3-}$, PO$_2$S$_2^{3-}$, POS$_3^{3-}$ or PS$_4^{3-}$ formed with a cation), thio phosphate esters ((R$^i$O)$_2$PS(OR$^i$), R$^i$SH, R$^i$SOH, R$^i$SO$_2$H, R$^i$SO$_3$H), various amines (hydroxylamine (e.g., NH$_2$OH), hydrazine (e.g., NH$_2$NH$_2$), NH$_2$O—R$^i$, R$^{i'}$NH—R$^i$, NH$_2$—R$^i$), NH$_2$—CO—NH$_2$, NH$_2$—C(=S)—NH$_2$, thiosulfate (H$_2$S$_2$O$_3$ or a salt of S$_2$O$_3^{2-}$ formed with a cation), dithionite (H$_2$S$_2$O$_4$ or a salt of S$_2$O$_4^{2-}$ formed with a cation), phosphorodithioate (P(=S)(OR$^k$)(SH)(OH) or a salt thereof formed with a cation), hydroxamic acid (R$^k$C(=O)NHOH or a salt formed with a cation), hydrazide (R$^k$CONHNH$_2$), formaldehyde sulfoxylate (HOCH$_2$SO$_2$H or a salt of HOCH$_2$SO$_2^-$ formed with a cation, such as HOCH$_2$SO$_2^-$Na$^+$), glycated nucleotide (such as GDP-mannose), fludarabine or a mixture thereof, wherein R$^i$ and R$^{i'}$ are each independently a linear or branched alkyl having 1 to 10 carbon atoms and are substituted with at least one substituent selected from —N(R$^j$)$_2$, —CO$_2$H, —SO$_3$H, and —PO$_3$H; R$^i$ and R$^{i'}$ can be further optionally substituted with a substituent for an alkyl described herein; R$^j$ is a linear or branched alkyl having 1 to 6 carbon atoms; R$^k$ is a linear, branched or cyclic alkyl, alkenyl or alkynyl having 1 to 10 carbon atoms, aryl, heterocyclyl or heteroaryl.

In certain embodiments, Y is —SO$_3$M; and M is —H or a pharmaceutically acceptable cation.

In certain embodiments, the CBA is huMy9-6.

Representative Compounds and Conjugates

The structures of representative compounds and conjugates of the present invention are shown in Tables 1-5 and formulas below (e.g., (B1)-(B3), (C1), (D1)-(D3), etc.). These compounds and conjugates can be prepared according to the methods described herein, and are within the scope of the compounds and conjugates (and pharmaceutical composition and uses thereof) of the invention.

TABLE 1
Structures of representative compounds in the present invention.
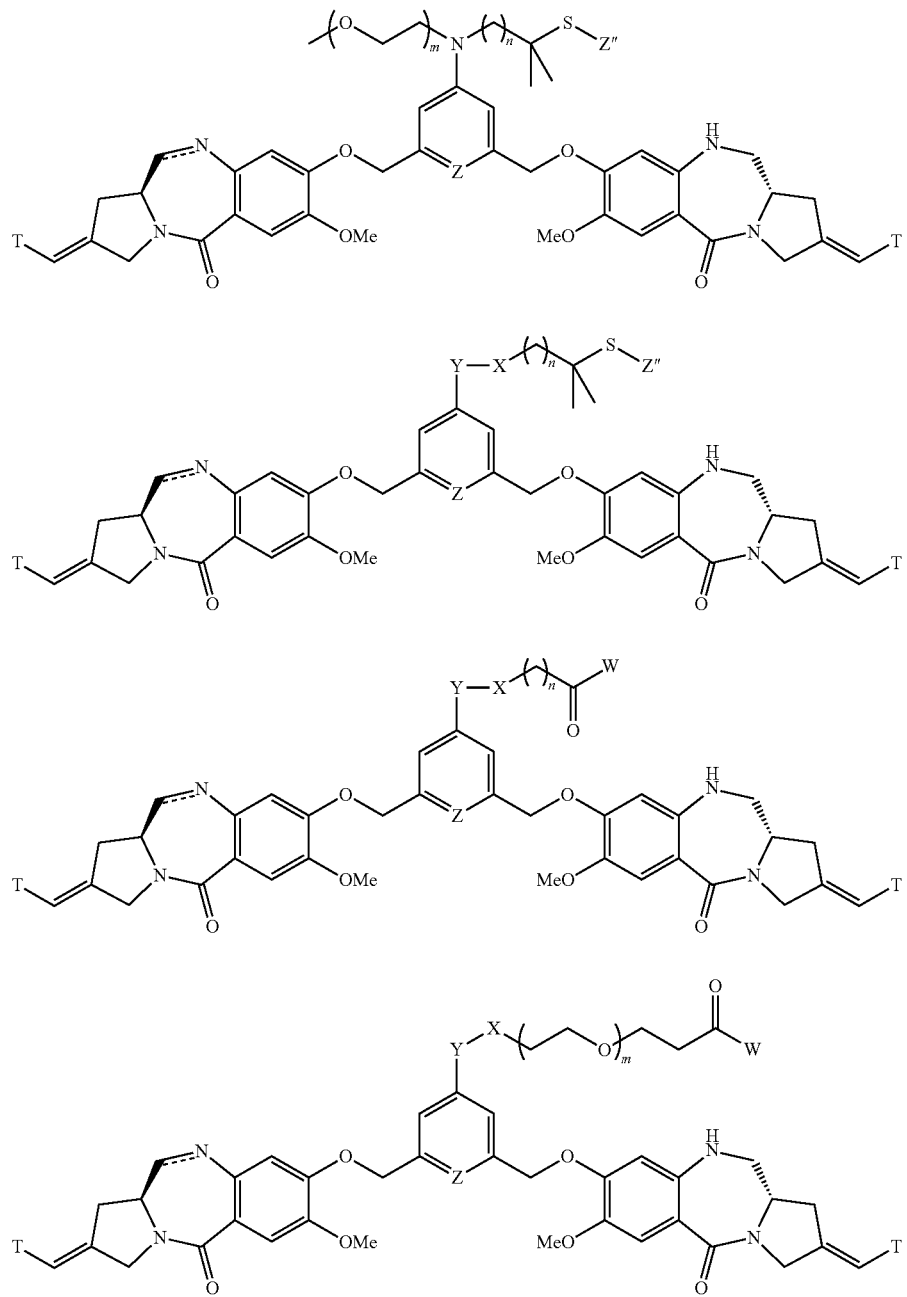
Note:
n = 1, 2 or 3
m = 3 or 4
T = H or Me
W = OH, OMe, ONHS, NHNH$_2$, H, Me, Ph, Peptide
X = CH$_2$, O, S, NH, NMe
Y = absent or CH$_2$
Z = CH or N
Z" = H, Me, SMe, S(CH$_2$)$_3$C(O)NHS or CH$_2$C(O)NHS or BMPS or SMCC or SPy or SPy—NO$_2$ TABLE 2
Structures of representative compounds in the present invention (Continue).
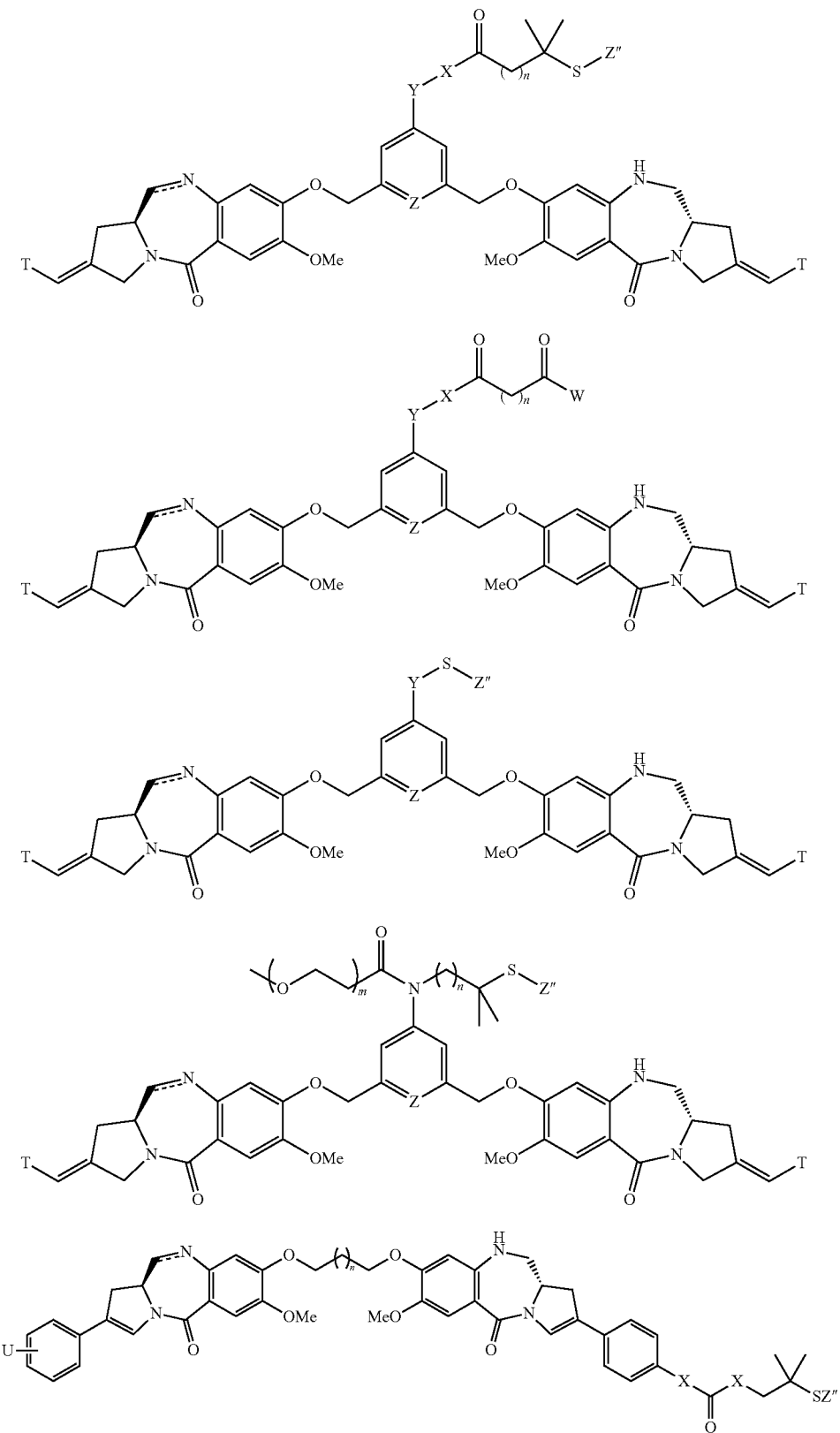

TABLE 2-continued
Structures of representative compounds in the present invention (Continue).
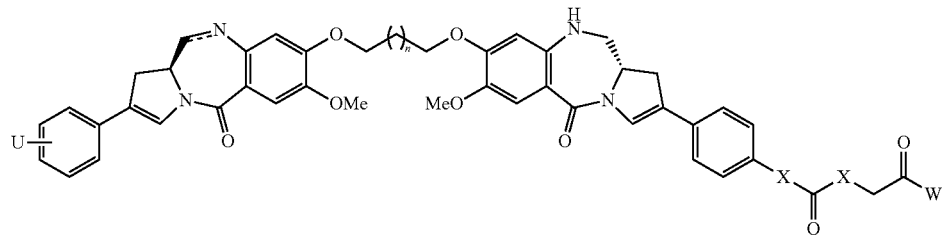
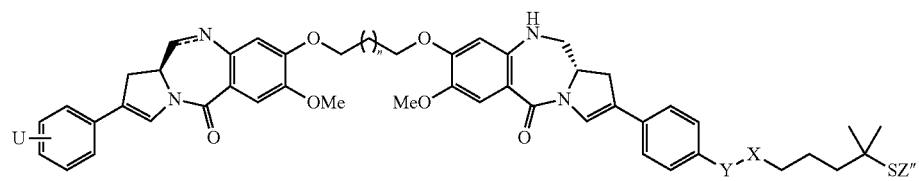
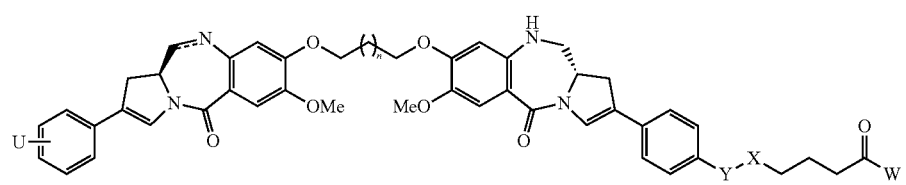
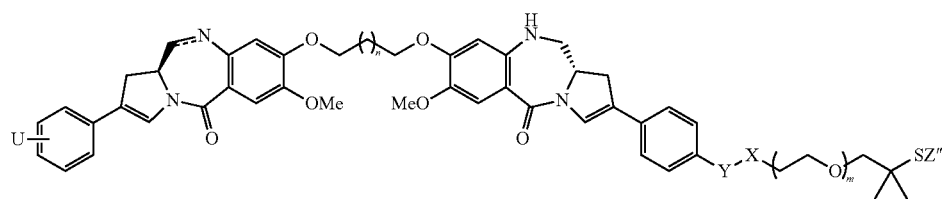
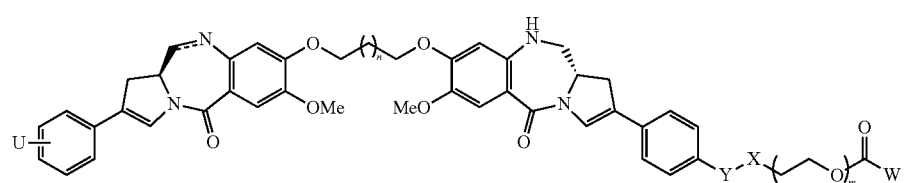
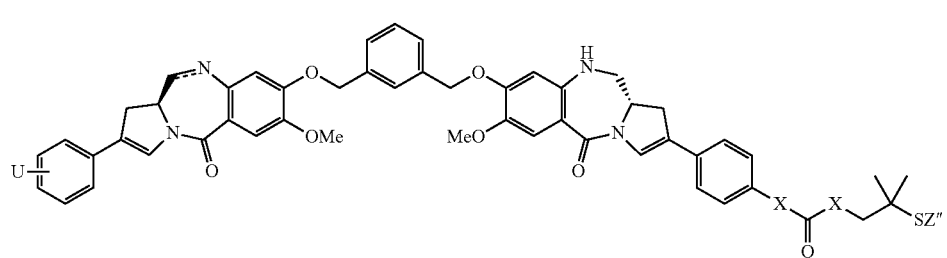

TABLE 2-continued

Structures of representative compounds in the present invention (Continue).

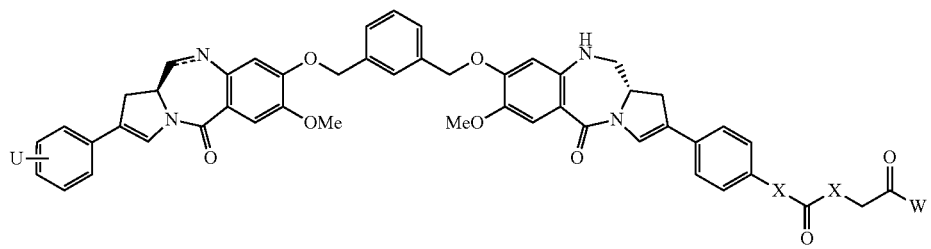

Note:
n = 1, 2 or 3
m = 3 or 4
T = H or Me
U = OH, OMe, SH, C(=O)OH, C(=O)H, N=C=O, NH$_2$, NR-Linker
W = OH, OMe, ONHS, NHNH$_2$, H, Me, Ph, Peptide
X = CH$_2$, O, S, NH, NMe
Y = absent or CH$_2$
Z = CH or N
Z" = H, Me, SMe, S(CH$_2$)$_3$C(O)NHS or CH$_2$C(O)NHS or BMPS or SMCC or SPy or SPy—NO$_2$

TABLE 3

Structures of representative compounds in the present invention (Continue).

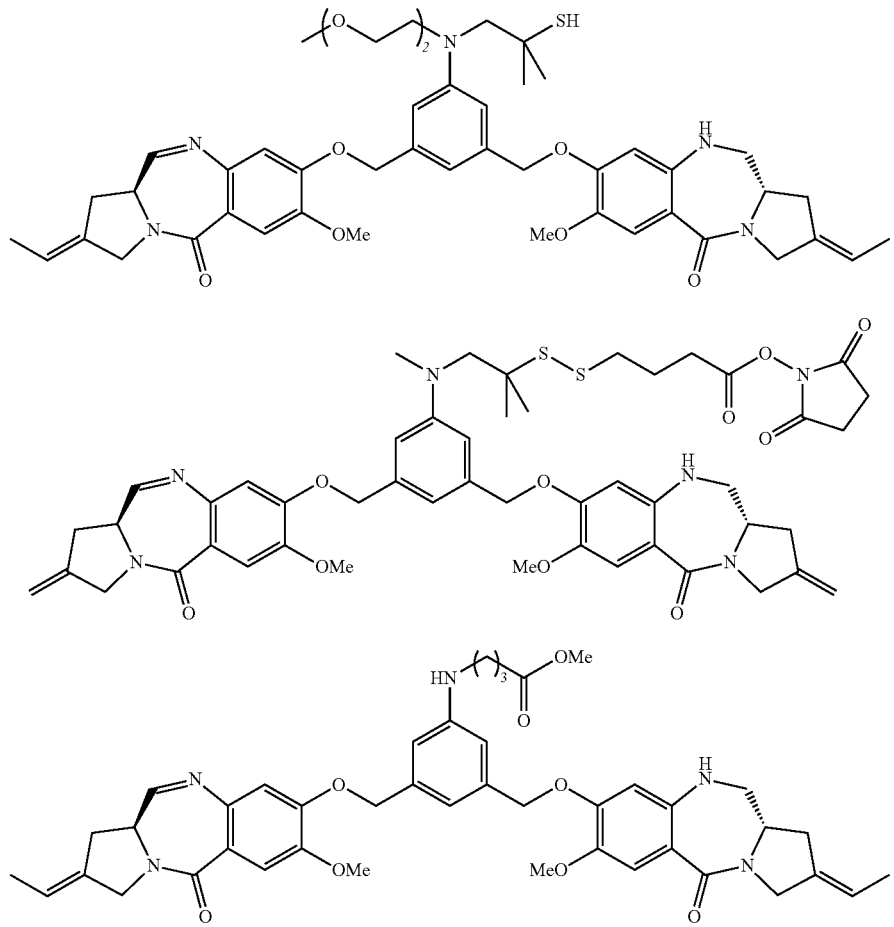

TABLE 3-continued
Structures of representative compounds in the present invention (Continue).
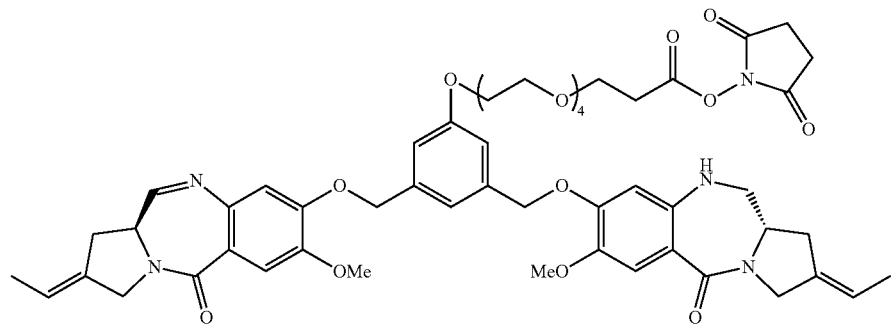
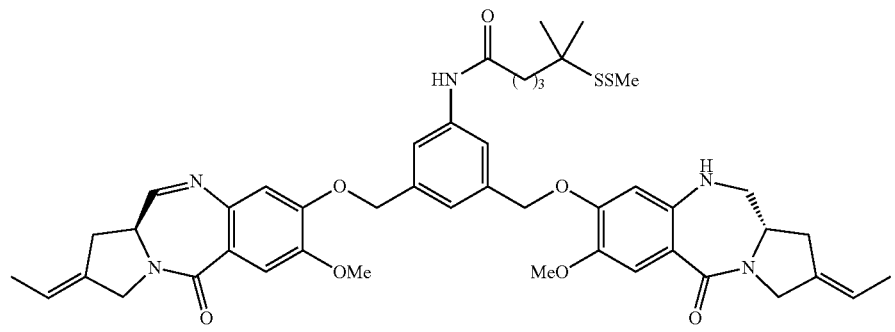
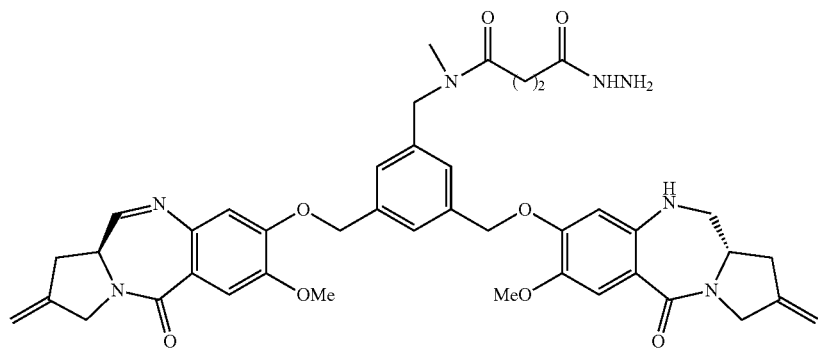
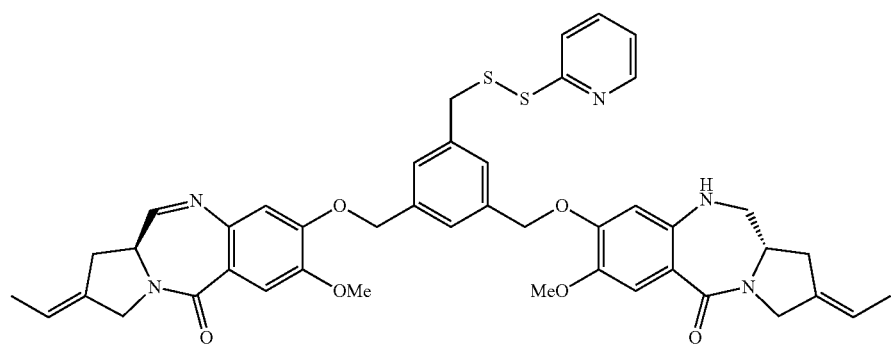 [SMILES: C/C=C1\C[C@H]2CNc3cc(OCc4cc(COc5cc6c(cc5OC)C(=O)N5C/C(=C/C)C[C@H]5C=N6)cc(CSSc5ccccn5)c4)c(OC)cc3C(=O)N2C1]

TABLE 3-continued
Structures of representative compounds in the present invention (Continue).
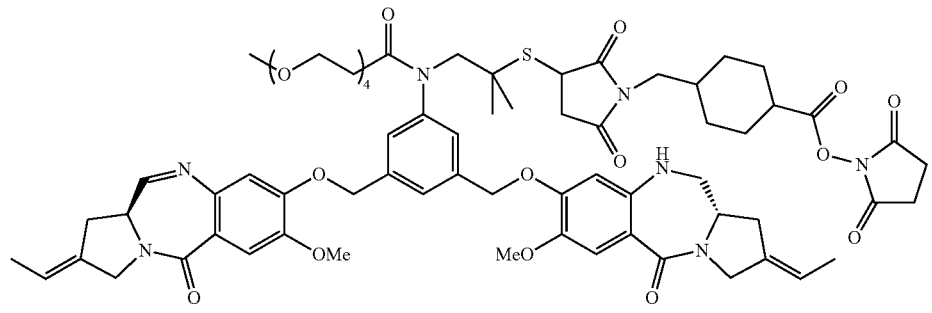
TABLE 4
Structures of representative compounds in the present invention (Continue).
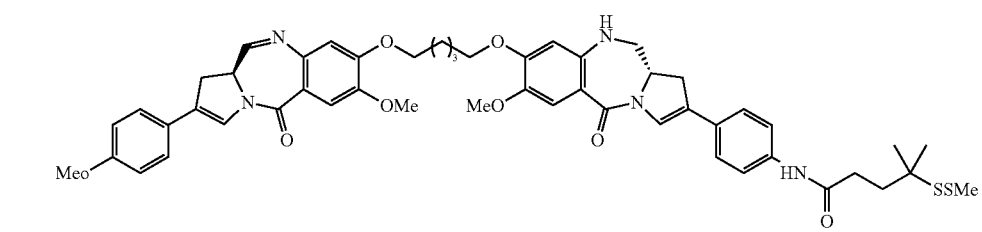
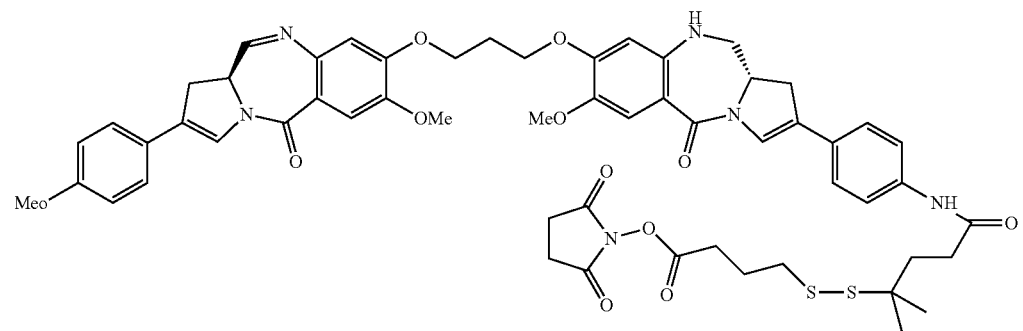
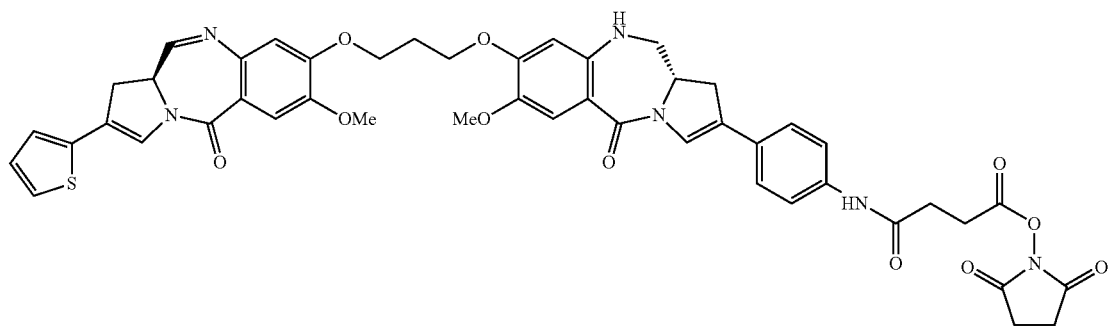 [SMILES: COc1cc2c(cc1OCCCOc1cc3c(cc1OC)C(=O)N1C=C(c4ccc(NC(=O)CCC(=O)ON5C(=O)CCC5=O)cc4)C[C@H]1CN3)N=C[C@@H]1CC(c3cccs3)=CN1C2=O]

TABLE 4-continued
Structures of representative compounds in the present invention (Continue).
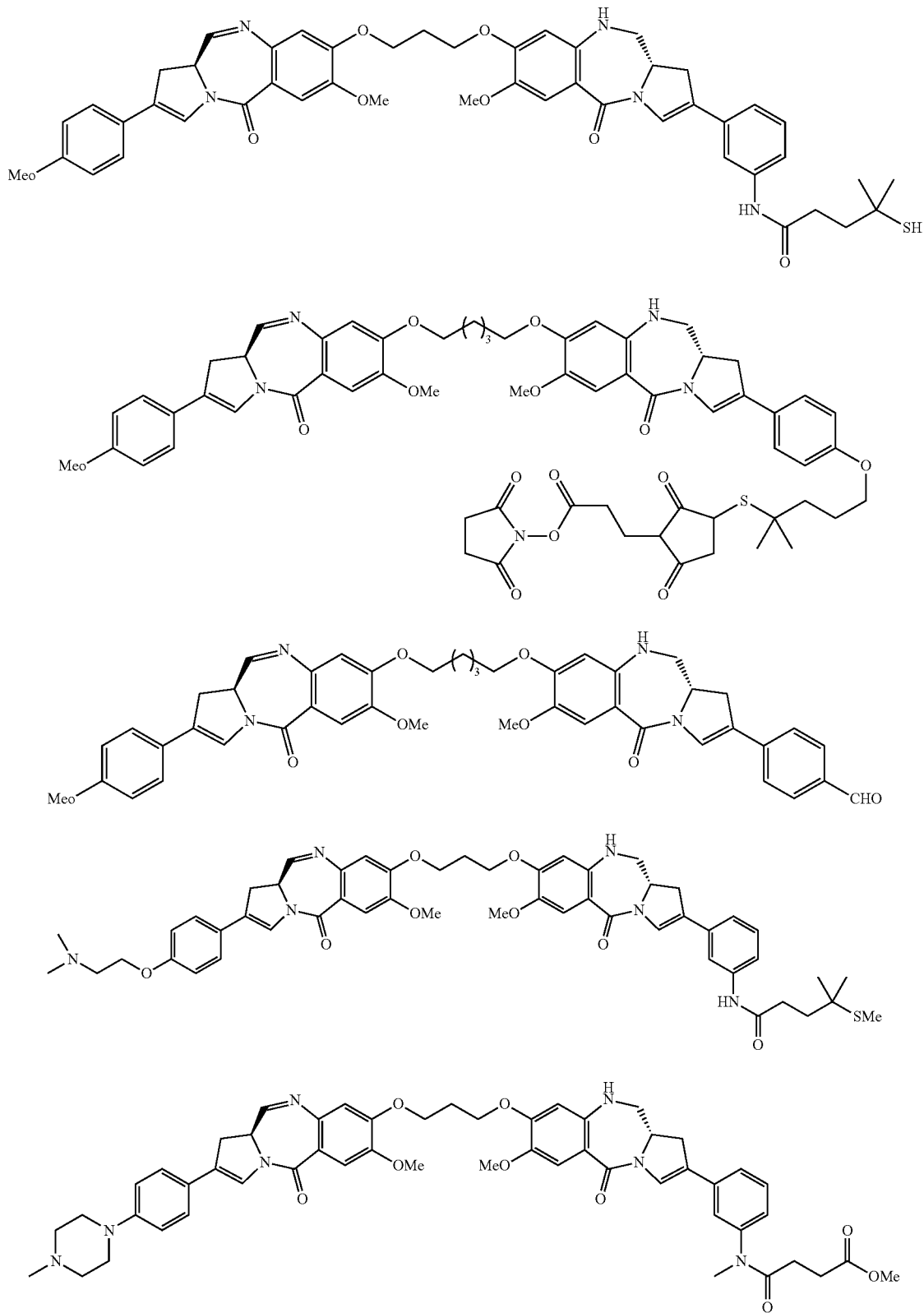

TABLE 4-continued
Structures of representative compounds in the present invention (Continue).
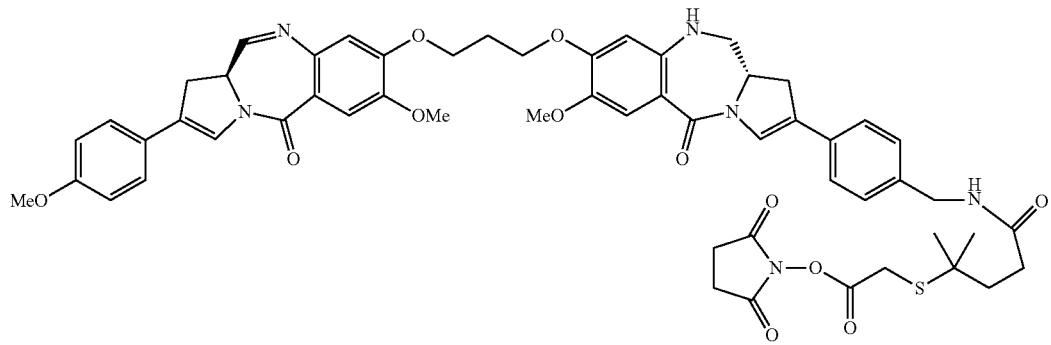 [SMILES: COc1ccc(C2=CN3C(=O)c4cc(OC)c(OCCCOc5cc6c(cc5OC)C(=O)N5C=C(c7ccc(CNC(=O)CCC(C)(C)SCC(=O)ON8C(=O)CCC8=O)cc7)C[C@H]5CN6)cc4N=C[C@@H]3C2)cc1]
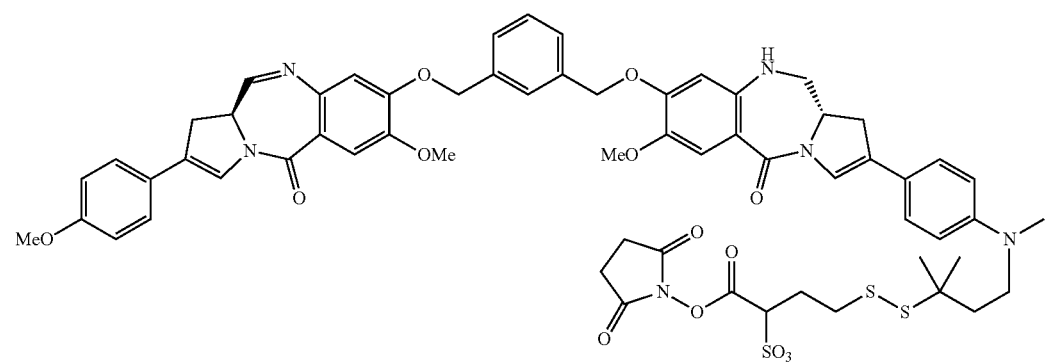
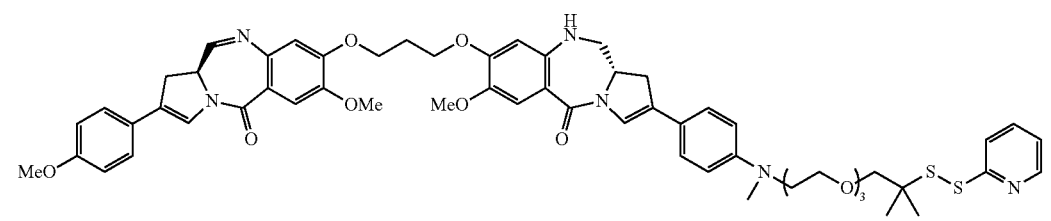
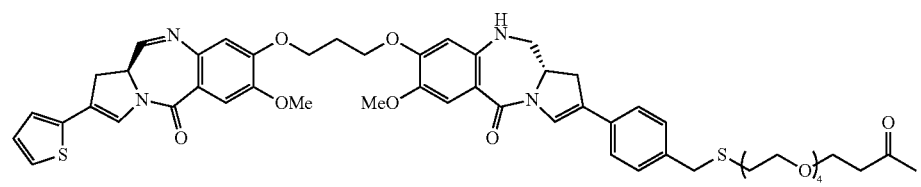

TABLE 5
Structures of representative conjugates of the present invention.
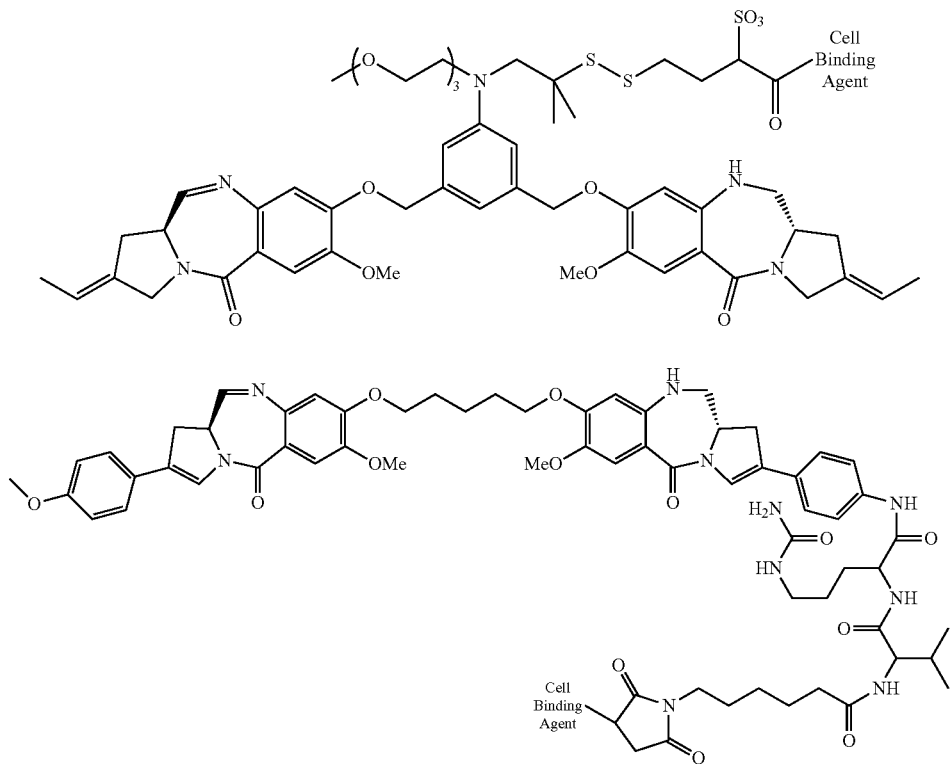
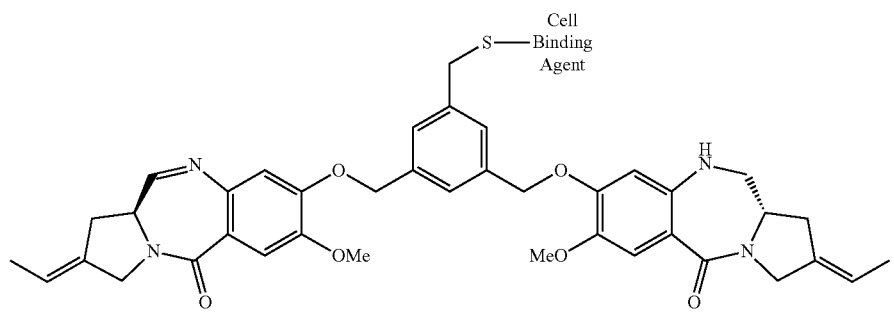 [SMILES: C/C=C1\C[C@H]2CNc3cc(OCc4cc(COc5cc6c(cc5OC)C(=O)N5C/C(=C/C)C[C@H]5C=N6)cc(CSC)c4)c(OC)cc3C(=O)N2C1]
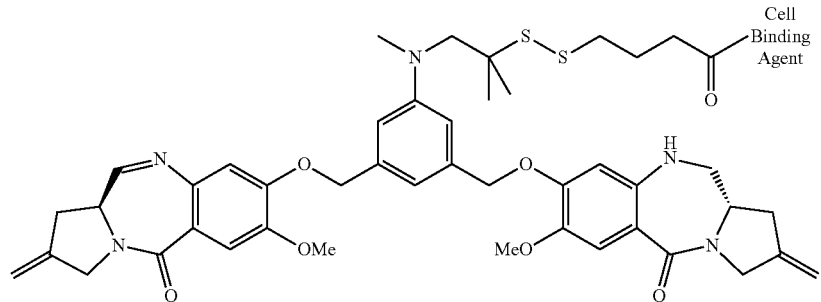

TABLE 5-continued

Structures of representative conjugates of the present invention.

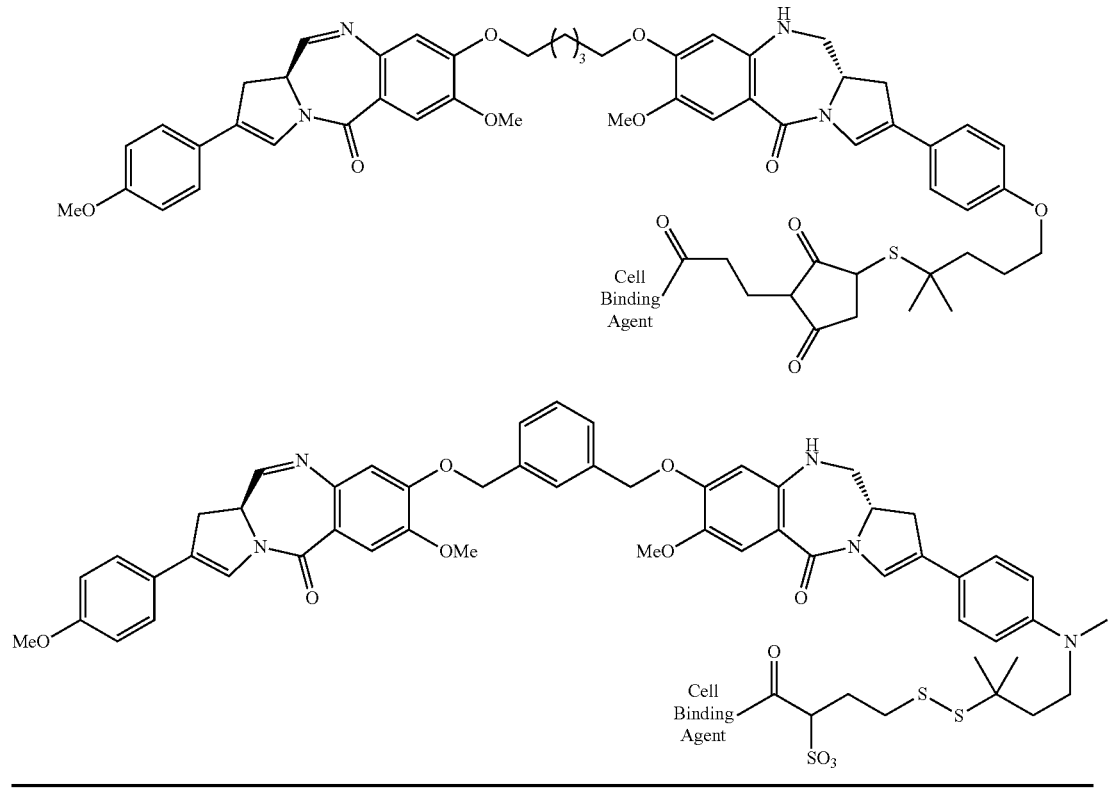

In another embodiment, the drugs that can be used in the methods of the present invention are represented by formula (B1):

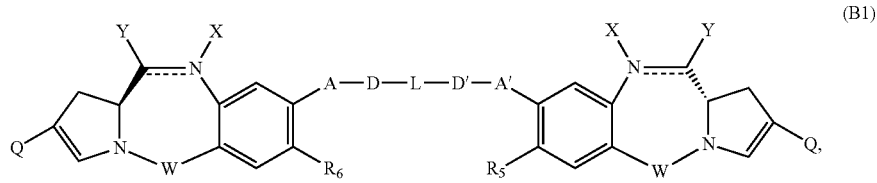

wherein:

Q is $Q_1$-Ar-$Q_2$;

Q' is $Q_1'$-Ar'-$Q_2'$;

$Q_1$ and $Q_1'$ are each independently absent, a linear, branched or cyclic alkyl from 1 to 6 carbon atoms or a CH=CH unit;

Ar and Ar' are each independently absent or represent an aryl group;

$Q_2$ and $Q_2'$ are each independently selected from —H, a linking group, a substituted or unsubstituted linear, branched or cyclic alkyl, alkenyl or alkynyl having from 1 to 10 carbon atoms, a polyethylene glycol unit $R^{c'}(OCH_2CH_2)_n$—$R^c$, or a substituent selected from a halogen, guanidinium [—NH(C=NH)NH$_2$], OR, NR'R", NO$_2$, —NCO, NR'COR", SR, a sulfoxide represented by SOR', a sulfone represented by —SO$_2$R', —SO$_2$M, a sulfonate —SO$_3$M, a sulfate —OSO$_3$M, a sulfonamide represented by SO$_2$NR'R", cyano, an azido, —COR', OCOR' or OCONR'R";

$R^{c'}$ is absent or selected from linear or branched alkyl, alkenyl or alkynyl having 1 to 5 carbon atoms;

$R^c$ is —H or a linear or branched alkyl having 1 to 4 carbon atoms, or a linking group; and the remainder of the variables are as described above for formula (VIIa), provided that at least one of the double line ⚌ between N and C represents a double bond.

In a preferred embodiment, for drugs of formula (B1):

the double line ⚌ between N and C represents a single bond or a double bond, provided that when it is a double bond X is absent and Y is —H. Preferably, the double line ⚌ between N and C represents a double bond;

when the double line ⚌ between N and C represents a single bond, X is —H or an amine protecting group (preferably, X is —H); and Y is selected from —OR, —OCOR', —SR, —NR'R", an optionally substituted 5 or 6-membered nitrogen-containing heterocycle (e.g., piperidine, tetrahydropyrrole, pyrazole, morpholine, etc.), —$SO_3M$, —$SO_2M$ or a sulfate —$OSO_3M$, wherein M is —H or a cation such as $Na^+$ or $K^+$. Preferably, M is —H or $Na^+$. Preferably, Y is selected from —$SO_3M$, —OH, —OMe, —OEt or —NHOH. More preferably, Y is —$SO_3M$ or —OH.

R, for each occurrence, is independently selected from the group consisting of —H, an optionally substituted linear, branched or cyclic alkyl, alkenyl or alkynyl having from 1 to 10 carbon atoms or phenyl;

R' and R" are same or different and are independently selected from —H, —OH, —OR, an optionally substituted linear, branched or cyclic alkyl, alkenyl or alkynyl having from 1 to 10 carbon atoms or phenyl;

W is C=O.

$R_6$ is —$OR^c$ or —$SR^c$, wherein $R^c$ is H, a linear or branched alkyl having 1 to 4 carbon atoms. Preferably, $R_6$ is —OMe or —SMe. Even more preferably, $R_6$ is OMe.

X' is selected from the group consisting of —H, —OH, an optionally substituted linear, branched or cyclic alkyl, alkenyl or alkynyl having from 1 to 10 carbon atoms, phenyl, a linking group, and an amine-protecting group. Preferably, X' is —H, —OH, -Me or a linking group. More preferably, X' is —H.

Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or oxo. More preferably, Y' is —H;

A and A' are the same or different and are selected from O, S, $NR_5$ and oxo (C=O). Preferably, A and A' are same or different and selected from O and S. More preferably, A and A' are O.

D and D' are same or different and independently selected from a polyethylene glycol unit —(—$OCH_2CH_2$)$_n$—, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more (e.g., 2, 3, 4, 5, 6 or more) substituents independently selected from the group consisting of halogen, —OR, —NR'COR", —SR and —COR'.

Preferably, D and D' are same or different and independently selected from linear, branched or cyclic alkyl, alkenyl or alkynyl having from 1 to 10 carbon atoms. More preferably, D and D' are linear or branched alkyl bearing 1 to 4 carbon atoms. Still more preferably, D and D' are same or different and selected from a linear alkyl having 1 to 4 carbon atoms.

L is absent, or is selected from an optionally substituted phenyl group and an optionally substituted pyridyl group, wherein the phenyl and the pyridyl group bears a linking group that enables linkage to a cell binding agent via a covalent bond, or L is an amine group bearing a linking group that enables linkage to a cell binding agent via a covalent bond (i.e., —N(linking group)-), or L is a linear, branched or cyclic alkyl or alkenyl having from 1 to 6 carbon atoms and bearing a linking group that enables linkage to a cell binding agent via a covalent bond.

In certain embodiments, compounds of formula (B1) are represented by the following formula:

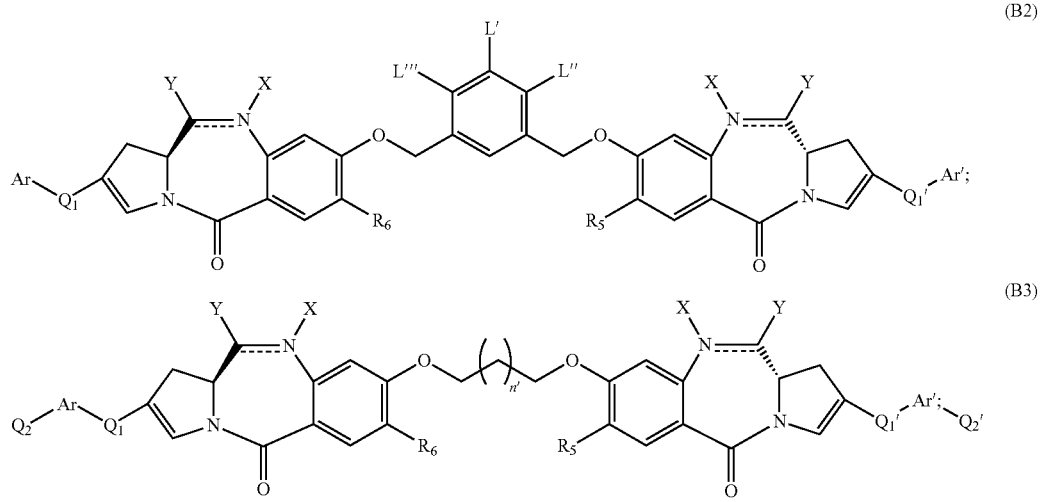

(B2)

(B3)

wherein the values and preferred values for X, Y, L', L", L''', and $R_6$ are as described above for formulas (IA) and (IIA), including any of the alternative specific embodiments; $Q_1$, $Q_1'$, Ar and Ar' are as described above for formula (B1); and one of $Q_2$ and $Q_2'$ is selected from —H, R, OR, NR'R", NR'(C=O)OR", SR and $NO_2$, the other is a linking group. Preferably, Y" is O, S or NR'. More preferably, Y" is O.

In another preferred embodiment, $Q_1$ and $Q_1'$ are absent; Ar and Ar' are an optionally substituted phenyl.

In another embodiment, L' in formula (B2), and one of $Q_2$ and $Q_2'$ in formula (B3) is a linking group represented by the following formula:

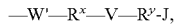

—W'—$R^x$—V—$R^y$-J, wherein:

W', $R^x$, V, $R^y$ and J are as defined in the alternative 4$^{th}$ specific embodiment above.

More preferably, W' is absent, —$CR^eR^e$—, —O—, —O—C(=O)—, —S—, —$CH_2$—S—, —O—(C=O)O—, —O—(C=O)N($R^e$)—, —N($R^e$)—, —N($R^e$)—C(=O)—, —N($R^e$)—C(=O)O—, or —C(=O)—;

R$^x$ is absent or an optionally substituted linear, branched or cyclic alkyl, alkenyl or alkynyl having 1 to 10 carbon atoms;

V is absent, —(CH$_2$—CH$_2$—O)$_n$—, —O—, —O—C(=O)—, —S—, —O—(C=O)O—, O—(C=O)N(R$^e$)—, —N(R$^e$)—, —N(R$^e$)—C(=O)—, —N(R$^e$)—C(=O)O—, —C(=O)—, an amino acid, or a peptide having 2 to 8 amino acids;

R$^y$ is absent or a linear, branched or cyclic alkyl having 1 to 10 carbon atoms;

R$^{e'}$ is —H or a linear or branched alkyl having 1 to 4 carbon atoms;

R$^e$ is H, a linear, branched or cyclic alkyl, alkenyl or alkynyl having 1 to 10 carbon atoms or —(CH$_2$—CH$_2$—O)$_n$—R$^c$, n is an integer from 1 to 24.

Preferably, R$^{e'}$ is H or Me; R$^e$ is a linear or branched alkyl having 1 to 6 carbon atoms or —(CH$_2$—CH$_2$—O)$_n$—R$^c$; n is an integer from 2 to 8; and the remainder of the variables are as described above in the alternative fourth specific embodiment.

In another preferred embodiment, V is an amino acid or a peptide having 2 to 8 amino acids. More preferably, V is valine-citrulline, gly-gly-gly or ala-leu-ala-leu.

Preferably, J is SH, —SSR$^d$ or —COE as described above.

In certain embodiments, for compounds of formulas (B2) and (B3) described above, L" and L''' are H, and L' is represented by —W'—R$^x$—S—Z$^s$, wherein the variables are as described in the alternative eighth and alternative ninth specific embodiments.

In another embodiment, the drugs that can be used in the methods of the present invention are represented by:

erably W and W' are the same or different and are OH, OMe, OEt, NHCONH$_2$, SMe;

and when ≡≡≡≡ represents a double bond, U and U' are absent and W and W' represent H;

R1, R2, R1', R2' are the same or different and independently chosen from Halide or Alkyl optionally substituted by one or more Hal, CN, NRR', CF$_3$, OR, Aryl, Het, S(O)$_q$R, or R1 and R2 and R1' and R2' form together a double bond containing group =B and =B' respectively. Preferably, R1=R2=R1'=R2'=H, or more preferably R1 and R2 and R1' and R2' form together a double bond containing group =B and =B' respectively.

B and B' are the same or different and independently chosen from Alkyl being optionally substituted by one or more Hal, CN, NRR', CF$_3$, OR, Aryl, Het, S(O)$_q$R or B and B' represent an oxygen atom. Preferably, B=B'. More preferably, B=B'=CH$_2$ or =CH—CH$_3$;

X, X' are the same or different and independently chosen from one or more —O—, —NR—, —(C=O)— and —S(O)$_q$—. Preferably, X=X'. More preferably, X=X'=O.

A, A' are the same or different and independently chosen from Alkyl or Alkenyl optionally containing an oxygen, a nitrogen or a sulfur atom and optionally substituted by one or more Hal, CN, NRR', CF$_3$, OR, S(O)$_q$R, Aryl, Het, Alkyl, Alkenyl. Preferably, A=A'. More preferably, A=A'=linear unsubstituted alkyl.

Y, Y' are the same or different and independently chosen from H, OR. Preferably, Y=Y'. More preferably, Y=Y'=OAlkyl, more preferably OMethyl.

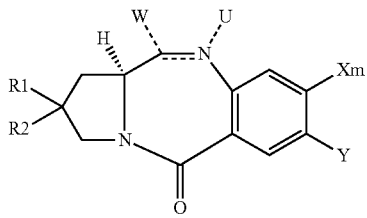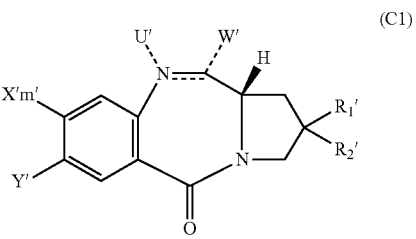

(C1)

---- represents an optional single bond;

≡≡≡≡ represents either a single bond or a double bond; provided that at least one of ≡≡≡≡ represents a double bond, and when ≡≡≡≡ represents a single bond, U and U', the same or different, independently represent H, and W and W', the same or different, are independently selected from the group consisting of —OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphite such as —SO$_3$, a bisulphite such as —OSO$_3$, a sulfonamide such as —NRSOOR, an amine such as —NRR', optionally cyclic amine such that N10 and C11 are a part of the cycle, a hydroxylamine derivative such as —NROR', an amide such as —NRCOR, an azido such as —N$_3$, a cyano, a halo, a trialkyl or triarylphosphonium, an aminoacid-derived group; Pref- T is —NR—, —O—, —S(O)$_q$—, or a 4 to 10-membered aryl or heteroaryl, all being optionally substituted by one or more Hal, CN, NRR', CF$_3$, OR, S(O)$_q$R, Alkyl, and/or linker(s), or a branched Alkyl, optionally substituted by one or more Hal, CN, NRR', CF$_3$, OR, S(O)$_q$R and/or linker(s), or a linear Alkyl substituted by one or more Hal, CN, NRR', CF$_3$, OR, S(O)$_q$R and/or linker(s).

Preferably, T is a 4 to 10-membered aryl or heteroaryl, more preferably phenyl or pyridyl, optionally substituted by one or more linker(s).

Suitable linking groups are well known in the art and include thiol, sulfide, disulfide groups, thioether groups, acid labile groups, photolabile groups, peptidase labile groups and esterase labile groups. Preferred are disulfide groups and thioether groups.

When the linking group is a thiol-, sulfide (or so-called thioether —S—) or disulfide (—S—S—)-containing group, the side chain carrying the thiol, the sulfide or disulfide group can be linear or branched, aromatic or heterocyclic. One of ordinary skill in the art can readily identify suitable side chains.

Specific examples of the thiol-, sulfide- or disulfide-containing substituents include —$(CR_{13}R_{14})_t(CR_{15}R_{16})_u(OCH_2CH_2)_ySZ'$,
—$(CR_{13}R_{14})_t(CR_{17}=CR_{18})(CR_{15}R_{16})_y(OCH_2CH_2)_ySZ'$,
—$(CR_{13}R_{14})_t(NR_{19}CO)(CR_{15}R_{16})_u(OCH_2CH_2)_ySZ'$,
—$(CR_{13}R_{14})_t(OCO)(R_{15}R_{16})_u(OCH_2CH_2)_ySZ'$,
—$(CR_{13}R_{14})_t(CO)(CR_{15}R_{16})_u(OCH_2CH_2)_ySZ'$,
—$(CR_{13}R_{14})_t(CONR_{19})(CR_{15}R_{16})_u(OCH_2CH_2)_ySZ'$,
—$(CR_{13}R_{14})_t$-phenyl-$CO(CR_{15}R_{16})_uSZ'$,
—$(CR_{13}R_{14})_t$-furyl-$CO(CR_{15}R_{16})_uSZ'$,
—$(CR_{13}R_{14})_t$-oxazolyl-$CO(CR_{15}R_{16})_uSZ'$,
—$(CR_{13}R_{14})_t$-thiazolyl-$CO(CR_{15}R_{16})_uSZ'$,
—$(CR_{13}R_{14})_t$-thienyl-$CO(CR_{15}R_{16})_uSZ'$,
—$(CR_{13}R_{14})_t$-imidazolyl-$CO(CR_{15}R_{16})_uSZ'$,
—$(CR_{13}R_{14})_t$-morpholino-$CO(CR_{15}R_{16})_uSZ'$,
—$(CR_{13}R_{14})_t$piperazino-$CO(CR_{15}R_{16})_uSZ'$,
—$(CR_{13}R_{14})_t$—N-methylpiperazin-$CO(CR_{15}R_{16})_uSZ'$,
—$(CR_{13}R_{14})_t$-phenyl-$QSZ'$,
—$(CR_{13}R_{14})_t$-furyl-$QSZ'$,
—$(CR_{13}R_{14})_t$-oxazolyl-$QSZ'$,
—$(CR_{13}R_{14})_t$-thiazolyl-$QSZ'$,
—$(CR_{13}R_{14})_t$-thienyl-$QSZ'$,
—$(CR_{13}R_{14})_t$-imidazolyl-$QSZ'$,
—$(CR_{13}R_{14})_t$-morpholino-$QSZ'$,
—$(CR_{13}R_{14})_t$-piperazino-$QSZ'$,
—$(CR_{13}R_{14})_t$—N-methylpiperazino-$QSZ'$, or
—$O(CR_{13}R_{14})_t(CR_{15}R_{16})_u(OCH_2CH_2)_ySZ'$,
—$O(CR_{13}R_{14})_t(NR_{19}CO)(CR_{15}R_{16})_u(OCH_2CH_2)_ySZ'$,
—$O(CR_{13}R_{14})_t(CR_{17}=CR_{18})(CR_{15}R_{16})_t(OCH_2CH_2)_ySZ'$,
—O-phenyl-$QSZ'$,
—O-furyl-$QSZ'$,
—O-oxazolyl-$QSZ'$,
—O-thiazolyl-$QSZ'$,
—O-thienyl-$QSZ'$,
—O-imidazolyl-$QSZ'$,
—O-morpholino-$QSZ'$,
—O-piperazino-$QSZ'$,
—O—N-methylpiperazino-$QSZ'$,
—$OCO(CR_{13}R_{14})_t(NR_{19}CO)_v(CR_{15}R_{16})_u(OCH_2CH_2)_ySZ'$,
—$OCO$—$(CR_{13}R_{14})_t(CR_{17}=CR_{18})(CR_{15}R_{16})_u(OCH_2CH_2)_ySZ'$,
—$OCONR_{12}(CR_{13}R_{14})_t(CR_{15}R_{16})_u(OCH_2CH_2)_ySZ'$,
—OCO-phenyl-$QSZ'$,
—OCO-furyl-$QSZ'$,
—OCO-oxazolyl-$QSZ'$,
—OCO-thiazolyl-$QSZ'$,
—OCO-thienyl-$QSZ'$,
—OCO-imidazolyl-$QSZ'$,
—OCO-morpholine-$QSZ'$,
—OCO-piperazino-$QSZ'$,
—OCO—N-methylpiperazino-$QSZ'$, or
—$CO(CR_{13}R_{14})_t(CR_{15}R_{16})_u(OCH_2CH_2)_ySZ'$,
—$CO$—$(CR_{13}R_{14})_t(CR_{17}=CR_{18})(CR_{15}R_{16})_u(OCH_2CH_2)_ySZ'$,
—$CONR_{12}(CR_{13}R_{14})_t(CR_{15}R_{16})_u(OCH_2CH_2)_ySZ'$,
—CO-phenyl-$QSZ'$,
—CO-furyl-$QSZ'$,
—CO-oxazolyl-$QSZ'$,
—CO-thiazolyl-$QSZ'$,
—CO-thienyl-$QSZ'$,
—CO-imidazolyl-$QSZ'$,
—CO-morpholino-$QSZ'$,
—CO-piperazino-$QSZ'$,
—CO-piperidino-$QSZ'$,
—CO—N-methylpiperazino-$QSZ'$,
—$NR_{19}(CR_{13}R_{14})_t(CR_{15}R_{16})_u(OCH_2CH_2)_ySZ'$,
—$NR_{19}CO(CR_{13}R_{14})_t(CR_{15}R_{16})_u(OCH_2CH_2)_ySZ'$,
—$NR_{19}(CR_{13}R_{14})_t(CR_{17}=CR_{18})(CR_{15}R_{16})_t(OCH_2CH_2)_ySZ'$,
—$NR_{19}CO(CR_{13}R_{14})_t$ $(CR_{17}=CR_{18})(CR_{15}R_{16})_t(OCH_2CH_2)_ySZ'$,
—$NR_{19}CONR_{12}(CR_{13}R_{14})_t(CR_{15}R_{16})_u(OCH_2CH_2)_ySZ'$,
—$NR_{19}CONR_{12}(CR_{13}R_{14})_t(CR_{17}=CR_{18})(CR_{15}R_{16})_t(OCH_2CH_2)_ySZ'$,
—$NR_{19}CO$-phenyl-$QSZ'$,
—$NR_{19}CO$-furyl-$QSZ'$,
—$NR_{19}CO$-oxazolyl-$QSZ'$,
—$NR_{19}CO$-thiazolyl-$QSZ'$,
—$NR_{19}CO$-thienyl-$QSZ'$,
—$NR_{19}CO$-imidazolyl-$QSZ'$,
—$NR_{19}CO$-morpholino-$QSZ'$,
—$NR_{19}CO$-piperazino-$QSZ'$,
—$NR_{19}CO$-piperidino-$QSZ'$,
—$NR_{19}CO$—N-methylpiperazino-$QSZ'$,
—$NR_{19}$-phenyl-$QSZ'$,
—$NR_{19}$-furyl-$QSZ'$,
—$NR_{19}$-oxazolyl-$QSZ'$,
—$NR_{19}$-thiazolyl-$QSZ'$,
—$NR_{19}$-thienyl-$QSZ'$,
—$NR_{19}$-imidazolyl-$QSZ'$,
—$NR_{19}$-morpholino-$QSZ'$,
—$NR_{19}$-piperazino-$QSZ'$,
—$NR_{19}$-piperidino-$QSZ'$,
—$NR_{19}$—N-methylpiperazino-$QSZ'$,
—$NR_{19}CO$—$NR_{12}$-phenyl-$QSZ'$,
—$NR_{19}CO$—$NR_{12}$-oxazolyl-$QSZ'$,
—$NR_{19}CO$—$NR_{12}$-thiazolyl-$QSZ'$,
—$NR_{19}CO$—$NR_{12}$-thienyl-$QSZ'$,
—$NR_{19}CO$—$NR_{12}$-piperidino-$QSZ'$,
—$S(O)_q(CR_{13}R_{14})_t(CR_{15}R_{16})_u(OCH_2CH_2)_ySZ'$,
—$S(O)_q(CR_{13}R_{14})_t(CR_{17}=CR_{18})(CR_{15}R_{16})_t(OCH_2CH_2)_ySZ'$,
—$SCONR_{12}(CR_{13}R_{14})_t(CR_{15}R_{16})_u(OCH_2CH_2)_ySZ'$,
—SCO-morpholino-$QSZ'$,
—SCO-piperazino-$QSZ'$,
—SCO-piperidino-$QSZ'$, and
—SCO—N-methylpiperazino-$QSZ'$, wherein:

$Z'$ is H, a thiol protecting group such as Ac, $R_{19}'$ or $SR_{19}'$, wherein Q is a direct link or a linear alkyl or branched alkyl having from 1-10 carbon atoms or a polyethylene glycol spacer with 2 to 20 repeating ethylene oxy units;

$R_{19}'$ and $R_{12}$ are the same or different and are linear alkyl, branched alkyl or cyclic alkyl having from 1 to 10 carbon atoms, or simple or substituted aryl or heterocyclic, and $R_{12}$ can in addition be H, $R_{13}$, $R_{14}$, $R_{15}$ and $R_{16}$ are the same or different and are H or a linear or branched alkyl having from 1 to 4 carbon atoms, $R_{17}$, $R_{18}$ and $R_{19}$ are H or alkyl, u is an integer from 1 to 10 and can also be 0, t is an integer from 1 to 10 and can also be 0, y is an integer from 1 to 20 and can also be 0.

m, n, m', n', equal or different are 0 or 1.

q is 0, 1 or 2.

R, R' are equal or different and independently chosen from H, Alkyl, Aryl, optionally substituted by Hal, CN, NRR', $CF_3$, OR, Aryl, Het;

or their pharmaceutically acceptable salts, hydrates, or hydrated salts, or the polymorphic crystalline structures of these compounds or their optical isomers, racemates, diastereomers or enantiomers.

In a preferred embodiment, compounds of the invention are those of formula (C1) where T=aryl optionally substituted by one or more Hal, CN, NRR', CF$_3$, OR, S(O)$_q$R, Alkyl, and/or linker(s) and A, A', X, X', U, U', W, W', m, m', n, n', ----, ==== are defined as above.

According to another preferred embodiment, compounds of formula (C1) are selected from the group consisting in:

8,8'-[1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-methoxy-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[4-(3-tert-butoxycarbonylaminopropyloxy)-2,6-pyridinediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(3-aminopropyloxy)-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(N-methyl-3-tert-butoxycarbonylaminopropyl)-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-{5-[3-(4-methyl-4-methyldisulfanyl-pentanoylamino)propyloxy]-1,3-benzenediylbis(methyleneoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methyleneoxy)]-bis[(S)-2-methylene-7-methoxy-1,2,3,11a-tetrahydro-5H-pyrrolo[2,1-c][1,4]benzodiazepin-5-one]

bis-{2-[(S)-2-methylene-7-methoxy-5-oxo-1,3,11a-tetrahydro-5H-pyrrolo[2,1-c][1,4]benzodiazepin-8-yloxy]-ethyl-}-carbamic acid tert-butyl ester 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

or their pharmaceutically acceptable salts, hydrates, or hydrated salts, or the polymorphic crystalline structures of these compounds or their optical isomers, racemates, diastereomers or enantiomers.

In another preferred embodiment, compounds of formula (C1) are represented by the following formula:

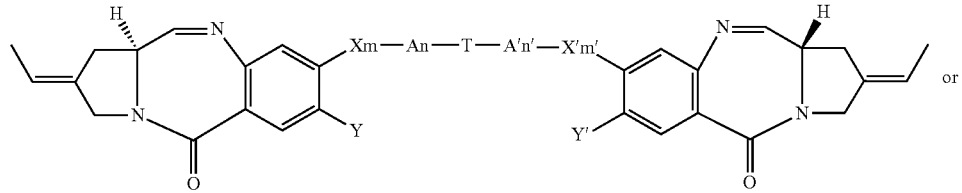

or

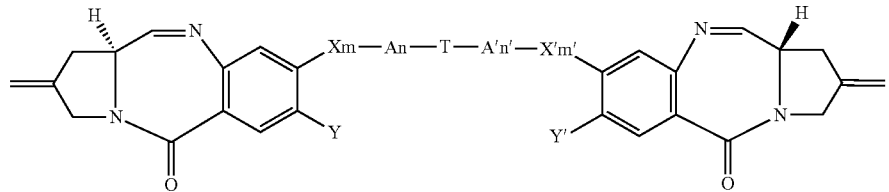

where X, X', A, A', Y, Y', T, n, n', m, m' are defined as above for formula (C1).

In another embodiment, drugs that can be used in the methods of the present invention are represented by formula (D1):

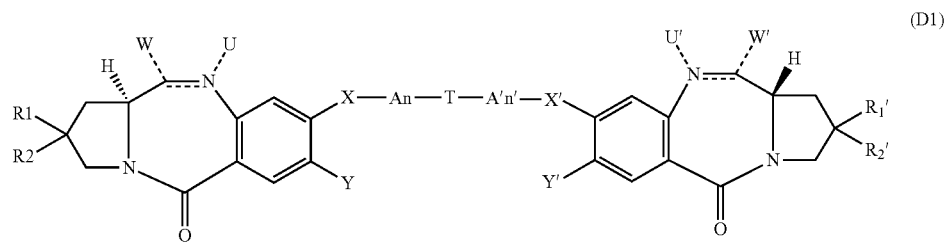

wherein

---- represents an optional single bond;

≡≡≡≡ represents either a single bond or a double bond;

provided that at least one of the ≡≡≡≡ represents a double bond and when ≡≡≡≡ represents a single bond, U and U', the same or different, independently represent H, and W and W', the same or different, are independently selected from the group consisting of OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO$_3^-$, a sulfonamide such as —NRSOOR', an amine such as NRR', optionally cyclic amine such that N10 and C11 are a part of the cycle, a hydroxylamine derivative such as —NROR', an amide such as NRCOR', an azido such as —N$_3$, a cyano, a halo, a trialkyl or triarylphosphonium, an aminoacid-derived group; Preferably W and W' are the same or different and are OH, OMe, OEt, NHCONH$_2$, SMe;

and when ≡≡≡≡ represents a double bond, U and U' are absent and W and W' represent H.

R1, R2, R1', R2' are the same or different and independently chosen from H, Halide or Alkyl optionally substituted by one or more Hal, CN, NRR', CF$_3$, OR, Aryl, Het, S(O)$_q$R, or R1 and R2 and R1' and R2' form together a double bond containing group =B and =B' respectively. Preferably, R1 and R2 and R1' and R2' form together a double bond containing group: =B and =B' respectively.

B and B' are the same or different and independently chosen from Alkenyl being optionally substituted by one or more Hal, CN, NRR', CF$_3$, OR, Aryl, Het, S(O)$_q$R or B and B' represent an oxygen atom. Preferably, B=B'. More preferably, B=B'==CH$_2$ or =CH—CH$_3$, X, X' are the same or different and independently chosen from one or more —O—, —NR—, —(C=O)—, —S(O)$_q$—. Preferably, X=X'. More preferably, X=X'=O.

A, A' are the same or different and independently chosen from Alkyl or Alkenyl optionally containing an oxygen, a nitrogen or a sulfur atom, each being optionally substituted by one or more Hal, CN, NRR', CF$_3$, OR, S(O)$_q$R, Aryl, Het, Alkyl, Alkenyl. Preferably, A=A'. More preferably, A=A'=linear unsubstituted alkyl.

Y, Y' are the same or different and independently chosen from H and OR. Preferably, Y=Y'. More preferably, Y=Y'=OAlkyl, more preferably OMethyl.

T is —NR— or a 4 to 10-membered aryl, cycloalkyl, heterocyclic, heteroaryl or a linear or branched alkyl, each being substituted by one or more non-cleavable linker(s) and optionally substituted by one or more of Hal, CN, NRR', CF$_3$, R, OR, S(O)$_q$R. Preferably, T is a 4 to 10-membered aryl or heteroaryl, more preferably phenyl or pyridyl, substituted by one or more non-cleavable linker(s) and optionally substituted by one or more of Hal, CN, NRR', CF$_3$, R, OR, S(O)$_q$R; the non-cleavable linker comprises a chain terminated by a linking group. Preferably, said linker does not contain cleavable groups such as disulfide groups, acid labile groups, photolabile groups, peptidase labile groups and esterase labile groups. According to the present invention, said linker contains non-cleavable groups. The non-cleavable linker comprises a terminal linking group. Said terminal linking group is preferably a carboxy or amide group, at the terminal end of the side chain. The side chain can be linear or branched, aromatic or heterocyclic. One of ordinary skill in the art can readily identify suitable side chains. Preferred linkers are composed of linear chains containing solubilizing functions such as amino, hydroxy, ether, sulfonic and carboxylic groups.

Preferably, said linker is of formula:

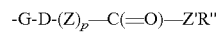

where

G is a single, a double or a triple bond, —O—, —S— or NR—;

D is a single bond or -E-, -E-NR—, -E-NR—F—, -E-O—, -E-O—F—, -E-NR—CO—, -E-CO—NR—, -E-NR—CO—F—, -E-CO—NR—F—, -E-CO—, —CO-E-, -E-CO—F, -E-S—, -E-S—F—, -E-NR—CS—, -E-CS—NR—, -E-NR—CS—F—, -E-CS—NR—F—;

where E and F are the same or different and are independently chosen from linear or branched —(OCH$_2$CH$_2$)$_i$Alkyl(OCH$_2$CH$_2$)$_j$—, -Alkyl(OCH$_2$CH$_2$)$_i$-Alkyl-, —(OCH$_2$CH$_2$)$_j$—, —(OCH$_2$CH$_2$)$_i$Cycloalkyl(OCH$_2$CH$_2$)$_j$—, —(OCH$_2$CH$_2$)$_i$Heterocyclic(OCH$_2$CH$_2$)$_j$—, —(OCH$_2$CH$_2$)$_i$Aryl(OCH$_2$CH$_2$)$_j$—, —(OCH$_2$CH$_2$)$_i$Heteroaryl(OCH$_2$CH$_2$)$_j$—, -Alkyl-(OCH$_2$CH$_2$)$_i$Alkyl(OCH$_2$CH$_2$)$_j$—, -Alkyl-(OCH$_2$CH$_2$)$_i$—, -Alkyl-(OCH$_2$CH$_2$)$_i$Cycloalkyl(OCH$_2$CH$_2$)$_j$—, Alkyl(OCH$_2$CH$_2$)$_i$Heterocyclic(OCH$_2$CH$_2$)$_j$—, -Alkyl-(OCH$_2$CH$_2$)$_i$Aryl(OCH$_2$CH$_2$)$_j$—, -Alkyl(OCH$_2$CH$_2$)$_i$Heteroaryl(OCH$_2$CH$_2$)$_j$—, -Cycloalkyl-Alkyl-,-Alkyl-Cycloalkyl-,-Heterocyclic-Alkyl-,-Alkyl- Heterocyclic-,-Alkyl-Aryl-,-Aryl-Alkyl-,-Alkyl-Heteroaryl-,-Heteroaryl-Alkyl-;

where i and j, identical or different are integers and independently chosen from 0, 1 to 2000;

Z is linear or branched Alkyl, cycloalkyl, Aryl, heteroaryl, heterocyclyl, aralkyl, cycloalkyl, heteroaralkyl, or heterocyclylalkyl, optionally substituted by solubilizing functions such as amino, ether, sulfonic and carboxylic groups;

p is 0 or 1;

—C(=O)—Z'R" is a carbonyl containing function wherein

Z' represents a single bond or substituted O, —S(O)$_q$—, NR— and

R" represents H, Alkyl, Cycloalkyl, Aryl, heteroaryl or heterocyclic, each being optionally substituted by one or more Hal, CN, NRR', CF$_3$, R, OR, S(O)$_q$R, Aryl, Het.

n, n', equal or different are 0 or 1.

q is 0, 1 or 2.

R, R' are equal or different and independently chosen from H, Alkyl, Aryl, each being optionally substituted by Hal, CN, NRR', CF$_3$, R, OR, S(O)$_q$R, Aryl, Het; or their pharmaceutically acceptable salts, hydrates, or hydrated salts, or the polymorphic crystalline structures of these compounds or their optical isomers, racemates, diastereomers or enantiomers.

The present invention refers to following preferred embodiments or any combination of any of them:

G is a single, a double or a triple bond or —O—, —S— or —NR—;

G is a single bond or —O—;

D is a single bond or -E- or -E-O—;

D is -E-;
E is linear or branched -Alkyl-, -Alk(OCH$_2$CH$_2$)$_i$—;
Z is linear or branched -Alkyl-;
p is 0;
Z' is a single bond or O;
Z' is O;
R" is H or linear or branched -Alkyl- or optionally substituted heterocyclic;
R" is H or alkyl or a succinimide group.

Specific examples of the non-cleavable linkers include
—(CR$_{13}$R$_{14}$)$_t$(CR$_{15}$R$_{16}$)$_u$(OCH$_2$CH$_2$)$_y$COZ'R",
—(CR$_{13}$R$_{14}$)$_t$(OCH$_2$CH$_2$)$_y$O(CR$_{15}$R$_{16}$)$_u$COZ'R",
—(CR$_{13}$R$_{14}$)$_t$(CR$_{17}$=CR$_{18}$)(CR$_{15}$R$_{16}$)$_y$(OCH$_2$CH$_2$)$_y$COZ'R",
—(CR$_{13}$R$_{14}$)$_t$(NR$_{19}$CO)(CR$_{15}$R$_{16}$)$_u$(OCH$_2$CH$_2$)$_y$COZ'R",
—(CR$_{13}$R$_{14}$)$_t$(OCO)(R$_{15}$R$_{16}$)$_u$(OCH$_2$CH$_2$)$_y$COZ'R",
—(CR$_{13}$R$_{14}$)$_t$(CO)(CR$_{15}$R$_{16}$)$_u$(OCH$_2$CH$_2$)$_y$COZ'R",
—(CR$_{13}$R$_{14}$)$_t$(CONR$_{19}$)(CR$_{15}$R$_{16}$)$_u$(OCH$_2$CH$_2$)$_y$COZ'R",
—(CR$_{13}$R$_{14}$)$_t$-phenyl-CO(CR$_{15}$R$_{16}$)$_u$SZ',
—(CR$_{13}$R$_{14}$)$_t$-furyl-CO(CR$_{15}$R$_{16}$)$_u$COZ'R",
—(CR$_{13}$R$_{14}$)$_t$-oxazolyl-CO(CR$_{15}$R$_{16}$)$_u$SZ',
—(CR$_{13}$R$_{14}$)$_t$-thiazolyl-CO(CR$_{15}$R$_{16}$)$_u$COZ'R",
—(CR$_{13}$R$_{14}$)$_t$-thienyl-CO(CR$_{15}$R$_{16}$)$_u$SZ',
—(CR$_{13}$R$_{14}$)$_t$-imidazolyl-CO(CR$_{15}$R$_{16}$)$_u$COZ'R",
—(CR$_{13}$R$_{14}$)$_t$piperazino-CO(CR$_{15}$R$_{16}$)$_u$COZ'R",
—(CR$_{13}$R$_{14}$)$_t$-phenyl-QCOZ'R",
—(CR$_{13}$R$_{14}$)$_t$-furyl-QCOZ'R",
—(CR$_{13}$R$_{14}$)$_t$-oxazolyl-QCOZ'R",
—(CR$_{13}$R$_{14}$)$_t$-thiazolyl-QCOZ'R",
—(CR$_{13}$R$_{14}$)$_t$-thienyl-QCOZ'R",
—(CR$_{13}$R$_{14}$)$_t$-imidazolyl-QCOZ'R",
—(CR$_{13}$R$_{14}$)$_t$-piperazino-QCOZ'R", or
—O(CR$_{13}$R$_{14}$)$_t$(CR$_{15}$R$_{16}$)$_u$(OCH$_2$CH$_2$)$_y$COZ'R",
—O(CR$_{13}$R$_{14}$)$_t$(NR$_{19}$CO)(CR$_{15}$R$_{16}$)$_u$(OCH$_2$CH$_2$)$_y$COZ'R",
—O(CR$_{13}$R$_{14}$)$_t$ (CR$_{17}$=CR$_{18}$)(CR$_{15}$R$_{16}$)$_t$ (OCH$_2$CH$_2$)$_y$COZ'R",
—O-phenyl-QCOZ'R",
—O-furyl-QCOZ'R",
—O-oxazolyl-QCOZ'R",
—O-thiazolyl-Q COZ'R",
—O-thienyl-QCOZ'R",
—O-imidazolyl-QSCOZ'R",
—O-morpholino-QCOZ'R",
—OCO(CR$_{13}$R$_{14}$)$_t$(NR$_{19}$CO)$_v$(CR$_{15}$R$_{16}$)$_u$ (OCH$_2$CH$_2$)$_y$COZ'R",
—OCO—(CR$_{13}$R$_{14}$)$_t$ (CR$_{17}$=CR$_{18}$)(CR$_{15}$R$_{16}$)$_u$(OCH$_2$CH$_2$)$_y$COZ'R",
—OCONR$_{12}$(CR$_{13}$R$_{14}$)$_t$(CR$_{15}$R$_{16}$)$_u$(OCH$_2$CH$_2$)$_y$COZ'R",
—OCO-phenyl-QCOZ'R",
—OCO-furyl-QCOZ'R",
—OCO-oxazolyl-QCOZ'R",
—OCO-thiazolyl-QCOZ'R",
—OCO-thienyl-QCOZ'R",
—OCO-imidazolyl-QCOZ'R",
—OCO-piperazine-QCOZ'R", or
—CO(CR$_{13}$R$_{14}$)$_t$(CR$_{15}$R$_{16}$)$_u$ (OCH$_2$CH$_2$)$_y$COZ'R",
—CO—(CR$_{13}$R$_{14}$)$_t$ (CR$_{17}$=CR$_{18}$)(CR$_{15}$R$_{16}$)$_u$(OCH$_2$CH$_2$)$_y$COZ'R",
—CONR$_{12}$(CR$_{13}$R$_{14}$)$_t$(CR$_{15}$R$_{16}$)$_u$ (OCH$_2$CH$_2$)$_y$COZ'R",
—CO-phenyl-QCOZ'R",
—CO-furyl-QCOZ'R",
—CO-oxazolyl-QCOZ'R",
—CO-thiazolyl-QCOZ'R",
—CO-thienyl-QCOZ'R",
—CO-imidazolyl-QCOZ'R",
—CO-piperazino-QCOZ'R",
—CO-piperidino-QCOZ'R",
—NR$_{19}$(CR$_{13}$R$_{14}$)$_t$(CR$_{15}$R$_{16}$)$_u$(OCH$_2$CH$_2$)$_y$COZ'R",
—NR$_{19}$CO(CR$_{13}$R$_{14}$)$_t$(CR$_{15}$R$_{16}$)$_u$(OCH$_2$CH$_2$)$_y$COZ'R",
—NR$_{19}$(CR$_{13}$R$_{14}$)$_t$ (CR$_{17}$=CR$_{18}$)(CR$_{15}$R$_{16}$)$_t$ (OCH$_2$CH$_2$)$_y$COZ'R",
—NR$_{19}$CO(CR$_{13}$R$_{14}$)$_t$ (CR$_{17}$=CR$_{18}$)(CR$_{15}$R$_{16}$)$_t$ (OCH$_2$CH$_2$)$_y$COZ'R",
—NR$_{19}$CONR$_{12}$(CR$_{13}$R$_{14}$)$_t$(CR$_{15}$R$_{16}$)$_u$ (OCH$_2$CH$_2$)$_y$COZ'R",
—NR$_{19}$CO NR$_{12}$ (CR$_{13}$R$_{14}$)$_t$ (CR$_{17}$=CR$_{18}$)(CR$_{15}$R$_{16}$)$_t$ (OCH$_2$CH$_2$)$_y$COZ'R",
—NR$_{19}$CO-phenyl-QCOZ'R", —NR$_{19}$CO-furyl-QSZ';
—NR$_{19}$CO-oxazolyl-QCOZ'R",
—NR$_{19}$CO-thiazolyl-QCOZ'R", —NR$_{19}$CO-thienyl-QCOZ'R",
—NR$_{19}$CO-imidazolyl-QCOZ'R",
—NR$_{19}$CO-morpholino-QCOZ'R",
—NR$_{19}$CO-piperazino-QCOZ'R",
—NR$_{19}$CO-piperidino-QCOZ'R",
—NR$_{19}$-phenyl-QCOZ'R",
—NR$_{19}$-furyl-QCOZ'R",
—NR$_{19}$-oxazolyl-QCOZ'R",
—NR$_{19}$-thiazolyl-QCOZ'R",
—NR$_{19}$-thienyl-QCOZ'R",
—NR$_{19}$-imidazolyl-QCOZ'R",
—NR$_{19}$-piperazino-QCOZ'R",
—NR$_{19}$-piperidino-QCOZ'R",
—NR$_{19}$CO—NR$_{12}$-phenyl-QCOZ'R",
—NR$_{19}$CO—NR$_{12}$-oxazolyl-QCOZ'R",
—NR$_{19}$CO—NR$_{12}$-thiazolyl-QCOZ'R",
—NR$_{19}$CO—NR$_{12}$-thienyl-QCOZ'R",
—NR$_{19}$CO—NR$_{12}$-piperidino-QCOZ'R",
—S(O)$_q$(CR$_{13}$R$_{14}$)$_t$(CR$_{15}$R$_{16}$)$_u$(OCH$_2$CH$_2$)$_y$COZ'R",
—S(O)$_q$(CR$_{13}$R$_{14}$)$_t$(CR$_{17}$=CR$_{18}$)(CR$_{15}$R$_{16}$)$_t$ (OCH$_2$CH$_2$)$_y$COZ'R",
—SCONR$_{12}$(CR$_{13}$R$_{14}$)$_t$(CR$_{15}$R$_{16}$)$_u$(OCH$_2$CH$_2$)$_y$COZ'R",
—SCO-piperazino-QCOZ'R", and —SCO-piperidino-QCOZ'R", and more preferably:
—(CR$_{13}$R$_{14}$)$_t$(CR$_{15}$R$_{16}$)$_u$(OCH$_2$CH$_2$)$_y$COZ'R",
—(CR$_{13}$R$_{14}$)$_t$(OCH$_2$CH$_2$)$_y$O(CR$_{15}$R$_{16}$)$_u$COZ'R",
—O(CR$_{13}$R$_{14}$)$_t$(CR$_{15}$R$_{16}$)$_u$(OCH$_2$CH$_2$)$_y$COZ'R", wherein:
Q is a direct link or a linear alkyl or branched alkyl having from 1-10 carbon atoms or a polyethylene glycol spacer with 2 to 20 repeating ethylene oxy units;
R$_{19}$ and R$_{12}$ are the same or different and are linear alkyl, branched alkyl or cyclic alkyl having from 1 to 10 carbon atoms, or simple or substituted aryl or heterocyclic, and R$_{12}$ can in addition be H,
R$_{13}$, R$_{14}$, R$_{15}$ and R$_{16}$ are the same or different and are H or a linear or branched alkyl having from 1 to 4 carbon atoms,
R$_{17}$ and R$_{18}$ are H or alkyl,
u is an integer from 1 to 10 and can also be 0,
t is an integer from 1 to 10 and can also be 0,
y is an integer from 1 to 20 and can also be 0.

When compound of formula (C2) is in the form of an ion (eg. sulphonate), the counter ion may be present (eg. Na$^+$ or K$^+$).

According to a preferred aspect, for compounds of formula (C2), T=aryl substituted by one or more non-cleavable linker(s) and optionally substituted by one or more Hal, CN, NRR', CF$_3$, R, OR, S(O)$_q$R, and/or linker(s) and A, A', X, X', U, U', W, W', m, m', n, n', ----, ==== are defined as above.

According to another preferred aspect, compounds of formula (C2) are selected from the group consisting in:

4-(3,5-Bis-[(S)-2-eth-(E)-ylidene-7-dimethoxy-1,2,3,11a-tetrahydro-pyrrolo[2,1c][1,4]benzodiazepin-5-one-8-yloxymethyl]-phenoxy)-butyric acid 4-(3,5-Bis-[(S)-2-eth-(E)-ylidene-7-dimethoxy-1,2,3,11a-tetrahydro-pyrrolo[2,1c][1,4]benzodiazepin-5-one-8-yloxymethyl]-phenoxy)-butyric acid methyl ester 4-(3,5-Bis-[(S)-2-eth-(E)-ylidene-7-dimethoxy-1,2,3,11a-tetrahydro-pyrrolo[2,1c][1,4]benzodiazepin-5-one-8-yloxymethyl]-phenoxy)-acetic acid 4-(3,5-Bis-[(S)-2-eth-(E)-ylidene-7-dimethoxy-1,2,3,11a-tetrahydro-pyrrolo[2,1c][1,4]benzodiazepin-5-one-8-yloxymethyl]-phenoxy)-acetic acid methyl ester 4-(3,5-Bis-[(S)-2-methylidene-7-dimethoxy-1,2,3,11a-tetrahydro-pyrrolo[2,1c][1,4]benzodiazepin-5-one-8-yloxymethyl]-phenyl)-propanoic acid methyl ester 4-(3,5-Bis-[(S)-2-methylidene-7-dimethoxy-1,2,3,11a-tetrahydro-pyrrolo[2,1c][1,4]benzodiazepin-5-one-8-yloxymethyl]-phenyl)-propanoic acid (2-{2-[2-(2-{3-[3,5-Bis-(7-methoxy-2-methylene-5-oxo-2,3,5,11a-tetrahydro-1H-benzo[e]pyrrolo[1,2-a][1,4]diazepin-8-yloxymethyl)-phenyl]-propoxy}-ethoxy)ethoxy]-ethoxy}-ethoxy)-acetic acid methyl ester (2-{2-[2-(2-{3-[3,5-Bis-(7-methoxy-2-methylene-5-oxo-2,3,5,11a-tetrahydro-1H-benzo[e]pyrrolo[1,2-a][1,4]diazepin-8-yloxymethyl)-phenyl]-propoxy}-ethoxy)ethoxy]-ethoxy}-ethoxy)-acetic acid as well as their corresponding N-hydroxysuccinimide ester or their pharmaceutically acceptable salts, hydrates, or hydrated salts, or the polymorphic crystalline structures of these compounds or their optical isomers, racemates, diastereomers or enantiomers.

In another preferred embodiment, compounds of formula (D1) are represented by one of the following formulas:

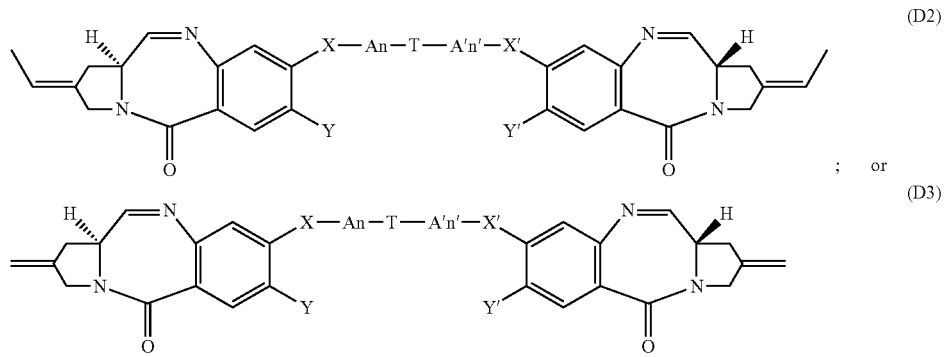

where X, X', A, A', Y, Y', T, n, n' are defined as above for formula (D1).

In one embodiment, the imine-containing drug bearing a linking moiety are those having a reactive ester group, a thiol or a thiol reactive group described above.

Alternatively, the drug described above can further react with bifunctional crosslinking agent to form a drug bearing a linking moiety. Any bifunctional crosslinking agents described can be used.

In any of the compounds or conjugates described above in the Tables, the imine double bond may react with/have reacted with any of the imine-reactive reagent (such as those described herein) according to the methods of the invention to form adducts, including bisulfite adducts. Such imine-protected adducts in the compounds of the Tables may be used in further reactions according to the methods of the invention to produce conjugates of the invention. Similarly, compounds comprising imine-protected adducts may be used in the methods of the invention to produce the conjugates in the Tables.

Any compounds or conjugates of these Tables and formulas may have at least one of its imine bonds reacted with a subject imine reactive reagent, thus forming an adduct, such as bisulfite adduct.

Specifically, in each of the compounds described herein, including those in Tables 1-5 and in the formulas above, the imine bond on the cytotoxic compounds may be reacted with an imine-reactive reagent to produce derivative compounds with the following structure:

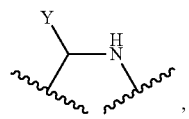

wherein:

Y is a leaving group, and is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydrosulfite, or a metabisulfite, or salts thereof (such as sodium salt).

Suitable imine reactive reagents for this reaction includes: sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetrathiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters ($(R^iO)_2PS(OR^i)$, $R^iSH$, $R^iSOH$, $R^iSO_2H$, $R^iSO_3H$), various amines (hydroxylamine (e.g., $NH_2OH$), hydrazine (e.g., $NH_2NH_2$), $NH_2$—$R^i$, $R^{i'}NH$—$R^i$, $NH_2$—$R^i$), $NH_2$—CO—$NH_2$, $NH_2$—C(=S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)($OR^k$)(SH)(OH) or a salt thereof formed with a cation), hydroxamic acid ($R^kC$(=O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-Na^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —$N(R^j)_2$, —$CO_2H$, —$SO_3H$, and —$PO_3H$; $R^i$ and $R^{i'}$ can be further optionally substituted with a substituent for an alkyl described herein; $R^j$ is a linear or branched alkyl having 1 to 6 carbon atoms; $R^k$ is a linear, branched or cyclic alkyl, alkenyl or alkynyl having 1 to 10 carbon atoms, aryl, heterocyclyl or heteroaryl.

Conjugates comprising any of such derivative compounds with the bisulfite adduct (or the Y group being —H), pharmaceutical compositions thereof, and methods of making or using thereof, are within the scope of the invention.

In Vitro Cytotoxicity of Compounds and Conjugates

The cytotoxic compounds and cell-binding agent-drug conjugates of the invention can be evaluated for their ability to suppress proliferation of various cancer cell lines in vitro. For example, cell lines such as the human colon carcinoma line COLO 205, the rhabdomyosarcoma cell line RH-30, and the multiple myeloma cell line MOLP-8 can be used for the assessment of cytotoxicity of these compounds and conjugates. Cells to be evaluated can be exposed to the compounds or conjugates for 1-5 days and the surviving fractions of cells measured in direct assays by known methods. $IC_{50}$ values can then be calculated from the results of the assays. Alternatively or in addition, an in vitro cell line sensitivity screen, such as the one described by the U.S. National Cancer Institute (see Voskoglou-Nomikos et al., 2003, Clinical Cancer Res. 9: 42227-4239, incorporated herein by reference) can be used as one of the guides to determine the types of cancers that may be sensitive to treatment with the compounds or conjugates of the invention.

All of the conjugates are expected to be extremely cytotoxic on the antigen positive cancer cells with an $IC_{50}$ in the low picomolar range. Antigen negative cell lines are expected to remain viable when exposed to the same conjugates. Related indolinobenzodiazepine dimers showed target specific potency being 160 fold less potent when blocked with unconjugated antibody huMy9-6 (anti-CD33) and 40 less potent when blocked with unconjugated antibody FOLR1 (anti-folate receptor antibody). For example, the huMy9-6-SPDB-If conjugate killed antigen positive HL60/QC cells with an $IC_{50}$ value of 10.5 pM, while the addition of an excess of unconjugated huMy9-6 antibody reduced this cytotoxic effect ($IC_{50}$=1.69 nM), demonstrating antigen specificity. In addition, the huMy9-6-SPDB-1f conjugate is also highly potent towards both the HL60/ATCC cell line with an $IC_{50}$ value of 21 pM and the NB-4 cell line with an $IC_{50}$ value of 190 pM.

Similarly, the huFOLR1-SPDB-1f conjugate was highly potent, with an $IC_{50}$ value of 55 pM for antigen positive KB cells. Addition of an excess of unconjugated huFOLR1 antibody reduced this cytotoxic effect >40 fold, demonstrating antigen-specificity.

The effect of conjugation on antibody binding can be measured by comparing the binding of both unconjugated huMy9-6 antibody and the huMy9-6-SPDB conjugate towards the HL60/QC cell line. FACS analysis will reveal that there is no change in binding capability of the conjugate to naked antibody, indicating that there is no compromise in binding due to conjugation of the cytotoxic agent to the antibody.

In vivo efficacy of a cell binding agent/cytotoxic agent conjugate can be experimentally measured. For example, nude mice bearing human HL60/QC tumors can be treated with huMy9-6-SPDB-cytotoxic compound conjugate, and significant tumor regression is expected at multiple doses while untreated mice grow tumors rapidly.

Compositions and Methods of Use

The present invention includes a composition (e.g., a pharmaceutical composition) comprising novel benzodiazepine compounds described herein (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds described herein (e.g., indolinobenzodiazepine or oxazolidinobenzodiazepine), derivatives thereof, or conjugates thereof, (and/or solvates and salts thereof) or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung (small cell and non-small cell), breast, colon, brain, prostate, kidney, pancreas, ovary, head and neck, skin (melanoma), Merkel cell carcinoma, glioblastoma, neuroblastoma, and cancers of lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index

By Manufacturer

Products (by company's or trademarked drug name)

Category index

Generic/chemical index (non-trademark common drug names)

Color images of medications

Product information, consistent with FDA labeling

Chemical information

Function/action

Indications & Contraindications

Trial research, side effects, warnings

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument and

Example 1

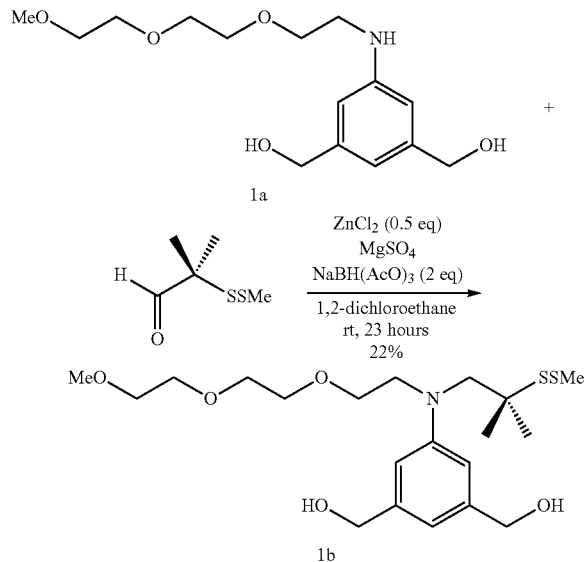

Compound 1b

To a stirred solution of the aniline 1a (1.55 g, 5.18 mmol) and 2-(methyldithio)-isobutyraldehyde (0.7 mL, 5.18 mmol) in anhydrous 1,2-dichloromethane (20 mL) was added sodium triacetoxyborohydride (1.1 g, 5.18 mmol) and zinc chloride powder (353 mg, 2.59 mmol) followed by the addition of anhydrous magnesium sulfate (800 mg). The mixture was stirred at room temperature (rt) for 6 hours then a second portion of 2-(methyldithio)-isobutyraldehyde (0.7 mL, 5.18 mmol) and sodium triacetoxyborohydride (1.1 g, 5.18 mmol) were added. It continued to be stirred at rt overnight. The reaction mixture was filtered through celite and washed with dichloromethane. The filtrate was concentrated and the remainder was purified by silica gel chromatography (Combiflash, 40 g column, dichloromethane/MeOH) to give compound 1b (487 mg y=22%) as colorless oil. Unreacted starting material aniline 1a (1.02 g) was also recovered in 65% yield. $^1$H NMR (400 Hz, CDCl$_3$): δ 6.76 (s, 2H), 6.63 (s, 1H), 4.55 (s, 4H), 3.65-3.51 (m, 14H), 3.35 (s, 3H), 2.44 (s, 3H), 1.33 (s, 6H); $^{13}$C NMR (400 Hz, CDCl$_3$): E. 149.0, 142.35, 114.0, 111.1, 71.98, 70.7, 70.6, 70.5, 67.6, 65.5, 59.75, 59.1, 53.9, 51.9, 26.6, 25.7, 20.75; MS (m/z). found 456.2 (M+Na)$^+$. See FIG. 1.

Example 2

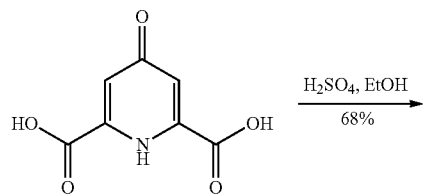

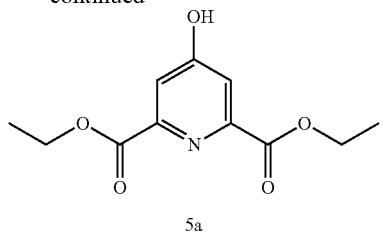

Compound 5a

A mixture of chelidamic acid hydrate (3.0 g, 15.56 mmol) and sulfuric acid (0.6 mL, 11.26 mmol) in absolute ethanol (40 mL) was refluxed for 20 hours. The reaction was cooled to ambient temperature, neutralized with aqueous sodium carbonate, and then acidified with concentrated HCl. Water was added and the mixture was extracted with dichloromethane. The extracts were dried with anhydrous magnesium sulfate, filtered and concentrated. The crude material was purified by silica gel chromatography (5% methanol/dichloromethane) to yield diethyl 4-hydroxypyridine-2,6-dicarboxylate (5a) (2.5 g, 68%) as a white solid. See FIG. 32.

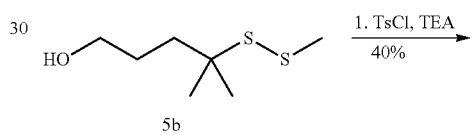

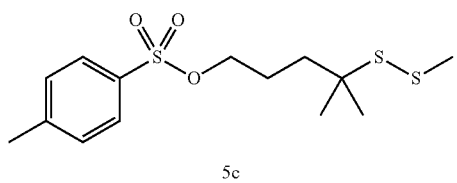

Compound 5c

A solution of 4-methyl-4-(methyldisulfanyl)pentan-1-ol (5b) (2.0 g, 11.09 mmol) in anhydrous dichloromethane (55.5 mL) was cooled to 0° C. in an ice bath. Triethylamine (5.41 mL, 38.8 mmol) and toluene sulfonyl chloride (3.17 g, 16.64 mmol) were added at 0° C. The reaction stirred for three hours at ambient temperature. The mixture was extracted with ethyl acetate and washed with brine. The organic extracts were dried with anhydrous sodium sulfate, filtered and concentrated. Purification by silica gel chromatography (5% ethyl actetate/hexanes) resulted in 4-methyl-4-(methyldisulfanyl)pentyl 4-methylbenzenesulfonate (5c) (1.5 g, 40%). 5b: $^1$H NMR (400 Hz, CDCl$_3$): δ3.42 (m, 2H), 2.19 (s, 3H), 1.77 (bs, 1H), 1.43 (m, 4H), 1.09 (s, 6H). 5c: $^1$H NMR (400 Hz, CDCl$_3$): δ7.66 (d, 2H, J=7.6 Hz), 7.22 (d, 2H, J=8.0 Hz), 3.90 (t, 2H, J=6.4 Hz), 2.32 (s, 3H), 2.23 (s, 3H), 1.60 (m, 2H), 1.44 (m, 2H), 1.11 (s, 6H). See FIG. 32.

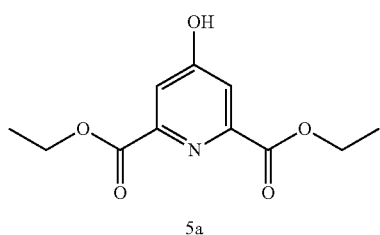

5a

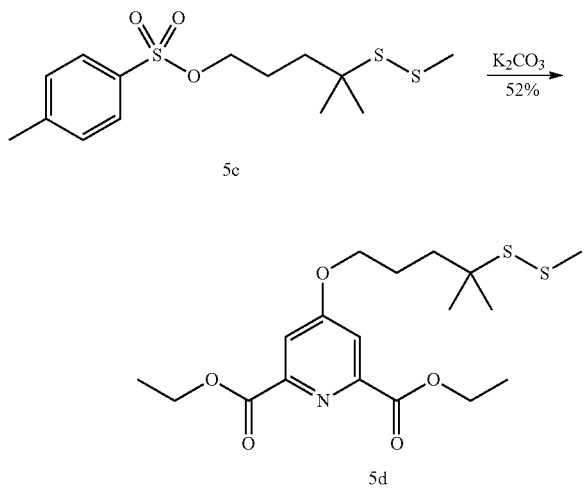

5c

5d

Compound 5d

To a stirred solution of 4-methyl-4-(methyldisulfanyl) pentyl 4-methylbenzenesulfonate (5c) (0.48 g, 1.435 mmol) and diethyl 4-hydroxypyridine-2,6-dicarboxylate (5a)(0.343 g, 1.435 mmol) in anhydrous dimethylformamide (6.5 mL) was added Potassium carbonate (0.297 g, 2.152 mmol). The reaction was stirred at 90° C. for 18 hours. Then allowed to cool to ambient temperature and quenched with saturated ammonium chloride. The mixture was extracted three times with ethyl acetate. The extracts were dried with anhydrous sodium sulfate, filtered and concentrated under reduced pressure. Purification by silica gel chromatography (30% hexanes/ethyl acetate) yielded diethyl 4-(4-methyl-4-(methyldisulfanyl)pentyloxy)pyridine-2,6-dicarboxylate (5d)(300 mg, 52%); $^1$H NMR (400 Hz, CDCl$_3$): δ 7.70 (s, 2H), 4.40 (q, 4H, J=7.2, 14.4 Hz), 4.07 (t, 2H, J=6. Hz), 2.35 (s, 3H), 1.86 (m, 2H), 1.70 (m, 2H), 1.38 (t, 6H, J=7.2 Hz), 1.27 (s, 6H); MS (m/z). found 424.1 (M+Na), 440.1 (M+K). See FIG. 32.

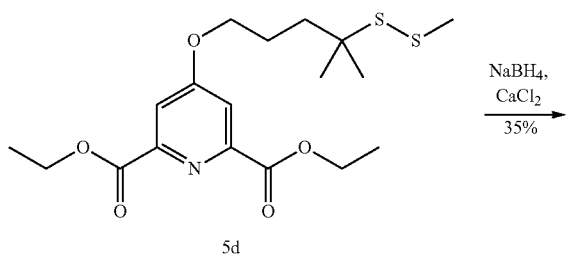

5d

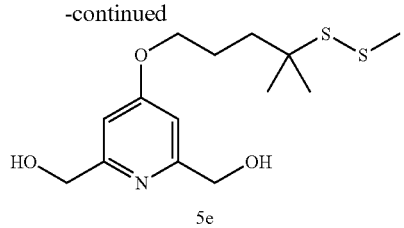

5e

Compound 5e

To a stirred solution of diethyl 4-(4-methyl-4-(methyldisulfanyl)pentyloxy)pyridine-2,6-dicarboxylate (5d) (270 mg, 0.672 mmol) in absolute ethanol (7.0 mL) was added calcium chloride (224 mg, 2.017 mmol) and sodium borohydride (76 mg, 2.017 mmol). The reaction was allowed to stir at ambient temperature for 90 minutes after which it was quenched with water and concentrated in vacuo to remove the ethanol. The mixture was then extracted twice with dichloromethane. The organic extracts were combined, washed with water, dried with anhydrous magnesium sulfate and filtered through celite. The filtrate was concentrated under reduced pressure and the crude material was purified by silica gel chromatography eluting with 10% methanol/dichloromethane to yield (4-(4-methyl-4-(methyldisulfanyl)pentyloxy)pyridine-2,6-diyl)dimethanol (5e)(75 mg, 35%); $^1$H NMR (400 Hz, CDCl$_3$): δ 6.63 (s, 2H), 4.60 (s, 4H), 3.95 (t, 2H, J=6.2 Hz), 3.54 (bs, 2H), 2.35 (s, 3H), 1.82 (m, 2H), 1.66 (m, 2H), 1.26 (s, 6H); MS (m/z). found 340.1 (M+Na). See FIG. 32.

Example 3

Preparation of Antibody-SPDB-Drug Conjugate

Compound 5g is pre-treated with 3 molar equivalents of sodium bisulfite (using a freshly prepared NaHSO$_3$ solution in water) in 96-98% DMA in water for 4-5 hrs at 25° C. For conjugation, the humanized antibody at 2 mg/mL is reacted with 5-7 molar equivalents of compound 5g (pre-treated with NaHSO$_3$) for 6 h at 25° C. in 85-90% PBS, pH 7.4, aqueous buffer, or 50 mM HEPES, pH 8.5, aqueous buffer, containing 10-15% N,N-dimethylacetamide (DMA) and then purified over a G25 gel filtration column in PBS, pH 7.4, to remove unreacted or hydrolyzed drug compound. The humanized antibody-SPDB-drug conjugates are dialyzed in 10 mM Histidine, 250 mM Glycine, 1% sucrose, pH 6.5 buffer.

The Drug Antibody Ratio (DAR) of the conjugates are expected to be measured at about 2-3 by UV absorbance measurements at 280 and 320 nm and using the extinction coefficients of the drug and antibody at 280 nm (215,000 M$^{-1}$ cm$^{-1}$) and 320 nm (9137 M$^{-1}$ cm$^{-1}$). The percentage of monomer in the conjugates are expected to be >90% by SEC (Size Exclusion Chromatography) using TSK-Gel G300SWXL column (7.8 mm×300 mm, 5 μm particle size). Based on the UV absorbance of the monomer peak in SEC it is also expected that the monomer conjugate peaks have linked drug molecules.

For free (unconjugated) drug assay, the conjugate is acetone extracted to remove protein, dried, and reconstituted in mobile phase and injected onto a VYDAC 208TP C8 reverse phase HPLC column (4.6×250 mm, 7 μm particle size) and compared to standards. The percentage of free drug compound in the conjugate is expected to be <0.5% of conjugated drug compound. See FIG. 29.

Preparation of Humanized Ab-SPDB-5d, -4-e, -43d, and -13c Conjugates

Humanized Ab at 8 mg/mL is derivatized with 4-6 molar equivalents of SPDB hetrobifunctional linker for 1.5 h at 25° C. in 95% PBS, PH 7.4, containing 5% DMA (v/v), and then purified over a G25 desalting column into citrate buffer (35 mM citrate buffer, pH 5.5, containing 2 mM EDTA, 150 mM NaCl) to remove unreacted linker. The LAR (Linker Antibody Ratio) are measured using UV absorbance at 280 and 343 nm without and with 50 mM dithiothreitol addition (to measure total antibody and dithiothreitol-released SPy) and are expected to be about 2-4 LAR. The SPDB-modified antibody at 2 mg/mL is reacted with 2 molar equivalents of compound-5d, -4-e, -43d, or -13c (HCl salt) per linked SPDB for 20 h at ambient temperature in 85% citrate buffer, 15% DMA (v/v) and then purified over a G25 desalting column into PBS, pH 7.4 to remove unconjugated drug compound. The DAR of the final humanized Ab-SPDB-5d, -4-e, -43d, and -13c conjugates are measured by UV spectrophotometry at 280 and 350 nm and calculated to be about 1.5-2.5 DAR. The percentage of monomer and linked drug compound on the monomer in the conjugate is determined by HPLC using an SEC (size exclusion chromatography) column. See FIG. 30.

Example 4

In Vitro Potency of Free Drugs and Conjugates

General Procedure Used: Samples of unconjugated free drug compounds or drug conjugates are added to 96-well flat bottomed tissue culture plates and titrated using serial dilutions to cover the desired molar range. Antigen positive ($Ag^+$) or Antigen negative ($Ag^-$) cells are added to the wells in specific cell densities in such a way that there are triplicate samples for each drug concentration for each corresponding cell line. The plates are then incubated at 37° C. in an atmosphere of 5% $CO_2$ for 4-5 days depending on the cell line. COLO 205 (1,000 cells/well), Namalwa (3,000 cells/well), HEL 92.1.7 (3,000 cells/well)—4 days; RH30(1,000 cells/well), HL60/QC (5,000 cells/well), Ramos (10,000 cells/well), KB (2,000 cells/well), BJAB (2,000 cells/well), NB4 (3,000 cells/well) 5 days, RPMI 8226 (8,000 cells/well)—6 days.

At the end of the incubation period cytotoxic potencies are then assessed using a WST-8 based cell viability assay and surviving cells are measured by developing with WST-8 (2-7 hours). The absorbance in each well is measured and the surviving fraction of cells at each concentration is plotted to reveal the cytotoxicity and/or antigen specificity (of the conjugates).

Using the general procedure described above, the cytotoxicity of the unconjugated free drug compounds is measured against seven cell lines: KB, a HeLa cell contaminant, HL60/QC, an acute myeloid leukemia cell line, Namalwa, a Burkitt lymphoma cell line, NB4, an acute promyelocytic leukemia cell line, HEL92.1.7, an erythroleukemia cell line, RPMI8226, a multiple myeloma cell line and BJAB, a B-cell leukemia cell line. The results are expected to show that the high potency of these compounds across a wide range of cell types. The potency and specificity of the antibody-drug conjugates are measured against antigen-expressing cells, with and without the additions of an excess amount of blocking unconjugated antibody to show specificity of the killing effect. The MY9-6-drug conjugate is expected to be extremely potent towards multiple different antigen-expressing cells, such as HL60/ATCC, HL60/QC and NB-4, despite the very low antigen expression in NB4 cells. The specific potency should be blocked by addition of excess unconjugated antibody, demonstrating that the cell killing effect is antigen-specific. Similarly, the huFOLR1-drug conjugate is expected to be effective in killing antigen-expressing KB cells in a specific manner.

Note that conjugates may preferably be prepared in the presence of sodium bisulfite.

To compare in vitro potency measurements for the subject conjugates prepared with and without imine reactive reagent, such as sodium bisulfite, multiple huMy9-6 conjugates with linkers such as BMPS, sulfo-SPDB, and SPDB are prepared with and without sodium bisulfite using the in situ sulfonation method (wherein the respective compounds of the invention is first mixed with sodium bisulfite and a bifunctional crosslinker bearing a reactive group, then the reaction mixture, without further purification, is reacted with the huMy9-6 monoclonal antibody as the cell-binding agent). $IC_{50}$s for the conjugates on HL60-QC cells are measured. The data is expected to indicate that the inclusion of imine reactive group (such as sodium bisulfite) in the conjugate preparation step does not negatively impact the in vitro potency of the subject conjugates.

It is expected that pre-treatment of the drug compounds with sodium bisulfite (5 molar equivalents, 22 h, 4° C., 90:10 DMA: pH 5.5 water) prior to conjugation with huMy9-6 has no significant effect on the antigen dependent or antigen independent (antigen blocking with 1 µM unconjugated huMy9-6) in vitro potency of the conjugates.

Example 5

Binding of Antibody-Drug Conjugate is Similar to that of Unmodified Antibody

The binding of huMY9-6-drug conjugate is compared with that of the unmodified huMY9-6 antibody against antigen-expressing HL60/QC cells using flow cytometry. Briefly, the antigen-positive cells are incubated with conjugates or unmodified antibodies at 4° C., then with a secondary antibody-FITC conjugate at 4° C., fixed with formaldehyde (1% in PBS) and analyzed by flow cytometry. No significant difference is expected to be observed between the binding of the conjugate versus that of the unmodified antibody. That is, a huMY9-6-drug conjugate binds to antigen-positive cells with a high affinity similar to that of the unmodified antibody.

Example 6

The tolerability of huFOLR-1 conjugates is investigated in female CD-1 mice. Animals are observed for seven days prior to study initiation and found to be free of disease or illness. The mice are administered a single i.v. injection of the conjugate and the animals are monitored daily for body weight loss, morbidity or mortality. The huFOLR1 conjugate is expected to be tolerated at only the lowest dose tested (e.g., about 50 µg/kg). In contrast, the corresponding monoimine conjugates are expected to be better tolerated with a maximum tolerated dose of at least about 4, 5, 10, 15, and 20 folds (e.g., about 200-600 µg/kg).

Example 7

Preparation of Humanized Antibody-sulfoSPDB Conjugates

A reaction containing 2.5 mg/mL huMy9-6 antibody and 10 molar equivalents of a cytotoxic compound (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-dimethylacetamide) cosolvent is allowed to conjugate for 6 hours at 25° C. Post-reaction, the conjugate is purified and buffer exchanged into 250 mM Glycine, 10 mM Histidine, 1% sucrose, 0.01% Tween, 50 µM sodium bisulfite formulation buffer, using NAP desalting columns (Illustra Sephadex G-25 DNA Grade, GE Healthcare). Dialysis is performed in the same buffer for 4 hours at room temperature utilizing Slide-a-Lyzer dialysis cassettes (ThermoScientific 20,000 MWCO). The purified conjugate is expected to have a DAR of about 2-3 (by UV-Vis using molar extinction coefficients $\epsilon_{330\ nm}=15,484\ cm^{-1}M^{-1}$ and $\epsilon_{280\ nm}=30,115\ cm^{-1}M^{-1}$ for 1f, and $\epsilon_{280\ nm}=146,000\ cm^{-1}M^{-1}$ for My9-6 antibody), >95% monomer (by size exclusion chromatography), <1% unconjugated free drug compound (by acetone extraction/reverse-phase HPLC) and a final protein concentration of ~1.5 mg/mL.

In vitro potency of antibody-sulfoSPDB-cytotoxic compound conjugates are measured according to general procedure described in Example 4. The antibody-sulfoSPDB-cytotoxic compound conjugates have comparable or higher potency than the antibody-SPDB-cytotoxic compound conjugates.

Use of covalent imine reactants, such as sodium bisulfite, improves Ab-compound conjugate specifications (e.g., % monomer and drug load). In one experiment, adduct formation is carried out with 5 molar equivalents of imine reactant over NHS-BMPS-cytotoxic compound in 90% DMSO/10% PBS pH 7.4 for 4 h at 25° C. The reaction mixture is then added to huMy9-6 antibody (4 molar equivalents of cytotoxic compound, 2 mg/ml, 10% v/v DMSO, 50 mM HEPES buffer, pH 8.5, 5 h, 25° C.). Conjugates made using sodium hydrosulfite, sodium bisulfite, or sodium metabisulfite are expected to have similar cytotoxic compound/Ab ratios and % monomer, while conjugates made with no additive treatment are expected to have very low drug incorporation.

Example 8

Preparation of Humanized Antibody-BMPS-Cytotoxic Compound Conjugate

A reaction containing 2.0 mg/mL huMy9-6 antibody and 5 molar equivalents of cytotoxic compound (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-dimethylacetamide) cosolvent is allowed to react for 6 hours at 25° C. Post-reaction, the conjugate is purified and buffer exchanged into 250 mM Glycine, 10 mM Histidine, 1% sucrose, 0.01% Tween, 50 µM sodium bisulfite formulation buffer, using NAP desalting, columns (Illustra Sephadex G-25 DNA Grade, GE Healthcare). Dialysis is performed in the same buffer for 4 hours at room temperature utilizing Slide-a-Lyzer dialysis cassettes (ThermoScientific 20,000 MWCO). The purified conjugate is found to have a DAR of about 2-3 (by UV-Vis using molar extinction coefficients $\epsilon_{330\ nm}=15,484\ cm^{-1}M^{-1}$ and $\epsilon_{280\ nm}=30,115\ cm^{-1}M^{-1}$ for 1f, and $\epsilon_{280\ nm}=146,000\ cm^{-1}M^{-1}$ for My9-6 antibody), >90% monomer (by size exclusion chromatography), <1% unconjugated free drug compound (by acetone extraction/reverse-phase HPLC) and a final protein concentration of about 1-2 mg/mL.

In vitro potency of antibody-BMPS-cytotoxic compound conjugates are measured according to general procedure described in Example 4. The antibody-BMPS-cytotoxic compound conjugates are expected to have comparable potency to the antibody-SPDB-cytotoxic compound conjugates.

Example 9

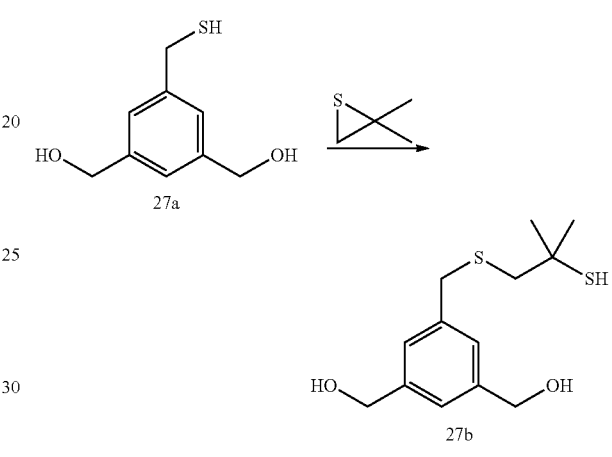

Compound 27b (5-((2-mercapto-2-methylpropylthio)methyl)-1,3-phenylene)dimethanol: (5-(mercaptomethyl)-1,3-phenylene)dimethanol (0.163 g, 0.885 mmol) was dissolved in methanol (3 mL) in a small vial and a stir bar was added. To this solution was added triethylamine (0.016 mL, 0.118 mmol) followed by 2,2-dimethylthiirane (0.058 mL, 0.590 mmol) and the resulting mixture was capped and stirred overnight (16 hrs) at room temperature. The reaction was then concentrated, redissolved in dichloromethane, loaded onto a silica ptlc plate (1000 micron) and the plate was developed using 10% methanol in dichloromethane. The band corresponding to the product was scraped, filtered with neat ethyl acetate, and concentrated to give (5-((2-mercapto-2-methylpropylthio)methyl)-1,3-phenylene)dimethanol (0.095 g, 0.349 mmol, 59.1% yield). $^1$H NMR (400 Hz, CDCl$_3$): δ 7.26 (s, 3H), 4.69 (s, 4H), 3.82 (s, 2H), 2.74 (s, 2H), 2.17 (s, 1H), 2.12 (br s, 2H), 1.43 (s, 6H); $^{13}$C NMR (400 Hz, CDCl$_3$): δ 141.6, 138.9, 126.7, 124.3, 65.0, 49.0, 45.4, 38.4, 31.5; MS (m/z), expected: 272.4. found 295.0 (M+Na).

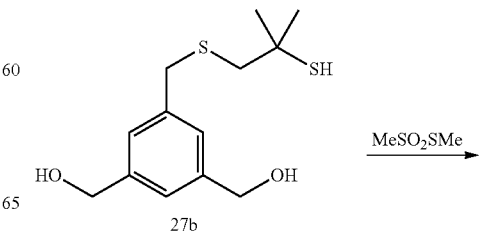

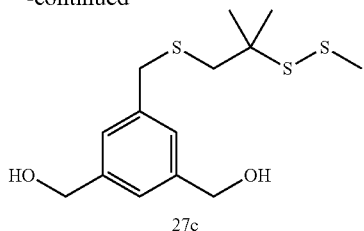

Compound 27c (5-((2-methyl-2-(methyldisulfanyl)propylthio)methyl)-1,3-phenylene)dimethanol: (5-((2-mercapto-2-methylpropylthio)methyl)-1,3-phenylene)dimethanol (0.120 g, 0.440 mmol) was dissolved in ethanol (5 mL) and 1.0 M potassium phosphate buffer (pH 7) (5.00 mL) and cooled in an ice bath (a ppt formed but it was ignored). S-methyl methanesulfonothioate (0.083 mL, 0.881 mmol) was added and the mixture stirred overnight with gradual (over 30 minutes) warming to room temperature. The reaction was diluted with dichloromethane and the organic layer was removed, washed with water, dried over anhydrous sodium sulfate, and concentrated in vacuo. The residue was dissolved in dichloromethane and loaded onto a 500 micron ptlc plate and developed with 66% ethyl acetate in hexane. The band corresponding to the product was scraped, filtered using ethyl acetate, and concentrated to give (5-((2-methyl-2-(methyldisulfanyl)propylthio)methyl)-1,3-phenylene)dimethanol (0.091 g, 0.286 mmol, 64.9% yield). $^1$H NMR (400 Hz, CDCl$_3$): δ 7.27 (s, 3H), 4.71 (s, 4H), 3.78 (s, 2H), 2.77 (s, 2H), 2.41 (s, 3H), 1.94 (br s, 2H), 1.38 (s, 6H); $^{13}$C NMR (400 Hz, CDCl$_3$): δ 141.6, 139.0, 126.7, 124.2, 65.0, 51.8, 44.0, 38.2, 26.7, 25.3; MS (m/z), expected: 341.5. found 341.1 (M+Na).

Example 10

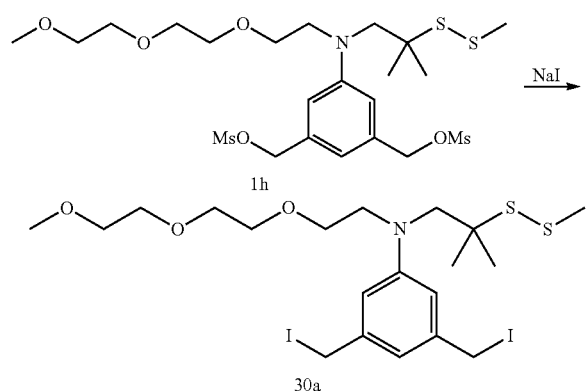

Compound 30a (5-((2-(2-(2-methoxyethoxy)ethoxy)ethyl)(2-methyl-2-(methyldisulfanyl)propyl)amino)-1,3-phenylene)bis(methylene) dimethanesulfonate (0.566 g, 0.960 mmol) was dissolved in acetone (30 mL) and a solution of sodium iodide (0.544 g, 3.63 mmol) dissolved in acetone (2 mL) was added with vigorous stirring. The reaction was monitored by tlc (50% ethyl acetate in hexane) and after 2 hours the reaction was filtered, concentrated in vacuo and dichloromethane was added to the residue. The solid salt left behind was filtered, the filtrate was concentrated and the resulting residue was purified on silica gel using a 3:5:2 mixture of ethyl acetate:hexane:dichloromethane to give 3,5-bis(iodomethyl)-N-(2-(2-(2-methoxyethoxy)ethoxy)ethyl)-N-(2-methyl-2-(methyldisulfanyl)propyl)aniline (0.505 g, 0.773 mmol, 74.5% yield) as a yellow oil. $^1$H NMR (400 Hz, CDCl$_3$): δ 6.75 (s, 2H), 6.73 (s, 1H), 4.38 (s, 4H), 3.63 (m, 14H), 3.40 (s, 3H), 2.50 (s, 3H), 1.38 (s, 6H); $^{13}$C NMR (400 Hz, CDCl$_3$): δ 148.7, 140.3, 117.3, 113.4, 71.9, 70.7, 70.6, 67.2, 59.8, 59.1, 53.5, 53.4, 51.8, 26.5, 25.6, 6.11; MS (m/z), Calcd 676.0 (M+Na)$^+$. found 675.8 (M+Na)$^+$.

Example 11

Synthesis of Compound 32a

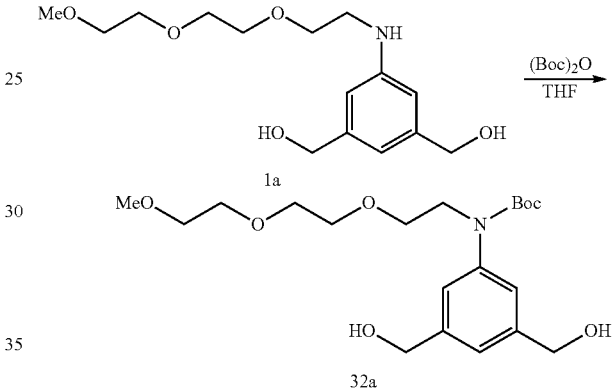

Compound 32a

To a stirred solution of the aniline 1a (339 mg, 1.1 mmol) in anhydrous tetrahydrofuran (4.0 mL) was added Boc anhydride (272 mg, 1.2 mmol). The mixture was continued to be stirred at room temperature for three days. The reaction mixture was concentrated under reduced pressure and the residue was purified by silica gel chromatography (CH$_2$Cl$_2$/MeOH) to give compound 32a (405 mg, y=90%) as colorless oil. $^1$H NMR (400 Hz, CDCl$_3$): δ 7.00 (s, 2H), 6.97 (s, 1H), 4.38 (s, 4H), 4.12 (s, 2h), 3.64 (t, J=5.6 Hz, 2H), 3.48-3.44 (m, 8H), 3.40-3.38 (m, 2H), 3.21 (s, 3H), 1.31 (s, 9H); $^{13}$C NMR (400 Hz, CDCl$_3$): δ 154.65, 142.3, 142.1, 124.1, 122.7, 80.2, 71.6, 70.3, 70.1, 69.9, 68.5, 63.9, 58.65, 49.4, 28.1.

Example 12

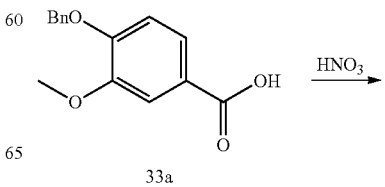

-continued

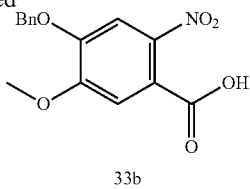

Compound 33b

Compound 33a (20 g, 77 mmol) was added as a thick suspension in anhydrous dichloromethane (100 mL) and was cooled to 0° C. Acetic acid (191 mL) was added, resulting in a clear solution which stirred at 0° C. until cool. Nitric acid (26 mL, 581 mmol) was added slowly dropwise through an addition funnel. The ice bath was removed and the solution continued to stir at room temperature. After 3 hours, the reaction was diluted with deionized water and extracted with dichloromethane. The organic layer was washed with brine, dried over anhydrous magnesium sulfate and the filtrate concentrated in vacuo. The crude residue was recrystallized using ethyl acetate and hexanes. The solid was filtered and washed with hexanes to give compound 33b as a yellow fluffy solid (13.8 g, y=59%). $^1$H NMR (400 Hz, CDCl$_3$): δ 7.48-7.43 (m, 6H), 7.25 (s, 1H), 5.25 (s, 2H), 4.02 (s, 3H), MS (m/z): 326.1 (M+Na)$^+$. See FIG. 33.

Example 13

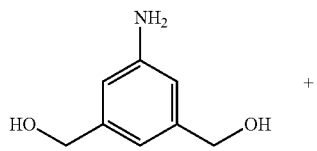

+

-continued

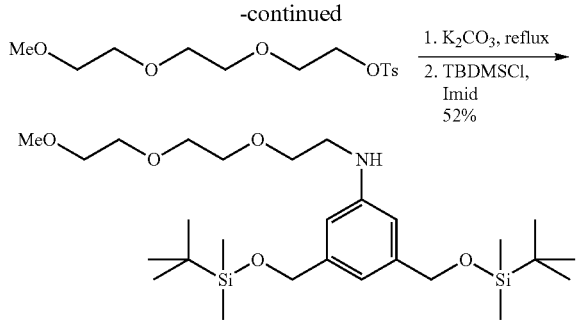

3,5-bis(((tert-butyldimethylsilyl)oxy)methyl)-N-(2-(2-(2-methoxyethoxy)ethoxy)ethyl)aniline A mixture of (5-amino-1,3-phenylene)dimethanol (11.78 g, 77 mmol), 2-(2-(2-methoxyethoxy)ethoxy)ethyl 4-methylbenzenesulfonate (15.3 g, 48.1 mmol), and potassium carbonate (13.28 g, 96 mmol) in DMF (96 ml) was refluxed for 20 hours. The reaction was cooled to ambient temperature and diluted with dichloromethane. The mixture was filtered through celite and concentrated in vacuo. The resulting orange oil was dissolved in dichloromethane (240 ml) and 1-butyldimethylsilyl chloride (18.09 g, 120 mmol) and imidazole (9.80 g, 144 mmol) were added. The reaction was stirred at ambient temperature for 20 hours upon which it was diluted with dichloromethane and filtered through celite. Purification by silica gel chromatography (EtOAc/Hex) yielded 3,5-bis(((tert-butyldimethylsilyl)oxy)methyl)-N-(2-(2-(2-methoxyethoxy)ethoxy)ethyl)aniline (13 g, 52%). $^1$H NMR (400 Hz, CDCl$_3$): δ6.52 (s, 1H), 6.40 (s, 2H), 4.56 (s, 4H), 3.60 (t, 2H, J=5.2 Hz), 3.56 (m, 6H), 3.46 (m, 2H), 3.29 (s, 3H), 3.20 (t, 2H, J=5.2 Hz), 0.84 (s, 18H), 0.00 (s, 12H). MS (m/z). found 550.1 (M+Na)$^+$. See FIG. 34.

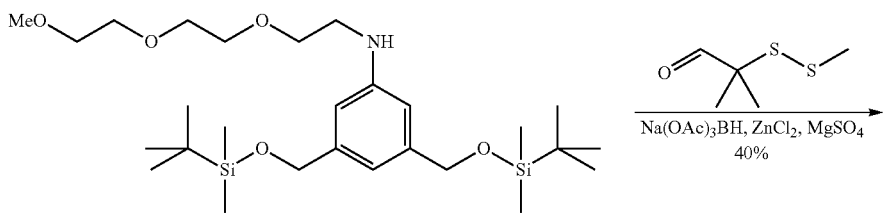

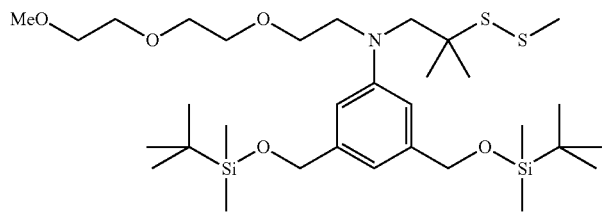

3,5-bis(((tert-butyldimethylsilyl)oxy)methyl)-N-(2-(2-(2-methoxyethoxy)ethoxy)ethyl)-N-(2-methyl-2-(methyldisulfanyl)propyl)aniline To a solution of 3,5-bis(((tert-butyldimethylsilyl)oxy)methyl)-N-(2-(2-(2-methoxyethoxy)ethoxy)ethyl)aniline (6.7 g, 12.69 mmol) in anhydrous 1,2-dichloroethane (50 ml) was added 2-(methyldithio)isobutyraldehyde (2.74 ml, 19.04 mmol), sodium triacetoxyborohydride (2.8 g, 1 eq), zinc(II) chloride (0.865 g, 6.35 mmol) and magnesium sulfate (2.292 g, 19.04 mmol). The mixture was stirred for five hours at ambient temperature. Sodium triacetoxyborohydride (2.8 g, 1 eq) was added. The reaction continued to stir at ambient temperature for 20 hours. The mixture was filtered through celite rinsing with dichloromethane and concentrated under reduced pressure then extracted with ethyl acetate and water. The organic extracts were washed with brine, dried over magnesium sulfate, filtered, concentrated and purified by combiflash (EtOAc/Hex) to give 3,5-bis(((tert-butyldimethylsilyl)oxy)methyl)-N-(2-(2-(2-methoxyethoxy)ethoxy)ethyl)-N-(2-methyl-2-(methyldisulfanyl)propyl)aniline (3.5 g, 40%). $^1$H NMR (400 Hz, CDCl3): δ 6.73 (s, 2H), 6.59 (s, 1H), 4.56 (s, 4H), 3.65-3.51 (m, 14H), 3.30 (s, 3H), 2.38 (s, 3H), 1.28 (s, 6H), 0.84 (s, 18H), 0.00 (s, 12H). MS (m/z). found 684.2 (M+Na)$^+$. See FIG. 34.

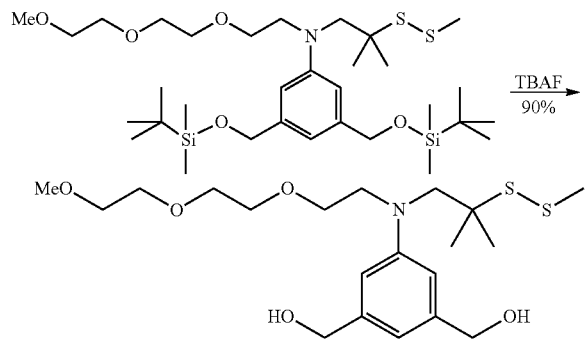

(5-((2-(2-(2-methoxyethoxy)ethoxy)ethyl)(2-methyl-2-(methyldisulfanyl)propyl)amino)-1,3-phenylene)dimethanol (1b)

Tetrabutylammonium fluoride (1M in THF) (10.57 ml, 10.57 mmol) was added dropwise to stirring solution of 3,5-bis(((tert-butyldimethylsilyl)oxy)methyl)-N-(2-(2-(2-methoxyethoxy)ethoxy)ethyl)-N-(2-methyl-2-(methyldisulfanyl)propyl)aniline (3.5 g, 5.29 mmol) in anhydrous THF (65 ml) at 0° C. in an ice bath. Following addition the mixture was stirred at ambient temperature for two hours. The mixture was quenched with saturated ammonium chloride and extracted with ethyl acetate. The extracts were washed with water and brine, dried with magnesium sulfate, filtered and concentrated under reduced pressure. Purification by silica gel chromatography (MeOH/DCM) yielded (5-((2-(2-(2-methoxyethoxy)ethoxy)ethyl)(2-methyl-2-(methyldisulfanyl)propyl)amino)-1,3-phenylene)dimethanol (2 g, 87%). $^1$H NMR (400 Hz, CDCl3): δ 6.76 (s, 2H), 6.63 (s, 1H), 4.55 (s, 4H), 3.65-3.51 (m, 14H), 3.35 (s, 3H), 2.44 (s, 3H), 1.33 (s, 6H); 13C NMR (400 Hz, CDCl3): δ 149.0, 142.35, 114.0, 111.1, 71.98, 70.7, 70.6, 70.5, 67.6, 65.5, 59.75, 59.1, 53.9, 51.9, 26.6, 25.7, 20.75; MS (m/z). found 456.2 (M+Na)$^+$.

Example 14

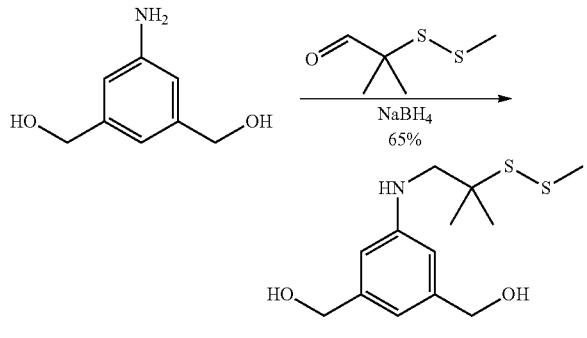

(5-(2-methyl-2-(methyldisulfanyl)propylamino)-1,3-phenylene)dimethanol (5-amino-1,3-phenylene)dimethanol (2.5 g, 16.32 mmol) and 2-(methyldithio)isobutyraldehyde (2.347 ml, 16.32 mmol) were stirred at ambient temperature in absolute ethanol (82 ml) until completely dissolved (3 hours). The mixture was cooled to 0° C. in an ice bath and sodium borohydride (0.741 g, 19.59 mmol) was added. The reaction was stirred for 1 hour at 0° C., and was then quenched slowly with cold 5% HCl solution. The mixture was diluted with dichloromethane and the pH was adjusted to pH=8 with saturated sodium bicarbonate solution then extracted with dichloromethane and then washed with brine. The organic extracts were dried over anhydrous sodium sulfate, filtered, and concentrated under reduced pressure. Purification by silica gel chromatography (MeOH/DCM) yielded (5-(2-methyl-2-(methyldisulfanyl)propylamino)-1,3-phenylene)dimethanol (3 g, 65%) as a white solid. $^1$H NMR (400 Hz, CDCl$_3$): δ6.62 (s, 1H), 6.54 (s, 2H), 4.53 (s, 4H), 3.13 (s, 2H), 2.30 (s, 3H), 1.32 (s, 6H). See FIG. 35.

Example 15

In Vivo Efficacy of Various Conjugates in Tumor Bearing Nude Mice

In this study, the anti-tumor activity of several conjugates of the invention are investigated in immune-compromised mice (nude or SCID), preferably female nude mice, bearing various tumors. In some cases, in addition or as an alternative, nude rats may be employed. The conjugates to be tested include any one or more of the conjugates described herein. The various tumor cell lines that can be used for inoculating the nude mice included HL60/QC, MOLM-13, NB4, HEL92.1.7, OCI-AML3, KB, and/or any other cancer cell lines recognized in the art as a proper model for a disease indication (e.g., cancer). Some criteria that may be applied for the selection of tumor cell lines suitable for in vivo evaluation include: a) expression of the target antigen on the tumor cell, and, b) sensitivity of tumor cells to the unconjugated drug in vitro. For example, an in vitro cell line sensitivity screen, such as the 60-cell line screen described by the U.S. National Cancer Institute (see Voskoglou-Nomikos et al., 2003, Clinical Cancer Res. 9; 42227-4239, incorporated herein by reference) can be used as one of the guides to determine the types of cancers that may be suitable for treatment with the compounds of the invention. The potency of the various conjugates against the various tumor cell lines, as expressed by $IC_{50}$ values (nM), is measured accordingly.

The various tumor cell lines are inoculated to nude or SCID mice using substantially the same protocol as outlined herein. For example, about $1\times10^6$-$5\times10^7$ tumor cells (typically $1\times10^7$) cells/mouse are subcutaneously inoculated at a volume of approximately 0.1-0.2 mL/mouse, in the area over the right shoulder of female athymic nude mice, 6 weeks of age. When the tumor has reached an average size of ~100 mm$^3$ (typically 6 to 8 days after tumor cell inoculation), mice are randomized into groups (e.g., n=5-8 per group) by tumor volume. Treatment is initiated the day after randomization, and groups includes a control group dosed with the appropriate vehicle (200 µL/injection), or a single treatment at various doses (5 to 700 µg/kg) of the above referenced drug conjugates (50 µg/kg linked drug dose corresponded to about 2 mg/kg antibody dose). Multiple dosing schedules (for example treatment at day 1, 3, 5, or day 1, 4, 7) may also be employed.

Median and mean tumor volume vs time is measured, with the data demonstrating a dose-dependent anti-tumor activity of the subject conjugates. The minimum effective dose is then calculated and compared to the maximum tolerated dose.

Example 16

Humanized My9-6 antibody at 2 mg/ml is conjugated with 9 molar equivalents of 2-NHS ester (of a subject cytotoxic compound) for 3 hrs at 25° C. in 85% PBS, pH 7.4, containing 15% DMA (v/v) and then purified over a G25 desalting column in PBS, pH 7.4, to remove unreacted or hydrolyzed, unconjugated drug. The conjugate is dialyzed in 10 mM Histidine, 250 mM Glycine, pH 6.5 buffer, containing 1% sucrose. The conjugate drug/antibody ratio (DAR) is determined to be about 1.5 DAR based on UV absorbance at 280 and 320 nm and calculation using the extinction coefficients of the drug and antibody at 280 nm and 320 nm.

The conjugate is analyzed for monomer % by size exclusion chromatography (SEC) on a TSK-Gel G300SWXL column (7.8 mm×300 mm, 5 µm particle size) using an isocratic mobile phase of 400 mm sodium perchlorate, 150 mM potassium phosphate buffer, pH 7.0, at 1 ml/min. The percentage of monomer (% monomer) and aggregate are determined by monitoring the UV absorbance of all antibody species at 280 nm and measuring the area-under-the-curve (AUC) of each antibody peak. Additionally, the percentage (%) of drug on both the monomer and the aggregate are determined by monitoring the UV absorbance of all antibody species at 320 nm and 280 nm and measuring the AUC of each antibody peak.

For free (unconjugated) drug assay, the conjugate is acetone extracted to remove protein, dried, and reconstituted in mobile phase and injected onto a VYDAC 208TP C8 reverse phase HPLC column (4.6×250 mm, 7 µm particle size) using a linear gradient of 20% acetonitrile and 80% deionized going up to 100% acetonitrile, all containing 0.025% acetic acid, at 1 ml/min over 48 min and compared to drug-methyl ester standards. The percentage of free, unconjugated drug in the conjugate is expected to be <1% of conjugated drug.

Example 17

For the conjugation of 2-NHS ester (a cytotoxic compound) using sodium bisulfite, the 2-NHS ester (cytotoxic compound) is pre-incubated with 0.9 molar equivalents of sodium bisulfite (freshly prepared $NaHSO_3$ in deionized water) in 66% DMA (dimethylacetamide) in water for 30 min at 25° C. HuMy9-6 antibody at 2 mg/ml is conjugated with 9 molar equivalents of 2-NHS ester (with added $NaHSO_3$) for 3 h at 25° C. in 85% PBS, pH 7.4, 15% DMA (v/v) and then purified over a G25 desalting column in PBS, pH 7.4 to remove unreacted or hydrolyzed drug. The conjugate is dialyzed in 10 mM histidine, 250 mM glycine, 1% sucrose, pH 6.5 buffer.

The DAR of the conjugate prepared using sodium bisulfite is measured by UV spectrophotometry at 280 and 320 nm and calculated to be about 3 DAR. The % monomer of the conjugate is expected to be about 95% and the % cytotoxic compound on the monomer is about 90%.

The MS of a huMy9-6 conjugate prepared using sodium bisulfite following deglycosylation is expected to show the largest peak of D1 with one linked drug, and possibly D2, D3, D4, D5, D6 peaks with 2-6 linked drugs per antibody.

The conjugate prepared with sodium bisulfite is expected to show a much greater drug incorporation than the conjugate prepared without sodium bisulfite. The MS of the conjugate prepared with sodium bisulfite is expected to show conjugate peaks of 1-6 linked drugs with the highest D1 peak with 1 linked drug. In contrast, the MS of conjugate prepared without sodium bisulfite is expected to show the highest peak of unconjugated antibody (D0) and much smaller D1, D2 and D3 linked drug conjugate peaks. The overall conjugate quality for the conjugate prepared with sodium bisulfite, therefore, is expected to be much superior than by the traditional conjugation procedure without sodium bisulfite.

The conjugate prepared with sodium bisulfite is expected to show a similar in vitro cytotoxicity to the conjugate prepared without sodium bisulfite. Therefore a better quality conjugate of higher DAR and higher % drug on monomer is prepared using sodium bisulfite without any loss of cytotoxic potency.

A huMy9-6 conjugate prepared using sodium bisulfite is analyzed by non-reducing SDS-PAGE using a gel chip analyzer. The conjugate is expected to show only the intact antibody band; no heavy and light chain bands are observed, showing an unexpected advantage that the added sodium bisulfite does not cause any unwanted reduction of native interchain disulfide bonds in the antibody.

2-NHS ester or SPDB-NHS esters of several cytotoxic compounds are pre-incubated with 0.5 to 3 molar equivalents of sodium bisulfite (freshly prepared NaHSO3 in deionized water) in 66-98% DMA (dimethylacetamide) in water from 15 min to 4 h at 25° C. Some of these reactions are left overnight at 4° C. and used for conjugations 20 h later.

The 2-NHS ester in DMA treated with sodium bisulfite or without added sodium bisulfite is analyzed by HPLC using a VYDAC C8 reversed phase column with a linear gradient of 20% acetonitrile and 80% deionized water going up to 100% acetonitrile, all containing 0.025% acetic acid, at 1 ml/min over 48 min. No undesirable peak of sulfonated hydrolyzed cytotoxic compound is observed. Therefore, a favorable reaction of sodium bisulfite toward addition to the imine bond without reaction with the NHS ester is expected to be observed.

Similarly drug NHS esters are treated with imine reactive reagents other than sodium bisulfite before conjugation with antibody. An alternative conjugation approach is to treat a mixture of drug-NHS ester and antibody with sodium bisulfite or other imine reactive reagent.

Example 18

The disulfide-linked antibody-SPDB-cytotoxic compound conjugate is prepared using synthesized SPDB-NHS ester linked cytotoxic compound. The cytotoxic compound-SPDB-NHS ester is pre-treated with 3 molar equivalents of sodium bisulfite (using a freshly prepared NaHSO$_3$ solution in water) in 96-98% DMA in water for 4-5 h at 25° C. The sodium bisulfite-treated cytotoxic compound-SPDB-NHS ester in DMA is analyzed using VYDAC C8 reversed phase-HPLC column using a linear gradient of 20% acetonitrile and 80% deionized water containing 0.025% acetic acid at 1 ml/min for 48 mM. The reversed phase HPLC analysis shows only the desired reaction of bisulfite addition to the imine bond without the undesired reaction of bisulfite with the NHS ester.

For conjugation, a humanized antibody at 2 mg/ml is reacted with 5-7 molar equivalents of cytotoxic compound-SPDB-NHS ester (pre-treated with NaHSO$_3$) for 6 h at 25° C. in 85% PBS, pH 7.4, aqueous buffer containing 15% N,N-dimethylacetamide (DMA) and then purified over a G25 gel filtration column in PBS, pH 7.4, to remove unreacted or hydrolyzed drug. The humanized antibody-SPDB-cytotoxic compound conjugates are dialyzed in 10 mM Histidine, 250 mM Glycine, 1% sucrose, pH 6.5 buffer. The drug/antibody ratio (DAR) of the conjugates are measured to be about 2-3 by UV absorbance measurements at 280 and 320 nm and using the extinction coefficients of the drug and antibody at 280 nm and 320 nm. The percentage of monomer in the conjugate preparation is determined by SEC (Size Exclusion Chromatography) as 90%. Based on the UV absorbance of the monomer peak in SEC it is also expected that the monomer conjugate peak has linked drug molecules. The unconjugated drug % by acetone extraction and reversed-phase HPLC is expected to be less than 1%.

The MS of the deglycosylated antibody-SPDB-cytotoxic compound conjugates prepared with sodium bisulfite added before conjugation shows a much superior conjugate than that obtained without sodium bisulfite conjugation. The MS of the conjugate prepared without sodium bisulfite has an average of about 1.5 drug/Ab ratio, and antibody species with up to three linked drug molecules. In contrast, the MS of the conjugate prepared with sodium bisulfite showed an average of about 2.5 drug/Ab and antibody species with up to seven linked drug molecules.

The disulfide-linked antibody-SPDB-cytotoxic compound conjugate prepared using sodium bisulfite shows only intact antibody band by non-reducing SDS-PAGE gel chip analysis. The gel chip assay is performed using Agilent Protein 230 Protein Chip and analyzed using an Agilent 2300 Bioanalyzer. No heavy and light chain bands are observed, showing an unexpected advantage that the added sodium bisulfite does not cause any unwanted reduction of native antibody-interchain disulfide bonds. The linked drug obtained in the antibody-SPDB-cytotoxic compound conjugate prepared using sodium bisulfite also demonstrate's that the disulfide linker in the conjugate is stable to the added sodium bisulfite.

Example 19

For conjugate preparation, cytotoxic compound-SPDB-NHS ester is pre-incubated with 3 molar equivalents of sodium bisulfite (freshly prepared NaHSO$_3$ in deionized water) in 96% DMA (dimethylacetamide) in water for 5 h at 25° C. and then incubated overnight at 4° C. until needed for conjugation. Humanized antibody at 2-3 mg/ml is derivatized with 8 molar equivalents of cytotoxic compound-SPDB-NHS ester in the absence or presence of sodium bisulfite (−/+NaHSO$_3$) for 4 h at 25° C. in 95% 50 mM HEPES, pH 8.5, aqueous buffer containing 5% DMA (v/v) and then both are purified over G25 desalting columns into PBS, pH 7.4, to remove unreacted, hydrolyzed drug. The conjugates are dialyzed in 10 mM histidine, 250 mM glycine, 1% sucrose, pH 6.5 buffer. The conjugate DAR is measured by UV spectrophotometry at 280 and 320 nm. The monomer % and % drug on the monomer in the conjugate are determined by SEC. The unconjugated drug in the conjugate is determined by reverse phase HPLC after acetone extraction.

Example 20

To conjugate drug thiols with reactive disulfide linker incorporated in antibody, humanized mAb at 8 mg/ml is derivatized with 4-6 molar equivalents of SPDB heterobifunctional linker for 1.5 h at 25° C. in 90% PBS, pH 7.5, aqueous buffer with 5% DMA (v/v) and then purified over a G25 desalting column into 35 mM citrate, 2 mM EDTA, 150 mM NaCl, pH 5.5 buffer to remove unreacted, hydrolyzed linker. The LAR (linker antibody ratio) is measured by UV absorbance at 280 and 343 nm without and with added 50 mM dithiothreitol (to measure total antibody and releasable SPy). The SPDB-modified antibody at 2 mg/ml is reacted with 2 molar equivalents of sodium bisulfite-treated drug thiol per linker for 2 to 20 h at 25° C. in 85-90% of 50 mM potassium phosphate, 50 mM NaCl, pH 7.5 buffer and then purified over a G25 desalting column in PBS, pH 7.4, to remove unreacted, hydrolyzed drug. The DAR of the antibody-SPDB-drug conjugate is measured by UV absorbance at 280 and 320 nm and the percentage of monomer and the percentage of drug on the monomer in the conjugate preparation is determined by SEC.

Example 21

Preparation of huMy9-6-Sulfo-SPDB-Cytotoxic Compound (2-Step Method)

A reaction containing 6 mg/mL huMy9-6 antibody and 9 molar equivalents sulfo-SPDB linker (20 mM stock in DMA) is incubated for 3 h at 25° C. in 50 mM EPPS buffer pH 8. Unreacted linker is removed using a NAP desalting column (Illustra Sephadex G-25 DNA Grade, GE Healthcare) and the linker to antibody ratio (LAR) is determined to be about 4 based on antibody concentration and DTT-released thiopyridine concentration by UV-Vis ($\epsilon_{343\ nm}$=8,080 cm$^{-1}$M$^{-1}$ for 2-thiopyridone).

Sulfo-SPDB modified huMy9-6 is diluted to 2 mg/ml in 50 mM EPPS pH 8.5, 10% v/v DMA, and reacted with 2 molar equivalents of a cytotoxic compound per linker (5 mM stock in DMA; 7.4 equivalents per antibody) for 3 h at 25° C.

Post-reaction, the conjugate is purified and buffer exchanged into 250 mM Glycine, 10 mM Histidine, 1% sucrose, 0.01% Tween-20, 50 μM sodium bisulfite at pH 6.2 using a desalting column (G-25 Sephadex, fine grade, GE Healthcare).

The purified conjugate is expected to have an average of 3 cytotoxic compound molecules linked per antibody (by UV-Vis using molar extinction coefficients $E_{330\ nm}$=15,484 cm$^{-1}$M$^{-1}$ and $\epsilon_{280\ nm}$=30,115 cm$^{-1}$M$^{-1}$ for compound 1, and $\epsilon_{280\ nm}$=207,000 cm$^{-1}$ M$^{-1}$ for My9-6 antibody), >95% monomer (by size exclusion chromatography), <1% unconjugated compound (by acetone extraction/reverse-phase HPLC), a 60% yield based on the amount of the antibody used, and a 20% overall yield based on the amount of compound used. The conjugate made using this method can be concentrated (by stirred cell or Amicon centrifugal filter device) to >3 mg/ml without conjugate precipitation.

Example 22

Preparation of huMy9-6-SPDB-Cytotoxic Compound

Method 1 (One-Step Reagent Method):
A reaction containing 2 mg/mL huMy9-6 antibody and 7 molar equivalents cytotoxic compound-SPDB-NHS (pre-treated with 5-fold excess of sodium bisulfite in 90:10 DMA:water, v/v for 1 h at 25° C. and then overnight at 4° C.) in 50 mM HEPES (4-(2-hydroxyethyl)-1-piperazine ethanesulfonic acid) pH 8.5 buffer and 10% v/v DMA (N,N-Dimethylacetamide) cosolvent is allowed to incubate for 3 h at 25° C.

Post-reaction, the conjugate is purified and buffer exchanged into 250 mM Glycine, 10 mM Histidine, 1% sucrose, 0.01% Tween, 50 µM sodium bisulfite formulation buffer, using NAP desalting columns (Illustra Sephadex G-25 DNA Grade, GE Healthcare). Dialysis is performed in the same buffer for 4 hours at room temperature utilizing Slide-a-Lyzer dialysis cassettes (ThermoScientific 20,000 MWCO).

The purified conjugate is expected to have an average of 4.0 cytotoxic compound molecules linked per antibody (by UV-Vis using molar extinction coefficients $\epsilon_{330\ nm}$=15,484 cm$^{-1}$M$^{-1}$ and $\epsilon_{280\ nm}$=30,115 cm$^{-1}$M$^{-1}$ for compound, and $\epsilon_{280\ nm}$=207,000 cm$^{-1}$M$^{-1}$ for My9-6 antibody), >90% monomer (by size exclusion chromatography, TSK3000, TOSOH Biosciences), <1% unconjugated compound (by acetone extraction/reverse-phase HPLC) a 70% yield based on the amount of the antibody used, a 40% overall yield based on the amount of cytotoxic compound-SPDB-NHS used, and a final protein concentration of 1.0 mg/ml.

Method 2 (Two-Step Method):
A reaction containing 4.8 mg/mL huMy9-6 antibody and 6 molar equivalents SPDB linker (18.5 mM stock in ethanol) is incubated for 3 h at 25° C. in PBS pH 7.4. Unreacted linker is removed using a NAP desalting column (Illustra Sephadex G-25 DNA Grade, GE Healthcare) and the linker to antibody ratio (LAR) is determined to be 4.0 based on antibody concentration and DTT-released 2-thiopyridone concentration by UV-Vis ($\epsilon_{343\ nm}$=8,080 cm$^{-1}$M$^{-1}$ for 2-thiopyridone).

SPDB modified huMy9-6 is diluted to 2 mg/ml in 50 mM EPPS pH 8.5, 10% v/v DMA and reacted with 1.75 molar equivalents of compound per linker (5 mM stock in DMA; 7 equivalents per antibody) for 3 h at 25° C.

Post-reaction, the conjugate is purified and buffer exchanged into 250 mM Glycine, 10 mM Histidine, 1% sucrose, 0.01% Tween-20, 50 µM sodium bisulfite at pH 6.2 using a desalting column (Illustra Sephadex G-25 DNA Grade, GE Healthcare).

The purified conjugate is found to have an average of 4 compound molecules linked per antibody (by UV-Vis using molar extinction coefficients $\epsilon_{330\ nm}$=15,484 cm$^{-1}$ M$^{-1}$ and $\epsilon_{280\ nm}$=30,115 cm$^{-1}$M$^{-1}$ for compound 1, and $\epsilon_{280\ nm}$=207,000 cm$^{-1}$M$^{-1}$ for My9-6 antibody), >90% monomer (by size exclusion chromatography, TSK3000, TOSOH Biosciences), <1% unconjugated compound (by acetone extraction/reverse-phase HPLC), a 40% yield based on the amount of the antibody used, a 20% overall yield based on the amount of compound used, and a final protein concentration of 0.5 mg/ml.

Example 23

Preparation of huMy9-6-Cytotoxic Compound

Method 1 (In-Situ One-Step Reagent Method):
A DMA solution containing 1.9 mM cytotoxic compound, 1 mM CX1-1 heterobifunctional linker with N-hydroxysuccinimide (NHS) and maleimide groups, and 20 mM diisopropyl ethyl amine (DIPEA) is allowed to react at ambient temperature for 8 min. Then 3 mM maleimido proprionic acid (MPA) is added to quench excess compound. The 1-CX1-1-NHS reaction mixture is stored frozen at −80° C., and later upon thawing is added in two portions to a buffered solution of huMy9-6 at 25° C. (2 mg/ml, 100 mM EPPS, pH 8.0, 10% v/v DMA); 4.8 molar equivalents per antibody (based on linker concentration) followed by 4.2 equivalents 30 min later. After 2 h reaction, the conjugate is purified and buffer exchanged into 250 mM Glycine, 10 mM Histidine, 1% sucrose, 0.01% Tween-20, 50 µM sodium bisulfite at pH 6.2 using a desalting column (Quick-spin protein, G-25 fine resin, Roche), dialysis, and finally 0.22 µm sterile filtration.

The purified conjugate is expected to have an average of about 3.5 compound molecules linked per antibody (by UV-Vis using molar extinction coefficients $\epsilon_{330\ nm}$=15,484 cm$^{-1}$ M$^{-1}$ and $\epsilon_{280\ nm}$=30,115 cm$^{-1}$ M$^{-1}$ for compound, and $\epsilon_{280\ nm}$=207,000 cm$^{-1}$ M$^{-1}$ for My9-6), 95% monomer (by size exclusion chromatography, TSK3000, TOSOH Biosciences), <1% unconjugated compound (by acetone extraction/reverse-phase HPLC), a 45% yield based on the amount of the antibody used, a 20% overall yield based on the amount of compound used, and a final protein concentration of 0.7 mg/ml.

Method 2 (One-Step Method):
To a buffered solution of huMy9-6 antibody (2 mg/ml, 50 mM EPPS, pH 8.5, 8% v/v DMA) is added 14 molar equivalents compound (5 mM stock in DMA) followed by 7 molar equivalents of CX1-1 linker (15 mM stock solution in ethanol) and incubated for 3 h at 25° C.

Post-reaction, the conjugate is purified and buffer exchanged into 250 mM Glycine, 10 mM Histidine, 1% sucrose, 0.01% Tween-20, 50 µM sodium bisulfite at pH 6.2 using a desalting column (Illustra Sephadex G-25 DNA Grade, GE Healthcare), followed by 2× dialysis at 4° C. in Slide-a-Lyzer dialysis cassettes (ThermoScientific 20,000 MWCO).

The purified conjugate is expected to have an average of about 3.5 compound molecules linked per antibody (by UV-Vis using molar extinction coefficients $\epsilon_{330\ nm}$=15,484 cm$^{-1}$M$^{-1}$ and $\epsilon_{280\ nm}$=30,115 cm$^{-1}$M$^{-1}$ for compound, and $\epsilon_{280\ nm}$=207,000 cm$^{-1}$M$^{-1}$ for My9-6 antibody), 90% monomer (by size exclusion chromatography, TSK3000, TOSOH Biosciences), <1% unconjugated compound (by acetone extraction/reverse-phase HPLC), a 45% yield based on the amount of the antibody used, an 10% overall yield based on the amount of used, and a final protein concentration of 1.5 mg/ml.

Example 24

Use of Covalent Imine Reactants to Improve Ab-Drug Conjugate Specifications (% Monomer and Drug Load)

Adduct formation is carried out with 5 molar equivalents of imine reactant over NHS-BMPS-cytotoxic compound in 90% DMSO/10% PBS pH 7.4 for 4 hr at 25° C. The reaction mixture is then added to huMy9-6 antibody (4 molar equivalents drug, 2 mg/ml, 10% v/v DMSO, 50 mM HEPES buffer, pH 8.5, 5 h, 25° C.). Conjugates made using sodium hydrosulfite, sodium bisulfite, or sodium metabisulfite have similar drug/Ab ratios and % monomer, while conjugates made with no additive treatment led to very low drug incorporation.

Example 25

Effect of Propylene Flycol in Formulation and Conjugation

This example demonstrates that the subject conjugation reactions carried out in the presence of propylene glycol as co-solvent do not show precipitation of the conjugates, and that as high as 40% (and possibly even higher) propylene glycol can be used without a decrease in the % monomer of the resulting conjugate (in the presence of 2% dimethylacetamide—data not shown).

More importantly, the presence of propylene glycol during purification leads to significant increases in yield.

While not wishing to be bound by any particular theory, Applicants believe that one of the primary source of problems during the conjugation of the subject conjugates is the inherent hydrophobicity of the molecular components of the conjugates. This may at least partially explain the low purified yields, and sometimes aberrant mass distribution profiles observed with the subject conjugations.

It is also worth noting that the addition of isopropanol during size exclusion chromatography of the subject conjugates greatly decreases the apparent aggregate population. This observation suggests that small hydrophobic cosolvents may increase the solubility of the drug and conjugate of the invention.

Thus the subject conjugation reactions, the purification steps after the reaction, and/or the formulation of the formed conjugates are preferably carried out in the presence of small hydrophobic cosolvents, such as Propylene Glycol (e.g., 5, 10, 15, 20, 25, 30, 35, 40, 45%).

Antibody-sulfo-SPDB is prepared according to previously described methods by the addition of the N-hydroxysuccinimidyl (NHS) ester form of sulfo-SPDB to antibody (huMy9-6) in water containing 3% DMA, and buffered at pH 8.5 for 3 hours. The resulting intermediate (antibody-sulfo-SPDB) is purified over G25 Sephadex to remove excess linker. Antibody and linker are quantitated by UV-vis spectroscopy by measuring absorbance at 280 nm in the absence of reductant, and at 343 nm in the presence of ~50 mM DTT to measure 2-thiopyridine release from conjugated linker.

To conjugate drug, the antibody-sulfo-SPDB prepared above is reacted at 2 mg/mL antibody with a 2-fold molar excess of compound in the presence of the indicated co-solvents, and with the pH maintained at 8.5 with EPPS buffer (final concentration 60 mM). Dimethylacetamide (SAFC) and propylene glycol (Alfa Aesar) are used as received with no further purification. All buffers are sterilized by passage through 0.22 micron filter (Corning) and water is purified by reverse osmosis/deionization. The reactions are incubated at 25° C. for 3 hrs and then purified using disposable G25 Sephadex columns (Nap 25, GE Healthcare) into a formulation buffer consisting of 10 mM histidine, 250 glycine, 1% sucrose, 0.01% polysorbate 20, 50 µM sodium bisulfite and buffered to pH 6.2, as well as the indicated percentage of propylene glycol (v/v). Reaction yields and drug load are determined by absorbance spectroscopy. All samples are expected to show >95% monomer by analytical size exclusion chromatography.

Similar examples, data, and associated figures are found in the co-owned co-pending PCT applications filed on the same day and claiming priority to the same U.S. provisional applications as the instant application.

I claim:

1. A cytotoxic compound comprising a linking group with a reactive group bonded thereto capable of covalently linking the cytotoxic compound to a cell binding agent (CBA), wherein said cytotoxic compound is represented by the following formula:

or a pharmaceutically acceptable salt thereof, wherein:

the double line == between N and C represents a single bond or a double bond, provided that when it is a double bond X is absent and Y is —H, or a linear or branched alkyl having 1 to 4 carbon atoms, and when it is a single bond, X is —H or an amine protecting moiety;

Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle, a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or, Y is HSO$_3$, HSO$_2$ or a salt of HSO$_3^-$, SO$_3^{2-}$ or HSO$_2^-$ formed with a cation, H$_2$S$_2$O$_5$ or a salt of S$_2$O$_5^{2-}$ formed with a cation, PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation, (R$^i$O)$_2$PS(OR$^i$), R$^i$S—, R$^i$SO, R$^i$SO$_2$, R$^i$SO$_3$, HS$_2$O$_3$ or a salt of S$_2$O$_3^{2-}$ formed with a cation, HS$_2$O$_4$ or a salt of S$_2$O$_4^{2-}$ formed with a cation, P(=S)(OR$^{k'}$)(S)(OH) or a salt thereof formed with a cation, R$^{k'}$C(=O)NOH or a salt formed with a cation, HOCH$_2$SO$_2^-$ or a salt of HOCH$_2$SO$_2^-$ formed with a cation, HOCH$_2$SO$_2^-$Na$^+$, or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group with the reactive group bonded thereto;

n is an integer from 1 to 24;

W is selected from C=O, C=S, CH$_2$, BH, SO and SO$_2$;

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R_6$ is —H, —R, —OR, —SR, —NR'R", —NO$_2$, halogen or the linking group with the reactive group bonded thereto;

A and A' are the same or different, and are independently selected from —O—, oxo (—C(=O)—), —CRR'O—, —CRR'—, —S—, —CRR'S—, —NR$_5$ and —CRR'N(R$_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto;

X" and X'" are the same or different, and are independently selected from —(CH$_2$)$_{n'}$—, —NR'—, —CO—, —BH—, —SO— or —SO$_2$—;

Y" and Y'" are the same or different, and are independently selected from —O, —(CH$_2$)$_{n'}$—, —NR'— or —S—;

Z" and Z'" are the same or different, and are independently selected from —(CH$_2$)$_{n'}$—, —CR$_7$R$_8$—, —NR$_9$—, —O—, and —S—;

n' is selected from 0, 1, 2 and 3;

$R_7$ and $R_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —(OCH$_2$CH$_2$)$_n$—;

$R_a$, $R_{a'}$, $R_b$ and $R_{b'}$ are the same or different, and are independently selected from the group consisting of —H, halide, or an optionally substituted branched, linear or cyclic alkyl having 1 to 10 carbon atoms; or $R_a$ and $R_{a'}$ and/or $R_b$ and $R_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent, or represent an aryl group;

Q$_2$ and Q$_2$' are each independently selected from —H, the linking group with the reactive group bonded thereto, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and R$^{c'}$ is absent or selected from linear or branched alkyl, alkenyl or alkynyl having 1 to 5 carbon atoms.

2. The compound of claim 1, wherein the compound is represented by the following formula:

wherein:

L', L", and L'" are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, an azido, —COR', —OCOR', —OCONR'R" and the linking group with the reactive group bonded thereto, provided only one of L', L", and L'" is the linking group with the reactive group bonded thereto;

R$_a$" and R$_b$" are the same or different, and are selected from —H and -Me;

one of Q$_2$ and Q$_2$' is selected from —H, —R, —OR, —NR'R", —NR'(C=O)OR", —SR, and —NO$_2$, the other is the linking group with the reactive group bonded thereto.

3. The compound of claim 2, wherein L' is the linking group with the reactive group bonded thereto, and L" and L'" are —H.

4. The compound of claim 3, wherein L' in formula (VIIAa), or one of Q$_2$ and Q$_2$' in formula (VIIA2a) is the linking group with the reactive group bonded thereto, represented by the following formula:

—W'—R$^x$—V—R$^y$-J, wherein:

W' and V are the same or different, and are each independently absent, or selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ and R$^y$ are the same or different, and are each independently absent or an optionally substituted linear, branched or cyclic alkyl, alkenyl or alkynyl having 1 to 10 carbon atoms, an aryl bearing 6 to 10 carbon atoms or a 3- to 8-membered heterocyclic ring bearing 1 to 3 heteroatoms selected from O, N or S;

R$^e$ and R$^{e'}$ are the same or different, and are selected from —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a —NHR$^{101}$ or —NR$^{101}$R$^{102}$ group or a 5- or 6-membered nitrogen containing heterocycle, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24;

J comprises the reactive group bonded thereto, and is selected from a maleimide, a haloacetamido, —SH, —SSR$^d$, —CH$_2$SH, —CH(Me)SH, —C(Me)$_2$SH, —NHR$^{c1}$, —CH$_2$NHR$^{c1}$, —NR$^{c1}$NH$_2$, —COOH, and —COE, wherein —COE represents a reactive ester selected from, but not limited to, N-hydroxysuccinimde ester, N-hydroxy sulfosuccinimide ester, nitrophenyl ester, dinitrophenyl ester, sulfo-tetraflurophenyl ester, and pentafluorophenyl ester, and wherein R$^{c1}$ is —H or a substituted or unsubstituted linear or branched alkyl having 1 to 4 carbon atoms, and, R$^d$ is selected from phenyl, nitrophenyl, dinitrophenyl, carboxynitrophenyl, pyridyl or nitropyridyl.

5. The compound of claim 4, wherein J is —SH, —SSR$^d$, a maleimide, or a N-hydroxysuccinimide ester.

6. The compound of claim 4, wherein:
W' is —O—, —N(R$^e$)— or —N(R$^e$)—C(=O)—;
R$^e$ is —H, -Me, or —(CH$_2$—CH$_2$—O)$_n$-Me;
n is an integer from 2 to 6;
R$^x$ is linear or branched alkyl bearing 1 to 6 carbon atoms;
V and R$^y$ are absent; and
J is —COE.

7. The compound of claim 6, wherein —COE is N-hydroxysuccinimide ester.

8. The compound of claim 4, wherein L' in formula (VIIAa), or one of Q$_2$ and Q$_2$' in formula (VIIA2a) is represented by the following formula:

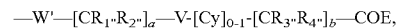

wherein:

R$_{1''}$, R$_{2''}$, and R$_{3''}$ are each independently —H or -Me;

R$_{4''}$ is —H, -Me, —SO$_3$H, or —SO$_3^-$M$^+$, wherein M$^+$ is a pharmaceutically acceptable cation;

a is an integers from 0-2, b is an integer from 0-3; and,

Cy is an optionally substituted 5-membered heterocyclic ring bearing an N heteroatom, preferably Cy is

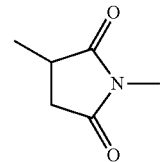

9. The compound of claim 4, wherein W' is —N(R$^e$)—; R$^e$ is —(CH$_2$—CH$_2$—O)$_{2-6}$—R$^k$, wherein R$^k$ is a —H, a linear, branched, or cyclic alkyl having 1 to 6 carbon atoms; and V is —S— or —SS—.

10. The compound of claim 4, wherein L' in formula (VIIAa), or one of Q$_2$ and Q$_2$' in formula (VIIA2a) is represented by the following formula:

11. The compound to claim 4, wherein L' in formula (VIIAa), or one of Q$_2$ and Q$_2$' in formula (VIIA2a) is:

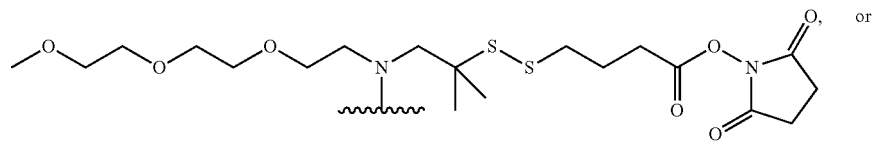

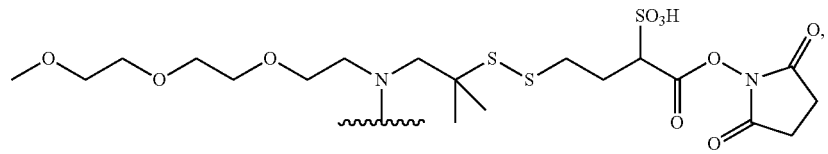

wherein Y is —H or —SO$_3$M, and M is —H or a pharmaceutically acceptable cation.

12. The compound of claim 4, wherein L' in formula (VIIAa), or one of Q$_2$ and Q$_2$' in formula (VIIA2a) is represented by the following formula:

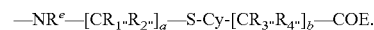

13. The compound of claim 4, wherein L' in formula (VIIAa), or one of Q$_2$ and Q$_2$' in formula (VIIA2a) is:

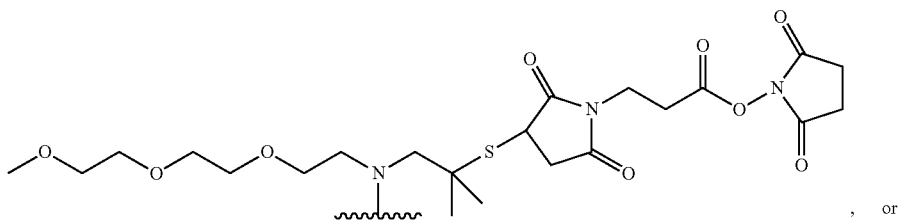

, or

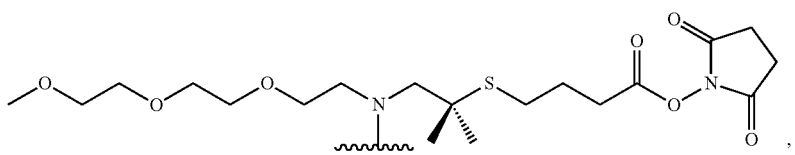

, wherein Y is —H or —SO₃M, and M is —H or a pharmaceutically acceptable cation.

14. The compound of claim 2, wherein L' in formula (VIIAa), or one of Q₂ and Q₂' in formula (VIIA2a) is represented by the following formula:

—W'—Rˣ—S—Zˢ wherein:
- the double line == between N and C represents a single bond or a double bond, provided that when it is a double bond, X is absent and Y is —H, and when it is a single bond, X is selected from —H, the linking group with the reactive group bonded thereto, or an amine protecting group;
- Y is —H, or a leaving group selected from —OR, —OCOR', —SR, —NR'R," —SO₃M, —SO₂M or —OSO₃M, wherein M is —H or a pharmaceutically acceptable cation;
- R is —H, an optionally substituted linear, branched or cyclic alkyl, alkenyl or alkynyl having from 1 to 10 carbon atoms or a PEG group —(CH₂CH₂O)ₙ—Rᶜ, wherein n is an integer from 1 to 24, and Rᶜ is a linear or branched alkyl having 1 to 4 carbon atoms;
- R' and R" are the same or different, and are selected from —H, —OH, —OR, —NRRᵍ′, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH₂CH₂O)ₙ—Rᶜ, wherein n is an integer from 1 to 24, preferably n is 2, 4 or 8; and Rᵍ′ is —H, an optionally substituted linear, branched or cyclic alkyl, alkenyl or alkynyl having from 1 to 10 carbon atoms or a PEG group —(CH₂CH₂O)ₙ—R;
- X' is selected from the group consisting of —H, —OH, a substituted or unsubstituted linear, branched or cyclic alkyl, alkenyl or alkynyl having from 1 to 10 carbon atoms, phenyl, and an amine-protecting group;
- Y' is selected from the group consisting of —H, an oxo group, a substituted or unsubstituted linear, branched or cyclic alkyl, alkenyl or alkynyl having from 1 to 10 carbon atoms;
- A and A' are selected from —O— and —S—;
- W' is absent, or selected from —O—, —N(Rᵉ)—, —N(Rᵉ)—C(=O)—, —N(C(=O)Rᵉ)—, —S—, —CH₂—S—, or —CH₂NRᵉ—;
- Rˣ is absent or selected from a linear, branched or cyclic alkyl having 1 to 10 carbon atoms;
- Rᵉ is —H, a linear, branched or cyclic alkyl, alkenyl or alkynyl having 1 to 10 carbon atoms or —(CH₂—CH₂—O)ₙ—Rᵏ, wherein Rᵏ is a —H, a linear, branched cyclic alkyl having 1 to 6 carbon atoms, optionally bearing a —NHR¹⁰¹ or —NR¹⁰¹R¹⁰² group or a 5- or 6-membered nitrogen containing heterocycle, wherein R¹⁰¹ and R¹⁰² are each independently a linear, branched, or cyclic alkyl, alkenyl or alkynyl having 1 to 10 carbon atoms;
- Zˢ is —H, or is selected from any one of the following formulas:

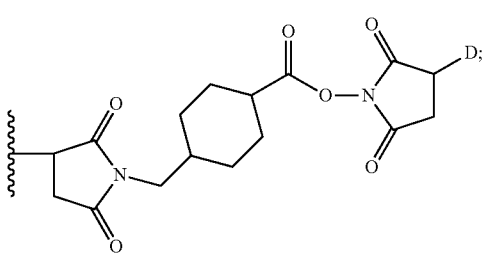 (a1)

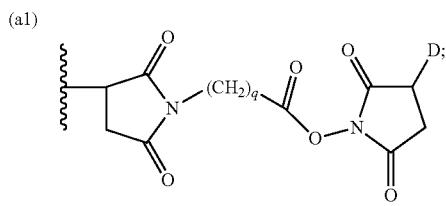 (a2)

-continued
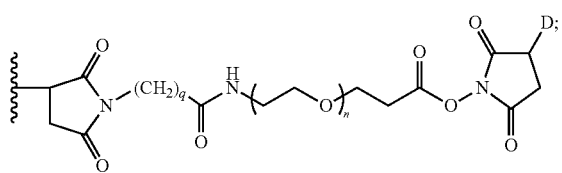 (a3)
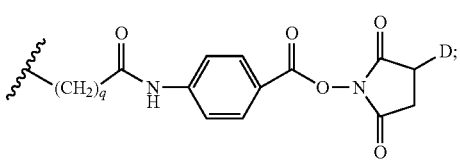 (a4)
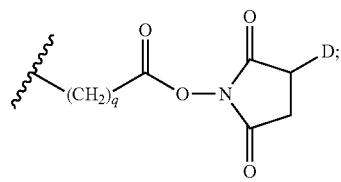 (a5)
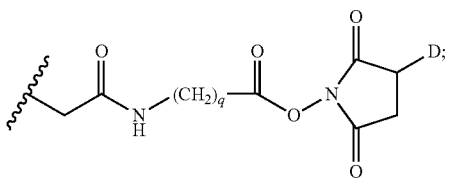 (a6)
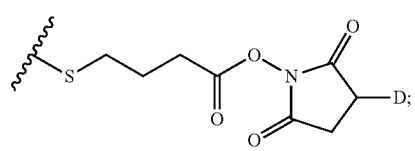 (a7)
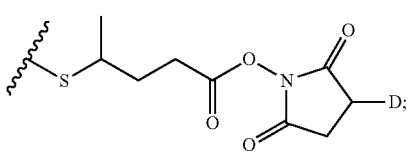 (a8)
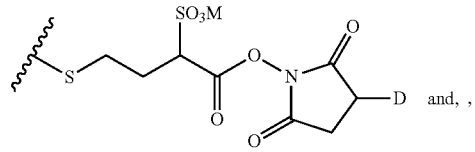 (a9)
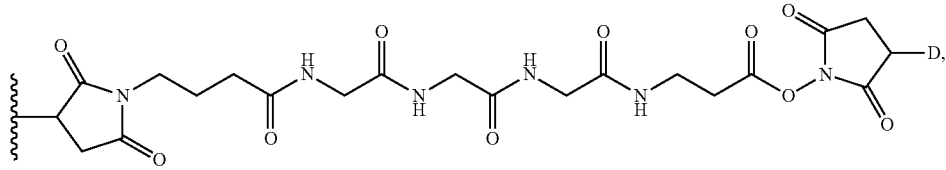 (a10)
wherein:
- q is an integer from 1 to 5;
- n is an integer from 2 to 6;
- D is —H or —SO₃M;
- M is —H or a pharmaceutically acceptable cation.
15. The compound of claim 14, wherein $Z^s$ is represented by any one of the following formulas:
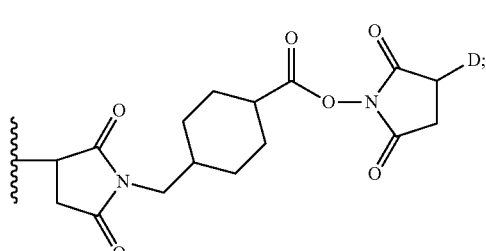 (a1)
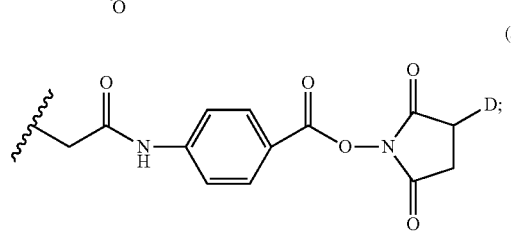 (a4')
-continued
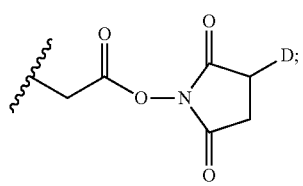 (a5')
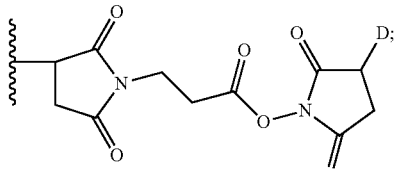 (a12)
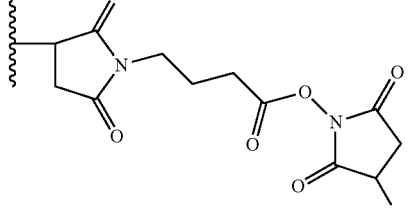 (a13)

16. The compound of claim 14, wherein W' is —N(R$^e$)—; and R$^e$ is —(CH$_2$—CH$_2$—O)$_n$—R$^k$, wherein R$^k$ is a —H, a linear, branched, or cyclic alkyl having 1 to 6 carbon atoms.

17. The compound of claim 16, wherein R$^k$ is —H or -Me, n is 4, and q is 2.

18. The compound of claim 17, wherein R$^x$ is a linear or branched alkyl having 1 to 6 carbon atoms.

19. The compound of claim 17, wherein R$^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3.

20. The compound of claim 19, wherein R$^f$ and R$^g$ are the same or different, and are selected from —H and -Me; and p is 1.

21. The compound of claim 14, wherein:
the double line == between N and C represents a single bond or a double bond, provided that when it is a double bond X is absent and Y is —H, and when it is a single bond, X is —H; Y is —OH or —SO$_3$M;
M is —H or a pharmaceutically acceptable cation;
X' and Y' are both —H;
A and A' are both —O—;
R$_6$ is —OMe; and
R$^x$ is a linear or branched alkyl having 1 to 6 carbon atoms.

22. The compound of claim 1, wherein the double line == between N and C represents a double bond.

23. The compound of claim 1, wherein the double line == between N and C represents a single bond, X is —H or an amine protecting group; and Y is selected from —H, —OR, —OCOR', —SR, —NR'R," an optionally substituted 5- or 6-membered nitrogen-containing heterocycle, —SO$_3$M, —SO$_2$M and a sulfate —OSO$_3$M.

24. The compound of claim 1, wherein W is C=O.

25. A conjugate comprising: a cytotoxic compound and a cell binding agent (CBA), wherein the cytotoxic compound comprises a linking group which covalently links the cytotoxic compound to the CBA, and wherein said cytotoxic compound is represented by the following formula:
or a pharmaceutically acceptable salt thereof, wherein:
the double line == between N and C represents a single bond or a double bond, provided that when it is a double bond X is absent and Y is —H, or a linear or branched alkyl having 1 to 4 carbon atoms, and when it is a single bond, X is —H or an amine protecting moiety;
Y is —H or a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine), a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$M, —SO$_3$M, —OSO$_3$M, halogen, cyano and an azido; or,
Y is a sulfite (HSO$_3$, HSO$_2$ or a salt of HSO$_3$$^-$, SO$_3$$^{2-}$ or HSO$_2$$^-$ formed with a cation), metabisulfite (H$_2$S$_2$O$_5$ or a salt of S$_2$O$_5$$^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2$$^{3-}$, POS$_3$$^{3-}$ or PS$_4$$^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3$$^{2-}$ formed with a cation), dithionite (HS$_2$O$_4$ or a salt of S$_2$O$_4$$^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2$$^-$ or a salt of HOCH$_2$SO$_2$$^-$ formed with a cation, such as HOCH$_2$SO$_2$$^-$Na$^{+)}$ or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R' is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group;

n is an integer from 1 to 24;

W is selected from C=O, C=S, CH$_2$, BH, SO and SO$_2$;

X' is selected from —H, an amine-protecting group, the linking group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$_6$ is —H, —R, —OR, —SR, —NR'R", —NO$_2$, halogen or the linking group;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group, a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can be the linking group;

X" and X''' are the same or different, and are independently selected from —(CH$_2$)$_{n'}$—, —NR'—, —CO—, —BH—, —SO— or —SO$_2$—;

Y" and Y''' are the same or different, and are independently selected from —O—, —(CH$_2$)$_{n'}$—, —NR'— or —S—;

Z" and Z''' are the same or different, and are independently selected from —(CH$_2$)$_{n'}$—, —CR$_7$R$_8$—, —NR$_9$—, —O—, and —S—;

n' is selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

R$_a$, R$_{a'}$, R$_b$ and R$_{b'}$ are the same or different, and are independently selected from the group consisting of —H, halide, or an optionally substituted branched, linear or cyclic alkyl having 1 to 10 carbon atoms; or R$_a$ and R$_{a'}$ and/or R$_b$ and R$_{b'}$ together form a double bond containing group =B and =B' respectively;

=B and =B' are the same or different and independently selected from an optionally substituted branched or linear alkenyl or a carbonyl group;

Q is Q$_1$-Ar-Q$_2$;

Q' is Q$_1$'-Ar'-Q$_2$';

Q$_1$ and Q$_1$' are each independently absent, a linear, branched or cyclic alkyl from 1 to 6 carbon atoms or a —CH=CH unit;

Ar and Ar' are each independently absent or represent an aryl group;

Q$_2$ and Q$_2$' are each independently selected from —H, the linking group, a substituted or unsubstituted linear, branched or cyclic alkyl, alkenyl or alkynyl having from 1 to 10 carbon atoms, a polyethylene glycol unit —R$^{c'}$—(OCH$_2$CH$_2$)$_n$—R$^c$, or a substituent selected from a halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$M, a sulfate —OSO$_3$M, a sulfonamide represented by SO$_2$NR'R", cyano, an azido, —COR', —OCOR' or —OCONR'R"; and R$^{c'}$ is absent or selected from linear or branched alkyl, alkenyl or alkynyl having 1 to 5 carbon atoms.

26. The compound of claim 1, wherein the compound is represented by the following formula:

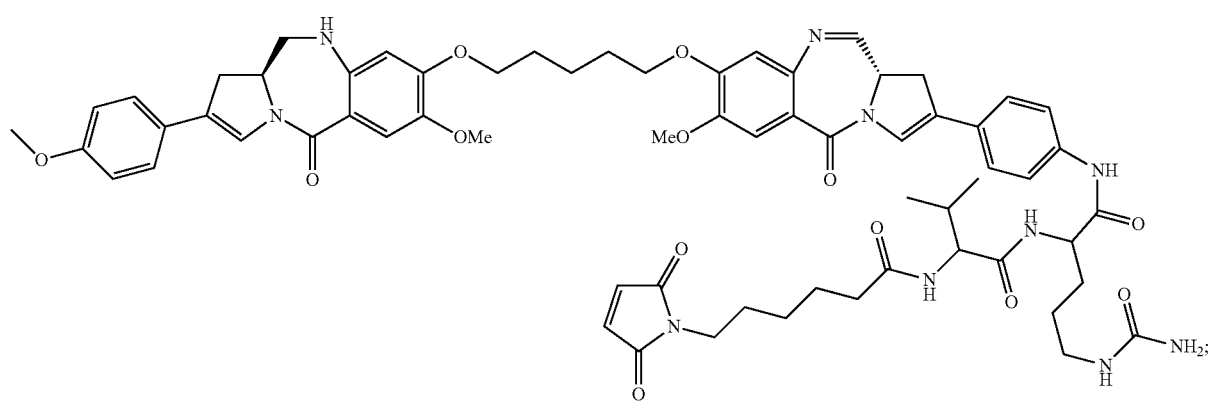

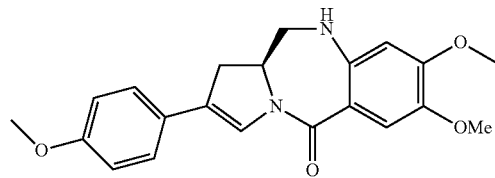
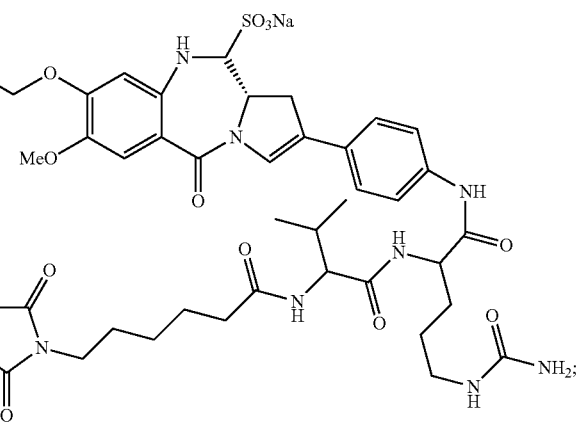
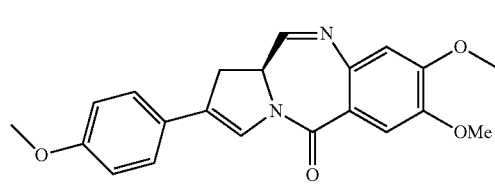
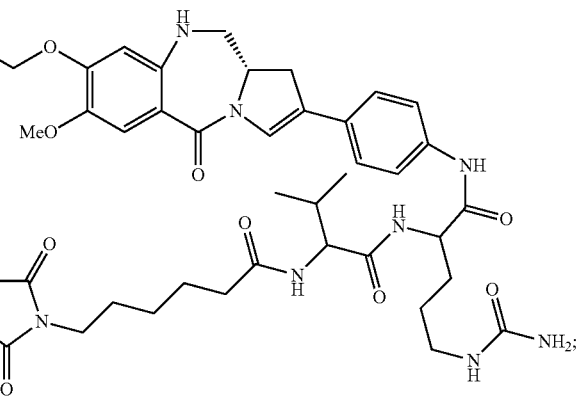
or
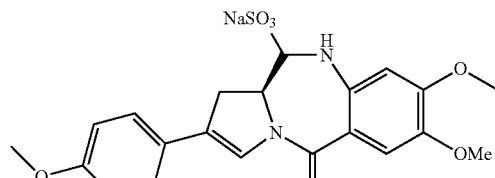
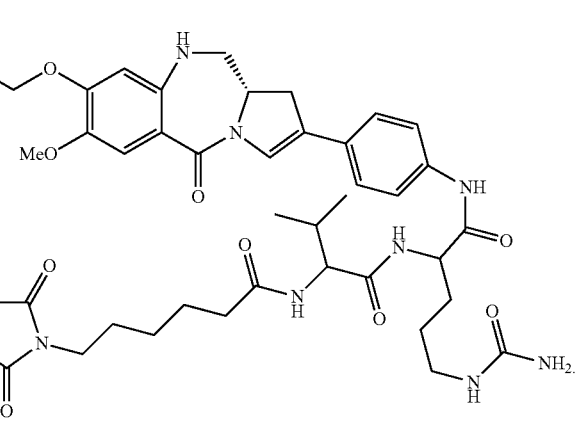

27. The conjugate of claim 25, wherein the cytotoxic compound is represented by the following formula:
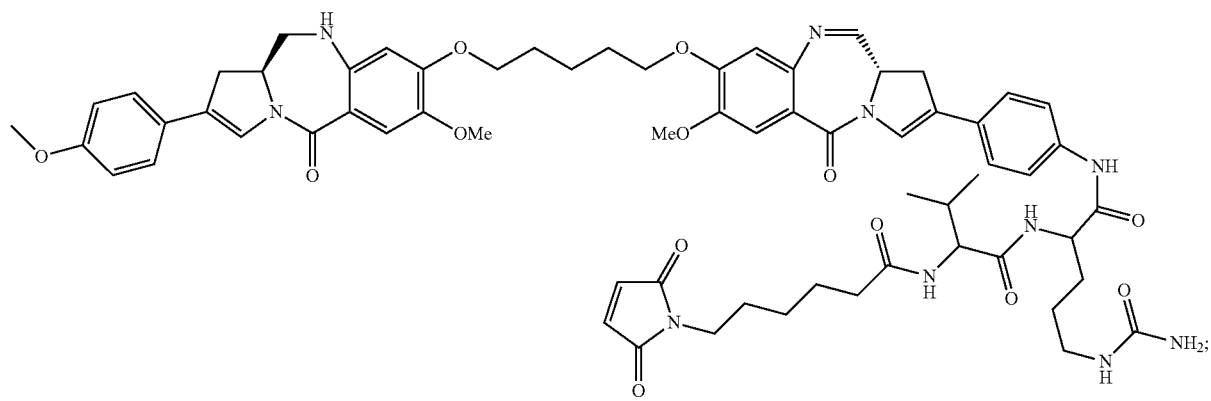
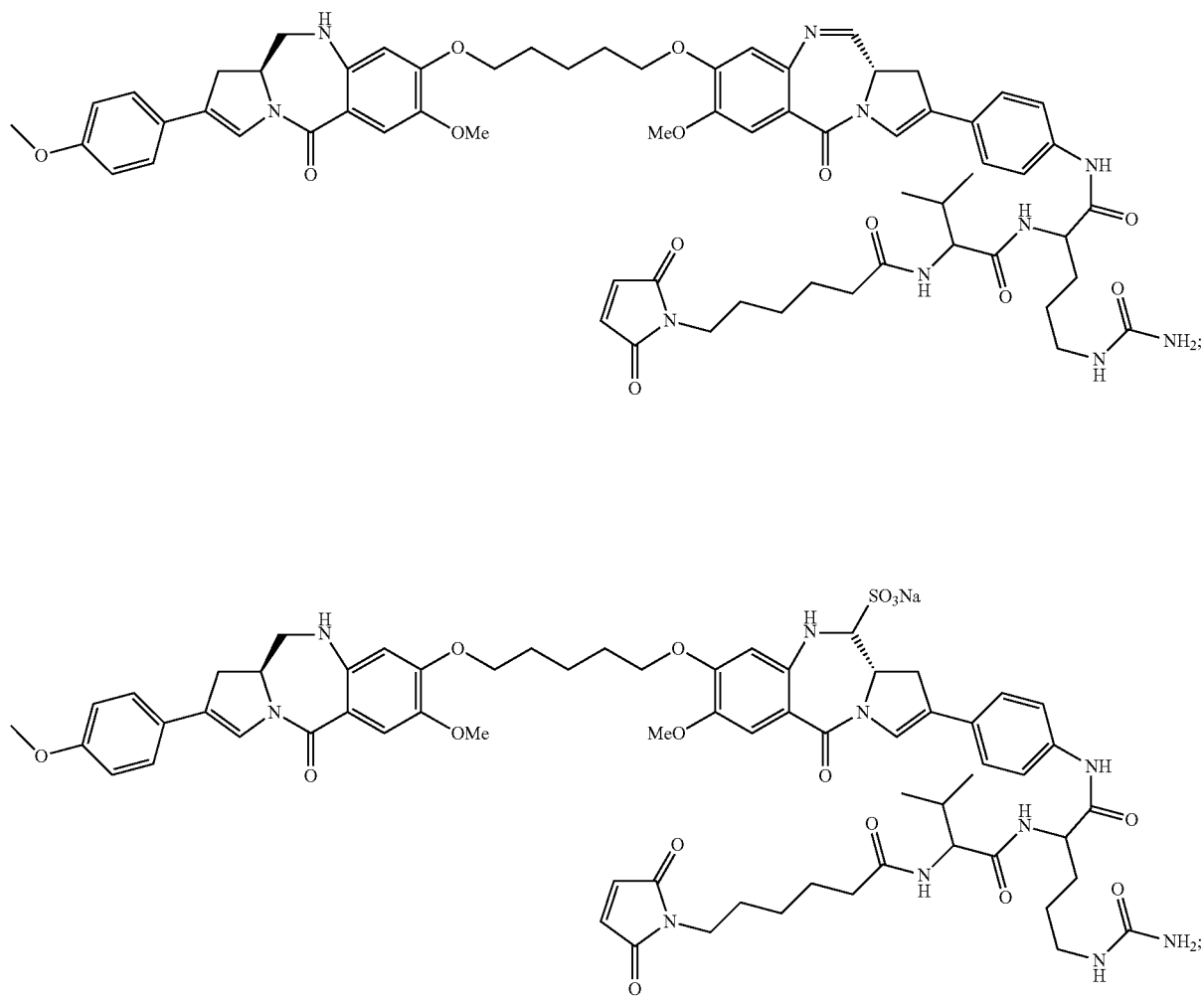
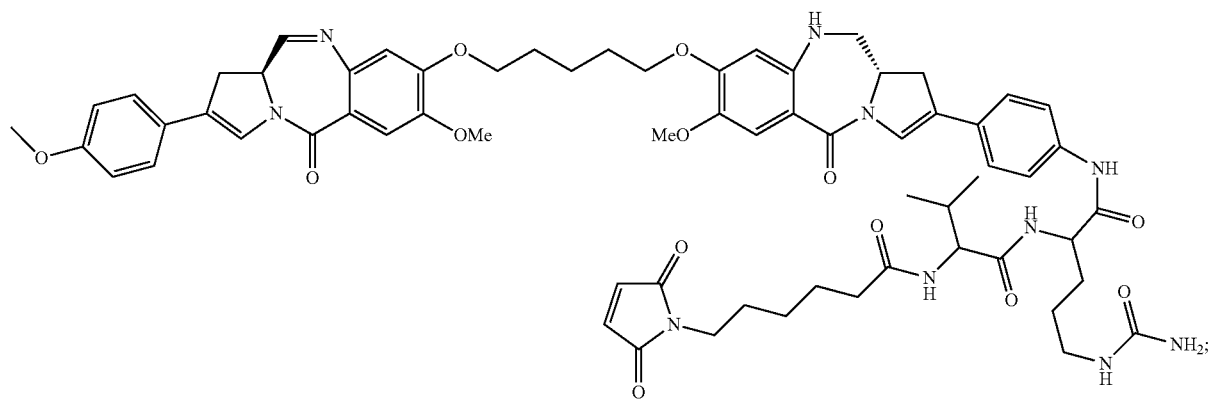

or
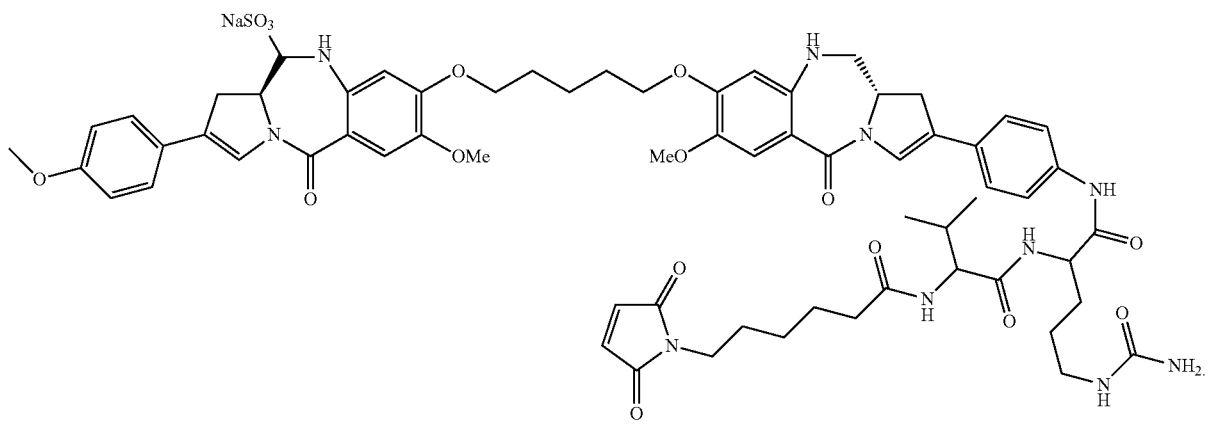
20
28. The conjugate of claim 25, wherein the conjugate is represented by the following formula:
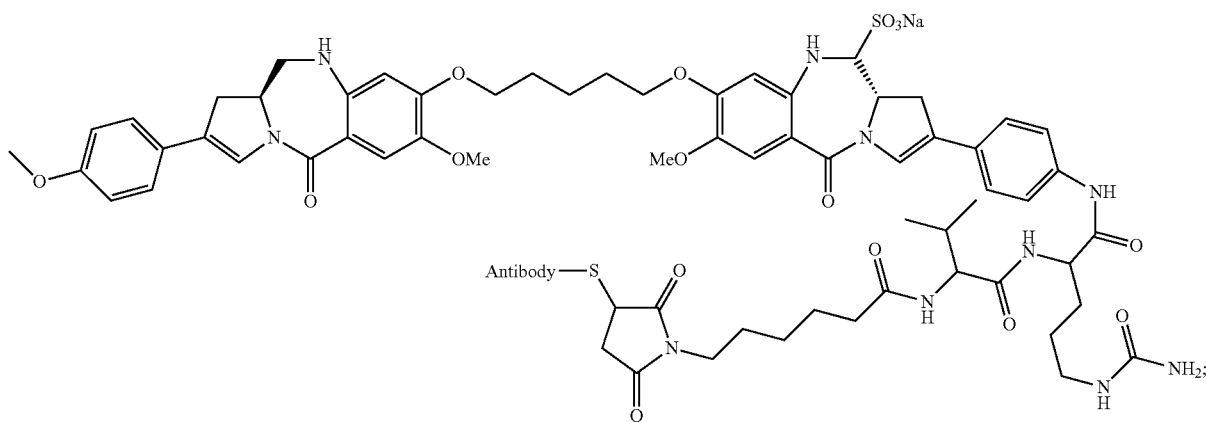
or
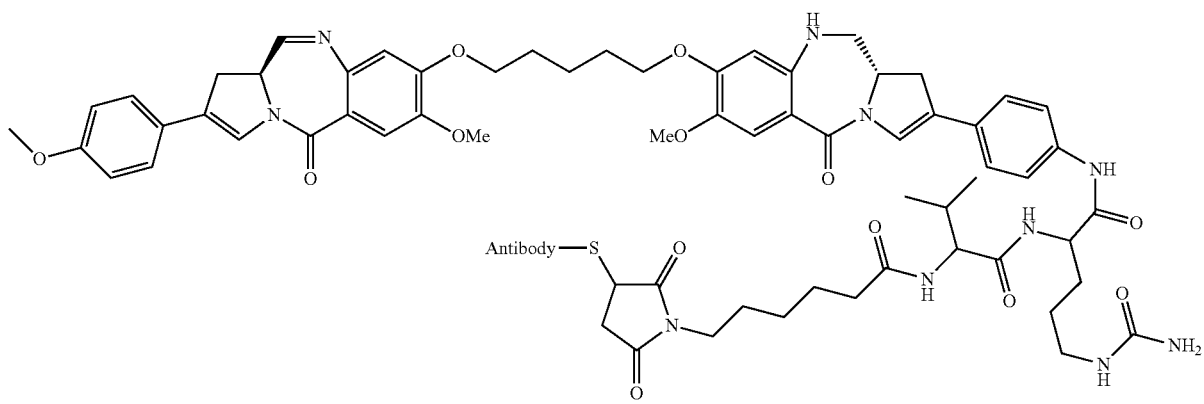
* * * * *

UNITED STATES PATENT AND TRADEMARK OFFICE
CERTIFICATE OF CORRECTION

PATENT NO. : 9,534,000 B2
APPLICATION NO. : 13/984762
DATED : January 3, 2017
INVENTOR(S) : Ravi V. J. Chari Page 1 of 2

It is certified that error appears in the above-identified patent and that said Letters Patent is hereby corrected as shown below:

In the Claims

At Column 263, Claim number 1, Line number 34, add the following formula:

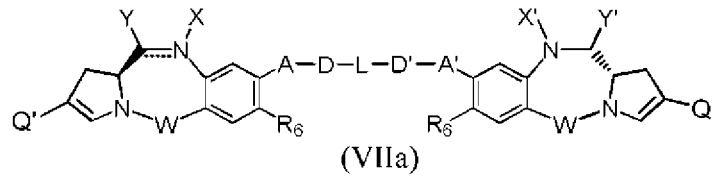

(VIIa)

At Column 266, Claim number 2, Line number 31, add the following formula:

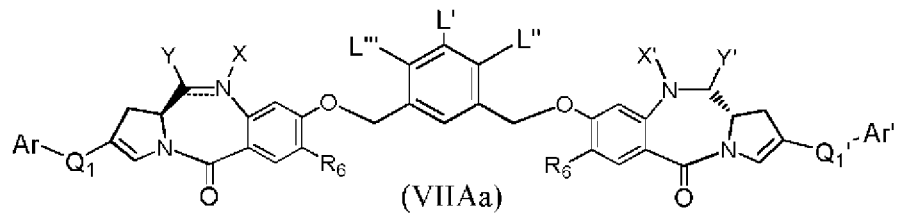

(VIIAa)

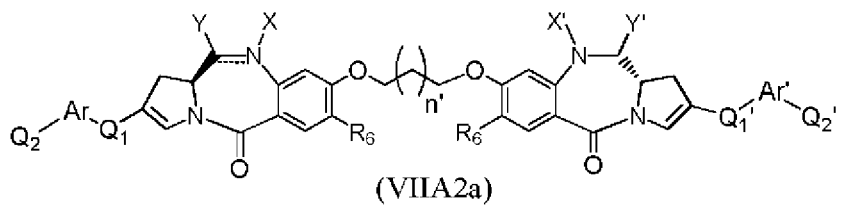

(VIIA2a)

Signed and Sealed this
Twenty-ninth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)

At Column 273, Claim number 25, Line number 39, add the following formula:

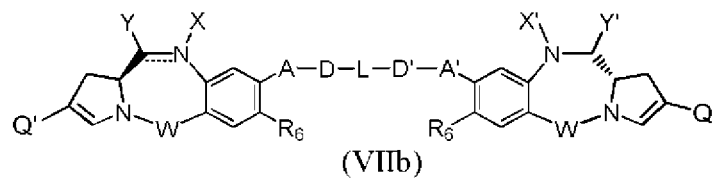

(VIIb)

```
                        SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Phe Met Asn
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (14)..(14)
<223> OTHER INFORMATION: /replace="Gln" or "His" or "Arg"
<220> FEATURE:
```

```
<221> NAME/KEY: misc_feature
<222> LOCATION: (14)..(14)
<223> OTHER INFORMATION: /note="Residue given in the sequence has no
      preference with respect to the annotations for said position"
<220> FEATURE:
<221> NAME/KEY: VARIANT
<222> LOCATION: (16)..(16)
<223> OTHER INFORMATION: /replace="His" or "Asn" or "Arg"
<220> FEATURE:
<221> NAME/KEY: VARIANT
<222> LOCATION: (17)..(17)
<223> OTHER INFORMATION: /replace="Glu" or "Thr" or "Ser" or "Ala" or
      "Val"
<220> FEATURE:
<221> NAME/KEY: misc_feature
<222> LOCATION: (16)..(17)
<223> OTHER INFORMATION: /note="Residues given in the sequence have no
      preference with respect to those in the annotations for said
      positions"

<400> SEQUENCE: 2

Arg Ile His Pro Tyr Asp Gly Asp Thr Phe Tyr Asn Gln Lys Phe Gln
1               5                   10                  15

Gly

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 9
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

```
                 130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 10
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 11
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
            115

<210> SEQ ID NO 12
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 13
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

```
Gly Thr Ser Leu Met His Trp Tyr His Gln Lys Pro Gly Gln Gln Pro
             35              40              45
Arg Leu Leu Ile Tyr Arg Ala Ser Asn Leu Glu Ala Gly Val Pro Asp
 50              55              60
Arg Phe Ser Gly Ser Gly Ser Lys Thr Asp Phe Thr Leu Thr Ile Ser
 65              70              75              80
Pro Val Glu Ala Glu Asp Ala Ala Thr Tyr Tyr Cys Gln Gln Ser Arg
                 85              90              95
Glu Tyr Pro Tyr Thr Phe Gly Gly Gly Thr Lys Leu Glu Ile Lys Arg
            100             105             110

<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Leu Ala Leu
1
```